(12) United States Patent
Puri et al.

(10) Patent No.: US 12,195,549 B2
(45) Date of Patent: *Jan. 14, 2025

(54) IMMUNOMODULATORY ANTIBODIES AND METHODS OF USE THEREOF

(71) Applicant: OncoResponse, Inc., Seattle, WA (US)

(72) Inventors: Kamal D. Puri, Seattle, WA (US); Siddarth Chandrasekaran, Issaquah, WA (US); Melissa L. Conerly, Seattle, WA (US); Peter Probst, Seattle, WA (US); Tyrel T. Smith, Seattle, WA (US); Mark E. Branum, Seattle, WA (US); Randi M. Simmons, Seattle, WA (US)

(73) Assignee: OncoResponse, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/185,736

(22) Filed: Mar. 17, 2023

(65) Prior Publication Data

US 2024/0101696 A1 Mar. 28, 2024

Related U.S. Application Data

(63) Continuation of application No. 17/597,706, filed as application No. PCT/US2020/042668 on Jul. 17, 2020, now Pat. No. 11,634,501.

(60) Provisional application No. 62/878,265, filed on Jul. 24, 2019, provisional application No. 62/876,580, filed on Jul. 19, 2019, provisional application No. 62/876,579, filed on Jul. 19, 2019.

(51) Int. Cl.
*A61P 35/00* (2006.01)
*C07K 16/28* (2006.01)
*A61K 39/00* (2006.01)
*A61K 45/06* (2006.01)

(52) U.S. Cl.
CPC .......... *C07K 16/2896* (2013.01); *A61P 35/00* (2018.01); *A61K 2039/507* (2013.01); *A61K 45/06* (2013.01); *C07K 2317/31* (2013.01); *C07K 2317/33* (2013.01); *C07K 2317/52* (2013.01); *C07K 2317/56* (2013.01); *C07K 2317/622* (2013.01); *C07K 2317/71* (2013.01); *C07K 2317/76* (2013.01); *C07K 2317/77* (2013.01); *C07K 2317/92* (2013.01)

(58) Field of Classification Search
CPC .................................................. C07K 16/2896
USPC ...................................................... 424/139.1
See application file for complete search history.

(56) References Cited

U.S. PATENT DOCUMENTS

| | | | |
|---|---|---|---|
| 3,773,919 A | 11/1973 | Boswell et al. | |
| 4,676,980 A | 6/1987 | Segal et al. | |
| 5,229,275 A | 7/1993 | Goroff | |
| 5,545,806 A | 8/1996 | Lonberg et al. | |
| 5,545,807 A | 8/1996 | Surani et al. | |
| 5,567,610 A | 10/1996 | Borrebaeck et al. | |
| 5,569,825 A | 10/1996 | Lonberg et al. | |
| 5,571,894 A | 11/1996 | Wels et al. | |
| 5,587,458 A | 12/1996 | King et al. | |
| 5,591,669 A | 1/1997 | Krimpenfort et al. | |
| 5,627,052 A | 5/1997 | Schrader | |
| 5,641,870 A | 6/1997 | Rinderknecht et al. | |
| 5,731,168 A | 3/1998 | Carter et al. | |
| 5,869,046 A | 2/1999 | Presta et al. | |
| 6,121,022 A | 9/2000 | Presta et al. | |
| 7,112,439 B2 | 9/2006 | Johnson et al. | |
| 9,476,890 B2 | 10/2016 | Moestrup et al. | |
| 9,724,426 B2 | 8/2017 | Graversen et al. | |
| 11,034,770 B2 | 6/2021 | Puri et al. | |
| 11,634,501 B2 * | 4/2023 | Puri ................... | C07K 16/2803 424/139.1 |
| 11,827,715 B2 * | 11/2023 | Puri ................... | C07K 16/2809 |
| 2007/0082380 A1 | 4/2007 | Pardridge et al. | |
| 2010/0146647 A1 | 6/2010 | Logtenberg et al. | |
| 2012/0316071 A1 | 12/2012 | Smider et al. | |
| 2014/0170168 A1 | 6/2014 | Reiter et al. | |
| 2018/0201681 A1 | 7/2018 | Seldon et al. | |
| 2018/0208654 A1 | 7/2018 | Xiao et al. | |
| 2019/0119407 A1 | 4/2019 | Hsu et al. | |
| 2019/0153471 A1 | 5/2019 | Paul et al. | |
| 2019/0192691 A1 | 6/2019 | Barrett et al. | |
| 2019/0194307 A1 | 6/2019 | Barelle et al. | |
| 2019/0211100 A1 | 7/2019 | Bakker et al. | |
| 2019/0336615 A1 | 11/2019 | Thompson et al. | |
| 2019/0359937 A1 | 11/2019 | Pigott et al. | |
| 2020/0017602 A1 | 1/2020 | Sexton et al. | |
| 2020/0023076 A1 | 1/2020 | Fotin-Mleczek et al. | |
| 2020/0071409 A1 | 3/2020 | Attinger et al. | |
| 2020/0079865 A1 | 3/2020 | Wang et al. | |

(Continued)

FOREIGN PATENT DOCUMENTS

| | | |
|---|---|---|
| CN | 102686612 A | 9/2012 |
| CN | 106459182 A | 2/2017 |

(Continued)

OTHER PUBLICATIONS

U.S. Appl. No. 18/491,682, filed Oct. 20, 2023, Pending.

(Continued)

*Primary Examiner* — Sean E Aeder
(74) *Attorney, Agent, or Firm* — Goodwin Procter LLP

(57) ABSTRACT

Provided herein are antibodies and methods of use thereof. The antibodies as disclosed herein bind to CD163+ on cells, such as on macrophages. These antibodies can be used in methods of treatment, such as methods of treating cancer.

14 Claims, 44 Drawing Sheets

Specification includes a Sequence Listing.

(56) References Cited

U.S. PATENT DOCUMENTS

| | | |
|---|---|---|
| 2020/0109213 A1 | 4/2020 | Sexton et al. |
| 2020/0115463 A1 | 4/2020 | Wang et al. |
| 2021/0253733 A1 | 8/2021 | Puri et al. |
| 2022/0289861 A1 | 9/2022 | Puri et al. |
| 2023/0181732 A1 | 6/2023 | Chandrasekaran et al. |

FOREIGN PATENT DOCUMENTS

| | | |
|---|---|---|
| EP | 1367393 A1 | 12/2003 |
| JP | 2019509017 A | 4/2019 |
| WO | WO-199100360 A1 | 1/1991 |
| WO | WO-199202551 A1 | 2/1992 |
| WO | WO-199220373 A1 | 11/1992 |
| WO | WO-1993/008829 A1 | 5/1993 |
| WO | WO-199316185 A2 | 8/1993 |
| WO | WO-1994/004690 A1 | 3/1994 |
| WO | WO-1996/027011 A1 | 9/1996 |
| WO | WO-199717852 A1 | 5/1997 |
| WO | WO-2003100419 A1 | 12/2003 |
| WO | WO-2011039510 A2 | 4/2011 |
| WO | WO-2015103072 A1 | 7/2015 |
| WO | WO-2017027316 A1 | 2/2017 |
| WO | WO-2017/189964 A2 | 11/2017 |
| WO | WO-2018019990 A1 | 2/2018 |
| WO | WO-2018094112 A1 | 5/2018 |
| WO | WO-2019084060 | 5/2019 |
| WO | WO-2019126194 | 6/2019 |
| WO | WO-2019126398 A1 | 6/2019 |
| WO | WO-2019160501 A1 | 8/2019 |
| WO | WO-202018434 A1 | 1/2020 |
| WO | WO-2020004492 A1 | 1/2020 |
| WO | WO-2020058372 A1 | 3/2020 |
| WO | WO-2021016128 A1 | 1/2021 |
| WO | WO-2023034963 A2 | 3/2023 |

OTHER PUBLICATIONS

U.S. Appl. No. 17/597,706, filed Jan. 19, 2022, U.S. Pat. No. 11,634,501, Apr. 25, 2023, Issued.
U.S. Appl. No. 17/302,032, filed Apr. 22, 2021, U.S. Pat. No. 11,827,715, Nov. 28, 2023, Issued.
U.S. Appl. No. 16/935,814, filed May 26, 2021, U.S. Pat. No. 11,034,770, Jun. 15, 2021, Issued.
Altschul, S.F., et al. Gapped BLAST and PSI-BLAST: a new generation of protein database search programs. Nucleic Acids Res. 25(17): 3389-3402 (1997).
Arber, D.A., et al., The 2016 revision to the World Health Organization classification of myeloid neoplasms and acute leukemia, Blood, 127(20): 2391-2405 (2016).
Babcook, U.S., et al. A novel strategy for generating monoclonal antibodies from single, isolated lymphocytes producing antibodies of defined specificities, PNAS USA, 93(15):7843-7848 (1996).
Brennen, M., et al. Preparation of bispecific antibodies by chemical recombination of monoclonal immunoglobulin fragments, Science 229(4708): 81-83 (1985).
Brüggemann, M., et al. Designer mice: the production of human antibody repertoires in transgenic animals, Year Immunol. 7: 33-40 (1993).
Carter, P., et al. High Level *Escherichia coli* expression and production of a bivalent humanized antibody fragment, Bio/Technology 10: 163-167 (1992).
Casset, F., et al., A peptide mimetic of an anti-CD4 monoclonal antibody by rational design, Biochem Biophys Res Commun, 307: 198-205 (2003).
Chen, L., et al. Epitope-directed antibody selection by site-specific photocrosslinking, Sci Adv 6(14):eaaz7825 (2020).
Chen, T., et al., CD163, a novel therapeutic target, regulates the proliferation and stemness of glioma cells via casein kinase 2, Oncogene, 38(8): 1183-1199 (2019).
Chen, Y., et al., Selection and analysis of an optimized anti-VEGF antibody: Crystal structure of an affinity-matured Fab in complex with an antigen, J Mol Biol, 293: 865-881 (1999).
De Pascalis, R., et al., Grafting of "abbreviated" complementarity-determining regions containing specificity-determining residues essential for ligand contact to engineer a less immunogenic humanized monoclonal antibody, J Immunol, 169: 3076-3084 (2002).
Devereux, J., et al. A comprehensive set of sequence analysis programs for the VAX, Nucl. Acids Res. 12(1): 387-395 (1984).
Etzerodt, A., et al., Efficient intracellular drug-targeting of macrophages using stealth liposomes directed to the hemoglobin scavenger receptor CD163, Journal of Controlled Release, 160(1): 72-80 (2012).
Gruber, M., et al. Efficient tumor cell lysis mediated by a bispecific single chain antibody expressed in *Escherichia coli*, J. Immunol. 152: 5368-5374 (1994).
Holliger, P., et al., "Diabodies": Small bivalent and bispecific antibody fragments, PNAS USA 90: 6444-6448 (1993).
Ishikawa, F., et al., The differentiative and regenerative properties of human hematopoietic stem/progenitor cells in NOD-SCID/IL2γ (null) mice, Curr Top Microbiol Immunol 324: 87-94 (2008).
Jakobovits, A., et al. Analysis of homozygous mutant chimeric mice: deletion of the immunoglobulin heavy-chain joining region blocks B-cell development and antibody production, PNAS 90: 2551-2555 (1993).
Jakobovits, A., et al., Germ-line transmission and expression of a human-derived yeast artificial chromosome, Nature 362(6417): 255-258 (1993).
Kipriyanov, S.M., et al., Single-chain antibody streptavidin fusions: Tetrameric bifunctional scFv-complexes with biotin binding activity and enhanced affinity to antigen, Hum Antibodies Hybridomas 6(3): 93-101 (1995).
Klockenbusch, C., et al., Optimization of Formaldehyde Cross-Linking for Protein Interaction Analysis of Non-Tagged Integrin β1, J Biomed Biotechnol 2010: 927585 (2010).
Kostelny, S.A., et al., Formation of a bispecific antibody by the use of leucine zippers, J. Immunol. 148(5): 1547-1553 (1992).
Lahn, M., et al., Aerosolized anti-T-cell-receptor antibodies are effective against airway inflammation and hyperreactivity. Int Arch Allergy Immunol, 134(1): 49-55 (2004).
Liljeblad, M., et al., Analysis of agalacto-IgG in rheumatoid arthritis using surface plasmon resonance, Glycoconj J, 17(5): 323-9 (2000).
MacCallum, R.M., et al., Antibody-antigen interactions: Contact analysis and binding site topography, J Mol Biol, 262: 732-745 (1996).
Matthews, K., et al., Therapeutic Targeting of CD163 on Hematopoietic Progenitor Cells By Novel Monoclonal Antibody TBI 304H Demonstrates an Increase in Erythropoiesis in Humanized Mice, Blood, 126(23): 1163 (2015).
Milstein, C., et al., Hybrid hybridomas and their use in immunohistochemistry, Nature 305: 537-539 (1983).
Morimoto, K., et al., Single-step purification of F(ab')2 fragments of mouse monoclonal antibodies (immunoglobulins G1) by hydrophobic interaction high performance liquid chromatography using TSKgel Phenyl-5PW, J Biochem Biophys Methods 24: 107-117 (1992).
Muraoka, S., et al., Structural requirements for IgM assembly and cytolytic activity. Effects of mutations in the oligosaccharide acceptor site at Asn402, J Immunol. 142(2):695-701 (1989).
Myers, E.W., et al., Optimal alignments in linear space, Comput Appl Biosci. 4(1): 11-17 (1988).
Neri, D., et al., High-affinity antigen binding by chelating recombinant antibodies (CRAbs), J Mol Biol. 246: 367-373 (1995).
Nimrod, G., et al., Computational Design of Epitope-Specific Functional Antibodies, Cell Reports 25: 2121-2131 (2018).
PCT/US2020/042668 International Search Report and Written Opinion dated Jan. 5, 2021.
Pearson, T., et al., Creation of "humanized" mice to study human immunity, Curr Protoc Immunol; Chapter 15: Unit 15.21 (2008).
Pearson, W.R., et al., Improved Tools for Biological Sequence Comparison, PNAS USA 85: 2444-2448 (1988).
Pearson, W.R., Rapid and sensitive sequence comparison with FASTP and FASTA, Meth. Enzymol. 183: 63-98 (1990).
Plückthun, A., et al., Expression of functional antibody Fv and Fab fragments in *Escherichia coli*, Methods Enzymol. 178: 497-515 (1989).

(56) References Cited

OTHER PUBLICATIONS

Rudikoff, S., et al., Single amino acid substitution altering antigen-binding specificity, Proc Natl Acad Sci USA, 79: 1979-1983 (1982).
Sanger, F., et al., DNA sequencing with chain-terminating inhibitors, PNAS USA, 74(12): 5463-5467 (1977).
Schultz, L.D., et al., Humanized mice for immune system investigation: progress, promise and challenges, Nat Rev Immunol 12(11): 786-798 (2012).
Schultz, L.D., et al., Humanized mice in translational biomedical research, Nat Rev Immunol 7(2): 118-30 (2007).
Shalaby, M.R., Development of humanized bispecific antibodies reactive with cytotoxic lymphocytes and tumor cells overexpressing the HER2 protooncogene, J Exp Med. 175(1): 217-25 (1992).
Sox, H.C., et al., Attachment of Carbohydrate to the variable region of myeloma immunoglobulin light chains, PNAS USA 66(3): 975-982 (1970).
Suresh, M.R., et al., Bispecific monoclonal antibodies from hybrid hybridomas, Methods Enzymol, 121: 210-228 (1986).
Swerdlow, S.H., et al., The 2016 revision of the World Health Organization classification of lymphoid neoplasms, Blood, 127(20): 2375-2390 (2016).
Tao, M., et al., Studies of aglycosylated chimeric mouse-human IgG. Role of carbohydrate in the structure and effector functions mediated by the human IgG constant region, J. Immunol, 143: 2595-2601 (1989).
Taylor, A.K., et al., Selective removal of alpha heavy-chain glycosylation sites causes immunoglobulin A degradation and reduced secretion, Mol Cell Biol, 8(10): 4197-4203 (1988).
Traunecker, A., et al., Bispecific single chain molecules (Janusins) target cytotoxic lymphocytes on HIV infected cells, EMBO J, 10(12): 3655-3659 (1991).
Troegeler, A., et al., An efficient siRNA-mediated gene silencing in primary human monocytes, dendritic cells and macrophages, Immunol Cell Biol, 92: 699-708 (2014).
U.S. Appl. No. 16/935,814 dated Jan. 1, 2021.
Ward, E.S., et al., Binding activities of a repertoire of single immunoglobulin variable domains secreted from *Escherichia coli*, Nature 341(6242): 544-546 (1989).
Wu, H., et al., Humanization of a murine monoclonal antibody by simultaneous optimization of framework and CDR residues, J Mol Biol, 294: 151-162 (1999).
Yan, W., et al., Index-ion triggered MS2 ion quantification: a novel proteomics approach for reproducible detection and quantification of targeted proteins in complex mixtures, Mol Cell Proteomics, 10.3: M110.005611 (2011).
Zapata, G., et al., Engineering linear F(ab')2 fragments for efficient production in *Escherichia coli* and enhanced antiproliferative activity, Protein Eng, 8(10): 1057-1062 (1995).

\* cited by examiner

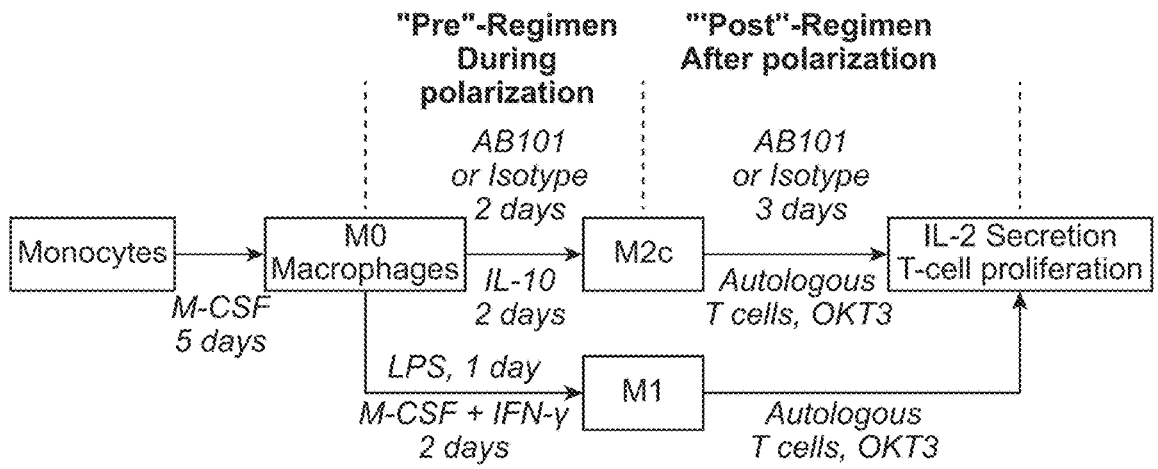
FIG. 28
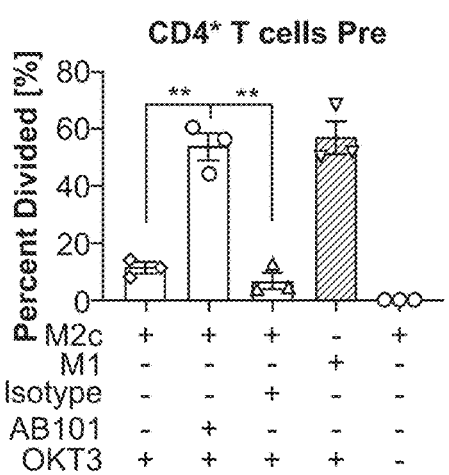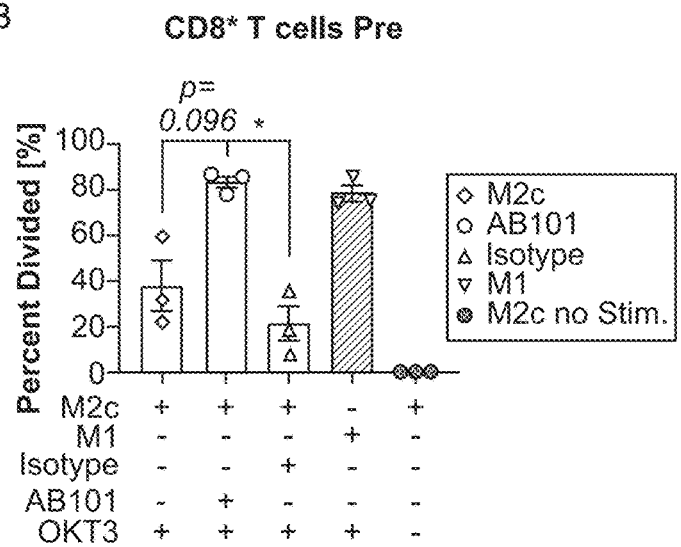
FIG. 29

```
         10         20         30         40         50         60
GTDKELRLVD GERKCSGRVE VKVQEEWGTV CNNGWSMEAV SVICNQLGCP TAIKAFSWAN 70         80         90        100        110        120
SSAGSGRIWM DHVSCRGNES ALWDCKHDGW GKHSNCTHQQ DAGVTCSDGS NLEMRLTRGG 130        140        150        160        170        180
NMCSGRIEIK FQSRWGTVCD DNFNIDHASV ICRQLECGSA VSFSGSSNFG EGSGPIWFDD 190        200        210        220        230        240
LICRNESSAL NWCRHGWGK HWCDHASDAG VICSKGADLS LRLVDGVTEC SGRLEVRFQG 250        260        270        280        290        300
EWGTICDDGW DSYEAAVACK QLGCPTAVTA IGRVNASKGF GHIWLDSVEC QHEPRVWQC 310        320        330        340        350        360
KHHEWGRETC NHNEDAGVTC SGGSDLEIRL RQGGBRCAGT VEVEIQRLLG KVCDRGWGLR 370        380        390        400        410        420
EADYVCRQLG CGSAIKTSYQ VYSKIQATNT WLFLSSPNGW STSIMDCKMM QWGGLTCDRI 430        440        450        460        470        480
EEAKITCSAH REPRLVGGDI PCSGRVEVKH GDTWGSICDS DFSLEAASVL CRELQCGTVV 490        500        510        520        530        540
SILGGAHFGE GNGQIWASEF QCEGHESHLS LCPVAPRPEG TCSHSRDVGV VCSRYTEIRL 550        560        570        580        590        600
VNGKTPCEGR VELKTLGAWG SLCNSHWDIE DAHVLCQQLK CGVALSTPGG ARFGRGNGQI 610        620        630        640        650        660
WRHMFHCTGT EQHMGDCPVT ALGASLCPSE QVASVICSGN QSQTLSSCNS SSLGPTRPTI 670        680        690        700        710        720
PESSAVACIE SGQLRLVNGG GRCAGRVEIY HEGSWGTICD DSWDLSDAHV VCRQLGCGEA 730        740        750        760        770        780
INATGSAHFG EGTGPIWLDE MKCNGKESRI WQCHSHGWGQ QNCRHKSIAG VICSEFMSLR 790        800        810        820        830        840
LTSEASREAC AGRLEVFYNG AWGTVGKSSM SETTVGVVCR QLGCADKGKI NPASLDKAMS 850        860        870        880        890        900
IPMWVDNVQC PKGPDTLWQC PSSPWEKRLA SPSEETWITC DNKIRLQESP TECSGRVEIW 910        920        930        940        950        960
HGGSWGTVCD DSWDLDDAQV VCQQLGCGEA LKAFKEAEFG QGTGPIWLNE VKCKGNESSL 970        980        990       1000       1010
WDCPARRWGH SECGHKEDAA VMCTDISVQK TFQKATTERS SKQSSHHHHH HHHHH
```

More flexible ◼◼◼◼◼◼◼◼◼◼◼◼ More protected
No change

FIG. 47

```
         10         20         30         40         50         60
GTDKELRLVD GENKCSGRVE VK?????STV ???????EAV SVICNQLGCP TAIK??????

70         80         90        100        110        120
??????IWM DHVS?????? A?NDCKHDGW GK??????Q? ?????????? ?????LTRGG 130        140        150        160        170        180
NMCSGRIEI? ?????????? DNFNIDHASV ICRQL???SA VSFSGSSNFG EGSGPIWFDD 190        200        210        220        230        240
LICNGNESAL WNCKHQGWGK HNCDHAEDAG VICSKGADLS LRLVDGVTEC SGRLEVRFQG 250        260        270        280        290        300
EWGTICDDGW DSYDAAVACK QLGCPTAVTA ?????????? GHIWLDSVSC QGHEPAVWQC 310        320        330        340        350        360
KHHEWGKHYC NHHEDAGVTC SDGSDLELRL RGGGSRCAGT VEVE?????? ??????????

370        380        390        400        410        420
?ADVVCRQLG CGSALKTSYQ VYSKIQATNT WLF??????? ?????????? ?????TCDHY 430        440        450        460        470        480
EEAKITCSAH REPRLVGEDI PCSGRVEVKH GDTWGSICD? ?????????? CRELQCGTVV 490        500        510        520        530        540
SIL??????? ?????????? QCEGHESHLS LCPVA????? ?????RDVGV VCSRYTEIRL 550        560        570        580        590        600
VNGKTPCEGR VE??????? ?LCNSHWDIE DAHVLCQQLK CGVALSTPGG ARFGKGNGQI 610        620        630        640        650        660
WRHMFECTGT EQHMGDCFVT ALGASLCPSE QVASVICSGN QSQTL????? ??????????

670        680        690        700        710        720
?????????? SGQLRLV??? ?????????Y HEGSWGTICD ?????SDAHV VCRQL?????

730        740        750        760        770        780
??????????  EGTGPIWLDE MKCNGKESRI WQCH????? ??CRHKEDAG VIC???????

790        800        810        820        830        840
LTSEASREAC AGRLEVFYNG AWGTVGKSSM SETTVGVVCR QLGCA????? ??????????

850        860        870        880        890        900
IPMWVDNVQC PKGPDTLWQC PSSPWEKRLA SPSEETWITC DNKIRLQ??? ??????????

910        920        930        940        950        960
?????????? ?????????? VCQQL?CGPA LKAF?????? ?????????? ??????????

970        980        990       1000       1010
??????RWGH SE???????? ?????????R TPKA????? ??????????  ??????
```

More flexible ▬▬▬▬▬▬▬▬▬▬▬▬▬▬ More protected
No change

FIG. 48

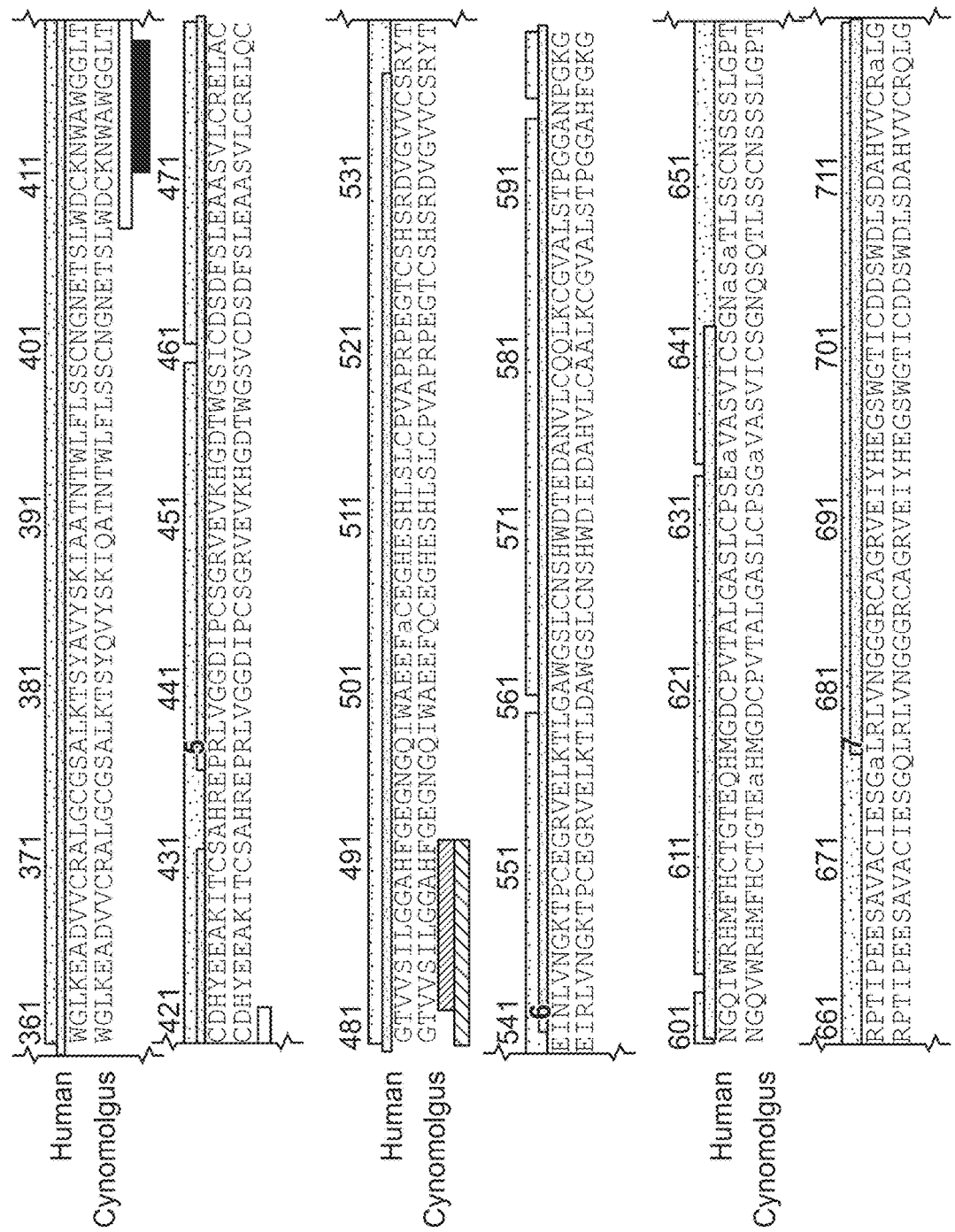
FIG. 51 (Cont. 1)

FIG. 51 (Cont. 2)

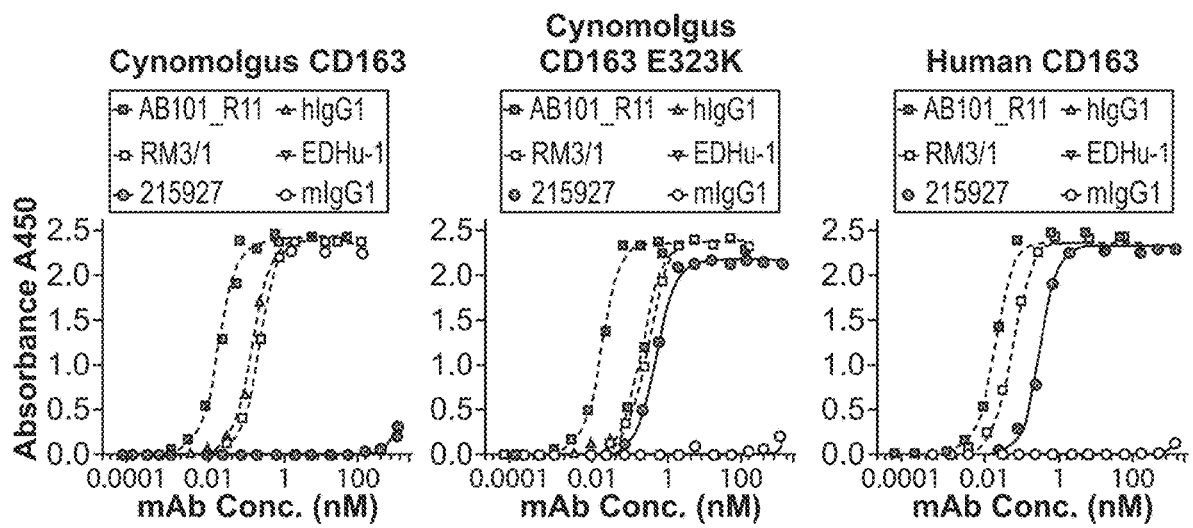
FIG. 52
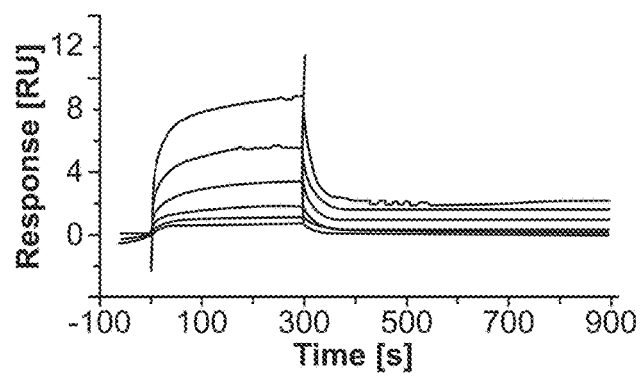
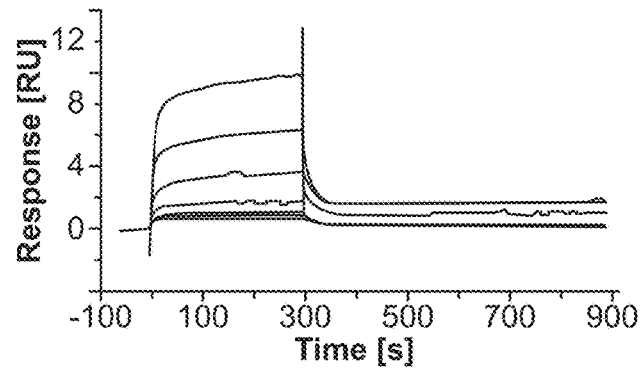
FIG. 53

IMMUNOMODULATORY ANTIBODIES AND METHODS OF USE THEREOF

CROSS-REFERENCE TO RELATED APPLICATIONS

This application is a continuation of U.S. application Ser. No. 17/597,706, filed Jan. 19, 2022, now issued as U.S. Pat. No. 11,634,501 on Apr. 25, 2023, which is the U.S. National Stage entry of International Application No. PCT/US2020/042668, filed on Jul. 17, 2020, which claims priority to and benefit of U.S. Provisional Application Nos. 62/876,580, filed Jul. 19, 2019, 62/876,579, filed Jul. 19, 2019, and 62/878,265, filed Jul. 24, 2019, the entire contents of each of which are herein incorporated by reference in their entireties.

SEQUENCE LISTING

The contents of the electronic sequence listing (ONR-003C2_SL.xml; Size: 41,871 bytes; and Date of Creation: Mar. 16, 2023) is herein incorporated by reference in its entirety.

SUMMARY OF THE DISCLOSURE

Provided herein are antibodies, including antigen-binding fragments and other antigen-binding polypeptides, that are useful in the treatment of cancer and other disorders. In some embodiments the antibodies specifically bind to M2 and M2-like immune-suppressive macrophages but not to M1 and M1-like anti-tumor macrophages. The disclosed antibodies bind to M2 and M2-like tumor-associated macrophages and modulate the physical and functional characteristics of tumor-associated M2 and M2-like macrophages to relieve immunosuppression of the tumor microenvironment and increase cytotoxic T-cell activation and proliferation, which promotes tumor cell killing. The antibody molecules of the present disclosure specifically bind to human CD163 expressed on the surface of M2 and M2-like macrophages.

Disclosed herein, in certain embodiments, are an antibody or a recombinant antibody comprising a heavy chain variable region (VH) having at least 80% identity to amino acid sequence SEQ ID NO: 8.

Disclosed herein, in certain embodiments, are an antibody or a recombinant antibody comprising a heavy chain variable region (VH) having at least 90% identity to amino acid sequence SEQ ID NO: 8.

Disclosed herein, in certain embodiments, are an antibody or a recombinant antibody comprising a heavy chain variable region (VH) having at least 95% identity to amino acid sequence SEQ ID NO: 8.

Disclosed herein, in certain embodiments, are an antibody or a recombinant antibody comprising a heavy chain variable region (VH) having at least 99% identity to amino acid sequence SEQ ID NO: 8.

Disclosed herein, in certain embodiments, are an antibody or a recombinant antibody comprising a heavy chain variable region (VH) having at least 100% identity to amino acid sequence SEQ ID NO: 8. In some embodiments, the antibody or the recombinant antibody further comprises a light chain variable region (VL) having at least 80% identity to amino acid sequence SEQ ID NO: 7. In some embodiments, the antibody or the recombinant antibody further comprises a light chain variable region (VL) having at least 90% identity to amino acid sequence SEQ ID NO: 7. In some embodiments, the antibody or the recombinant antibody further comprises a light chain variable region (VL) having at least 95% identity to amino acid sequence SEQ ID NO: 7. In some embodiments, the antibody or the recombinant antibody further comprises a light chain variable region (VL) having at least 99% identity to amino acid sequence SEQ ID NO: 7. In some embodiments, the antibody or the recombinant antibody further comprises a light chain variable region (VL) having at least 100% identity to amino acid sequence SEQ ID NO: 7.

Disclosed herein, in certain embodiments, are a light chain variable region (VL) having at least 80% identity to amino acid sequence SEQ ID NO: 7.

Disclosed herein, in certain embodiments, are an antibody or a recombinant antibody comprising a light chain variable region (VL) having at least 90% identity to amino acid sequence SEQ ID NO: 7.

Disclosed herein, in certain embodiments, are an antibody or a recombinant antibody comprising a light chain variable region (VL) having at least 95% identity to amino acid sequence SEQ ID NO: 7

Disclosed herein, in certain embodiments, are an antibody or a recombinant antibody comprising a light chain variable region (VL) having at least 99% identity to amino acid sequence SEQ ID NO: 7.

Disclosed herein, in certain embodiments, are an antibody or a recombinant antibody comprising a light chain variable region (VL) having at least 100% identity to amino acid sequence SEQ ID NO: 7. In some embodiments, the antibody or the recombinant antibody further comprises a heavy chain variable region (VH) having at least 80% identity to amino acid sequence SEQ ID NO: 8. In some embodiments, the antibody or the recombinant antibody further comprises a heavy chain variable region (VH) having at least 90% identity to amino acid sequence SEQ ID NO: 8. In some embodiments, the antibody or the recombinant antibody further comprises a heavy chain variable region (VH) having at least 95% identity to amino acid sequence SEQ ID NO: 8. In some embodiments, the antibody or the recombinant antibody further comprises a heavy chain variable region (VH) having at least 99% identity to amino acid sequence SEQ ID NO: 8. In some embodiments, the antibody or the recombinant antibody further comprises a heavy chain variable region (VH) having at least 100% identity to amino acid sequence SEQ ID NO: 8.

Disclosed herein, in certain embodiments, are an antibody or a recombinant antibody comprising a heavy chain variable region ($V_H$) having at least 80% identity to amino acid sequence SEQ ID NO: 8 and a light chain variable region ($V_L$) having at least 80% identity to amino acid sequence SEQ ID NO: 7. In some embodiments, the antibody or the recombinant antibody comprises the light chain variable region ($V_L$) having at least 85% identity to amino acid sequence SEQ ID NO: 7. In some embodiments, the antibody or the recombinant antibody comprises the light chain variable region ($V_L$) having at least 90% identity to amino acid sequence SEQ ID NO: 7. In some embodiments, the antibody or the recombinant antibody comprises the light chain variable region ($V_L$) having at least 95% identity to amino acid sequence SEQ ID NO: 7. In some embodiments, the antibody or the recombinant antibody comprises the light chain variable region ($V_L$) having at least 99% identity to amino acid sequence SEQ ID NO: 7. In some embodiments, the antibody or the recombinant antibody comprises the light chain variable region ($V_L$) having at least 100% identity to amino acid sequence SEQ ID NO: 7. In some embodiments, the antibody or the recombinant antibody comprises the heavy chain variable region (V$_H$) having at least 85% identity to amino acid sequence SEQ ID NO: 8. In some embodiments, the antibody or the recombinant antibody comprises the heavy chain variable region (V$_H$) having at least 90% identity to amino acid sequence SEQ ID NO: 8. In some embodiments, the antibody or the recombinant antibody comprises the heavy chain variable region (V$_H$) having at least 95% identity to amino acid sequence SEQ ID NO: 8. In some embodiments, the antibody or the recombinant antibody comprises the heavy chain variable region (V$_H$) having at least 99% identity to amino acid sequence SEQ ID NO: 8. In some embodiments, the antibody or the recombinant antibody comprises the heavy chain variable region (V$_H$) having at least 100% identity to amino acid sequence SEQ ID NO: 8.

Disclosed herein, in certain embodiments, are an antibody or a recombinant antibody comprising a heavy chain sequence comprising a complementarity determining region (CDR) H1 having at least 80% identity to amino acid sequence SEQ ID NO: 4, a CDR H2 having at least 80% identity to amino acid sequence SEQ ID NO: 5, and a CDR H3 having at least 80% identity to amino acid sequence SEQ ID NO: 6, and a light chain sequence comprising a CDR L1 having at least 80% identity to amino acid sequence SEQ ID NO: 1, a CDR L2 having at least 80% identity to amino acid sequence SEQ ID NO: 2, and a CDR L3 having at least 80% identity to amino acid sequence SEQ ID NO: 3. In some embodiments, the antibody or the recombinant antibody comprises the light chain sequence comprising the CDR L1 having at least 85% identity to amino acid sequence SEQ ID NO: 1, the CDR L2 having at least 85% identity to amino acid sequence SEQ ID NO: 2, and the CDR L3 having at least 85% identity to amino acid sequence SEQ ID NO: 3. In some embodiments, the antibody or the recombinant antibody comprises the light chain sequence comprising the CDR L1 having at least 90% identity to amino acid sequence SEQ ID NO: 1, the CDR L2 having at least 90% identity to amino acid sequence SEQ ID NO: 2, and the CDR L3 having at least 90% identity to amino acid sequence SEQ ID NO: 3. In some embodiments, the antibody or the recombinant antibody comprises light chain sequence comprising the CDR L1 having at least 95% identity to amino acid sequence SEQ ID NO: 1, the CDR L2 having at least 95% identity to amino acid sequence SEQ ID NO: 2, and the CDR L3 having at least 95% identity to amino acid sequence SEQ ID NO: 3. In some embodiments, the antibody or the recombinant antibody comprises the light chain sequence comprising the CDR L1 having at least 99% identity to amino acid sequence SEQ ID NO: 1, the CDR L2 having at least 99% identity to amino acid sequence SEQ ID NO: 2, and the CDR L3 having at least 99% identity to amino acid sequence SEQ ID NO: 3. In some embodiments, the antibody or the recombinant antibody comprises the light chain sequence comprising the CDR L1 having at least 100% identity to amino acid sequence SEQ ID NO: 1, the CDR L2 having at least 100% identity to amino acid sequence SEQ ID NO: 2, and the CDR L3 having at least 100% identity to amino acid sequence SEQ ID NO: 3. In some embodiments, the antibody or the recombinant antibody comprises the heavy chain sequence comprising a the CDR H1 having at least 85% identity to amino acid sequence SEQ ID NO: 4, the CDR H2 having at least 85% identity to amino acid sequence SEQ ID NO: 5, and the CDR H3 having at least 85% identity to amino acid sequence SEQ ID NO: 6. In some embodiments, the antibody or the recombinant antibody comprises the heavy chain sequence comprising a the CDR H1 having at least 90% identity to amino acid sequence SEQ ID NO: 4, the CDR H2 having at least 90% identity to amino acid sequence SEQ ID NO: 5, and the CDR H3 having at least 90% identity to amino acid sequence SEQ ID NO: 6. In some embodiments, the antibody or the recombinant antibody comprises the heavy chain sequence comprising a the CDR H1 having at least 95% identity to amino acid sequence SEQ ID NO: 4, the CDR H2 having at least 95% identity to amino acid sequence SEQ ID NO: 5, and the CDR H3 having at least 95% identity to amino acid sequence SEQ ID NO: 6. In some embodiments, the antibody or the recombinant antibody comprises the heavy chain sequence comprising a the CDR H1 having at least 99% identity to amino acid sequence SEQ ID NO: 4, the CDR H2 having at least 99% identity to amino acid sequence SEQ ID NO: 5, and the CDR H3 having at least 99% identity to amino acid sequence SEQ ID NO: 6. In some embodiments, the antibody or the recombinant antibody comprises the heavy chain sequence comprising a the CDR H1 having at least 100% identity to amino acid sequence SEQ ID NO: 4, the CDR H2 having at least 100% identity to amino acid sequence SEQ ID NO: 5, and the CDR H3 having at least 100% identity to amino acid sequence SEQ ID NO: 6.

Disclosed herein, in certain embodiments, are an antibody or a recombinant antibody, comprising a heavy chain sequence comprising at least one of complementarity determining region (CDR) H1 having at least 80% identity to amino acid sequence SEQ ID NO: 4, a CDR H2 having at least 80% identity to amino acid sequence SEQ ID NO: 5, and a CDR H3 having at least 80% identity to amino acid sequence SEQ ID NO: 6.

Disclosed herein, in certain embodiments, are an antibody or a recombinant antibody, comprising a heavy chain sequence comprising at least one of complementarity determining region (CDR) H1 having at least 90% identity to amino acid sequence SEQ ID NO: 4, a CDR H2 having at least 90% identity to amino acid sequence SEQ ID NO: 5, and a CDR H3 having at least 90% identity to amino acid sequence SEQ ID NO: 6.

Disclosed herein, in certain embodiments, are an antibody or a recombinant antibody, comprising a heavy chain sequence comprising at least one of complementarity determining region (CDR) H1 having at least 95% identity to amino acid sequence SEQ ID NO: 4, a CDR H2 having at least 95% identity to amino acid sequence SEQ ID NO: 5, and a CDR H3 having at least 95% identity to amino acid sequence SEQ ID NO: 6.

Disclosed herein, in certain embodiments, are an antibody or a recombinant antibody, comprising a heavy chain sequence comprising at least one of complementarity determining region (CDR) H1 having at least 99% identity to amino acid sequence SEQ ID NO: 4, a CDR H2 having at least 99% identity to amino acid sequence SEQ ID NO: 5, and a CDR H3 having at least 99% identity to amino acid sequence SEQ ID NO: 6.

Disclosed herein, in certain embodiments, are an antibody or a recombinant antibody, comprising a heavy chain sequence comprising at least one of complementarity determining region (CDR) H1 having at least 100% identity to amino acid sequence SEQ ID NO: 4, a CDR H2 having at least 100% identity to amino acid sequence SEQ ID NO: 5, and a CDR H3 having at least 100% identity to amino acid sequence SEQ ID NO: 6.

In some embodiments, the antibody or the recombinant antibody further comprises a light chain sequence comprising at least one of complementarity determining region (CDR) L1 having at least 80% identity to amino acid sequence SEQ ID NO: 1, a CDR L2 having at least 80% identity to amino acid sequence SEQ ID NO: 2, and a CDR L3 having at least 80% identity to amino acid sequence SEQ ID NO: 3. In some embodiments, the CDR L1 has at least 90% identity to amino acid sequence SEQ ID NO: 1, the CDR L2 has at least 90% identity to amino acid sequence SEQ ID NO: 2, and the CDR L3 has at least 90% identity to amino acid sequence SEQ ID NO: 3. In some embodiments, the CDR L1 has at least 95% identity to amino acid sequence SEQ ID NO: 1, the CDR L2 has at least 95% identity to amino acid sequence SEQ ID NO: 2, and the CDR L3 has at least 95% identity to amino acid sequence SEQ ID NO: 3. In some embodiments, the CDR L1 has at least 99% identity to amino acid sequence SEQ ID NO: 1, the CDR L2 has at least 99% identity to amino acid sequence SEQ ID NO: 2, and the CDR L3 has at least 99% identity to amino acid sequence SEQ ID NO: 3. In some embodiments, the CDR L1 has at least 100% identity to amino acid sequence SEQ ID NO: 1, the CDR L2 has at least 100% identity to amino acid sequence SEQ ID NO: 2, and the CDR L3 has at least 100% identity to amino acid sequence SEQ ID NO: 3. In some embodiments, the light chain variable region (VL) has at least 80% identity to amino acid sequence SEQ ID NO: 7.

In some embodiments, the antibody or the recombinant antibody further comprises a light chain variable region (VL) having at least 80% identity to amino acid sequence SEQ ID NO: 7. In some embodiments, the antibody or the recombinant antibody comprises a heavy chain variable region (VH) having at least 80% identity to amino acid sequence SEQ ID NO: 8.

Disclosed herein, in certain embodiments, are an antibody or a recombinant antibody, comprising a light chain sequence comprising a complementarity determining region (CDR) L1 having at least 80% identity to amino acid sequence SEQ ID NO: 1, a CDR L2 having at least 80% identity to amino acid sequence SEQ ID NO: 2, and a CDR L3 having at least 80% identity to amino acid sequence SEQ ID NO: 3.

Disclosed herein, in certain embodiments, are an antibody or a recombinant antibody, comprising a light chain sequence comprising a complementarity determining region (CDR) L1 having at least 90% identity to amino acid sequence SEQ ID NO: 1, a CDR L2 having at least 90% identity to amino acid sequence SEQ ID NO: 2, and a CDR L3 having at least 90% identity to amino acid sequence SEQ ID NO: 3.

Disclosed herein, in certain embodiments, are an antibody or a recombinant antibody, comprising a light chain sequence comprising a complementarity determining region (CDR) L1 having at least 95% identity to amino acid sequence SEQ ID NO: 1, a CDR L2 having at least 95% identity to amino acid sequence SEQ ID NO: 2, and a CDR L3 having at least 95% identity to amino acid sequence SEQ ID NO: 3.

Disclosed herein, in certain embodiments, are an antibody or a recombinant antibody, comprising a light chain sequence comprising a complementarity determining region (CDR) L1 having at least 99% identity to amino acid sequence SEQ ID NO: 1, a CDR L2 having at least 99% identity to amino acid sequence SEQ ID NO: 2, and a CDR L3 having at least 99% identity to amino acid sequence SEQ ID NO: 3.

Disclosed herein, in certain embodiments, are an antibody or a recombinant antibody, comprising a light chain sequence comprising a complementarity determining region (CDR) L1 having at least 100% identity to amino acid sequence SEQ ID NO: 1, a CDR L2 having at least 100% identity to amino acid sequence SEQ ID NO: 2, and a CDR L3 having at least 100% identity to amino acid sequence SEQ ID NO: 3.

In some embodiments, the antibody or the recombinant antibody further comprises a heavy chain sequence comprising at least one of complementarity determining region (CDR) H1 having at least 80% identity to amino acid sequence SEQ ID NO: 4, a CDR H2 having at least 80% identity to amino acid sequence SEQ ID NO: 5, and a CDR H3 having at least 80% identity to amino acid sequence SEQ ID NO: 6. In some embodiments, the CDR H1 has at least 90% identity to amino acid sequence SEQ ID NO: 4, the CDR H2 has at least 90% identity to amino acid sequence SEQ ID NO: 5, and the CDR H3 has at least 90% identity to amino acid sequence SEQ ID NO: 6. In some embodiments, the CDR H1 has at least 95% identity to amino acid sequence SEQ ID NO: 4, the CDR H2 has at least 95% identity to amino acid sequence SEQ ID NO: 5, and the CDR H3 has at least 95% identity to amino acid sequence SEQ ID NO: 6. In some embodiments, the CDR H1 has at least 99% identity to amino acid sequence SEQ ID NO: 4, the CDR H2 has at least 99% identity to amino acid sequence SEQ ID NO: 5, and the CDR H3 has at least 99% identity to amino acid sequence SEQ ID NO: 6. In some embodiments, the CDR H1 has at least 100% identity to amino acid sequence SEQ ID NO: 4, the CDR H2 has at least 100% identity to amino acid sequence SEQ ID NO: 5, and the CDR H3 has at least 100% identity to amino acid sequence SEQ ID NO: 6. In some embodiments, the heavy chain variable region (VH) has at least 80% identity to amino acid sequence SEQ ID NO: 8.

In some embodiments, the antibody or the recombinant antibody further comprises a heavy chain variable region (VH) having at least 80% identity to amino acid sequence SEQ ID NO: 8. In some embodiments, the light chain variable region (VL) having at least 80% identity to amino acid sequence SEQ ID NO: 7.

In some embodiments, the antibody or the recombinant antibody further comprises a human heavy chain constant region or a human light chain constant region. In some embodiments, the human heavy chain constant region is IgG1 or IgG4 or a fragment thereof. In some embodiments, the heavy chain has at least 80% identity to the amino acid sequence of SEQ ID NO: 10. In some embodiments, the light chain has at least 80% identity to the amino acid sequence of SEQ ID NO: 9. In some embodiments, wherein the heavy chain has at least 80% identity to the amino acid sequence of SEQ ID NO: 12. In some embodiments, the heavy chain has at least 80% identity to the amino acid sequence of SEQ ID NO: 11. In some embodiments, heavy chain has at least 80% identity to the amino acid sequence of SEQ ID NO: 13. In some embodiments, the antibody or the recombinant antibody comprises a human variable framework region and a murine constant region. In some embodiments, the antibody or the recombinant antibody further comprises a murine heavy chain constant region or a murine light chain constant region. In some embodiments, the antibody or the murine heavy chain constant region is IgG2A. In some embodiments, the heavy chain has at least 80% identity to the amino acid sequence of SEQ ID NO: 15. In some embodiments, the heavy chain has at least 80% identity to the amino acid sequence of SEQ ID NO: 16. In some embodiments, the light chain has at least 80% identity to the amino acid sequence of SEQ ID NO: 14. In some embodiments, the antibody or the recombinant antibody is an antibody fragment comprising a single heavy chain, a single light chain, Fab, Fab', F(ab)', F(ab')2, Fd, scFv, a variable heavy domain, a variable light domain, a variable NAR domain, bi-specific scFv, a bi-specific Fab2, a tri-specific Fab3, a single chain binding polypeptide, a dAb fragment, or a diabody.

In some embodiments, the antibody or the recombinant antibody specifically binds to a CD163 protein expressed on an immunosuppressive human myeloid cell, wherein binding of the antibody or the recombinant antibody to the myeloid cell promotes an immune cell function as measured by one or both of the following parameters: (i) activation of a CD4$^+$ T cell, CD8$^+$ T cell, NK cell, or any combination thereof; and (ii) proliferation of a CD4$^+$ T cell, CD8$^+$ T cell, NK cell, or any combination thereof. In some embodiments, wherein activation of a CD4$^+$ T cell, CD8$^+$ T cell, NK cell, or any combination thereof is measured as an increased level of IFN-γ, TNF-α, or perforin, or any combination thereof. In some embodiments, the immunosuppressive human myeloid cell is a macrophage or a myeloid-derived suppressor cell. In some embodiments, the immune cell function is in a tumor microenvironment. In some embodiments, the immune cell function is in vivo. In some embodiments, the antibody or the recombinant antibody specifically binds to a CD163 protein expressed on a human macrophage, wherein binding of the antibody to the macrophage increases an immunostimulatory activity in a tumor microenvironment. In some embodiments, the tumor microenvironment is in vivo. In some embodiments, binding of the antibody or the recombinant antibody to the macrophage reduces an immunosuppression activity of the macrophage. In some embodiments, binding of the antibody or the recombinant antibody to the macrophage reduces a tumor promoting activity of the macrophage. In some embodiments, the macrophage is a tumor-associated macrophage. In some embodiments, the antibody or recombinant antibody alters expression of at least one marker on the macrophage. In some embodiments, the CD163 protein is a glycoform of CD163. In some embodiments, the CD163 protein is a 150 kDa glycoform of CD163. In some embodiments, the antibody does not specifically bind to a 130 kDa glycoform of CD163 expressed by the human macrophage.

In some embodiments, the antibody or the recombinant antibody has a constant domain that enables binding to an Fc receptor. In some embodiments, the Fc receptor is expressed on the macrophage. In some embodiments, the antibody or the recombinant antibody has an antibody fragment comprising a single heavy chain, a single light chain, Fab, Fab', F(ab)', F(ab')2, Fd, scFv, a variable heavy domain, a variable light domain, a variable NAR domain, bi-specific scFv, a bi-specific Fab2, a tri-specific Fab3, a single chain binding polypeptide, a dAb fragment, or a diabody. In some embodiments, at least one marker on the human macrophage is CD16, CD64, TLR2, or Siglec-15. In some embodiments, the human macrophage is an M2 macrophage or a M2-like macrophage. In some embodiments, the human macrophage is an M2a, M2b, M2c, or M2d macrophage. In some embodiments, the CD163 protein is a component of a cell surface complex comprising at least one other protein expressed by the macrophage. In some embodiments, the at least one other protein is a galectin-1 protein, a LILRB2 protein, a casein kinase II protein, or any combination thereof. In some embodiments, upon binding with the CD163 protein, the antibody or the recombinant antibody is internalized by the human macrophage. In some embodiments, binding to the CD163 protein is not cytotoxic to the macrophage. In some embodiments, binding to the CD163 protein promotes CD4$^+$ T cell activation, CD4$^+$ T cell proliferation, or both CD4$^+$ T cell activation and proliferation. In some embodiments, binding to the CD163 protein promotes expression of CD69, ICOS, OX40, PD1, LAG3, CTLA4, or any combination thereof by CD4$^+$ T cells. In some embodiments, binding to the CD163 protein promotes CD8$^+$ T cell activation, CD8$^+$ T cell proliferation, or both CD8$^+$ T cell activation and proliferation. In some embodiments, binding to the CD163 protein promotes expression of ICOS, OX40, PD1, LAG3, CTLA4, or any combination thereof by CD8$^+$ T cells. In some embodiments, binding to the CD163 protein reduces immunosuppression in a tumor microenvironment. In some embodiments, binding to the CD163 protein promotes tumor cell killing in a tumor microenvironment. In some embodiments, binding to the CD163 protein promotes cytotoxic lymphocyte-mediated killing of cancer cells. In some embodiments, binding to the CD163 protein promotes NK cell-mediated tumor cell killing. In some embodiments, binding to the CD163 protein promotes expression of IL-2 by T cells. In some embodiments, binding to the CD163 protein increases CD4$^+$ T cells, CD196$^-$ T cells, CXCR3$^+$ T cells, CCR4$^-$ T cells, or any combination thereof.

In some embodiments, binding to CD163 reduces immunosuppression in a tumor microenvironment caused by a macrophage. In some embodiments, the antibody or the recombinant antibody specifically binds to a CD163 protein expressed on a human macrophage, wherein binding results in at least one of the following effects: (a) reduced expression of at least one marker by the macrophage, wherein the at least one marker is CD16, CD64, TLR2, or Siglec-15; (b) internalization of the antibody by the macrophage; (c) activation of a CD4$^+$ T cell, CD8$^+$ T cell, NK cell, or any combination thereof; —(d) proliferation of a CD4$^+$ T cell, CD8$^+$ T cell, NK cell, or any combination thereof; and (e) promotion of tumor cell killing in a tumor microenvironment. In some embodiments, the binding results in: two or more of (a) through (e); three or more of (a) through (e); four or more of (a) through (e); or all of (a) through (e). In some embodiments, the antibody or the recombinant antibody specifically binds to a CD163$^+$ immunosuppressive myeloid cell in a tumor microenvironment, wherein the binding reduces suppression of cytotoxic T cell-mediated killing of tumor cells in the tumor microenvironment. In some embodiments, the antibody or the recombinant antibody specifically binds to a CD163 protein expressed on a human tumor-associated macrophage and reduces expression of CD16, CD64, TLR2, Siglec-15, or a combination thereof by the macrophage, for use in a method of treating cancer. In some embodiments, binding of the antibody or the recombinant antibody to the macrophage modulates an immune function of a cell in a tumor microenvironment. In some embodiments, binding of the antibody or the recombinant antibody to the macrophage promotes an anti-tumor immune function.

In some embodiments, the antibody or the recombinant antibody specifically binds to a CD163 epitope comprising amino acid sequence of SEQ ID NO: 18. In some embodiments, the antibody or the recombinant antibody specifically binds to a CD163 epitope comprising amino acid sequence of SEQ ID NO: 19. In some embodiments, the antibody or the recombinant antibody specifically binds to a CD163 epitope comprising amino acid sequence of SEQ ID NO: 20. In some embodiments, the antibody or the recombinant antibody specifically binds to a CD163 epitope comprising each of amino acid sequence SEQ ID NO: 18, SEQ ID NO: 19, and SEQ ID NO: 20. In some embodiments, the antibody or the recombinant antibody specifically binds to CD163 with a K$_D$ from 1 nM to 100 nM. In some embodiments, the antibody or the recombinant antibody specifically binds to CD163 with a $K_D$ from 1 nM to 50 nM. In some embodiments, the antibody or the recombinant antibody specifically binds to CD163 with a $K_D$ from 1 nM to 10 nM. In some embodiments, the CD163 is human CD163. In some embodiments, the antibody or the recombinant antibody specifically binds to M2c macrophages with a $K_D$ from 1 nM to 100 nM. In some embodiments, the antibody or the recombinant antibody specifically binds to M2c macrophages with a $K_D$ from 1 nM to 50 nM. In some embodiments, the antibody or the recombinant antibody specifically binds to M2c macrophages with a $K_D$ from 1 nM to 10 nM. In some embodiments, the M2c macrophages are human M2c macrophages.

Disclosed herein, in certain embodiments, are a composition comprising an antibody or a recombinant antibody and an excipient.

Disclosed herein, in certain embodiments, are a pharmaceutical composition, comprising an antibody or a recombinant antibody of any one of the previous embodiments and a pharmaceutically acceptable carrier.

Disclosed herein, in certain embodiments, are a use of an antibody or a recombinant antibody of any one of the previous embodiments for the manufacture of a medicament for treating cancer in a human subject.

Disclosed herein, in certain embodiments, are a use of an antibody or a recombinant antibody of any one of the previous embodiments for the manufacture of a medicament that reduces immunosuppression by a tumor-associated macrophage in a human subject having a cancer.

Disclosed herein, in certain embodiments, are a use of an antibody or a recombinant antibody of any one of the previous embodiments for the manufacture of a medicament that promotes T cell-mediated tumor cell killing in a human subject having a cancer.

Disclosed herein, in certain embodiments, are a method of promoting an immune cell function, the method comprising: administering an antibody or a recombinant antibody of any one of the previous embodiments to an individual in need thereof, and promoting an immune cell function as measured by one or both of the following parameters: (i) activation of a $CD4^+$ T cell, $CD8^+$ T cell, NK cell, or any combination thereof; and (ii) proliferation of a $CD4^+$ T cell, $CD8^+$ T cell, NK cell, or any combination thereof. In some embodiments, the activation of a $CD4^+$ T cell, $CD8^+$ T cell, NK cell, or any combination thereof is measured as an increased level of IFN-γ, TNF-α, or perforin, or any combination thereof. In some embodiments, the immunosuppressive human myeloid cell is a macrophage. In some embodiments, the immunosuppressive human myeloid cell is a myeloid-derived suppressor cell. In some embodiments, the antibody or the recombinant antibody is an antibody or a recombinant antibody of any one of the previous embodiments.

Disclosed herein, in certain embodiments, are a method of treating cancer in an individual in need thereof, the method comprising administering to the individual a therapeutically effective amount of an antibody or a recombinant antibody of any one of the previous embodiments, thereby treating the cancer in the individual.

Disclosed herein, in certain embodiments, are a method of treating cancer in an individual in need thereof, the method comprising administering to the individual a therapeutically effective amount of an antibody or a recombinant antibody of any one of the previous embodiments, whereby immunosuppression by a tumor-associated macrophage in the individual is reduced.

Disclosed herein, in certain embodiments, are a method of treating cancer in an individual in need thereof, the method comprising administering to the individual a therapeutically effective amount of an antibody or a recombinant antibody of any one of the previous embodiments, whereby T cell-mediated tumor cell killing in the individual is increased.

Disclosed herein, in certain embodiments, are a method of reducing a tumor-promoting activity of a tumor-associated macrophage in an individual in need thereof, the method comprising administering to the individual an amount of a pharmaceutical composition of any one of the previous embodiments that is effective to modulate a $CD4^+$ T cell activation, $CD4^+$ T cell proliferation, $CD8^+$ T cell activation, $CD8^+$ T cell proliferation, or any combination thereof in the tumor microenvironment.

Disclosed herein, in certain embodiments, are a method of promoting lymphocyte-mediated tumor cell killing in an individual in need thereof, the method comprising administering to the individual an effective amount of an antibody or a recombinant antibody of any one of the previous embodiments or a pharmaceutical composition of any one of the previous embodiments.

In some embodiments, the method further comprises promoting tumor cell killing in the tumor microenvironment. In some embodiments, the cancer is a lung cancer or sarcoma. In some embodiments, the lung cancer is a lung carcinoma or lung adenocarcinoma. In some embodiments, the method further comprises administering to the individual an additional anticancer therapeutic or anticancer therapy. In some embodiments, the additional anticancer therapy is surgical therapy, chemotherapy, radiation therapy, cryotherapy, hormonal therapy, immunotherapy, and cytokine therapy, and combinations thereof. In some embodiments, the additional anticancer therapy is an immunotherapy. In some embodiments, the immunotherapy is a composition comprising a checkpoint inhibitor.

Disclosed herein, in certain embodiments, are a method of modulating an activity of a tumor-associated macrophage in a tumor microenvironment, the method comprising contacting the tumor-associated macrophage with an antibody or a recombinant antibody that binds to a CD163-expressing human macrophage and comprises at least one of the following effects: (a) the binding of the antibody reduces expression of at least one marker on the macrophage, wherein the at least one marker is CD16, CD64, TLR2, or Siglec-15; (b) upon binding of the antibody with the CD163 protein, the antibody is internalized by the human macrophage; (c) the binding of the antibody is not cytotoxic to the macrophage; (d) the binding of the antibody or the recombinant antibody produces IFN-γ, TNF-α, perforin, or any combination thereof by a $CD4^+$ T cell, $CD8^+$ T cell, NK cell, or any combination thereof; (e) the binding of the antibody or the recombinant antibody promotes an activation of a $CD4^+$ T cell, $CD8^+$ T cell, NK cell, or any combination thereof; (f) the binding of the antibody or the recombinant antibody promotes a proliferation of a $CD4^+$ T cell, $CD8^+$ T cell, NK cell, or any combination thereof; and (g) the binding of the antibody or the recombinant antibody promotes tumor cell killing in the tumor microenvironment. In some embodiments, the binding results in: two or more of (a) through (g); three or more of (a) through (g); four or more of (a) through (g); five or more of (a) through (g); six or more of (a) through (g); or all of (a) through (g).

In some embodiments, the method occurs in a tumor microenvironment. In some embodiments, the method occurs in vivo. In some embodiments, binding of the antibody or the recombinant antibody to the macrophage modulates an immune function of a cell in a tumor microenvironment. In some embodiments, binding of the antibody or the recombinant antibody to the macrophage promotes an anti-tumor immune function. In some embodiments, the antibody or the recombinant antibody comprises a constant domain and the constant domain binds to an Fc receptor. In some embodiments, the Fc receptor is expressed on the macrophage. In some embodiments, the method further comprises internalizing the antibody or the recombinant antibody by the human macrophage upon binding with the CD163 protein. In some embodiments, binding to the CD163 protein is not cytotoxic to the human macrophage. In some embodiments, the method further comprises promoting expression of CD69, ICOS, OX40, PD1, LAG3, CTLA4, or any combination thereof by CD4$^+$ T cells. In some embodiments, the method further comprises promoting expression of ICOS, OX40, PD1, LAG3, CTLA4, or any combination thereof by CD8$^+$ T cells. In some embodiments, the method comprises reducing immunosuppression in a tumor microenvironment. In some embodiments, the method comprises promoting cytotoxic lymphocyte-mediated killing of cancer cells. In some embodiments, the method comprises promoting NK cell-mediated tumor cell killing. In some embodiments, the method comprises promoting expression of IL-2 by T cells. In some embodiments, the method comprises increasing CD4$^+$ T cells, CD196$^-$ T cells, CXCR3$^+$ T cells, CCR4$^-$ T cells, or any combination thereof.

Disclosed herein, in certain embodiments, is an antibody that specifically binds to a CD163 protein expressed on a immunosuppressive human myeloid cell, wherein binding of the antibody to the myeloid cell promotes an immune cell function as measured by one or both of the following parameters: (i) activation of a CD4$^+$ T cell, CD8$^+$ T cell, NK cell, or any combination thereof; and (ii) proliferation of a CD4$^+$ T cell, CD8$^+$ T cell, NK cell, or any combination thereof. In some embodiments, the immunosuppressive human myeloid cell is a macrophage or a myeloid-derived suppressor cell. In some embodiments, the activation of a CD4$^+$ T cell, CD8$^+$ T cell, NK cell, or any combination thereof is measured as increased production of IFN-$\gamma$, TNF-$\alpha$, perforin, or any combination thereof.

Disclosed herein, in certain embodiments, is an antibody that specifically binds to a CD163 protein expressed on a human macrophage, wherein binding of the antibody to the macrophage promotes an immune cell function as measured by one or both of the following parameters: (i) activation of a CD4$^+$ T cell, CD8$^+$ T cell, NK cell, or any combination thereof; and (ii) proliferation of a CD4$^+$ T cell, CD8$^+$ T cell, NK cell, or any combination thereof. In some embodiments, the immune cell function is in a tumor microenvironment. In some embodiments, the immune cell function is in vivo. In some embodiments, the activation of a CD4$^+$ T cell, CD8$^+$ T cell, NK cell, or any combination thereof is measured as increased production of IFN-$\gamma$, TNF-$\alpha$, perforin, or any combination thereof.

Disclosed herein, in certain embodiments, is an antibody that specifically binds to a CD163 protein expressed on a human macrophage, wherein binding of the antibody to the macrophage increases an immunostimulatory activity in a tumor microenvironment. In some embodiments, the tumor microenvironment is in vivo. In some embodiments, binding of the antibody to the macrophage reduces an immunosuppression activity of the macrophage. In some embodiments, binding of the antibody to the macrophage reduces a tumor promoting activity of the macrophage.

In some embodiments, the macrophage is a tumor-associated macrophage. In some embodiments, the antibody alters expression of at least one marker on the macrophage. In some embodiments, the CD163 protein is a glycoform of CD163. In some embodiments, the CD163 protein is a 150 kDa glycoform of CD163. In some embodiments, the antibody does not specifically bind to a 130 kDa glycoform of CD163 expressed by the human macrophage. In some embodiments, the antibody has a constant domain that enables binding to an Fc receptor. In some embodiments, the Fc receptor is expressed on the macrophage. In some embodiments, an antibody fragment comprises a single heavy chain, a single light chain, Fab, Fab', F(ab)', F(ab')$_2$, Fd, scFv, a variable heavy domain, a variable light domain, a variable NAR domain, bi-specific scFv, a bi-specific Fab$_2$, a tri-specific Fab$_3$, a single chain binding polypeptide, a dAb fragment, or a diabody. In some embodiments, at least one marker on the human macrophage is CD16, CD64, TLR2, or Siglec-15. In some embodiments, the human macrophage is an M2 macrophage or a M2-like macrophage. In some embodiments, the human macrophage is an M2a, M2b, M2c, or M2d macrophage. In some embodiments, the CD163 protein is a component of a cell surface complex comprising at least one other protein expressed by the macrophage. In some embodiments, the at least one other protein is a galectin-1 protein, a LILRB2 protein, a casein kinase II protein, or any combination thereof. In some embodiments, upon binding with the CD163 protein, the antibody is internalized by the human macrophage. In some embodiments, binding to the CD163 protein is not cytotoxic to the macrophage. In some embodiments, binding to the CD163 protein promotes CD4$^+$ T cell activation, CD4$^+$ T cell proliferation, or both CD4$^+$ T cell activation and proliferation. In some embodiments, binding to the CD163 protein promotes expression of CD69, ICOS, OX40, PD1, LAG3, CTLA4, or any combination thereof by CD4$^+$ T cells. In some embodiments, binding to the CD163 protein promotes CD8$^+$ T cell activation, CD8$^+$ T cell proliferation, or both CD8$^+$ T cell activation and proliferation. In some embodiments, binding to the CD163 protein promotes expression of ICOS, OX40, PD1, LAG3, CTLA4, or any combination thereof by CD8$^+$ T cells. In some embodiments, binding to the CD163 protein reduces immunosuppression in a tumor microenvironment. In some embodiments, binding to the CD163 protein promotes tumor cell killing in a tumor microenvironment. In some embodiments, binding to the CD163 protein promotes cytotoxic lymphocyte-mediated killing of cancer cells. In some embodiments, binding to the CD163 protein promotes NK cell-mediated tumor cell killing. In some embodiments, binding to the CD163 protein promotes expression of IL-2 by T cells. In some embodiments, binding to the CD163 protein increases CD4$^+$ T cells, CD196$^-$ T cells, CXCR3$^+$ T cells, CCR4$^-$ T cells, or any combination thereof. In some embodiments, binding to CD163 reduces immunosuppression in a tumor microenvironment caused by a macrophage.

Disclosed herein, in certain embodiments, is an antibody that specifically binds to a CD163 protein expressed on a human macrophage, wherein binding results in at least one of the following effects: (a) reduced expression of at least one marker by the macrophage, wherein the at least one marker is CD16, CD64, TLR2, or Siglec-15; (b) internalization of the antibody by the macrophage; (c) activation of a CD4$^+$ T cell, CD8$^+$ T cell, NK cell, or any combination thereof; (d) proliferation of a CD4$^+$ T cell, CD8$^+$ T cell, NK cell, or any combination thereof; and (e) promotion of tumor cell killing in a tumor microenvironment. In some embodiments, the binding results in: two or more of (a) through (e); three or more of (a) through (e); four or more of (a) through (e); or all of (a) through (e). In some embodiments, the activation of a CD4+ T cell, CD8+ T cell, NK cell, or any combination thereof is measured as increased production of IFN-γ, TNF-α, perforin, or any combination thereof.

Disclosed herein, in certain embodiments, is an antibody that specifically binds to a CD163+ immunosuppressive myeloid cell in a tumor microenvironment, wherein the binding reduces suppression of cytotoxic T cell-mediated killing of tumor cells in the tumor microenvironment.

Disclosed herein, in certain embodiments, is an antibody that specifically binds to a CD163 protein expressed on a human tumor-associated macrophage and reduces expression of CD16, CD64, TLR2, Siglec-15, or a combination thereof by the macrophage, for use in a method of treating cancer. In some embodiments, binding of the antibody to the macrophage modulates an immune function of a cell in a tumor microenvironment. In some embodiments, binding of the antibody to the macrophage promotes an anti-tumor immune function.

In some embodiments, a composition comprises an antibody according to any embodiment as disclosed herein, and an excipient.

In some embodiments, a pharmaceutical composition comprises an antibody according to any embodiment as disclosed herein and a pharmaceutically acceptable carrier.

In some embodiments, a use of an antibody as disclosed herein is for the manufacture of a medicament for treating cancer in a human subject.

In some embodiments, a use of an antibody as disclosed herein is for the manufacture of a medicament that reduces immunosuppression by a tumor-associated macrophage in a human subject having a cancer.

In some embodiments, a use of an antibody as disclosed herein is for the manufacture of a medicament that promotes T cell-mediated tumor cell killing in a human subject having a cancer.

Disclosed herein, in certain embodiments, is a method of promoting an immune cell function, the method comprising: specifically binding an antibody to a CD163 protein expressed on an immunosuppressive human myeloid cell; and promoting an immune cell function as measured by one or both of the following parameters: (i) activation of a CD4+ T cell, CD8+ T cell, NK cell, or any combination thereof; and (ii) proliferation of a CD4+ T cell, CD8+ T cell, NK cell, or any combination thereof. In some embodiments, the immunosuppressive human myeloid cell is a macrophage. In some embodiments, the immunosuppressive human myeloid cell is a myeloid-derived suppressor cell. In some embodiments, the antibody is any embodiment as disclosed herein.

Disclosed herein, in certain embodiments, is a method of treating cancer in an individual in need thereof, the method comprising administering to the individual a therapeutically effective amount of an antibody of any one of the embodiments disclosed herein, thereby treating the cancer in the individual.

Disclosed herein, in certain embodiments, is a method of treating cancer in an individual in need thereof, the method comprising administering to the individual a therapeutically effective amount of an antibody of any one of the embodiments disclosed herein, whereby immunosuppression by a tumor-associated macrophage in the individual is reduced.

Disclosed herein, in certain embodiments, is a method of treating cancer in an individual in need thereof, the method comprising administering to the individual a therapeutically effective amount of an antibody of any one of the embodiments disclosed herein, whereby T cell-mediated tumor cell killing in the individual is increased. In some embodiments, the cancer is a lung cancer or sarcoma. In some embodiments, the lung cancer is a lung carcinoma or lung adenocarcinoma.

Disclosed herein, in certain embodiments, is a method of reducing a tumor promoting activity of a tumor-associated macrophage in an individual in need thereof, the method comprising administering to the individual an amount of a pharmaceutical composition that is effective to modulate a CD4+ T cell activation, CD4+ T cell proliferation, CD8+ T cell activation, CD8+ T cell proliferation, or any combination thereof in the tumor microenvironment. In some embodiments, the method further comprises promoting tumor cell killing in the tumor microenvironment.

Disclosed herein, in certain embodiments, is a method of promoting lymphocyte-mediated tumor cell killing in an individual in need thereof, the method comprising administering to the individual an effective amount of a pharmaceutical composition of any one of the embodiments disclosed herein.

Disclosed herein, in certain embodiments, is a method of modulating an activity of a tumor-associated macrophage in a tumor microenvironment, the method comprising contacting the tumor-associated macrophage with an antibody that binds to a CD163-expressing human macrophage and comprises at least one of the following effects: (a) the binding of the antibody reduces expression of at least one marker on the macrophage, wherein the at least one marker is CD16, CD64, TLR2, or Siglec-15; (b) upon binding of the antibody with the CD163 protein, the antibody is internalized by the human macrophage; (c) the binding of the antibody is not cytotoxic to the macrophage; (d) the binding of the antibody promotes an activation of a CD4+ T cell, CD8+ T cell, NK cell, or any combination thereof; (e) the binding of the antibody promotes a proliferation of a CD4+ T cell, CD8+ T cell, NK cell, or any combination thereof; and (f) the binding of the antibody promotes tumor cell killing in the tumor microenvironment. In some embodiments, the binding results in: two or more of (a) through (f); three or more of (a) through (f); four or more of (a) through (f); five or more of (a) through (f); or all of (a) through (f). In some embodiments, the activation of a CD4+ T cell, CD8+ T cell, NK cell, or any combination thereof is measured as increased production of IFN-γ, TNF-α, perforin, or any combination thereof. In some embodiments, the method occurs in a tumor microenvironment. In some embodiments, the method occurs in vivo. In some embodiments, binding of the antibody to the macrophage modulates an immune function of a cell in a tumor microenvironment. In some embodiments, binding of the antibody to the macrophage promotes an anti-tumor immune function. In some embodiments, the antibody comprises a constant domain and the constant domain binds to an Fc receptor. In some embodiments, the Fc receptor is expressed on the macrophage. In some embodiments, the method further comprises internalizing the antibody by the human macrophage upon binding with the CD163 protein. In some embodiments, binding to the CD163 protein is not cytotoxic to the human macrophage. In some embodiments, the method further comprises promoting expression of CD69, ICOS, OX40, PD1, LAG3, CTLA4, or any combination thereof by CD4+ T cells. In some embodiments, the method further comprises promoting expression of ICOS, OX40, PD1, LAG3, CTLA4, or any combination thereof by CD8+ T cells. In some embodiments, the method comprises reducing immunosuppression in a tumor microenvironment. In some embodiments, the method comprises promoting cytotoxic lymphocyte-mediated killing of cancer cells. In some embodiments, the method comprises promoting NK cell-mediated tumor cell killing. In some embodiments, the method comprises promoting expression of IL-2 by T cells. In some embodiments, the method comprises increasing CD4+ T cells, CD196− T cells, CXCR3+ T cells, CCR4− T cells, or any combination thereof.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 28 shows the experimental design for M2c/T cell coculture assay to evaluate the effect of AB101 treatment on T cell proliferation and IL-2 production.

FIG. 29 shows that treatment with AB101 during M2c macrophage polarization restored T-cell proliferation in M2c/T cell coculture assay.

FIG. 47 shows a summary of changes based on pepsin digestion of AB101 bound to huCD163. Figure discloses SEQ ID NO: 24.

FIG. 48 shows a summary of changes based on Nepenthesin II digestion of AB101 bound to huCD163. Figure discloses SEQ ID NO: 24.

FIG. 52 shows that AB101 binds human and cynomolgus E323K mutant but does not bind wildtype cynomolgus CD163 ECD.

FIG. 53 shows SPR detection of binding of AB101 to human CD163. AB101 was serially diluted into different concentrations with (A) EDTA or (B) calcium-containing running buffer. GHI/61 was then injected into flow cell 2 with a flow rate at 30 μl/min, concentrations at 6.25/12.5/25/50/100/200 μg/ml, a contact time of 300 s, and a dissociation time of 600 s.

DETAILED DESCRIPTION OF THE DISCLOSURE

Figure 1:
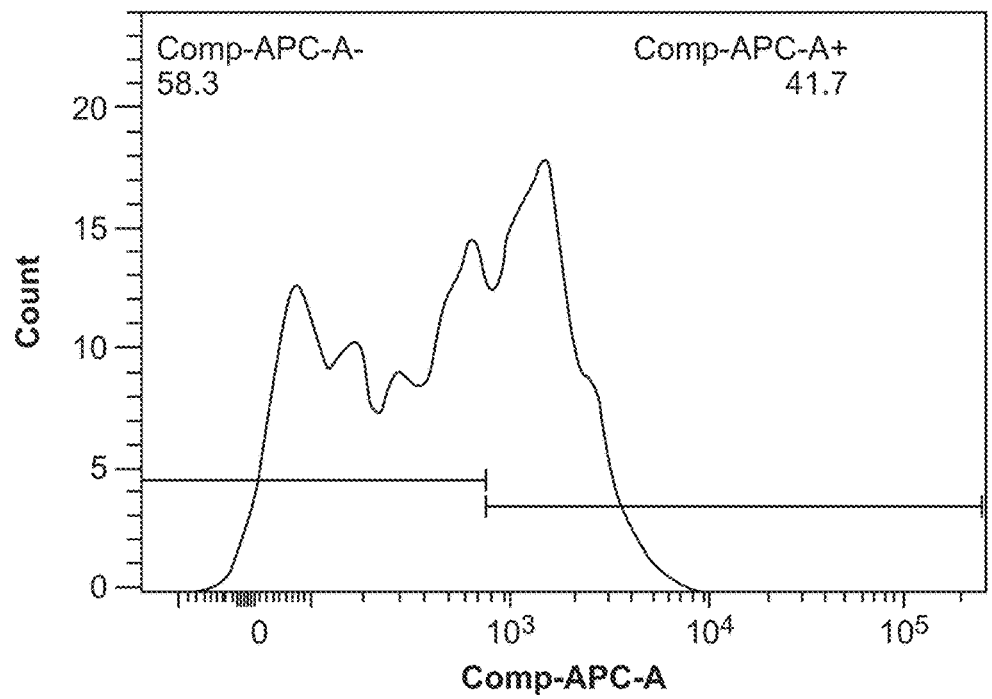
FIG. 1 shows the AB101 antibody binding to human MDSC populations.

Disclosed herein are antibodies that specifically bind to CD163+ cells. In some embodiments, the CD163+ cells are immunosuppressive myeloid cells. In some embodiments, the CD163+ cells are human CD163 expressing myeloid. In some embodiments, the CD163+ cells are tumor cells. In some embodiments, the CD163+ immunosuppressive myeloid cells are human macrophages. In some embodiments, the human CD163+ immunosuppressive macrophages are M2 or M2-like macrophages. In some embodiments, the immunosuppressive myeloid cells are myeloid-derived suppressor cells (MDSC). In some embodiments, the human macrophages express high levels of CD163 (CD163$^{Hi}$). By contrast, other human hematopoietic cells or primary non-immune human cells do not express CD163. For example, M1 and M1-like macrophages do not express CD163.

Monocytes and macrophages exposed to certain inflammatory cytokines or microbe-associated molecular patterns differentiate into pro-inflammatory (M1 or M1-like) or anti-inflammatory M2 or M2-like macrophages. M1 and M2 are classifications used to define macrophages activated in vitro as pro-inflammatory (when classically activated with IFN-γ and lipopolysaccharide) or anti-inflammatory (when alternatively activated with IL-4 or IL-10), respectively, whereas in vivo or ex vivo macrophages with M1 or M2 phenotypes are defined as M1-like or M2-like macrophages. In some embodiments, M2 macrophages are generated by their exposure to certain cytokines. In some embodiments, the M2 macrophages are differentiated by IL-4, IL-10, IL-13, or a combination thereof.

Sub-types of M2 macrophages include M2a, M2b, M2c, and M2d subtypes. M2a macrophages are induced by IL-4 and IL-13 which evokes upregulated expression of CD163, arginase-1, mannose receptor MRC1 (CD206), antigen presentation by MHC II system, and production of IL-10 and TGF-β, leading to tissue regeneration and the inhibition of pro-inflammatory molecules to prevent the inflammatory response. The M2b macrophages produce IL-1, IL-6, IL-10, TNF-α as a response to immune complexes. M2c macrophages are induced by IL-10, transforming growth factor beta (TGF-β) and glucocorticoids exposure, and produce IL-10 and TGF-β, leading to suppression of inflammatory response. M2d subtypes are activated as a response to IL-6 and adenosines.

M2 macrophages have functions and phenotypes corresponding to M2 macrophages and their subtypes. An M2-like macrophage is any in vivo or ex vivo macrophage having a subset of the functional or phenotypic characteristics of M2 macrophages.

In some embodiments, the antibodies of the present disclosure have high avidity and specific binding for immunosuppressive myeloid cells, in particular, for tumor-associated macrophages, such as M2 and M2-like macrophages. In some embodiments, the antibodies specifically bind to M2 and M2-like TAMs from human primary lung tumors. In some embodiments, the antibodies as disclosed herein do not have appreciable binding to M1 or M1-like macrophages. M1-activated macrophages express transcription factors such as Interferon-Regulatory Factor (IRF5), Nuclear Factor of kappa light polypeptide gene enhancer (NF-κB), Activator-Protein (AP-1) and STAT1. M1 macrophages secrete pro-inflammatory cytokines such as IFN-γ, IL-1, IL-6, IL-12, IL-23 and TNFα. M1 macrophages have functions and phenotypes corresponding to M1 macrophages. An M1-like macrophage is any in vivo or ex vivo macrophage having a subset of the functional or phenotypic characteristics of M1 macrophages.

In some embodiments, the antibodies of the present disclosure do not bind to primary human cells. In some embodiments, the antibodies of the present disclosure do not bind to hematopoietic stem cells, leukocytes, T cells, B cells, NK cells, and granulocytes.

Tumor-associated macrophages (TAMs) are a heterogeneous class of macrophage cells present in high numbers in the microenvironment of solid tumors. Most evidence suggests that TAMs have a tumor-promoting phenotype, appearing to be involved in tumor cell proliferation, tumor angiogenesis, motility, and invasion, metastasis, anticancer drug resistance, and tumor immune evasions.

Direct tumor cell killing by cytotoxic T cells among tumor-infiltrating lymphocytes (TIL) play a major role in the anti-tumor function of the immune system. TAMs in the tumor microenvironment (TME), however, suppress the T cell-mediated anti-tumor immune response.

TAMs have an immunosuppressive transcriptional profile and express factors including IL-10 and transforming growth factor β (TGFβ). In humans, TAMs have been shown to directly suppress T cell function through surface presentation of programmed death-ligand 1 (PD-L1) in hepatocellular carcinoma and B7-homologs in ovarian carcinoma, which activate programmed cell death protein 1 (PD-1) and cytotoxic T-lymphocyte-associated protein 4 (CTLA4), respectively, on T cells. Inhibitory signals to PD-1 and CTLA4 are immune checkpoints, and binding of these inhibitory receptors by their ligands inhibits T cell receptor signaling and T cell cytotoxic function, and promotes T cell apoptosis. HIF-1α induces TAMs to suppress T cell function. CD163 has been identified as an immunosuppressive molecule that is solely expressed on TAMs, and could be a potential therapeutic target for cancer immunotherapy.

TAMs generally fall into two categories, M1-like antitumor and M2-like immunosuppressive macrophages, based on their functional characteristics, including their relationships to T helper cell (CD4$^+$) types Th1 and Th2. M1 macrophages are a model of "classical" and can be generated with IFN-γ with either innate immune activators such as pathogen associated molecular patterns (PAMP) (e.g., lipopolysaccharide (LPS)) or damage-associated molecular patterns (DAMPs) as well as inflammatory cytokines (e.g., tumor necrosis factor-alpha (TNF-α). In addition, T cell dependent macrophage activation via the CD40-CD40 ligand pathway induce M1 differentiation. M1 macrophages have pro-inflammatory, bactericidal, and cytotoxic functions. These macrophages promote the antigen-dependent induction of Th1 cells and activation of Th1 and CD8$^+$ T cells. The promotion of T cell cytotoxic activity by M1-like anti-tumor macrophages is critical for tumor cell elimination. In some embodiments, M1-like anti-tumor macrophages are characterized by surface marker expression measured by flow cytometry and have either a CD80$^+$ CD86$^+$ CD163$^{Lo/-}$ or CD206$^{Lo/-}$ phenotype. M1 macrophages secrete IL-12, and low level of IL-10 and/or TGF-ß.

By contrast, M2-like immunosuppressive macrophages are a model of "alternative" or "non-classical" activation, which can be generated with IL-4 or IL-10 in vitro, are anti-inflammatory and promote wound healing and tissue repair. In some embodiments, M2-like immunosuppressive macrophages are polarized from monocyte-derived macrophages and recruited by factors secreted by tumors. M2-like immunosuppressive macrophages are the principal macrophage cell type involved in pro-tumoral function of TAMs, which includes promoting tumor growth, metastasis, and immune evasion. M2-like macrophages express the surface markers CD15, CD23, CD64, CD68, CD163$^{Hi}$, CD204$^{Hi}$, CD206$^{Hi}$, and/or other M2 macrophage markers determined by flow cytometry. M2 macrophages secrete high levels of IL-10 and TGF-beta1, and low levels of IL-12.

In many tumor types, TAM infiltration level has significant prognostic value. TAMs have been linked to poor prognosis in a wide variety of tumors. For example, it has been found that breast cancer patients with more M2-like tumor-associated macrophages had higher-grade tumors, greater microvessel density, and lower overall survival. Patients with more M1-like anti-tumor TAMs displayed the opposite effect.

Accordingly, there remains a need to identify compounds and methods to improve immunotherapeutic treatment of treating cancer.

CD163 (scavenger receptor cysteine-rich type 1 protein M130; hemoglobin scavenger receptor) is a cell surface protein which acts as a scavenger receptor for the hemoglobin-haptoglobin complex and protects tissues from free hemoglobin-mediated oxidative damage. Four isoforms of CD163 protein, with molecular weights of 125,451, 125,982, 121,609 and 124,958 Da have been reported. Isoform 1 is the most prevalent isoform of CD163, with a molecular weight of 125,451 Da, and consisting of 1115 amino acid-residue polypeptide comprising an extracellular domain, a transmembrane segment, and a cytoplasmic tail. The extracellular domain comprises nine cysteine-rich repeat domains. Isoform 1 of CD163 protein has four N-linked glycosylation sites, and in M2 macrophages CD163 protein shows two distinct bands, at ~150 kDa and ~130 kDa, in SDS-PAGE under reducing conditions.

CD163 mRNA expression is generally restricted to myeloid cells but is also expressed by certain human cancers. CD163 expression on TAMs has been associated with immunosuppressive M2-like phenotype, which has been shown to correlate with poor clinical outcome in cancer. CD163 is required for protumoral activation of macrophages in human and murine sarcoma. CD163 has also been reported to be a macrophage scavenger receptor and promote immunosuppression. In some embodiments, the interaction of the hemoglobin-haptoglobin complex with CD163 induces the secretion of the immunosuppressive cytokine IL-10 and the expression heme-oxygenase-1 (HO-1). HO-1 produces the anti-inflammatory metabolites $Fe^{2+}$, CO and biliverdin.

Soluble CD163 occurs in humans via ectodomain shedding and is reported to have anti-inflammatory properties, such as downregulating T-cell responses, including lymphocyte proliferation stimulated by phytohemagglutinin (PHA) or 12-O-tetradecanoylphorbol-13-acetate (TPA).

Antibodies targeting CD163 have been shown to modulate the innate immune response of CD163 expressing macrophages. For example, RM3/1 antibody, an antibody against CD163, is a mouse monoclonal IgG1 (kappa light chain) that was raised against human monocytes. The RM3/1 antibody binds to the cysteine-rich domain 9 of human CD163, reduces LPS-induced TNFα, and enhances IL-10 secretion by macrophages.

Certain Terminology

Unless defined otherwise, all technical and scientific terms used herein have the same meaning as is commonly understood by one of skill in the art to which the claimed subject matter belongs. Generally, nomenclatures utilized in connection with, and techniques of, immunology, oncology, cell and tissue culture, molecular biology, and protein and oligo- or polynucleotide chemistry and hybridization described herein are those well-known and commonly used in the art. It is to be understood that the foregoing general description and the following detailed description are exemplary and explanatory only and are not restrictive of any subject matter claimed. The section headings used herein are for organizational purposes only and are not to be construed as limiting the subject matter described.

As used herein, singular forms "a," "an," and "the" include plural referents unless the context clearly indicates otherwise. Thus, for example, reference to "an antibody" includes a plurality of antibodies and reference to "an antibody" in some embodiments includes multiple antibodies, and so forth.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. In another example, reference to a range of 1-5,000 fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5 fold, etc., 2.1, 2.2, 2.3, 2.4, 2.5 fold, etc., and so forth.

"About" a number, as used herein, refers to range including the number and ranging from 10% below that number to 10% above that number. "About" a range refers to 10% below the lower limit of the range, spanning to 10% above the upper limit of the range.

"Percent identity" and "% identity" refers to the extent to which two sequences (nucleotide or amino acid) have the same residue at the same positions in an alignment. For example, "an amino acid sequence is X % identical to SEQ ID NO: Y" refers to % identity of the amino acid sequence to SEQ ID NO:Y and is elaborated as X % of residues in the amino acid sequence are identical to the residues of sequence disclosed in SEQ ID NO: Y. Generally, computer programs are employed for such calculations. Exemplary programs that compare and align pairs of sequences, include ALIGN (Myers and Miller, Comput Appl Biosci. 1988 March; 4(1):11-7), FASTA (Pearson and Lipman, Proc Natl Acad Sci USA. 1988 April; 85(8):2444-8; Pearson, Methods Enzymol. 1990; 183:63-98) and gapped BLAST (Altschul et al., Nucleic Acids Res. 1997 Sep. 1; 25(17):3389-40), BLASTP, BLASTN, or GCG (Devereux et al., Nucleic Acids Res. 1984 Jan. 11; 12(1 Pt 1):387-95).

As used herein "antibody" refers to a protein that binds an antigen. An antibody often comprises a variable domain and a constant domain in each of a heavy chain and a light chain. Accordingly, most antibodies have a heavy chain variable domain (VH) and a light chain variable domain (VL) that together form the portion of the antibody that binds to the antigen. Within each variable domain are three complementarity-determining regions (CDR), which form loops in the heavy chain variable domain (VH) and light chain variable domain (VL) and contact the surface of the antigen. "Antibody" includes, but is not limited to, polyclonal, monoclonal, monospecific, multispecific (e.g., bispecific antibodies), natural, humanized, human, chimeric, synthetic, recombinant, hybrid, mutated, grafted, antibody fragments (e.g., a portion of a full-length antibody, generally the antigen binding or variable region thereof, e.g., Fab, Fab', F(ab')2, and Fv fragments), and in vitro-generated antibodies having the antigen-binding activity. The term also includes single chain antibodies, e.g., single chain Fv (sFv or scFv) antibodies, in which a variable heavy and a variable light chain are joined together (directly or through a peptide linker) to form a continuous polypeptide.

As used herein "complementarity-determining regions (CDRs)" refers to the part of the variable chains in antibodies that bind to the specific antigen. Multiple methods may be used to define a CDR. The current art utilizes various numbering schemes with different definitions of CDR lengths and positions. For example, the Kabat numbering scheme is based on sequence alignment and uses "variability parameter" of a given amino acid position (the number of different amino acids at a given position divided by the frequency of the most occurring amino acid at that position) to predict CDRs. The Chothia numbering scheme, on the other hand, is a structure-based numbering scheme where antibody crystal structures are aligned as define the loop structures as CDRs. The Martin numbering scheme focuses on the structure alignment of different framework regions of unconventional lengths. IMGT numbering scheme is a standardized numbering system based on alignments of sequences from a complete reference gene database including the whole immunoglobulin superfamily. Honneger's numbering scheme (AHo's) is based on structural alignments of the 3D structure of the variable regions and uses structurally conserved Ca positions to deduce framework and CDR lengths. One of skill in the art will note that the definition of a CDR will vary based on the method used. Any method of defining a CDR is contemplated with the sequences disclosed herein.

The terms "recipient," "individual," "subject," "host," and "patient," are used interchangeably herein and refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is a human.

As used herein, the terms "treatment," "treating," and the like, in some cases, refer to administering an agent, or carrying out a procedure, for the purposes of obtaining an effect. In some embodiments, the effect is prophylactic in terms of completely or partially preventing a disease or symptom thereof and/or is therapeutic in terms of effecting a partial or complete cure for a disease and/or symptoms of the disease. "Treatment," as used herein, includes treatment of a disease or disorder (e.g., cancer) in a mammal, particularly in a human, and includes: (a) preventing the disease or a symptom of a disease from occurring in a subject which is predisposed to the disease but has not yet been diagnosed as having it (e.g., including diseases that is associated with or caused by a primary disease); (b) inhibiting the disease, i.e., arresting its development; and (c) relieving the disease, i.e., causing regression of the disease. In some embodiments, treating refers to any indicia of success in the treatment or amelioration or prevention of a cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms is based on one or more objective or subjective parameters; including the results of an examination by a physician. Accordingly, the term "treating" includes the administration of the compounds or agents of the present disclosure to prevent or delay, to alleviate, or to arrest or inhibit development of the symptoms or conditions associated with diseases (e.g., cancer). The term "therapeutic effect" refers to the reduction, elimination, or prevention of the disease, symptoms of the disease, or side effects of the disease in the subject. A subject is "treated" for a disease or disorder if, after receiving a therapeutic amount of an antibody of the present disclosure, the patient shows observable and/or measurable change in a parameter or symptom of the disease or disorder, such as, in the case of treatment of a cancer, increased tumor cell killing activity as assessed ex vivo, lower levels of immunosuppressive secreted factors in blood, lower tumor volume or mass, increased cytotoxic lymphocytes and Th1 like T cell numbers in tumor biopsy, reduced morbidity or mortality, improvement in quality of life factors, or improvement in any objective indicia related to a parameter or symptom of the disease or disorder. In some embodiments, the parameters include converting immune cold tumors into immune hot, e.g., by increasing cytotoxic lymphocyte cell number as well as markers of T cell activation (CD69, ICOS, OX40, etc.) in tumor biopsy, or decreasing expression of CD16, CD64, TLR2, Siglec-15 on TAMs in tumor biopsy.

In some embodiments, "inducing a response" refers to the alleviation or reduction of signs or symptoms of illness in a subject, and specifically includes, without limitation, prolongation of survival.

The term "avidity" refers to the resistance of a complex of two or more agents to dissociation after dilution.

In some embodiments, antibody "effector functions" refers to those biological activities attributable to the Fc region (a native sequence Fc region or amino acid sequence variant Fc region) of an antibody and vary with the antibody isotype.

"Fc receptor" or "FcR" refers to a receptor that binds to the Fc region of an antibody.

"Human effector cells" as used herein refers to leukocytes that express one or more FcRs and perform effector functions. For example, the cells express at least FcγRIII and perform an ADCC effector function. Examples of human leukocytes that mediate ADCC include, but are not limited to, peripheral blood mononuclear cells (PBMC), NK cells, monocytes, macrophages, cytotoxic T cells, and neutrophils.

"Complement-dependent cytotoxicity" or "CDC" refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, for example, is performed.

An antibody that "internalizes" is one that is taken up by (i.e., enters) the cell upon binding to an antigen on a mammalian cell (e.g., a cell surface polypeptide or receptor). The internalizing antibody comprises antibody fragments, human or chimeric antibody, and antibody conjugates. In some cases, internalization of an antibody (e.g., such as disclosed herein) alter the biology of the cell, causing it to change its function.

An "antigen-binding domain," "antigen-binding region," or "antigen-binding site" is a portion of an antibody that contains amino acid residues (or other moieties) that interact with an antigen and contribute to the antibody's specificity and affinity for the antigen. For an antibody that specifically binds to its antigen, this will include at least part of at least one of its CDR domains.

The antigen-binding region of an antibody is referred to as a "paratope," which binds to an antigenic determinant, the "epitope" of an antigen, that is, a portion of the antigen molecule that is able to be bound by an antibody. In some embodiments, an antigen substance has one or more portions that are recognizable by antibodies, i.e., more than one epitope, and thus a single antigen substance is specifically bound by different antibodies each having specificity for a different epitope. In some embodiments, an epitope comprises non-contiguous portions of the antigen. For example, in a polypeptide, amino acid residues that are not contiguous in the polypeptide's primary sequence but that, in the context of the polypeptide's tertiary and quaternary structure, are near enough to each other to be bound by an antigen-binding protein, constitutes an epitope.

An "antibody fragment" comprises a portion of an intact antibody. In some embodiments, the antibody fragment comprises an antigen-binding or variable region of the intact antibody.

The terms "antigen-binding portion of an antibody," "antigen-binding fragment," "antigen-binding domain," "antibody fragment" are used interchangeably herein to refer to one or more fragments of an antibody that retain the ability to specifically bind to the antigen. Non-limiting examples of antibody fragments included within such terms include, but are not limited to, (i) a Fab fragment, a monovalent fragment consisting of the VL, VH, CL, and CHl domains; (ii) a F(ab')2 fragment, a bivalent fragment containing two Fab fragments linked by a disulfide bridge at the hinge region; (iii) a Fd fragment consisting of the VH and CH domains; (iv) a Fv fragment containing the VL and VH domains of a single arm of an antibody, (v) a dAb fragment (Ward et al., Nature 341(6242):544-6 (1989)), containing a VH domain; and (vi) an isolated CDR. Also included are "one-half" antibodies comprising a single heavy chain and a single light chain. Other forms of single chain antibodies, such as diabodies are also encompassed herein.

A "functional antibody fragment" as used herein refers in context to an antibody fragment that not only binds the antibody's antigen, but also possesses a functional attribute that characterizes the intact antibody. For example, if an antibody depends for a function on possessing a Fc domain that enables an effector function, such as ADCC, a functional fragment would possess such function. It is hypothesized that antibodies of the disclosure are effective in modulating the functional state of tumor-associated macrophages, or reorienting or dampening the M2-status macrophages, when they comprise an Fc portion that binds to a macrophage Fc receptor, such as CD16 (FcγRIIIa) or CD64 (FcγRI) in some embodiments.

The phrase "functional fragment or analog" of an antibody is a compound having qualitative biological activity in common with a full-length antibody. For example, a functional fragment or analog of an anti-IgE antibody is one that binds to an IgE immunoglobulin to prevent or substantially reduce the ability of such molecule from having the ability to bind to the high affinity receptor, FcγRI.

An "antigen-binding protein" is a protein comprising a portion that comprises an antigen-binding portion of an antibody, optionally also including a scaffold or framework portion that allows the antigen-binding portion to adopt a conformation that promotes binding of the antigen-binding protein to the antigen.

An "intact" antibody is one that comprises an antigen-binding site as well as a $C_L$ and at least heavy chain constant domains, $C_H1$, $C_H2$, and $C_H3$. In some embodiments, the constant domains are native sequence constant domains (e.g., human native sequence constant domains) or amino acid sequence variant thereof.

The term "recombinant antibody" as used herein refers to an antibody comprising an antigen-binding domain of a first antibody, such as, for example, a CDR, a VH region, or an intact light chain, and a domain from one or more other antibodies or proteins. Chimeric, hybrid, and humanized antibodies are examples of recombinant antibodies.

A "CDR-grafted antibody" is an antibody comprising one or more CDRs derived from an antibody of one species or isotype and the framework of another antibody of the same or different species or isotype.

The term "human antibody" includes all antibodies that have one or more variable and constant regions derived from human immunoglobulin sequences. In one embodiment, all of the variable and constant domains of the antibody are derived from human immunoglobulin sequences (referred to as a "fully human antibody").

As used herein, the term "affinity" refers to the equilibrium constant for the reversible binding of two agents and is expressed as $K_D$. In one embodiment, the antibodies or antigen-binding fragments thereof exhibit binding affinity as measured by $K_D$ (equilibrium dissociation constant) for CD163 in the range of $10^{-6}$ M or less, or ranging down to $10^{-16}$ M or lower, (e.g., about $10^{-7}$, $10^{-8}$, $10^{-9}$, $10^{-10}$, $10^{-11}$, $10^{-12}$, $10^{-13}$, $10^{-14}$, $10^{-15}$, $10^{-16}$ M or less). In certain embodiments, antibodies as describe herein specifically bind to a huCD163 polypeptide with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M.

The terms "preferentially binds" or "specifically binds" mean that the antibodies or fragments thereof bind to an epitope with greater affinity than it binds unrelated amino acid sequences, and, if cross-reactive to other polypeptides containing the epitope, are not toxic at the levels at which they are formulated for administration to human use. In some embodiments, such affinity is at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the antibody or fragment thereof for unrelated amino acid sequences.

The term "specific" refers to a situation in which an antibody will not preferentially bind to molecules other than the antigen containing the epitope recognized by the antibody. The term is also applicable where for example, an antigen-binding domain is specific for a particular epitope which is carried by a number of antigens, in which case the antibody or antigen-binding fragment thereof carrying the antigen-binding domain will be able to bind to the various antigens carrying the epitope.

As used herein, an antibody is said to be "immunospecific" or "specific" for, or to "specifically bind" to, an antigen if that antibody reacts at a detectable level with the antigen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^9$ $M^{-1}$.

The term "monospecific," as used herein, refers to an antibody composition that contains an antibody that displays a preferential affinity for one particular epitope. In some embodiments, monospecific antibody preparations are made up of about 10%, 20%, 30%, 40%, 50%, 60%, 70%, 75%, 80%, 85%, 90%, 95%, 97%, 99%, or 99.9% antibody having specific binding activity for the particular antigen.

The term "polypeptide" is used in its conventional meaning, i.e., as a sequence of amino acids. The polypeptides are not limited to a specific length of the product. Peptides, oligopeptides, and proteins are included within the definition of polypeptide, and such terms are used interchangeably herein unless specifically indicated otherwise. This term also does not refer to or exclude post-expression modifications of the polypeptide, for example, glycosylations, acetylations, phosphorylations, and the like, as well as other modifications known in the art, both naturally occurring and non-naturally occurring. In some embodiments, a polypeptide is an entire protein, or a subsequence thereof. Particular polypeptides of interest in the context of the antibodies of this disclosure are amino acid subsequences comprising CDRs and being capable of binding human M2 macrophages or CD163 protein expressed by such cells.

As used herein, "substantially pure," and "substantially free" refer to a solution or suspension containing less than, for example, about 20% or less extraneous material, about 10% or less extraneous material, about 5% or less extraneous material, about 4% or less extraneous material, about 3% or less extraneous material, about 2% or less extraneous material, or about 1% or less extraneous material.

The term "isolated" refers to a protein (e.g., an antibody), nucleic acid, or other substance that is substantially free of other cellular material and/or chemicals. In some embodiments, the antibodies, or antigen-binding fragments thereof, and nucleic acids of the disclosure are isolated. In some embodiments, the antibodies, or antigen-binding fragments thereof, and nucleic acids of the disclosure are substantially pure.

When applied to polypeptides, "isolated" generally means a polypeptide that has been separated from other proteins and nucleic acids with which it naturally occurs. Preferably, the polypeptide is also separated from substances such as antibodies or gel matrices (polyacrylamide) which are used to purify it. In some cases, the term means a polypeptide or a portion thereof which, by virtue of its origin or manipulation: (i) is present in a host cell as the expression product of a portion of an expression vector; or (ii) is linked to a protein or other chemical moiety other than that to which it is linked in nature; or (iii) does not occur in nature, for example, a protein that is chemically manipulated by appending, or adding at least one hydrophobic moiety to the protein so that the protein is in a form not found in nature. By "isolated" it is further meant a protein that is: (i) synthesized chemically; or (ii) expressed in a host cell and purified away from associated and contaminating proteins.

The term "effective amount" as used herein, refers to that amount of an antibody, or an antigen-binding portion thereof as described herein, that is sufficient to induce a response, e.g., to effect treatment, prognosis, or diagnosis of a disease associated with macrophage activity or TAM activity, as described herein, when administered to a subject. Therapeutically effective amounts of antibodies provided herein, when used alone or in combination, will vary depending upon the relative activity of the antibodies and combinations (e.g., in inhibiting tumor cell growth) and depending upon the subject and disease condition being treated, the weight and age of the subject, the severity of the disease condition, the manner of administration, and the like, which, in some cases, are readily determined by one of ordinary skill in the art.

The term "therapeutically effective amount" generally refers to an amount of an antibody or a drug effective to "treat" a disease or disorder in a subject or mammal. In some embodiments, a composition described herein is administered to a subject in an amount that is effective for producing some desired therapeutic effect by inhibiting a disease or disorder as described herein at a reasonable benefit/risk ratio applicable to any medical treatment. A therapeutically effective amount is an amount that achieves at least partially a desired therapeutic or prophylactic effect in an organ or tissue. The amount of an antibody necessary to bring about prevention and/or therapeutic treatment of a disease or disorder is not fixed per se. In some embodiments, the amount of the antibody administered varies with the type of disease, extensiveness of the disease, and size of the mammal suffering from the disease or disorder. When used in conjunction with therapeutic methods involving administration of a therapeutic agent after the subject presents symptoms of a disease or disorder, the term "therapeutically effective" means that, after treatment, one or more signs or symptoms of the disease or disorder is ameliorated or eliminated.

The phrase "pharmaceutically acceptable" refers to molecular entities and compositions that are physiologically tolerable and do not typically produce an allergic or similar untoward reaction, such as gastric upset, dizziness, and the like, when administered to a human.

The term "contacting" is defined herein as a means of bringing a composition as provided herein in physical proximity with a cell, organ, tissue, or fluid as described herein.

Immunomodulatory Antibodies

Disclosed herein, in certain embodiments, are antibodies that specifically bind to a CD163 protein expressed on human CD163$^+$ cell. In some embodiments, the CD163$^+$ cell is an immunosuppressive myeloid cell. In some embodiments, the immunosuppressive myeloid cell is human macrophage. In some embodiments, the binding of an antibody disclosed herein alters expression of at least one marker on the human macrophage.

In some embodiments, an antibody disclosed herein binds to a human CD163 (huCD163) protein expressed on a human M2 or M2-like immunosuppressive macrophage. In some embodiments, the antibody specifically binds to a CD163 protein that is an approximately 140 kDa glycoform of huCD163. In some embodiments, the antibody specifically binds to extracellular domain 3 of huCD163. In some embodiments, the antibody specifically binds to extracellular domain 4 of huCD163. In some embodiments, the antibody specifically binds to extracellular domain 3 and extracellular domain 4 of huCD163. In some embodiments, the antibody specifically binds to huCD163, resulting in a conformational change of huCD163. In some embodiments, the conformational change to humCD163 exposes extracellular domains 2, 5, and 9 of humCD163. In some embodiments, the antibody does not specifically bind a lower molecular weight (approximately 115 kDa) glycoform of huCD163.

In some embodiments, an antibody disclosed herein binds to a human CD163$^+$ immunosuppressive myeloid cell and causes an alteration in the expression of certain cell markers that characterize a M2 or M2-like immunosuppressive macrophage (such as a M2c macrophage), indicating a functional differentiation of the macrophages to a non- or less immunosuppressive as well as a more anti-tumor state. In some embodiments, an antibody disclosed herein binds to a M2 or M2-like immunosuppressive macrophage and causes a decrease in the expression of certain cell markers that characterize a M2 or M2-like macrophage, indicating a functional differentiation of the macrophages to an altered differentiation state. In some embodiments, an antibody disclosed herein reduces expression of one or more of CD16, CD64, TLR2, and Siglec-15 by the CD163$^+$ immunosuppressive myeloid cell.

In some embodiments, the binding of an antibody disclosed herein to a CD163$^+$ immunosuppressive myeloid cells results in a functional change in the CD163$^+$ immunosuppressive myeloid cell. In some embodiments, the binding of the antibody disclosed herein to the CD163$^+$ immunosuppressive myeloid cell results in changes in marker expression in the M2 or M2-like immunosuppressive macrophages. In some embodiments, the functional changes in the antibody-bound CD163$^+$ immunosuppressive myeloid cells result in modified interactions with other cells, such as effector T cells, which subsequently modifies their effects on and interaction with target tumor cells.

In some embodiments, an antibody of the present disclosure reduces immunosuppression caused by tumor-associated macrophages in tumor microenvironments. In some embodiments, a reduction in immunosuppression by tumor-associated macrophages in the tumor microenvironment corresponds to an increase in immunostimulation, e.g., production of promotion of T cell activation, T cell proliferation, NK cell activation, NK cell proliferation, or any combination thereof. In some embodiments, T cell activation and/or NK cell activation results in increased production of IFN-γ, TNF-α, perforin, or a combination thereof by T cells and/or NK cells. In some embodiments, the antibodies of the present disclosure increase immunostimulation, e.g., production of promotion of T cell activation, T cell proliferation, NK cell activation, NK cell proliferation, or any combination thereof. In some embodiments, T cell activation and/or NK cell activation results in increased production of IFN-γ, TNF-α, perforin, or a combination thereof by T cells and/or NK cells. In some embodiments, antibodies of the present disclosure specifically bind to a CD163 protein expressed on a human macrophage, wherein the human macrophage has a first immunosuppression activity before binding the antibody and second immunosuppression activity after binding the antibody, and wherein the second immunosuppression activity lower than the first immunosuppression activity. In various embodiments, the first and second immunosuppression activities are each non-zero.

In some embodiments, an antibody of the present disclosure promotes T cell activation and proliferation. In some embodiments, the antibody skews a T cell population towards an anti-tumor T cell phenotype. In some embodiments, the antibody reduces or blocks myeloid cell suppression of T cell activation. In some embodiments, the antibody reduces the ability of TAMs to suppress T-cell activation, leading to greater T-cell stimulation and IL-2 production. In some embodiments, the antibody blocks the ability of TAMs to suppress T-cell activation, leading to greater T-cell stimulation and IL-2 production.

In some embodiments, an antibody disclosed herein reduces myeloid suppression of T cell proliferation. In some embodiments, the antibody reduces the ability of TAMs to suppress both CD4$^+$ and CD8$^+$ T cell activation and proliferation. In some embodiments, the antibody reduces TAM suppression of Th1 cell proliferation. Proliferated T cells show enhanced expression of activation markers on CD4$^+$ T cells.

In some embodiments, an antibody of the present disclosure alters an M2-polarized macrophage such that the macrophage exhibits a M1-like phenotype that alleviates immunosuppressive effects of M2 macrophages. In some embodiments, an antibody described herein influences monocyte-derived macrophages to differentiate to a less immunosuppressive and more anti-tumor differentiation state.

In some embodiments, provided herein are antibodies that specifically bind to a human CD163 protein (huCD163) that is expressed on a human macrophage and reduces expression of at least one of CD16, CD64, TLR2, or Siglec-15 by the macrophage. In some embodiments, the human macrophage is tumor-associated immunosuppressive macrophage. In some embodiments, the human macrophage is an M2-like immunosuppressive macrophage.

In some embodiments, an antibody disclosed herein binds to a CD163 protein that is expressed by a macrophage as a component of a complex comprising at least one other protein expressed by the macrophages. In some embodiments, the complex is a cell surface complex. In some embodiments, the complex comprises at least one other protein selected from a galectin-1 protein, a LILRB2 protein, and a casein kinase II protein.

In some embodiments, an antibody disclosed herein binds to a CD163 protein on a macrophage and is internalized by the macrophage.

In some embodiments, an antibody disclosed herein is not cytotoxic to a macrophage to which it is bound.

In some embodiments, an antibody disclosed herein promotes CD4$^+$ T cell activity or proliferation. In some embodiments, the antibody promotes expression of CD69, ICOS, OX40, PD1, LAG3, or CTLA4 by CD4$^+$ T cells.

In some embodiments, an antibody disclosed herein promotes CD8$^+$ T cell activity or proliferation. In some embodiments, the antibody promotes expression of ICOS, OX40, PD1, LAG3, or CTLA4 by CD8$^+$ T cells.

In some embodiments, an antibody disclosed herein promotes tumor cell killing in a tumor microenvironment by promoting CD8$^+$ T cell activity or proliferation. In some embodiments, the antibody promotes cytotoxic lymphocyte-mediated killing of cancer cells. In some embodiments, the antibody promotes NK cell-mediated tumor cell killing.

In some embodiments, an antibody disclosed herein promotes expression of IL-2 by T cells.

In some embodiments, the binding of antibodies of the present disclosure to CD163 protein increases CD4$^+$ T cells, CD196$^-$ T cells, CXCR3$^+$ T cells, CCR4$^-$ T cells, or any combination thereof. In some embodiments, the antibody increases CD4$^+$ CD196$^-$ CXCR3$^+$ CCR4$^-$ T cells.

In some embodiments, an antibody disclosed herein has a constant domain that binds to an Fc receptor expressed on a macrophage. In some embodiments, the antibody specifically binds huCD163 and has a constant domain that binds to an Fc receptor. In some embodiments, the antibody has a constant domain that binds to an Fc receptor expressed on CD163$^+$ immunosuppressive myeloid cells such as CD16 (FcγRIIIa) or CD64 (FcγRI). In some embodiments, the huCD163 and Fc receptor are expressed on the same cell. In some embodiments, the huCD163 and Fc receptor are expressed on different cells. In some embodiments, the antibody variable domain specifically binds huCD163 and the antibody constant domain binding to an Fc receptor simultaneously.

Disclosed herein, in certain embodiments, are antibodies that specifically bind to a CD163 protein expressed on human M2 and M2-like macrophages, wherein said binding results in at least one of the following effects:
  (a) reduced expression of at least one marker by the human macrophage, wherein the at least one marker is CD16, CD64, TLR2, or Siglec-15;
  (b) internalization of the antibody by the human macrophage;
  (c) activation of a CD4$^+$ T cell, CD8$^+$ T cell, NK cell, or any combination thereof;
  (d) proliferation of a CD4$^+$ T cell, CD8$^+$ T cell, NK cell, or any combination thereof; and
  (e) promotion of tumor cell killing in a tumor microenvironment.

Disclosed herein, in certain embodiments, are antibodies that specifically bind to a CD163 protein expressed on human M2 and M2-like macrophages, wherein said binding results in at least two of the following effects:
  (a) reduced expression of at least one marker by the human macrophage, wherein the at least one marker is CD16, CD64, TLR2, or Siglec-15;

(b) internalization of the antibody by the human macrophage;
(c) activation of a CD4+ T cell, CD8+ T cell, NK cell, or any combination thereof;
(d) proliferation of a CD4+ T cell, CD8+ T cell, NK cell, or any combination thereof; and
(e) promotion of tumor cell killing in a tumor microenvironment.

Disclosed herein, in certain embodiments, are antibodies that specifically bind to a CD163 protein expressed on human M2 and M2-like macrophages, wherein said binding results in at least three of the following effects:
(a) reduced expression of at least one marker by the human macrophage, wherein the at least one marker is CD16, CD64, TLR2, or Siglec-15;
(b) internalization of the antibody by the human macrophage;
(c) activation of a CD4+ T cell, CD8+ T cell, NK cell, or any combination thereof;
(d) proliferation of a CD4+ T cell, CD8+ T cell, NK cell, or any combination thereof; and
(e) promotion of tumor cell killing in a tumor microenvironment.

Disclosed herein, in certain embodiments, are antibodies that specifically bind to a CD163 protein expressed on human M2 and M2-like macrophages, wherein said binding results in at least four of the following effects:
(a) reduced expression of at least one marker by the human macrophage, wherein the at least one marker is CD16, CD64, TLR2, or Siglec-15;
(b) internalization of the antibody by the human macrophage;
(c) activation of a CD4+ T cell, CD8+ T cell, NK cell, or any combination thereof;
(d) proliferation of a CD4+ T cell, CD8+ T cell, NK cell, or any combination thereof; and
(e) promotion of tumor cell killing in a tumor microenvironment.

Disclosed herein, in certain embodiments, are antibodies that specifically bind to a CD163 protein expressed on human M2 and M2-like macrophages, wherein said binding results in at least five of the following effects:
(a) reduced expression of at least one marker by the human macrophage, wherein the at least one marker is CD16, CD64, TLR2, or Siglec-15;
(b) internalization of the antibody by the human macrophage;
(c) activation of a CD4+ T cell, CD8+ T cell, NK cell, or any combination thereof;
(d) proliferation of a CD4+ T cell, CD8+ T cell, NK cell, or any combination thereof; and
(e) promotion of tumor cell killing in a tumor microenvironment.

In some embodiments, an antibody disclosed herein selectively binds to human CD163+ immunosuppressive myeloid cells in a tumor-associated macrophage (TAM) population, in which the antibody specifically binds to a CD163 protein expressed on the M2 macrophages and reduces an immunosuppressive activity of the TAM population.

In some embodiments, an antibody disclosed herein selectively binds to human CD163+ immunosuppressive myeloid cells in a tumor microenvironment, in which the antibody specifically binds to a CD163 protein expressed on the M2 macrophages and reduces M2 macrophage-mediated suppression. In some embodiments, an antibody disclosed herein is human, humanized, or chimeric. In some embodiments, an antibody disclosed herein is an antigen-binding fragments thereof that bind as described.

In some embodiments the antibodies of the present disclosure are intact immunoglobulin molecules, such as, for example, a human antibody, as well as those portions of a humanized Ig molecule that contain the antigen-binding site (i.e., paratope) or a single heavy chain and a single light chain, including those portions known in the art as Fab, Fab', F(ab')', F(ab')2, Fd, scFv, a variable heavy domain, a variable light domain, a variable NAR domain, bi-specific scFv, a bi-specific Fab2, a tri-specific Fab3, a single chain binding polypeptide, a dAb fragment, a diabody, and others also referred to as antigen-binding fragments. When constructing an immunoglobulin molecule or fragments thereof, variable regions or portions thereof are, in some embodiments, fused to, connected to, or otherwise joined to one or more constant regions or portions thereof to produce any of the antibodies or fragments thereof described herein. Thus, in some embodiments, the antigen-binding fragment of any one of the antibodies described above is a Fab, a Fab', a Fd, a F(ab')2, a Fv, a scFv, a single chain binding polypeptide (e.g., a scFv with Fc portion) or any other functional fragment thereof as described herein.

In some embodiments, antibodies of the present disclosure are of any immunoglobulin class, and, therefore, in some embodiments, have a gamma, mu, alpha, delta, or epsilon heavy chain. In some embodiments, the gamma chain is gamma 1, gamma 2, gamma 3, or gamma 4. In some embodiments, the alpha chain is alpha 1 or alpha 2.

In some embodiments, an antibody of the present disclosure is an IgG immunoglobulin. In some embodiments, antibodies of the present disclosure are of any IgG subclass. In some embodiments the antibody is IgG1.

In some embodiments, antibodies of the present disclosure comprise a variable light chain that is either kappa or lambda. In some embodiments, the lambda chain is of any of subtype, including, e.g., lambda 1, lambda 2, lambda 3, and lambda 4. In some embodiments, the light chain is kappa.

In some embodiments, antibodies disclosed herein comprise a human variable framework region and a human constant region. In some embodiments the antibodies comprise a human light chain variable framework region and a human light chain constant region. In some embodiments the antibodies comprise a human heavy chain variable framework region and a human heavy chain constant region. In some embodiments the antibodies comprise a human light chain variable framework region, a human light chain constant region, a human heavy chain variable framework region, and a human heavy chain constant region.

In some embodiments, the human heavy chain constant region is IgG1 or IgG4 or a fragment thereof. In some embodiments, the heavy chain constant region is human IgG1. One example of an antibody having an IgG1 is AB101. AB101 comprises a light chain comprising SEQ ID NO: 9 and a heavy chain comprising SEQ ID NO: 10, as described in Example 1 below.

In some embodiments, the heavy chain constant region is human IgG1 that has reduced ADCC function (i.e., a Fc-null antibody). An exemplary Fc-null antibody of the present disclosure is AB102. AB102 comprises a light chain comprising SEQ ID NO: 9 and a heavy chain comprising SEQ ID NO: 11, which contains the variable regions of AB101 and in which the heavy chain constant region is a Fc-null form of human IgG1. AB102 is described further in the examples below.

In some embodiments, the heavy chain constant region is a human IgG1 modified to enhance ADCC function. An exemplary antibody of the present disclosure having enhanced ADCC function is AB103. AB103 comprises a light chain comprising SEQ ID NO: 9 and a heavy chain comprising SEQ ID NO: 12, which contains the variable regions of AB101 and in which the heavy chain constant region is an enhanced ADCC form of human IgG1.

In some embodiments, the heavy chain constant region is a human IgG4. An exemplary antibody of the present disclosure having an IgG4 is AB104. AB104 comprises a light chain comprising SEQ ID NO: 9 and a heavy chain comprising SEQ ID NO: 13, which contains the variable regions of AB101 and in which the heavy chain constant region is a human IgG4.

In some embodiments, an antibody of the present disclosure comprises a human variable framework region and a murine constant region. In some embodiments, an antibody of the present disclosure comprises a human heavy chain variable framework region and a murine heavy chain constant region. In some embodiments, an antibody of the present disclosure comprises a human light chain variable framework region, a murine light chain constant region, a human heavy chain variable framework region, and a murine heavy chain constant region.

In some embodiments, the heavy chain constant region is murine IgG2A. One example of an antibody having a murine IgG2A is AB211. AB211 comprises a light chain comprising SEQ ID NO: 14 and a heavy chain comprising SEQ ID NO: 15, which contains the human variable regions of AB101 and in which the heavy chain constant region is a Fc-null form of murine IgG1 and the light chain constant region is a murine kappa. AB211 is described further in the examples below.

In some embodiments, the heavy chain constant region is murine IgG2A. One example of an antibody having the heavy chain of a murine IgG2A is AB212. AB212 comprises a light chain comprising SEQ ID NO: 14 and a heavy chain comprising SEQ ID NO: 16, which contains the human variable regions of AB101 and in which the heavy chain constant region is a murine IgG2a and the light chain constant region is a murine kappa. AB212 is described further in the examples below.

Binding of an antibody or antigen-binding fragment to a CD163 protein expressed on M2 macrophages partially (e.g., 5%, 10%, 20%, 30%, 40%, 50%, 60%, 70%, 80%, 90%, 95%, 98%, 99% or any number therein) or completely modulates a biological function of such M2 macrophages in some embodiments. The activity of an antibody or antigen-binding fragment, for example, are determined using an in vitro assay and/or in vivo using art-recognized assays such as those described herein or otherwise known in the art.

In some embodiments, antibodies of the present disclosure are further modified to alter the specific properties of the antibody while retaining the desired functionality, if needed. For example, in one embodiment, an antibody of the present disclosure is modified to alter a pharmacokinetic property of the antibody, including, but not limited to, in vivo stability, solubility, bioavailability, or half-life.

In some embodiments, an antibody described herein has a dissociation constant (Kd) of about 1 to about 10 pM, from about 10 to about 20 pM, from about 1 to about 29 pM, from about 30 to about 40 pM, from about 10 to about 100 pM, or from about 20 to about 500 pM.

In some embodiments, an antibody described herein has a dissociation constant (Kd) of less than about 500 pM, less than about 400 pM, less than about 300 pM, less than about 200 pM, less than about 100 pM, less than about 75 pM, less than about 50 pM, less than about 30 pM, less than about 25 pM, less than about 20 pM, less than about 18 pM, less than about 15 pM, less than about 10 pM, less than about 7.5 pM, less than about 5 pM, less than about 2.5 pM, or less than about 1 pM.

In some embodiments, an antibody described herein has an affinity for a huCD163 protein or peptide of from about $10^{-9}$ to about $10^{-14}$, from about $10^{-10}$ to about $10^{-14}$, from about $10^{-11}$ to about $10^{-14}$, from about $10^{-12}$ to about $10^{-14}$, from about $10^{-13}$ to about $10^{-14}$, from about $10^{-10}$ to about $10^{-11}$, from about $10^{-11}$ to about $10^{-12}$, from about $10^{-12}$ to about $10^{-13}$, or $10^{-13}$ to about $10^{-14}$ M.

In some embodiments, an antibody described herein has more than one binding site. In some embodiments, the binding sites are identical to one another. In some embodiments, the binding sites are different from one another. A naturally occurring human immunoglobulin typically has two identical binding sites, while engineered antibodies, for example, have two or more different binding sites.

In some embodiments, an antibody of the present disclosure is bispecific or multi-specific. Bispecific antibodies are antibodies that have binding specificities for at least two different epitopes. Exemplary bispecific antibodies, in some embodiments, bind to two different epitopes of a single antigen. Other such antibodies, in some embodiments, combine a first antigen binding site with a binding site for a second antigen. In some embodiments, the bispecific antibodies bind at least two different epitopes and have constant domains that bind to Fc receptors. In some embodiments, the binding of one or more epitopes of the bispecific antibodies is simultaneous with binding of the constant domains of the bispecific antibodies to Fc receptors.

In some embodiments, an antibody of the present disclosure has two or more valencies, which are also referred to as multivalent. In some embodiments, an antibody of the present disclosure is trispecific. In some embodiments, the multivalent antibody is internalized (and/or catabolized) faster than a bivalent antibody by a cell expressing an antigen to which the antibodies bind. In some embodiments, the antibodies of the present disclosure are multivalent antibodies with three or more antigen binding sites (e.g., tetravalent antibodies). In some embodiments, the multivalent antibodies of the present disclosure are produced by recombinant expression of nucleic acid encoding the polypeptide chains of the antibody. In some embodiments, the multivalent antibody comprises a dimerization domain and three or more antigen binding sites. In some embodiments, the dimerization domain comprises (or consists of) an Fc region or a hinge region. In this scenario, the antibody will comprise an Fc region and three or more antigen binding sites amino-terminal to the Fc region. In some embodiments, the multivalent antibody herein comprises about three to about eight, but preferably four, antigen binding sites. The multivalent antibody comprises at least one polypeptide chain (and preferably two polypeptide chains), wherein the polypeptide chain(s) comprise two or more variable regions. For instance, the polypeptide chain(s) comprises VD1-$(X1)_n$-VD2-$(X2)_n$-Fc, wherein VD1 is a first variable region, VD2 is a second variable region, Fc is one polypeptide chain of an Fc region, X1 and X2 represent an amino acid or polypeptide, and n is 0 or 1. In some embodiments, the polypeptide chain(s) each independently comprise: $V_H$—$C_H$1-flexible linker-$V_H$-$C_H$1-Fc region chain; or $V_H$—$C_H1$-$V_H$-$C_H1$-Fc region chain. In some embodiments, the multivalent antibody herein further comprises at least two (and preferably four) light chain variable region polypeptides. In some embodiments, the multivalent antibody herein comprises from about two to about eight light chain variable region polypeptides. In some embodiments, the light chain variable region polypeptides described herein comprise a light chain variable region. In some embodiments, the light chain variable region polypeptides described herein further comprise a $C_L$ domain.

In some embodiments, an antibody of the present disclosure is constructed to fold into multivalent forms, which, in some embodiments, improves binding affinity, specificity, and/or increased half-life in blood. Multivalent forms of antibodies are prepared, for example, by techniques known in the art.

In some embodiments, an antibody of the present disclosure is an SMIP or binding domain immunoglobulin fusion protein specific for the target protein. These constructs are single-chain polypeptides comprising antigen-binding domains fused to immunoglobulin domains necessary to carry out antibody effector functions.

In some embodiments, an antibody of the present disclosure comprises a single chain binding polypeptide having a heavy chain variable region, and/or a light chain variable region which binds an epitope disclosed herein and has, optionally, an immunoglobulin Fc region. Such a molecule is a single chain variable fragment (scFv) optionally having effector function or increased half-life through the presence of the immunoglobulin Fc region.

Anti-CD163 Antibodies

Provided herein, in certain embodiments, are antibodies that specifically bind to CD163 proteins. In some embodiments, CD163-binding antibodies comprise at least one heavy chain and at least one light chain. In some embodiments, CD163-binding antibodies comprise at least one heavy chain comprising a heavy chain variable domain (VH) and at least one light chain comprising a light chain variable domain (VL). Each VH and VL comprises three complementarity determining regions (CDR). The amino acid sequences of the VH and VL and the CDRs determine the antigen binding specificity and antigen binding strength of the antibody. The VH and VL domains are summarized in Table 1. The light chains and heavy chains are summarized in Table 2. The amino acid sequences of the CDRs are summarized in Table 3.

In some embodiments, an antibody disclosed herein is a monoclonal antibody. In some embodiments, an antibody disclosed herein is an antigen binding fragment. In some embodiments, an antibody disclosed herein is selected from a whole immunoglobulin, an scFv, a Fab, a F(ab')2, or a disulfide linked Fv. In some embodiments, an antibody disclosed herein is an IgG or an IgM. In some embodiments, an antibody disclosed herein is humanized. In some embodiments, an antibody disclosed herein is chimeric.

Anti-CD163 Antibody Variable Domains

TABLE 1

Anti-CD163 Variable Domain Sequences.
Anti-CD163 Variable Domain Sequences

| | SEQUENCE | SEQ ID NO: |
|---|---|---|
| Light Chain Variable domain | DIQMTQSPSSLSASVGDRVTITCRASQSISSYLNWYQQKPGKAPK LLIYAASSLQSGVPSRFSGSGSGTDFTLTISSLQPEDFATYYCQQSY STPRGTFGQGTKVEIKR | 7 |
| Heavy Chain Variable domain | EVQLVESGGGVVQPGRSLRLSCAASGFTFSSYAMHWVRQAPGK GLEWVAVISYDGSNKYYADSVKGRFTISRDNSKNTLYLQMNSLR AEDTAVYYCARENVRPYYDFWSGYYSEYYYYGMDVWGQGTTV TVSSASTKGPSVFPLAPSSKSTSGGTAALGCLVKDYF | 8 |

Disclosed herein, in certain embodiments, are antibodies comprising a light chain variable domain (VL) having an amino acid sequence at least about 70% identical to an amino acid sequence set forth as SEQ ID NO: 7. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7. In some embodiments, the VL has an amino acid sequence 100% identical to an amino acid sequence set forth as SEQ ID NO: 7.

Disclosed herein, in certain embodiments, are antibodies comprising a heavy chain variable domain (VH) having an amino acid sequence at least about 70% identical to an amino acid sequence set forth as SEQ ID NO: 8. In some embodiments the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. In some embodiments, the VH has an amino acid sequence 100% identical to an amino acid sequence set forth as SEQ ID NO: 8.

Disclosed herein, in certain embodiments, are antibodies comprising a light chain variable domain (VL) having an amino acid sequence at least about 70% identical to an amino acid sequence set forth as SEQ ID NO: 7 and a heavy chain variable domain (VH) having an amino acid sequence at least about 70% identical to an amino acid sequence set forth as SEQ ID NO: 8. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. In some embodiments, the VL has an amino acid sequence 100% identical to an amino acid sequence set forth as SEQ ID NO: 7 and the VH has an amino acid sequence 100% identical to an amino acid sequence set forth as SEQ ID NO: 8.

Anti-CD163 Antibody Light Chain and Heavy Chain

TABLE 2

Anti-CD163 Light Chain and Heavy Chain Sequences
Anti-CD163 Light Chain and Heavy Chain Sequences

| | SEQUENCE | SEQ ID NO: |
|---|---|---|
| AB101, AB102, AB103, or AB104 Light Chain (hIgG1) | DIQMTQSPSSLSASVGDRVTITCRASQSISSYLNWYQQKPGKAP KLLIYAASSLQSGVPSRFSGSGSGTDFTLTISSLQPEDFATYYCQ QSYSTPRGTFGQGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC | 9 |
| AB101 Heavy Chain (hIgG1) | EVQLVESGGGVVQPGRSLRLSCAASGFTFSSYAMHWVRQAPG KGLEWVAVISYDGSNKYYADSVKGRFTISRDNSKNTLYLQMN SLRAEDTAVYYCARENVRPYYDFWSGYYSEYYYYGMDVWG QGTTVTVSSASTKGPSVFPLAPSSKSTSGGTAALGCLVKDYFPE PVTVSWNSGALTSGVHTFPAVLQSSGLYSLSSVVTVPSSSLGTQ TYICNVNHKPSNTKVDKRVEPKSCDKTHTCPPCPAPELLGGPS VFLFPPKPKDTLMISRTPEVTCVVVDVSHEDPEVKFNWYVDGV EVHNAKTKPREEQYNSTYRVVSVLTVLHQDWLNGKEYKCKV SNKALPAPIEKTISKAKGQPREPQVYTLPPSREEMTKNQVSLTC LVKGFYPSDIAVEWESNGQPENNYKTTPPVLDSDGSFFLYSKL TVDKSRWQQGNVFSCSVMHEALHNHYTQKSLSLSPGK | 10 |
| AB102 Heavy Chain (hIgG1 ADCC-Null) | EVQLVESGGGVVQPGRSLRLSCAASGFTFSSYAMHWVRQAPG KGLEWVAVISYDGSNKYYADSVKGRFTISRDNSKNTLYLQMN SLRAEDTAVYYCARENVRPYYDFWSGYYSEYYYYGMDVWG QGTTVTVSSASTKGPSVFPLAPSSKSTSGGTAALGCLVKDYFPE PVTVSWNSGALTSGVHTFPAVLQSSGLYSLSSVVTVPSSSLGTQ TYICNVNHKPSNTKVDKRVEPKSCDKTHTCPPCPAPEFEGGPS VFLFPPKPKDTLMISRTPEVTCVVVDVSHEDPEVKFNWYVDGV EVHNAKTKPREEQYNSTYRVVSVLTVLHQDWLNGKEYKCKV SNKALPASIEKTISKAKGQPREPQVYTLPPSREEMTKNQVSLTC LVKGFYPSDIAVEWESNGQPENNYKTTPPVLDSDGSFFLYSKL TVDKSRWQQGNVFSCSVMHEALHNHYTQKSLSLSPGK | 11 |
| AB103 Heavy Chain (hIgG1 eADCC) | EVQLVESGGGVVQPGRSLRLSCAASGFTFSSYAMHWVRQAPG KGLEWVAVISYDGSNKYYADSVKGRFTISRDNSKNTLYLQMN SLRAEDTAVYYCARENVRPYYDFWSGYYSEYYYYGMDVWG QGTTVTVSSASTKGPSVFPLAPSSKSTSGGTAALGCLVKDYFPE PVTVSWNSGALTSGVHTFPAVLQSSGLYSLSSVVTVPSSSLGTQ TYICNVNHKPSNTKVDKRVEPKSCDKTHTCPPCPAPELLGGPD VFLFPPKPKDTLMISRTPEVTCVVVDVSHEDPEVKFNWYVDGV EVHNAKTKPREEQYNSTYRVVSVLTVLHQDWLNGKEYKCKV SNKALPLPEEKTISKAKGQPREPQVYTLPPSREEMTKNQVSLTC LVKGFYPSDIAVEWESNGQPENNYKTTPPVLDSDGSFFLYSKL TVDKSRWQQGNVFSCSVMHEALHNHYTQKSLSLSPGK | 12 |
| AB104 Heavy Chain (hIgG4) | EVQLVESGGGVVQPGRSLRLSCAASGFTFSSYAMHWVRQAPG KGLEWVAVISYDGSNKYYADSVKGRFTISRDNSKNTLYLQMN SLRAEDTAVYYCARENVRPYYDFWSGYYSEYYYYGMDVWG QGTTVTVSSASTKGPSVFPLAPCSRSTSESTAALGCLVKDYFPE PVTVSWNSGALTSGVHTFPAVLQSSGLYSLSSVVTVPSSSLGTK TYTCNVDHKPSNTKVDKRVESKYGPPCPPCPAPEFLGGPSVFLF PPKPKDTLMISRTPEVTCVVVDVSQEDPEVQFNWYVDGVEVH NAKTKPREEQFNSTYRVVSVLTVLHQDWLNGKEYKCKVSNK GLPSSIEKTISKAKGQPREPQVYTLPPSQEEMTKNQVSLTCLVK GFYPSDIAVEWESNGQPENNYKTTPPVLDSDGSFFLYSRLTVD KSRWQEGNVFSCSVMHEALHNHYTQKSLSLSLGK | 13 |
| AB211 or AB212 Light Chain (muKappa) | DIQMTQSPSSLSASVGDRVTITCRASQSISSYLNWYQQKPGKAP KLLIYAASSLQSGVPSRFSGSGSGTDFTLTISSLQPEDFATYYCQ QSYSTPRGTFGQGTKVEIKRTDAAPTVSIFPPSSEQLTSGGASVV CFLNNFYPKDINVKWKIDGSERQNGVLNSWTDQDSKDSTYSM SSTLTLTKDEYERHNSYTCEATHKTSTSPIVKSFNRNEC | 14 |
| AB211 Heavy Chain (muIgG2A) | EVQLVESGGGVVQPGRSLRLSCAASGFTFSSYAMHWVRQAPG KGLEWVAVISYDGSNKYYADSVKGRFTISRDNSKNTLYLQMN SLRAEDTAVYYCARENVRPYYDFWSGYYSEYYYYGMDVWG QGTTVTVSSKTTAPSVYPLAPVCGDTTGSSVTLGCLVKYFPE PVTLTWNSGSLSSGVHTFPAVLQSDLYTLSSSVTVTSSTWPSQS ITCNVAHPASSTKVDKKIEPRGPTIKPCPPCKCPAPNLLGGPSVF IFPPKIKDVLMISLSPIVTCVVVDVSEDDPDVQISWFVNNVEVH TAQTQTHREDYNSTLRVVSALPIQHQDWMSGKEFKCKVNND LPAPIERTISKPKGSVRAPQVYVLPPPEEEMTKKQVTLTCMVTD FMPEDIYVEWTNNGKTELNYKNTEPVLDSDGSYFMYSKLRVE KKNWVERNSYSCSVVHEGLHNhHTTKSFSRTPGK | 15 |

TABLE 2-continued

Anti-CD163 Light Chain and Heavy Chain Sequences
Anti-CD163 Light Chain and Heavy Chain Sequences

| | SEQUENCE | SEQ ID NO: |
|---|---|---|
| AB212 Heavy Chain (muIgG2A ADCC-Null) | EVQLVESGGGVVQPGRSLRLSCAASGFTFSSYAMHWVRQAPG KGLEWVAVISYDGSNKYYADSVKGRFTISRDNSKNTLYLQMN SLRAEDTAVYYCARENVRPYYDFWSGYYSEYYYYGMDVWG QGTTVTVSSKTTAPSVYPLAPVCGDTTGSSVTLGCLVKGYFPE PVTLTWNSGSLSSGVHTFPAVLQSDLYTLSSSVTVTSSTWPSQS ITCNVAHPASSTKVDKKIEPRGPTIKPCPPCKCPAPNLEGGPSVF IFPPKIKDVLMISLSPIVTCVVVDVSEDDPDVQISWFVNNVEVH TAQTQTHREDYNSTLRVVSALPIQHQDWMSGKAFACAVNNK DLPAPIERTISKPKGSVRAPQVYVLPPPEEEMTKKQVTLTCMVT DFMPEDIYVEWTNNGKTELNYKNTEPVLDSDGSYFMYSKLRV EKKNWVERNSYSCSVVHEGLHNHHTTKSFSRTPGK | 16 |

Disclosed herein, in certain embodiments, are antibodies comprising a light chain having an amino acid sequence at least about 70% identical to an amino acid sequence set forth as SEQ ID NO: 9. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 9. In some embodiments, the light chain has an amino acid sequence 100% identical to an amino acid sequence set forth as SEQ ID NO: 9.

Disclosed herein, in certain embodiments, are antibodies comprising a heavy chain having an amino acid sequence at least about 70% identical to an amino acid sequence set forth as SEQ ID NO: 10. In some embodiments the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 10. In some embodiments, the heavy chain has an amino acid sequence 100% identical to an amino acid sequence set forth as SEQ ID NO: 10.

Disclosed herein, in certain embodiments, are antibodies comprising a heavy chain having an amino acid sequence at least about 70% identical to an amino acid sequence set forth as SEQ ID NO: 11. In some embodiments the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 11. In some embodiments, the heavy chain has an amino acid sequence 100% identical to an amino acid sequence set forth as SEQ ID NO: 11.

Disclosed herein, in certain embodiments, are antibodies comprising a heavy chain having an amino acid sequence at least about 70% identical to an amino acid sequence set forth as SEQ ID NO: 12. In some embodiments the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 12. In some embodiments, the heavy chain has an amino acid sequence 100% identical to an amino acid sequence set forth as SEQ ID NO: 12.

Disclosed herein, in certain embodiments, are antibodies comprising a heavy chain having an amino acid sequence at least about 70% identical to an amino acid sequence set forth as SEQ ID NO: 13. In some embodiments the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 13. In some embodiments, the heavy chain has an amino acid sequence 100% identical to an amino acid sequence set forth as SEQ ID NO: 13.

Disclosed herein, in certain embodiments, are antibodies comprising a light chain having an amino acid sequence at least about 70% identical to an amino acid sequence set forth as SEQ ID NO: 9 and a heavy chain having an amino acid sequence at least about 70% identical to an amino acid sequence set forth as SEQ ID NO: 10. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 9 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 10. In some embodiments, the light chain has an amino acid sequence 100% identical to an amino acid sequence set forth as SEQ ID NO: 9 and the heavy chain has an amino acid sequence 100% identical to an amino acid sequence set forth as SEQ ID NO: 10.

Disclosed herein, in certain embodiments, are antibodies comprising a light chain having an amino acid sequence at least about 70% identical to an amino acid sequence set forth as SEQ ID NO: 9 and a heavy chain having an amino acid sequence at least about 70% identical to an amino acid sequence set forth as SEQ ID NO: 11. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 9 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 11. In some embodiments, the light chain has an amino acid sequence 100% identical to an amino acid sequence set forth as SEQ ID NO: 9 and the heavy chain has an amino acid sequence 100% identical to an amino acid sequence set forth as SEQ ID NO: 11.

Disclosed herein, in certain embodiments, are antibodies comprising a light chain having an amino acid sequence at least about 70% identical to an amino acid sequence set forth as SEQ ID NO: 9 and a heavy chain having an amino acid sequence at least about 70% identical to an amino acid sequence set forth as SEQ ID NO: 12. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 9 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 12. In some embodiments, the light chain has an amino acid sequence 100% identical to an amino acid sequence set forth as SEQ ID NO: 9 and the heavy chain has an amino acid sequence 100% identical to an amino acid sequence set forth as SEQ ID NO: 12.

Disclosed herein, in certain embodiments, are antibodies comprising a light chain having an amino acid sequence at least about 70% identical to an amino acid sequence set forth as SEQ ID NO: 9 and a heavy chain having an amino acid sequence at least about 70% identical to an amino acid sequence set forth as SEQ ID NO: 13. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 9 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 13. In some embodiments, the light chain has an amino acid sequence 100% identical to an amino acid sequence set forth as SEQ ID NO: 9 and the heavy chain has an amino acid sequence 100% identical to an amino acid sequence set forth as SEQ ID NO: 13.

Disclosed herein, in certain embodiments, are antibodies comprising a light chain having an amino acid sequence at least about 70% identical to an amino acid sequence set forth as SEQ ID NO: 14. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 14. In some embodiments, the light chain has an amino acid sequence 100% identical to an amino acid sequence set forth as SEQ ID NO: 14.

Disclosed herein, in certain embodiments, are antibodies comprising a heavy chain having an amino acid sequence at least about 70% identical to an amino acid sequence set forth as SEQ ID NO: 15. In some embodiments the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 15. In some embodiments, the heavy chain has an amino acid sequence 100% identical to an amino acid sequence set forth as SEQ ID NO: 15.

Disclosed herein, in certain embodiments, are antibodies comprising a heavy chain having an amino acid sequence at least about 70% identical to an amino acid sequence set forth as SEQ ID NO: 16. In some embodiments the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 16. In some embodiments, the heavy chain has an amino acid sequence 100% identical to an amino acid sequence set forth as SEQ ID NO: 16.

Disclosed herein, in certain embodiments, are antibodies comprising a light chain having an amino acid sequence at least about 70% identical to an amino acid sequence set forth as SEQ ID NO: 14 and a heavy chain having an amino acid sequence at least about 70% identical to an amino acid sequence set forth as SEQ ID NO: 15. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 14 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 15. In some embodiments, the light chain has an amino acid sequence 100% identical to an amino acid sequence set forth as SEQ ID NO: 14 and the heavy chain has an amino acid sequence 100% identical to an amino acid sequence set forth as SEQ ID NO: 15.

Disclosed herein, in certain embodiments, are antibodies comprising a light chain having an amino acid sequence at least about 70% identical to an amino acid sequence set forth as SEQ ID NO: 14 and a heavy chain having an amino acid sequence at least about 70% identical to an amino acid sequence set forth as SEQ ID NO: 16. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 14 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 16. In some embodiments, the light chain has an amino acid sequence 100% identical to an amino acid sequence set forth as SEQ ID NO: 14 and the heavy chain has an amino acid sequence 100% identical to an amino acid sequence set forth as SEQ ID NO: 16.

Exemplary anti-CD163 Complementarity Determining Regions

TABLE 3 anti-CD163 CDR Sequences
Anti-CD163 CDR Sequences

| | SEQUENCE | SEQ ID NO: |
|---|---|---|
| Light Chain CDR1 | RASQSISSYLN | 1 |
| Light Chain CDR2 | AASSLQS | 2 |
| Light Chain CDR3 | QQSYSTPRGT | 3 |
| Heavy Chain CDR1 | SYAMH | 4 |
| Heavy Chain CDR2 | VISYDGSNKYYADSVKG | 5 |
| Heavy Chain CDR3 | ENVRPYYDFWSGYYSEYYYYGMDV | 6 |

Disclosed herein, in certain embodiments, are antibodies comprising at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, and a light chain CDR3 having an amino acid sequence at least about 70% identical to an amino acid sequence set forth as SEQ ID NO: 3. In some embodiments, antibodies binding to CD163 comprise at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, and a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3. In some embodiments, antibodies binding to CD163 comprise at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, and a light chain CDR3 having an amino acid sequence 100% identical to an amino acid sequence set forth as SEQ ID NO: 3.

Disclosed herein, in certain embodiments, are antibodies comprising at least one of a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, a heavy chain CDR3 having an amino acid sequence at least about 70% identical to an amino acid sequence set forth as SEQ ID NO: 6. In some embodiments, antibodies binding to CD163 comprise at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to CD163 comprise at least one of a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, a heavy chain CDR3 having an amino acid sequence 100% identical to an amino acid sequence set forth as SEQ ID NO: 6.

Disclosed herein, in certain embodiments, are antibodies comprising at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, a light chain CDR3 having an amino acid sequence at least about 70% identical to an amino acid sequence set forth as SEQ ID NO: 3, a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, and a heavy chain CDR3 having an amino acid sequence at least about 70% identical to an amino acid sequence set forth as SEQ ID NO: 6. In some embodiments, antibodies binding to CD163 comprise at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to CD163 comprise at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, a light chain CDR3 having an amino acid sequence 100% identical to an amino acid sequence set forth as SEQ ID NO: 3, a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, and a heavy chain CDR3 having an amino acid sequence 100% identical to an amino acid sequence set forth as SEQ ID NO: 6.

Binding Affinity and Immunoreactivity

Binding affinity and/or avidity of antibodies or antigen-binding fragments thereof are improved by modifying framework regions. Any suitable methods for modifications of framework regions are known in the art and are contemplated herein. Selection of one or more relevant framework amino acid positions to alter depends on a variety of criteria. One criterion for selecting relevant framework amino acids to change is, for example, the relative differences in amino acid framework residues between the donor and acceptor molecules. Selection of relevant framework positions to alter using this approach has the advantage of avoiding any subjective bias in residue determination or any bias in CDR binding affinity contribution by the residue.

Binding interactions are manifested as an intermolecular contact with one or more amino acid residues of one or more CDRs in some embodiments. Antigen-binding involves, for example, a CDR or a CDR pair or, in some cases, interactions of up to all six CDRs of the $V_H$ and $V_L$ chains.

Binding affinity and avidity of antibodies or antigen-binding fragments can be measured by surface plasmon resonance (SPR) measurements, AlphaLisa assays or flow cytometry of the equilibrium dissociation constant ($K_D$).

Disclosed herein are antibodies that specifically bind to human CD163 with a $K_D$ from 0.1 nM to 1000 nM. In some embodiments, the antibodies specifically bind to human CD163 with a $K_D$ from about 0.1 to about 500 nM, from about 0.1 to about 100 nM, from about 0.1 to about 50 nM, from about 0.1 to about 20 nM, from about 0.1 to about 10 nM, from about 0.1 to about 5 nM, from about 0.1 to about 2 nM, from about 0.1 to about 1 nM, from about 0.1 to about 0.5 nM, from about 0.5 to about 1000 nM, from about 0.5 to about 500 nM, from about 0.5 to about 100 nM, from about 0.5 to about 50 nM, from about 0.5 to about 20 nM, from about 0.5 to about 10 nM, from about 0.5 to about 5 nM, from about 0.5 to about 2 nM, from about 0.5 to about 1 nM, from about 1 to about 1000 nM, from about 1 to about 500 nM, from about 1 to about 100 nM, from about 1 to about 50 nM, from about 1 to about 20 nM, from about 1 to about 10 nM, from about 1 to about 5 nM, from about 1 to about 2 nM, from about 2 to about 1000 nM, from about 2 to about 500 nM, from about 2 to about 100 nM, from about 2 to about 50 nM, from about 2 to about 20 nM, from about 2 to about 10 nM, from about 2 to about 5 nM, from about 5 to about 1000 nM, from about 5 to about 500 nM, from about 5 to about 100 nM, from about 5 to about 50 nM, from about 5 to about 20 nM, from about 5 to about 10 nM, from about 10 to about 100 nM, from about 10 to about 500 nM, from about 10 to about 100 nM, from about 10 to about 50 nM, from about 10 to about 20 nM, from about 20 to about 1000 nM, from about 20 to about 500 nM, from about 20 to about 100 nM, from about 20 to about 50 nM, from about 50 to about 1000 nM, from about 50 to about 500 nM, from about 50 to about 100 nM, from about 100 to about 500 nM, from about 100 to about 100 nM, from about 500 to about 1000 nM. In some embodiments, the antibodies specifically bind to human CD163 with a $K_D$ of 1.8 nM, 12 nM, 45 nM or 89 nM.

The antibodies disclosed herein binds to the myeloid scavenger receptor CD163, which is highly expressed on tumor associated macrophages (TAMs) and has been detected on various tumor cells from different origins. The expression of CD163 in tumor tissue is associated with poor prognosis. The binding affinity between the antibodies disclosed herein and IL-10 polarized M2c macrophages are measured by flow cytometry assays.

Disclosed herein are antibodies that specifically binds to M2c macrophages with a $K_D$ from 0.1 nM to 100 nM. In some embodiments, the antibodies specifically bind to M2c macrophages with a $K_D$ from about 0.1 to about 500 nM, from about 0.1 to about 100 nM, from about 0.1 to about 50 nM, from about 0.1 to about 20 nM, from about 0.1 to about 10 nM, from about 0.1 to about 5 nM, from about 0.1 to about 2 nM, from about 0.1 to about 1 nM, from about 0.1 to about 0.5 nM, from about 0.5 to about 1000 nM, from about 0.5 to about 500 nM, from about 0.5 to about 100 nM, from about 0.5 to about 50 nM, from about 0.5 to about 20 nM, from about 0.5 to about 10 nM, from about 0.5 to about 5 nM, from about 0.5 to about 2 nM, from about 0.5 to about 1 nM, from about 1 to about 1000 nM, from about 1 to about 500 nM, from about 1 to about 100 nM, from about 1 to about 50 nM, from about 1 to about 20 nM, from about 1 to about 10 nM, from about 1 to about 5 nM, from about 1 to about 2 nM, from about 2 to about 1000 nM, from about 2 to about 500 nM, from about 2 to about 100 nM, from about 2 to about 50 nM, from about 2 to about 20 nM, from about 2 to about 10 nM, from about 2 to about 5 nM, from about 5 to about 1000 nM, from about 5 to about 500 nM, from about 5 to about 100 nM, from about 5 to about 50 nM, from about 5 to about 20 nM, from about 5 to about 10 nM, from about 10 to about 100 nM, from about 10 to about 500 nM, from about 10 to about 100 nM, from about 10 to about 50 nM, from about 10 to about 20 nM, from about 20 to about 1000 nM, from about 20 to about 500 nM, from about 20 to about 100 nM, from about 20 to about 50 nM, from about 50 to about 1000 nM, from about 50 to about 500 nM, from about 50 to about 100 nM, from about 100 to about 500 nM, from about 100 to about 100 nM, from about 500 to about 1000 nM. In some embodiments, the antibodies specifically bind to M2c macrophages with a $K_D$ of 7.7 nM.

Binding Epitopes

Antibody epitopes may be a linear peptide sequence (i.e., "continuous") or may be composed of noncontiguous amino acid sequences (i.e., "conformational" or "discontinuous"). In some embodiments, an antibody recognizes one or more amino acid sequences; therefore, an epitope defines more than one distinct amino acid sequence. Epitopes recognized by antibodies are determined, for example, by peptide mapping and sequence analysis techniques well known to one of skill in the art. Binding interactions are manifested as intermolecular contacts with one or more amino acid residues of a CDR.

Human CD163 protein is a protein that in humans is encoded by the CD163 gene. The amino acid sequence of human CD163 is:

```
                                              (SEQ ID NO: 17)
MSKLRMVLLEDSGSADFRRHFVNLSPFTITVVLLLSACFVTSSLGGTDKEL

RLVDGENKCSGRVEVKVQEEWGTVCNNGWSMEAVSVICNQLGCPTAIKAPG

WANSSAGSGRIWMDHVSCRGNESALWDCKHDGWGKHSNCTHQQDAGVTCSD

GSNLEMRLTRGGNMCSGRIEIKFQGRWGTVCDDNFNIDHASVICRQLECGS

AVSFSGSSNFGEGSGPIWFDDLICNGNESALWNCKHQGWGKHNCDHAEDAG

VICSKGADLSLRLVDGVTECSGRLEVRFQGEWGTICDDGWDSYDAAVACKQ

LGCPTAVTAIGRVNASKGFGHIWLDSVSCQGHEPAIWQCKHHEWGKHYCNH

NEDAGVTCSDGSDLELRLRGGGSRCAGTVEVEIQRLLGKVCDRGWGLKEAD

VVCRQLGCGSALKTSYQVYSKIQATNTWLFLSSCNGNETSLWDCKNWQWGG

LTCDHYEEAKITCSAHREPRLVGGDIPCSGRVEVKHGDTWGSICDSDFSLE

AASVLCRELQCGTVVSILGGAHFGEGNGQIWAEEFQCEGHESHLSLCPVAP

RPEGTCSHSRDVGVVCSRYTEIRLVNGKTPCEGRVELKTLGAWGSLCNSHW

DIEDAHVLCQQLKCGVALSTPGGARFGKGNGQIWRHMFHCTGTEQHMGDCP

VTALGASLCPSEQVASVICSGNQSQTLSSCNSSSLGPTRPTIPEESAVACI

ESGQLRLVNGGGRCAGRVEIYHEGSWGTICDDSWDLSDAHVVCRQLGCGEA

INATGSAHFGEGTGPIWLDEMKCNGKESRIWQCHSHGWGQQNCRHKEDAGV

ICSEFMSLRLTSEASREACAGRLEVFYNGAWGTVGKSSMSETTVGVVCRQL

GCADKGKINPASLDKAMSIPMWVDNVQCPKGPDTLWQCPSSPWEKRLASPS

EETWITCDNKIRLQEGPTSCSGRVEIWHGGSWGTVCDDSWDLDDAQVVCQQ
```

-continued

LGCGPALKAFKEAEFGQGTGPIWLNEVKCKGNESSLWDCPARRWGHSECGH

KEDAAVNCTDISVQKTPQKATTGRSSRQSSFIAVGILGVVLLAIFVALFFL

TKKRRQRQRLAVSSRGENLVHQIQYREMNSCLNADDLDLMNSSGGHSEPH.

Disclosed herein are antibodies that specifically bind to an epitope in human CD163. In some embodiments, an antibody disclosed herein binds to an epitope comprising noncontiguous amino acid sequences. In some embodiments, the antibody binds to an epitope of human CD163 comprising the amino acid sequence IGRVNASKGFGHIWLDSVSCQGHEPAI (SEQ ID NO: 18). In some embodiments, the antibody binds to an epitope of human CD163 comprising the amino acid sequence VVCRQLGCGSA (SEQ ID NO: 19). In some embodiments, the antibody binds to an epitope of human CD163 comprising the amino acid sequence WDCKNWQWGGLTCD (SEQ ID NO: 20). In some embodiments, the antibody binds to an epitope of human CD163 comprising the amino acid sequences of SEQ ID NOs:18-20.

Also disclosed herein are additional antibodies that specifically bind to the epitope disclosed herein. These additional antibodies, or antigen-binding fragments thereof that specifically bind to the epitope disclosed herein can be identified using techniques known in the art. For example, a computational approach is used to design epitope-specific antibodies. Nimrod et al., Computational Design of Epitope-Specific Functional Antibodies, Cell Reports 25, 2121-2131, Nov. 20, 2018, (incorporated herein by reference). Another approach can be used to identify antibodies that bind to specific epitopes from a library of antibodies that bind to the antigen, such as the following: first incorporate noncanonical amino acids (ncAAs) p-benzoyl-L-phenylalanine (pBpa) and p-azido-L-phenylalanine (pAzF) into the target epitope and then select the antibodies that cross-link with the ncAA incorporated epitope after UV irradiation. Because cross-linking only occurs when the distance between the antibody and the epitope is close enough, this method can efficiently select antibodies that specifically bind to the target epitope. Chen et al. Epitope-directed antibody selection by site-specific photocrosslinking, Science Advances, Vol. 6, no. 14, eaaz7825, 1 Apr. 2020 (incorporated herein by reference).

Modifications of Antibodies

Antibodies, or antigen-binding fragments thereof, are modified, in some cases, using techniques known in the art for various purposes such as, for example, by addition of polyethylene glycol (PEG). In some embodiments, PEG modification (PEGylation) leads to one or more of improved circulation time, improved solubility, improved resistance to proteolysis, reduced antigenicity and immunogenicity, improved bioavailability, reduced toxicity, improved stability, and easier formulation.

In some cases when an antigen-binding fragment does not contain an Fc portion, an Fc portion is added to (e.g., recombinantly) the fragment, for example, to increase half-life of the antigen-binding fragment in circulation in blood when administered to a subject. Choice of an appropriate Fc region and methods of to incorporate such fragments are known in the art. Incorporating an Fc region of an IgG into a polypeptide of interest so as to increase its circulatory half-life, but so as not to lose its biological activity is accomplished, for example, by using conventional techniques known in the art. In some embodiments, Fc portions of antibodies are further modified to increase half-life of the antigen-binding fragment in circulation in blood when administered to a subject. Modifications are, for example, determined using conventional means in the art.

Additionally, in some embodiments, antibodies and antigen-binding fragments thereof are produced or expressed so that they do not contain fucose on their complex N-glycoside-linked sugar chains. The removal of the fucose from the complex N-glycoside-linked sugar chains is known to increase effector functions of the antibodies and antigen-binding fragments, including but not limited to, antibody dependent cell-mediated cytotoxicity (ADCC) and complement dependent cytotoxicity (CDC). Similarly, antibodies or antigen-binding fragments thereof that bind an epitope are, in some cases, attached at their C-terminal end to all or part of an immunoglobulin heavy chain derived from any antibody isotype, e.g., IgG, IgA, IgE, IgD, and IgM, and any of the isotype sub-classes, particularly IgG1, IgG2, IgG3, and IgG4.

Additionally, the antibodies or antigen-binding fragments described herein are also modified so that they are able to cross the blood-brain barrier in some embodiments. Such modification of the antibodies or antigen-binding fragments described herein allows for the treatment of brain diseases such as glioblastoma multiforme (GBM). Exemplary modifications to allow proteins such as antibodies or antigen-binding fragments to cross the blood-brain barrier are described in US Pat. Publ. 2007/0082380.

Glycosylation of immunoglobulins has been shown to have significant effects on their effector functions, structural stability, and rate of secretion from antibody-producing cells. The carbohydrate groups responsible for these properties are generally attached to the constant (C) regions of the antibodies. For example, glycosylation of IgG at asparagine 297 in the $C_H2$ domain is required for full capacity of IgG to activate the classical pathway of complement-dependent cytolysis (Tao and Morrison, *J Immunol* 143:2595 (1989)). Glycosylation of IgM at asparagine 402 in the $C_H3$ domain is necessary for proper assembly and cytolytic activity of the antibody (Muraoka and Shulman, *J Immunol* 142:695 (1989)). Removal of glycosylation sites as positions 162 and 419 in the $C_H1$ and $C_H3$ domains of an IgA antibody led to intracellular degradation and at least 90% inhibition of secretion (Taylor and Wall, *Mol Cell Biol* 8:4197 (1988)). Additionally, in some embodiments, antibodies and antigen-binding fragments thereof are produced or expressed so that they do not contain fucose on their complex N-glycoside-linked sugar chains. The removal of the fucose from the complex N-glycoside-linked sugar chains is known to increase effector functions of the antibodies and antigen-binding fragments, including but not limited to, antibody dependent cell-mediated cytotoxicity (ADCC) and complement dependent cytotoxicity (CDC). These "defucosylated" antibodies and antigen-binding fragments are produced, in some embodiments, through a variety of systems utilizing molecular cloning techniques known in the art, including but not limited to, transgenic animals, transgenic plants, or cell-lines that have been genetically engineered so that they no longer contain the enzymes and biochemical pathways necessary for the inclusion of a fucose in the complex N-glycoside-linked sugar chains (also known as fucosyltransferase knock-out animals, plants, or cells). Non-limiting examples of cells that are engineered to be fucosyltransferase knock-out cells include CHO cells, SP2/0 cells, NS0 cells, and YB2/0 cells.

Glycosylation of immunoglobulins in the variable (V) region has also been observed. Sox and Hood reported that about 20% of human antibodies are glycosylated in the V region (*Proc Natl Acad Sci USA* 66:975 (1970)). Glycosylation of the V domain is believed to arise from fortuitous occurrences of the N-linked glycosylation signal Asn-Xaa-Ser/Thr in the V region sequence and has not been recognized in the art as playing a role in immunoglobulin function.

Glycosylation at a variable domain framework residue, in some cases, alters the binding interaction of the antibody with antigen. The present disclosure includes criteria by which a limited number of amino acids in the framework or CDRs of a humanized immunoglobulin chain are chosen to be mutated (e.g., by substitution, deletion, or addition of residues) to increase the affinity of an antibody.

In some embodiments, cysteine residue(s) are removed or introduced in the Fc region of an antibody or Fc-containing polypeptide, thereby eliminating or increasing interchain disulfide bond formation in this region. A homodimeric specific binding agent or antibody generated using such methods, in some embodiments, exhibit improved internalization capability and/or increased complement-mediated cell killing and antibody-dependent cellular cytotoxicity (ADCC).

It has been shown that sequences within the CDR cause an antibody to bind to MHC Class II and trigger an unwanted helper T-cell response in some cases. In some embodiments, a conservative substitution allows the antibody to retain binding activity yet reduce its ability to trigger an unwanted T-cell response. In one embodiment, one or more of the N-terminal 20 amino acids of the heavy or light chain is removed.

In some embodiments, antibody molecules are produced with altered carbohydrate structure resulting in altered effector activity, including antibody molecules with absent or reduced fucosylation that exhibit improved ADCC activity. A variety of ways are known in the art to accomplish this. For example, ADCC effector activity is mediated by binding of the antibody molecule to the FcγRIII receptor, which has been shown to be dependent on the carbohydrate structure of the N-linked glycosylation at the Asn-297 of the $C_H2$ domain. Non-fucosylated antibodies bind this receptor with increased affinity and trigger FcγRIII-mediated effector functions more efficiently than native, fucosylated antibodies. Some host cell strains, e.g., Lec13 or rat hybridoma YB2/0 cell line naturally produce antibodies with lower fucosylation levels. An increase in the level of bisected carbohydrate, e.g., through recombinantly producing antibody in cells that overexpress GnTIII enzyme, has also been determined to increase ADCC activity. In some embodiments, the absence of only one of the two fucose residues are sufficient to increase ADCC activity.

Covalent modifications of an antibody are also included herein. In some embodiments, they are made by chemical synthesis or by enzymatic or chemical cleavage of the antibody, if applicable. In some embodiments, other types of covalent modifications are introduced by reacting targeted amino acid residues with an organic derivatizing agent that is capable of reacting with selected side chains or the N- or C-terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

In some embodiments, histidyl residues are derivatized by reaction with diethylpyrocarbonate at pH 5.5-7.0 because this agent is relatively specific for the histidyl side chain. In some embodiments, para-bromophenacyl bromide also is useful; the reaction, in some embodiments, is performed in 0.1 M sodium cacodylate at pH 6.0.

In some embodiments, lysinyl and amino-terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

In some embodiments, arginyl residues are modified by reaction with one or several conventional reagents, such as phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents, in some embodiments, react with the groups of lysine as well as the arginine epsilon-amino group.

In some embodiments, the specific modification of tyrosyl residues are made, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and 3-nitro derivatives, respectively, in some embodiments. Tyrosyl residues are iodinated using $^{125}I$ or $^{131}I$ to prepare labeled proteins for use in radioimmunoassay.

Carboxyl side groups (aspartyl or glutamyl) are specifically modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

In some embodiments, glutaminyl and asparaginyl residues are deamidated to the corresponding glutamyl and aspartyl residues, respectively. These residues are deamidated under neutral or basic conditions.

Other modifications include hydroxylation of proline and lysine, phosphorylation of hydroxyl groups of seryl or threonyl residues, methylation of the alpha-amino groups of lysine, arginine, and histidine side chains, acetylation of the N-terminal amine, and amidation of any C-terminal carboxyl group.

Another type of covalent modification involves chemically or enzymatically coupling glycosides to the specific binding agent or antibody. These procedures do not require production of the polypeptide or antibody in a host cell that has glycosylation capabilities for N- or O-linked glycosylation. Depending on the coupling mode used, in some embodiments, the sugar(s) are attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine.

Removal of any carbohydrate moieties present on the polypeptide or antibody are, in some embodiments, accomplished chemically or enzymatically. Chemical deglycosylation involves exposure of the antibody to the compound trifluoromethanesulfonic acid, or an equivalent compound.

This treatment results in the cleavage of most or all sugars except the linking sugar (N-acetylglucosamine or N-acetylgalactosamine), while leaving the antibody intact. Enzymatic cleavage of carbohydrate moieties on an antibody is achieved by the use of a variety of endo- and exo-glycosidases in some embodiments.

Another type of covalent modification comprises linking an antibody to one of a variety of nonproteinaceous polymers, e.g., polyethylene glycol, polypropylene glycol, polyoxyethylated polyols, polyoxyethylated sorbitol, polyoxyethylated glucose, polyoxyethylated glycerol, polyoxyalkylenes, or polysaccharide polymers such as dextran. Such methods are known in the art.

Affinity for binding a pre-determined polypeptide antigen, generally, is modulated by introducing one or more mutations into the V region framework, typically in areas adjacent to one or more CDRs and/or in one or more framework regions. Typically, such mutations involve the introduction of conservative amino acid substitutions that either destroy or create the glycosylation site sequences but do not substantially affect the hydropathic structural properties of the polypeptide. Typically, mutations that introduce a proline residue are avoided.

Effector Functions

Examples of antibody effector functions include: C1q binding and complement dependent cytotoxicity; Fc receptor binding; antibody-dependent cell-mediated cytotoxicity (ADCC); phagocytosis; down-regulation of cell surface receptors (e.g., B cell receptor); and B cell activation. Typically, the Fc-mediated functions involve binding of the Fc portion of the antibody by specialized receptor molecules, "Fc receptors" or "FcR," expressed by the cell whose function is to be affected.

IgG is considered the most versatile immunoglobulin, because it carries out all of the functions of immunoglobulin molecules in some embodiments. IgG is the major Ig in serum, and the only class of Ig that crosses the placenta. IgG also fixes complement, although the IgG4 subclass does not. Macrophages, monocytes, polymorphonuclear leukocytes (PMNs), and some lymphocytes have receptors for the Fc region of IgG. Not all subclasses bind equally well: IgG2 and IgG4 do not bind to Fc receptors. A consequence of binding to the Fc receptors on PMNs, monocytes, and macrophages is that the cell now internalizes the antigen better in some cases. IgG is an opsonin that enhances phagocytosis. Binding of IgG to Fc receptors on other types of cells results in the activation of other functions.

In certain embodiments, the FcR is a native sequence human FcR. Moreover, a preferred FcR is one that binds an IgG antibody (a gamma ("γ") receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII, and FcγRIII. To assess ADCC activity of a molecule of interest, an in vitro ADCC assay is performed in some embodiments. Useful effector cells for such assays include peripheral blood mononuclear cells (PBMC) and Natural Killer (NK) cells.

Alternatively, or additionally, in some embodiments, ADCC activity of the molecule of interest is assessed in vivo, e.g., in an animal model.

In some embodiments, the antibodies of the disclosure bind to a surface membrane protein of and are internalized by M2-like macrophages. This internalization process is believed to be involved in the observed alteration of the functional immunosuppressive characteristics of these cells, i.e., the differentiation of the cells from M2 status to subtly activated state, without killing them or inhibiting their proliferation. In some embodiments, upon internalization, the antibodies decrease the expression of immunosuppressive soluble factors while increasing expression of soluble factors that stimulate or promote the activity or proliferation of T cells, including $CD4^+$ helper T cells and cytotoxic lymphocytes.

For certain therapeutic applications, the internalization process is employed for purposes of killing or decreasing the activity or proliferation of a target cell that expresses a CD163 protein. The number of antibody molecules internalized will be sufficient or adequate to kill a cell or inhibit its growth, especially a cancer cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the targeted cell.

In some embodiments, the antibody or antigen-binding fragment provided herein is conjugated or linked to a therapeutic moiety, an imaging or detectable moiety, or an affinity tag. Methods for conjugating or linking polypeptides are well known in the art. Associations (binding) between compounds and labels include any means known in the art including, but not limited to, covalent and non-covalent interactions, chemical conjugation, as well as recombinant techniques. An antibody or antigen-binding fragment thereof is conjugated to, or recombinantly engineered with, an affinity tag (e.g., a purification tag), in some embodiments. Affinity tags such as, for example, poly-histidine (e.g., His6) tags are conventional in the art.

In some embodiments, the antibody or antigen-binding fragment further comprises a detectable moiety. Detections accomplished, for example, in vitro, in vivo or ex vivo. In vitro assays for the detection and/or determination (quantification, qualification, etc.) of, e.g., huCD163 protein expressed by macrophages using the antibodies or antigen-binding fragments thereof include but are not limited to, for example, ELISAs, RIAs, and western blots. In some embodiments, in vitro detection, diagnosis, or monitoring of the antigen of the antibodies occurs by obtaining a sample (e.g., a blood sample) from a subject and testing the sample in, for example, a standard ELISA assay.

Also disclosed herein, in certain embodiments, are compositions comprising an antibody as disclosed herein, and a carrier.

Pharmaceutical Compostions

Disclosed herein, in certain embodiments, are pharmaceutical compositions comprising an antibody as disclosed herein and a pharmaceutically acceptable excipient.

Such compositions are useful for in vitro or in vivo analysis or, in the case of pharmaceutical compositions, for administration to a subject in vivo or ex vivo for treating a subject with the disclosed antibodies.

In some embodiments, the excipient is a carrier, buffer, stabilizer or other suitable materials known to those skilled in the art. Such materials should be non-toxic and should not interfere with the efficacy of the active ingredient. The precise nature of the carrier or other material will depend on the route of administration.

Pharmaceutical formulations comprising an antibody or antigen-binding fragment, identified by the methods described herein are prepared for storage by mixing the protein having the desired degree of purity with optional physiologically acceptable carriers, excipients or stabilizers (see, e.g., *Remington's Pharmaceutical Sciences*, 16$^{th}$ edition, Osol, A. Ed. (1980)), in the form of lyophilized formulations or aqueous solutions in some embodiments. Acceptable carriers, or stabilizers are those that are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG). In certain embodiments, the pharmaceutical composition comprises the antibody at a concentration of between 5-200 mg/mL; preferably between 10-100 mg/mL.

Acceptable carriers are physiologically acceptable to the administered subject and retain the therapeutic properties of the compounds with/in which it is administered. Acceptable carriers and their formulations are generally described in, for example, *Remington's Pharmaceutical Sciences*, supra. One exemplary carrier is physiological saline. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject compounds from the administration site of one organ, or portion of the body, to another organ, or portion of the body, or in an in vitro assay system. Each carrier is acceptable in the sense of being compatible with the other ingredients of the formulation and not injurious to a subject to whom it is administered. Nor should an acceptable carrier alter the specific activity of the subject compounds.

In another embodiment, a pharmaceutical composition disclosed herein further comprises an acceptable additive to improve the stability of the compounds in composition and/or to control the release rate of the composition. Acceptable additives do not alter the specific activity of the subject compounds. Exemplary acceptable additives include, but are not limited to, a sugar such as mannitol, sorbitol, glucose, xylitol, trehalose, sorbose, sucrose, galactose, dextran, dextrose, fructose, lactose, and mixtures thereof. Acceptable additives are combined with acceptable carriers and/or excipients such as dextrose in some embodiments. Alternatively, exemplary acceptable additives include, but are not limited to, a surfactant such as polysorbate 20 or polysorbate 80 to increase stability of the peptide and decrease gelling of the solution. In some embodiments, the surfactant is added to the composition in an amount of 0.01% to 5% of the solution. Addition of such acceptable additives increases the stability and half-life of the composition in storage.

In one embodiment, a pharmaceutical composition disclosed herein contains an isotonic buffer such as a phosphate, acetate, or TRIS buffer in combination with a tonicity agent such as a polyol, Sorbitol, sucrose or sodium chloride, which tonicifies and stabilizes. In some embodiments, a tonicity agent is present in the composition in an amount of about 5%.

In another embodiment, a pharmaceutical composition disclosed herein includes a surfactant such as to prevent aggregation and for stabilization at 0.01 to 0.02% wt/vol.

In another embodiment, the pH of a pharmaceutical composition disclosed herein ranges from 4.5-6.5 or 4.5-5.5.

In some embodiments, a pharmaceutical composition disclosed herein also contains more than one active compound as necessary for the indication being treated, such as those with complementary activities that do not adversely affect each other. For example, a method of treatment further provides an immunosuppressive agent. Such molecules are suitably present in combination in amounts that are effective for the purpose intended.

In some embodiments, active ingredients are entrapped in microcapsule prepared, for example, by coacervation techniques or by interfacial polymerization, for example, hydroxy methylcellulose or gelatin-microcapsule and poly-(methylmethacylate) microcapsule, respectively, in colloidal drug delivery systems (for example, liposomes, albumin microspheres, microemulsions, nano-particles, and nano-capsules) or in macroemulsions. Such techniques are disclosed in *Remington's Pharmaceutical Sciences*, supra.

Suspensions and crystal forms of antibodies are also contemplated herein; methods to make suspensions and crystal forms are known to one of skill in the art.

In some embodiments, a pharmaceutical composition disclosed herein is sterile. In some embodiments, a pharmaceutical composition disclosed herein is sterilized by conventional, well known sterilization techniques. For example, sterilization is readily accomplished by filtration through sterile filtration membranes. In some embodiments, the resulting solutions is packaged for use or filtered under aseptic conditions and lyophilized, the lyophilized preparation being combined with a sterile solution prior to administration.

Freeze-drying is employed to stabilize polypeptides for long-term storage, such as when a polypeptide is relatively unstable in liquid compositions, in some embodiments.

In some embodiments, some excipients such as, for example, polyols (including mannitol, sorbitol, and glycerol); sugars (including glucose and sucrose); and amino acids (including alanine, glycine, and glutamic acid), act as stabilizers for freeze-dried products. Polyols and sugars are also used to protect polypeptides from freezing and drying-induced damage and to enhance the stability during storage in the dried state in some embodiments. Sugars are, in some embodiments, effective in both the freeze-drying process and during storage. Other classes of molecules, including mono- and disaccharides and polymers such as PVP, have also been reported as stabilizers of lyophilized products.

For injection, in some embodiments, a pharmaceutical composition disclosed herein is a powder suitable for reconstitution with an appropriate solution as described above. Examples of these include, but are not limited to, freeze dried, rotary dried or spray dried powders, amorphous powders, granules, precipitates, or particulates. For injection, the compositions optionally contain stabilizers, pH modifiers, surfactants, bioavailability modifiers and combinations of these.

Sustained-release preparations is prepared in some embodiments. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (see, e.g., U.S. Pat. No. 3,773,919), copolymers of L-glutamic acid and γ ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. In some embodiments, while encapsulated antibodies remain in the body for a long time, they denature or aggregate as a result of exposure to moisture at 37° C., resulting in a loss of biological activity and possible changes in immunogenicity. Rational strategies devised for stabilization are, in some cases, dependent on the mechanism involved. For example, if the aggregation mechanism is discovered to be intermolecular S—S bond formation through thio-disulfide interchange, stabilization is achieved, in some cases, by modifying sulfhydryl residues, lyophilizing from acidic solutions, controlling moisture content, using appropriate additives, and developing specific polymer matrix compositions.

In some embodiments, a pharmaceutical composition disclosed herein is designed to be short-acting, fast-releasing, long-acting, or sustained-releasing as described herein. In one embodiment, a pharmaceutical composition disclosed herein is formulated for controlled release or for slow release.

The pharmaceutical composition is administered, for example, by injection, including, but not limited to, subcutaneous, intravitreal, intradermal, intravenous, intra-arterial, intraperitoneal, intracerebrospinal, or intramuscular injection. Excipients and carriers for use in formulation of compositions for each type of injection are contemplated herein. The following descriptions are by example only and are not meant to limit the scope of the compositions. Compositions for injection include, but are not limited to, aqueous solutions (where water soluble) or dispersions, as well as sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In some embodiments, the carrier is a solvent or dispersion medium containing, for example, water, ethanol, polyol (for example, glycerol, propylene glycol, and liquid polyetheylene glycol, and the like), and suitable mixtures thereof. Fluidity is maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid, and thimerosal. Isotonic agents, for example, sugars, polyalcohols such as mannitol, sorbitol, and sodium chloride is included in the composition in some embodiments. In some embodiments, the resulting solutions are packaged for use as is, or lyophilized; the lyophilized preparation is later be combined with a sterile solution prior to administration in some embodiments. For intravenous, injection, or injection at the site of affliction, the active ingredient will be in the form of a parenterally acceptable aqueous solution which is pyrogen-free and has suitable pH, isotonicity, and stability. Those of relevant skill in the art are well able to prepare suitable solutions using, for example, isotonic vehicles such as Sodium Chloride Injection, Ringer's Injection, and Lactated Ringer's Injection. Preservatives, stabilizers, buffers, antioxidants, and/or other additives are included, as needed, in some embodiments. Sterile injectable solutions are prepared by incorporating an active ingredient in the required amount in an appropriate solvent with one or a combination of ingredients enumerated above, as required, followed by filtered sterilization, in some embodiments. Generally, dispersions are prepared by incorporating the active ingredient into a sterile vehicle which contains a basic dispersion medium and the required other ingredients from those enumerated above. In the case of sterile powders for the preparation of sterile injectable solutions, the preferred methods of preparation are vacuum drying and freeze drying which yields a powder of the active ingredient plus any additional desired ingredient from a previously sterile-filtered solution thereof.

Compositions are conventionally administered intravenously in some embodiments, such as by injection of a unit dose, for example. For injection, in some embodiments, an active ingredient is in the form of a parenterally acceptable aqueous solution which is substantially pyrogen-free and has suitable pH, isotonicity, and stability. In some embodiments, one prepares suitable solutions using, for example, isotonic vehicles such as Sodium Chloride Injection, Ringer's Injection, Lactated Ringer's Injection. Preservatives, stabilizers, buffers, antioxidants, and/or other additives are included, as required, in some embodiments. Additionally, compositions are administered via aerosolization in some embodiments. (Lahn et al., *Int Arch Allergy Immunol* 134:49-55 (2004)).

For parenteral administration, the antibodies are formulated in a unit dosage injectable form (solution, suspension, emulsion) in association with a pharmaceutically acceptable, parenteral vehicle. Examples of such vehicles are water, saline, Ringer's solution, dextrose solution, and 5% human serum albumin. Nonaqueous vehicles such as fixed oils and ethyl oleate are also used. Liposomes are used as carriers. The vehicle contains minor amounts of additives such as substances that enhance isotonicity and chemical stability, e.g., buffers and preservatives. The antibodies are typically formulated in such vehicles at concentrations of about 1 mg/mL to 10 mg/mL.

In one embodiment, a pharmaceutical composition disclosed herein is lyophilized, for example, to increase shelf-life in storage. When the compositions are considered for use in medicaments or any of the methods provided herein, in some embodiments, it is contemplated that the composition are substantially free of pyrogens such that the composition will not cause an inflammatory reaction or an unsafe allergic reaction when administered to a human subject.

Testing compositions for pyrogens and preparing compositions substantially free of pyrogens are well understood to one of ordinary skill of the art and are accomplished using commercially available kits in some embodiments.

In some embodiments, acceptable carriers contain a compound that stabilizes, increases or delays absorption or clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. In some embodiments, detergents also be used to stabilize or to increase or decrease the absorption of the pharmaceutical composition, including liposomal carriers. To protect from digestion the compound, in some embodiments, is complexed with a composition to render it resistant to acidic and enzymatic hydrolysis, or the compound is, in some embodiments, complexed in an appropriately resistant carrier such as a liposome. Means of protecting compounds from digestion are known in the art.

The compositions are administered, in some embodiments, in a manner compatible with the dosage formulation, and in a therapeutically effective amount. The quantity to be administered depends on the subject to be treated, capacity of the subject's immune system to utilize the active ingredient, and degree of binding capacity desired. Precise amounts of active ingredient required to be administered depend on the judgment of the practitioner and are peculiar to each individual. Suitable regimes for initial administration and booster shots are also variable, but are typified by an initial administration followed by repeated doses at one or more hour intervals by a subsequent injection or other administration. Alternatively, continuous intravenous infusion that is sufficient to maintain concentrations in the blood are contemplated.

In some embodiments, the disclosure provides a use of the compositions described herein to make a medicament for treating a condition, disease, or disorder described herein. In some embodiments, medicaments are formulated based on the physical characteristics of the subject needing treatment, and are formulated in single or multiple formulations based on the stage of the condition, disease or disorder. Medicaments are packaged in a suitable package with appropriate labels for the distribution to hospitals and clinics in which the label is for the indication of treating a subject having a disease described herein in some embodiments. Medicaments are packaged as a single or multiple units in some embodiments. Instructions for the dosage and administration of the compositions are included with the packages as described below in some embodiments. The disclosure is further directed to medicaments comprising an antibody or antigen-binding fragment thereof described herein and a pharmaceutically acceptable carrier.

In some embodiments, a composition (an antibody or an antigen-binding fragment described herein) is administered alone or in combination with a second composition either simultaneously or sequentially dependent upon the condition to be treated. In one embodiment, a second therapeutic treatment is an anticancer therapy or an anticancer therapeutic. When two or more compositions are administered, the compositions are, for example, administered in combination (either sequentially or simultaneously). A composition is administered in a single dose or multiple doses in some embodiments.

In some embodiments, when formulated for administration to human subjects, the compositions are formulated to be free of pyrogens. Testing compositions for pyrogens and preparing pharmaceutical compositions free of pyrogens are well understood to one of ordinary skill in the art.

Antibodies, or antigen-binding fragments thereof, are formulated for any suitable route of administration to a subject including, but not limited to, injection, in some embodiments. Injection includes, for example, subcutaneous, peritoneal, intravenous injection, intramuscular injection, or spinal injection into the cerebrospinal fluid (CSF). In some embodiments, administration are in one, two, three, four, five, six, seven, or more injection sites. In one embodiment, administration is via six injection sites.

For in vivo applications, contacting occurs, for example, via administration of a composition (such as are described herein) to a subject by any suitable means. An antibody described herein, in some embodiments, is administered by any suitable means, either systemically or locally, including via parenteral, subcutaneous, intraperitoneal, intracerebrospinal, intrapulmonary, and intranasal administration, and, if desired for local treatment, intralesional administration. Parenteral routes include, for example, intravenous, intraarterial, intraperitoneal, epidural, intramuscular, and intrathecal administration. Such administration, in some embodiments, is as a bolus, continuous infusion, or pulse infusion. In some embodiments, compositions are administered by injection depending in part on whether the administration is brief or chronic. Other modes of administration methods are contemplated, including topical, particularly transdermal, transmucosal, rectal, oral or local administration e.g., through a catheter placed close to the desired site.

Methods of Treatment and Use

Disclosed herein, in certain embodiments, are methods of treating a cancer in an individual in need thereof, comprising administering to the individual an antibody disclosed herein. In some embodiments, the disclosure provides a use of an antibody as described herein, for the manufacture of a medicament for treating cancer in a human subject. In some embodiments, the antibody specifically binds to a CD163 protein expressed on human tumor associated macrophages and reduces expression of at least one of CD16, CD64, TLR2, or Siglec-15 by the macrophages.

Disclosed herein, in certain embodiments, are methods of modulating immune activity in a subject in need thereof, comprising administering to said subject an antibody described herein. In some embodiments, the antibody specifically binds to a CD163 protein expressed on human tumor associated macrophages and reduces expression of at least one of CD16, CD64, TLR2, or Siglec-15 by the macrophages.

Disclosed herein, in certain embodiments, are methods of treating a subject with pathologically or inappropriately elevated levels of M2 macrophages (e.g., inappropriately elevated relative to the level useful for promoting immune-mediated tumor cell killing in the subject), comprising administering to said subject an antibody described herein. In some embodiments, the antibody specifically binds to a CD163 protein expressed on human tumor associated macrophages and reduces expression of at least one of CD16, CD64, TLR2, or Siglec-15 by the macrophages.

In some embodiments, the antibody comprises at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, and a light chain CDR3 having an amino acid sequence at least about 70% identical to an amino acid sequence set forth as SEQ ID NO: 3. In some embodiments, the antibody comprises at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, and a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3. In some embodiments, the antibody comprises at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, and a light chain CDR3 having an amino acid sequence 100% identical to an amino acid sequence set forth as SEQ ID NO: 3.

In some embodiments, the antibody comprises at least one of a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, a heavy chain CDR3 having an amino acid sequence at least about 70% identical to an amino acid sequence set forth as SEQ ID NO: 6. In some embodiments, the antibody comprises at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, the antibody comprises at least one of a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, a heavy chain CDR3 having an amino acid sequence 100% identical to an amino acid sequence set forth as SEQ ID NO: 6.

In some embodiments, the antibody comprises at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, a light chain CDR3 having an amino acid sequence at least about 70% identical to an amino acid sequence set forth as SEQ ID NO: 3, a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, and a heavy chain CDR3 having an amino acid sequence at least about 70% identical to an amino acid sequence set forth as SEQ ID NO: 6. In some embodiments, the antibody comprises at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, the antibody comprises at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, a light chain CDR3 having an amino acid sequence 100% identical to an amino acid sequence set forth as SEQ ID NO: 3, a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, and a heavy chain CDR3 having an amino acid sequence 100% identical to an amino acid sequence set forth as SEQ ID NO: 6.

In some embodiments, the antibody comprises a light chain variable domain (VL) having an amino acid sequence at least about 70% identical to an amino acid sequence set forth as SEQ ID NO: 7. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7. In some embodiments, the VL has an amino acid sequence 100% identical to an amino acid sequence set forth as SEQ ID NO: 7.

In some embodiments, the antibody comprises a heavy chain variable domain (VH) having an amino acid sequence at least about 70% identical to an amino acid sequence set forth as SEQ ID NO: 8. In some embodiments the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. In some embodiments, the VH has an amino acid sequence 100% identical to an amino acid sequence set forth as SEQ ID NO: 8.

In some embodiments, the antibody comprises a light chain variable domain (VL) having an amino acid sequence at least about 70% identical to an amino acid sequence set forth as SEQ ID NO: 7 and a heavy chain variable domain (VH) having an amino acid sequence at least about 70% identical to an amino acid sequence set forth as SEQ ID NO: 8. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. In some embodiments, the VL has an amino acid sequence 100% identical to an amino acid sequence set forth as SEQ ID NO: 7 and the VH has an amino acid sequence 100% identical to an amino acid sequence set forth as SEQ ID NO: 8.

In some embodiments, the antibody comprises a light chain having an amino acid sequence at least about 70% identical to an amino acid sequence set forth as SEQ ID NO: 9. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 9. In some embodiments, the light chain has an amino acid sequence 100% identical to an amino acid sequence set forth as SEQ ID NO: 9.

In some embodiments, the antibody comprises a heavy chain having an amino acid sequence at least about 70% identical to an amino acid sequence set forth as SEQ ID NO: 10. In some embodiments the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 10. In some embodiments, the heavy chain has an amino acid sequence 100% identical to an amino acid sequence set forth as SEQ ID NO: 10.

In some embodiments, the antibody comprises a heavy chain having an amino acid sequence at least about 70% identical to an amino acid sequence set forth as SEQ ID NO: 11. In some embodiments the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 11. In some embodiments, the heavy chain has an amino acid sequence 100% identical to an amino acid sequence set forth as SEQ ID NO: 11.

In some embodiments, the antibody comprises a heavy chain having an amino acid sequence at least about 70% identical to an amino acid sequence set forth as SEQ ID NO: 12. In some embodiments the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 12. In some embodiments, the heavy chain has an amino acid sequence 100% identical to an amino acid sequence set forth as SEQ ID NO: 12.

In some embodiments, the antibody comprises a heavy chain having an amino acid sequence at least about 70% identical to an amino acid sequence set forth as SEQ ID NO: 13. In some embodiments the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 13. In some embodiments, the heavy chain has an amino acid sequence 100% identical to an amino acid sequence set forth as SEQ ID NO: 13.

In some embodiments, the antibody comprises a light chain having an amino acid sequence at least about 70% identical to an amino acid sequence set forth as SEQ ID NO: 9 and a heavy chain having an amino acid sequence at least about 70% identical to an amino acid sequence set forth as SEQ ID NO: 10. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 9 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 10. In some embodiments, the light chain has an amino acid sequence 100% identical to an amino acid sequence set forth as SEQ ID NO: 9 and the heavy chain has an amino acid sequence 100% identical to an amino acid sequence set forth as SEQ ID NO: 10.

In some embodiments, the antibody comprises a light chain having an amino acid sequence at least about 70% identical to an amino acid sequence set forth as SEQ ID NO: 9 and a heavy chain having an amino acid sequence at least about 70% identical to an amino acid sequence set forth as SEQ ID NO: 11. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 9 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 11. In some embodiments, the light chain has an amino acid sequence 100% identical to an amino acid sequence set forth as SEQ ID NO: 9 and the heavy chain has an amino acid sequence 100% identical to an amino acid sequence set forth as SEQ ID NO: 11.

In some embodiments, the antibody comprises a light chain having an amino acid sequence at least about 70% identical to an amino acid sequence set forth as SEQ ID NO: 9 and a heavy chain having an amino acid sequence at least about 70% identical to an amino acid sequence set forth as SEQ ID NO: 12. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 9 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 12. In some embodiments, the light chain has an amino acid sequence 100% identical to an amino acid sequence set forth as SEQ ID NO: 9 and the heavy chain has an amino acid sequence 100% identical to an amino acid sequence set forth as SEQ ID NO: 12.

In some embodiments, the antibody comprises a light chain having an amino acid sequence at least about 70% identical to an amino acid sequence set forth as SEQ ID NO: 9 and a heavy chain having an amino acid sequence at least about 70% identical to an amino acid sequence set forth as SEQ ID NO: 13. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 9 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 13. In some embodiments, the light chain has an amino acid sequence 100% identical to an amino acid sequence set forth as SEQ ID NO: 9 and the heavy chain has an amino acid sequence 100% identical to an amino acid sequence set forth as SEQ ID NO: 13.

In some embodiments, the antibody comprises a light chain having an amino acid sequence at least about 70% identical to an amino acid sequence set forth as SEQ ID NO: 14. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 14. In some embodiments, the light chain has an amino acid sequence 100% identical to an amino acid sequence set forth as SEQ ID NO: 14.

In some embodiments, the antibody comprises a heavy chain having an amino acid sequence at least about 70% identical to an amino acid sequence set forth as SEQ ID NO: 15. In some embodiments the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 15. In some embodiments, the heavy chain has an amino acid sequence 100% identical to an amino acid sequence set forth as SEQ ID NO: 15.

In some embodiments, the antibody comprises a heavy chain having an amino acid sequence at least about 70% identical to an amino acid sequence set forth as SEQ ID NO: 16. In some embodiments the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 16. In some embodiments, the heavy chain has an amino acid sequence 100% identical to an amino acid sequence set forth as SEQ ID NO: 16.

Also In some embodiments, the antibody comprises a light chain having an amino acid sequence at least about 70% identical to an amino acid sequence set forth as SEQ ID NO: 14 and a heavy chain having an amino acid sequence at least about 70% identical to an amino acid sequence set forth as SEQ ID NO: 15. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 14 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 15. In some embodiments, the light chain has an amino acid sequence 100% identical to an amino acid sequence set forth as SEQ ID NO: 14 and the heavy chain has an amino acid sequence 100% identical to an amino acid sequence set forth as SEQ ID NO: 15.

In some embodiments, the antibody comprises a light chain having an amino acid sequence at least about 70% identical to an amino acid sequence set forth as SEQ ID NO: 14 and a heavy chain having an amino acid sequence at least about 70% identical to an amino acid sequence set forth as SEQ ID NO: 16. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 14 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 16. In some embodiments, the light chain has an amino acid sequence 100% identical to an amino acid sequence set forth as SEQ ID NO: 14 and the heavy chain has an amino acid sequence 100% identical to an amino acid sequence set forth as SEQ ID NO: 16.

In some embodiments, the disclosure provides a use of an antibody as described herein, for the manufacture of a medicament that reduces immunosuppression by tumor-associated macrophages in a human subject having a cancer.

In some embodiments, the disclosure provides a use of an antibody as described herein, for the manufacture of a medicament that promotes T cell-mediated tumor cell killing in a human subject having a cancer.

In some embodiments, the disclosure provides a method of treating a human subject having a cancer, comprising administering to the subject a therapeutically effective amount of an antibody as described herein, whereby immunosuppression by tumor-associated macrophages in the subject is reduced.

In some embodiments, the disclosure provides a method of treating a human subject having a cancer, comprising administering to the subject a therapeutically effective amount of an antibody as described herein, whereby T cell-mediated tumor cell killing in the subject is increased.

Disclosed herein, in certain embodiments, are methods of functionally reorienting tumor-associated macrophages to reduce immunosuppression in a patient having cancer, comprising administering to the patient an amount of a pharmaceutical composition comprising an antibody as described herein that is effective to improve $CD4^+$ or $CD8^+$ T cell activity or proliferation in the tumor microenvironment.

Disclosed herein, in certain embodiments, are methods of promoting lymphocyte-mediated tumor cell killing in a human subject in need thereof, comprising administering to the subject an effective amount of a pharmaceutical composition comprising an antibody as described herein.

Disclosed herein, in certain embodiments, are methods of modulating an activity of a tumor-associated macrophage in a tumor microenvironment, the method comprising contacting the tumor-associated macrophage with an antibody disclosed herein, wherein the method results in at least one of the following effects:
  (a) reduced expression of at least one marker by the human macrophage, wherein the at least one marker is CD16, CD64, TLR2, or Siglec-15;
  (b) internalization of the antibody by the human macrophage;
  (c) activation of a $CD4^+$ T cell, $CD8^+$ T cell, NK cell, or any combination thereof;
  (d) proliferation of a $CD4^+$ T cell, $CD8^+$ T cell, NK cell, or any combination thereof; and
  (e) promotion of tumor cell killing in a tumor microenvironment.

Disclosed herein, in certain embodiments, are methods of modulating an activity of a tumor-associated macrophage in a tumor microenvironment, the method comprising contacting the tumor-associated macrophage with an antibody disclosed herein, wherein the method results in at least two of the following effects:
   (a) reduced expression of at least one marker by the human macrophage, wherein the at least one marker is CD16, CD64, TLR2, or Siglec-15;
   (b) internalization of the antibody by the human macrophage;
   (c) activation of a CD4$^+$ T cell, CD8$^+$ T cell, NK cell, or any combination thereof;
   (d) proliferation of a CD4$^+$ T cell, CD8$^+$ T cell, NK cell, or any combination thereof; and
   (e) promotion of tumor cell killing in a tumor microenvironment.

Disclosed herein, in certain embodiments, are methods of modulating an activity of a tumor-associated macrophage in a tumor microenvironment, the method comprising contacting the tumor-associated macrophage with an antibody disclosed herein, wherein the method results in at least three of the following effects:
   (a) reduced expression of at least one marker by the human macrophage, wherein the at least one marker is CD16, CD64, TLR2, or Siglec-15;
   (b) internalization of the antibody by the human macrophage;
   (c) activation of a CD4$^+$ T cell, CD8$^+$ T cell, NK cell, or any combination thereof;
   (d) proliferation of a CD4$^+$ T cell, CD8$^+$ T cell, NK cell, or any combination thereof; and
   (e) promotion of tumor cell killing in a tumor microenvironment.

Disclosed herein, in certain embodiments, are methods of modulating an activity of a tumor-associated macrophage in a tumor microenvironment, the method comprising contacting the tumor-associated macrophage with an antibody disclosed herein, wherein the method results in at least four of the following effects:
   (a) reduced expression of at least one marker by the human macrophage, wherein the at least one marker is CD16, CD64, TLR2, or Siglec-15;
   (b) internalization of the antibody by the human macrophage;
   (c) activation of a CD4$^+$ T cell, CD8$^+$ T cell, NK cell, or any combination thereof;
   (d) proliferation of a CD4$^+$ T cell, CD8$^+$ T cell, NK cell, or any combination thereof; and
   (e) promotion of tumor cell killing in a tumor microenvironment.

Disclosed herein, in certain embodiments, are methods of modulating an activity of a tumor-associated macrophage in a tumor microenvironment, the method comprising contacting the tumor-associated macrophage with an antibody disclosed herein, wherein the method results in at least five of the following effects:
   (a) reduced expression of at least one marker by the human macrophage, wherein the at least one marker is CD16, CD64, TLR2, or Siglec-15;
   (b) internalization of the antibody by the human macrophage;
   (c) activation of a CD4$^+$ T cell, CD8$^+$ T cell, NK cell, or any combination thereof;
   (d) proliferation of a CD4$^+$ T cell, CD8$^+$ T cell, NK cell, or any combination thereof; and
   (e) promotion of tumor cell killing in a tumor microenvironment.

In some embodiments, a method disclosed herein reduces myeloid cell suppression of CD8 T cell activation and proliferation.

M2 to M1 macrophage polarization refers to the process by which a M2 or M2-like macrophage of the present disclosure is altered such that the resulting macrophage has certain functional or phenotypic attributes associated with M1 or M1-like macrophages. In some embodiments, an M2 or M2-like macrophage is polarized when it no longer expresses CD163.

In some embodiments, the antibodies reduce myeloid cell suppression of CD19-CD3 BiTE-mediated killing of Raji cells by CD8 T cells.

In some embodiments, the antibodies reduce myeloid cell suppression of CAR T-cell-mediated killing of cancer cells.

In some embodiments, the antibodies reduce myeloid cell suppression of NK cell-mediated killing of cancer cells by ADCC.

Any of the methods disclosed herein, in some instances, further comprise administering to said subject an additional anticancer therapy. Anticancer therapies include, but are not limited to, surgical therapy, chemotherapy, radiation therapy, cryotherapy, hormonal therapy, immunotherapy, and cytokine therapy, and combinations thereof. In one embodiment, the antibody or antigen-binding fragment thereof and the anticancer therapy are administered concurrently or sequentially.

In some embodiments, the additional anticancer therapy is an immunotherapy. In some embodiments, the immunotherapy is a composition comprising a checkpoint inhibitor. In some embodiments, the additional anticancer therapy is an immune checkpoint inhibitor.

In some embodiments, the disclosure provides an in vitro or ex vivo method for identifying huCD163-expressing macrophages in a cell sample suspected of comprising huCD163-expressing macrophages, comprising contacting the cell sample with an antibody as described herein and measuring binding to cells in the sample, a positive signal indicating the presence of huCD163-expressing macrophages in the sample.

In some embodiments, the disclosure provides a method for identifying human M2c macrophages in a cell sample, which comprises contacting a cell sample comprising blood cells suspected of comprising human M2c macrophages with an antibody as described herein and measuring binding to cells in the sample, a positive signal indicating the presence of human M2c macrophages in the sample. In some embodiments, the cell sample comprises cells obtained from a human subject. In some embodiments, the cell sample comprises cultured cells. In some embodiments, the methods for detecting M2 cells in a sample include using an antibody or fragment that is not internalized by the cells upon binding, but remains bound to the exterior of the cells to facilitate detection.

In some embodiments, the disclosure provides a method for identifying huCD163-expressing cancer cells in a cell sample, which comprises contacting a cell sample comprising cells suspected of comprising huCD163-expressing cancer cells with an antibody as described herein and measuring binding to cells in the sample, a positive signal indicating the presence of huCD163-expressing cancer cells in the sample. In some embodiments, the cell sample comprises cells obtained from a human subject. In some embodiments, the cell sample comprises cultured cells.

In some embodiments, the disclosure provides a method of modulating expression of cell surface markers on M2c macrophages. In some embodiments, the expression of at least one of CD16 (FcγRIIIa), CD64 (FcγRI), Siglec-15, and TLR2 is decreased. In some embodiments, the expression of CD16, CD64, Siglec-15, and TLR2 are decreased.

In some embodiments, the disclosure provides a method of reducing myeloid cell suppression of T cell activation. In some embodiments the method induces increased IL-2 production by T cells. In some embodiments, the disclosure provides a method for increasing Th1 cell proliferation. In some embodiments, the disclosure provides a method for increasing the proportion of Th1 cells in proliferating T cells. In each of these aspects, the methods comprise administering an antibody as described herein in vivo, or contacting the antibody with a complex immune cell system in vitro or ex vivo, in which macrophages and effector T cells, and optional tumor target cells, are allowed to interact in ways that recapitulate or model in vivo interactions.

In some embodiments, the disclosure provides a method of reducing myeloid cell suppression of T cell proliferation. In some embodiments, the disclosure provides a method for increasing $CD4^+$ cell proliferation or $CD8^+$ T cell proliferation, or both.

In some embodiments, the disclosure provides a method for increasing T cell expression of at least one of CD69, ICOS, OX40, PD-1, LAG3, and CTLA4 in a patient in need thereof. In some embodiments the method increases expression of at least one of CD69, ICOS, OX40, PD-1, LAG3, and CTLA4 by $CD4^+$ T cells. In some embodiments the method increases expression of at least one of ICOS, OX40, PD-1, LAG3, and CTLA4 by $CD8^+$ T cells.

In some embodiments, the disclosure provides a method for increasing cancer cell killing. In some embodiments cancer cell killing by cytotoxic lymphocytes (CTL) is increased. In some embodiments, T cell-mediated killing of MHC-mismatched cancer cells is increased.

In some embodiments, the disclosure provides a method for contacting myeloid cells with an antibody described herein, to reduce macrophage-mediated suppression of $CD8^+$ T cell activation or $CD8^+$ T cell proliferation. In some embodiments, the antibody is contacted with myeloid cells comprising M0 macrophages. In some embodiments, the antibody is contacted with myeloid cells comprising M2 macrophages. In some embodiments, the antibody is contacted with myeloid cells comprising M0 and M2 macrophages.

In some embodiments the disclosure provides a method of treating a human patient having lung cancer, comprising administering an effective amount of an antibody as described herein to the patient. In some embodiments, the lung cancer is a carcinoma or an adenocarcinoma. In some embodiments, the lung cancer is non-small cell lung cancer.

An effective response of the present disclosure is achieved when the subject experiences partial or total alleviation or reduction of signs or symptoms of illness and, in the case of the treatment of cancer, specifically includes, without limitation, cure, remission, prolongation of survival, or other objective responses. In some embodiments, the expected progression-free survival times are measured in months to years, depending on prognostic factors including the number of relapses, stage of disease, and other factors. Prolonging survival includes without limitation times of at least 1 month (mo.), about at least 2 mos., about at least 3 mos., about at least 4 mos., about at least 6 mos., about at least 1 year, about at least 2 years, about at least 3 years, etc. Overall survival is also measured, for example, in months to years. Alternatively, an effective response, in some embodiments, is that a subject's symptoms remain static. Further indications of treatment of indications are described in more detail below.

In some embodiments, administration of a therapeutic agent in a prophylactic method occurs prior to the manifestation of symptoms of an undesired disease or disorder, such that the disease or disorder is prevented or, alternatively, delayed in its progression. Thus, when used in conjunction with prophylactic methods, the term "therapeutically effective" means that, after treatment, a smaller number of subjects (on average) develop the undesired disease or disorder or progress in severity of symptoms.

In some embodiments, amounts of the active ingredients in the compositions, the composition formulation, and the mode of administration, are among the factors that are varied to provide an amount of the active ingredient that is effective to achieve the desired therapeutic response for each subject, without being unduly toxic to the subject. The selected dosage level will depend upon a variety of factors including the activity of the particular compound employed, the route of administration, the time of administration, the rate of excretion or metabolism of the particular compound being employed, the duration of the treatment, other drugs, compounds and/or materials used in combination with the particular composition employed, the age, sex, weight, condition, general health, diet and prior medical history of the subject being treated, and like factors well known in the medical arts.

In some embodiments, the antibodies and antigen-binding fragments described herein are administered to a subject in various dosing amounts and over various time frames. Non-limiting doses include about 0.01 mg/kg, about 0.05 mg/kg, about 0.1 mg/kg, about 0.5 mg/kg, about 1 mg/kg, about 5 mg/kg, about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or any integer in between. Additionally, the dose(s) of an antibody or antigen-binding fragment are administered, in some embodiments, twice a week, weekly, every two weeks, every three weeks, every 4 weeks, every 6 weeks, every 8 weeks, every 12 weeks, or any combination of weeks therein. Dosing cycles are also contemplated such as, for example, administering antibodies or antigen-binding fragments thereof once or twice a week for 4 weeks, followed by two weeks without therapy. Additional dosing cycles including, for example, different combinations of the doses and weekly cycles described herein are also contemplated within the disclosure.

Therapeutically effective amounts of a composition, in some embodiments, varies and depends on the severity of the disease and the weight and general state of the subject being treated, but generally range from about 1.0 µg/kg to about 100 mg/kg body weight, or about 10 µg/kg to about 30 mg/kg, or about 0.1 mg/kg to about 10 mg/kg or about 1 mg/kg to about 10 mg/kg per application. Administration can be daily, on alternating days, weekly, twice a month, monthly or more or less frequently, as necessary depending on the response to the disorder or condition and the subject's tolerance of the therapy. In some embodiments, maintenance dosages over a longer period of time, such as 4, 5, 6, 7, 8, 10, or 12 weeks or longer is needed until a desired suppression of disorder symptoms occurs, and dosages are adjusted as necessary. The progress of this therapy is easily monitored by conventional techniques and assays.

In some embodiments, the antibody of the disclosure is administered intravenously in a physiological solution at a dose ranging between 0.01 mg/kg to 100 mg/kg at a frequency ranging from daily to weekly to monthly (e.g., every day, every other day, every third day, or 2, 3, 4, 5, or 6 times per week), preferably a dose ranging from 0.1 to 45 mg/kg, 0.1 to 15 mg/kg or 0.1 to 10 mg/kg at a frequency of 2 or 3 times per week, or up to 45 mg/kg once a month.

A response is achieved when the subject experiences partial or total alleviation, or reduction of signs or symptoms of illness, and specifically includes, without limitation, prolongation of survival. The expected progression-free survival times are measured, for example, in months to years, depending on prognostic factors including the number of relapses, stage of disease, and other factors. Prolonging survival includes without limitation times of at least 1 month (mo), about at least 2 months (mos.), about at least 3 mos., about at least 4 mos., about at least 6 mos., about at least 1 year, about at least 2 years, about at least 3 years, or more. Overall survival is also be measured in months to years in some embodiments. The subject's symptoms remain static or decrease in some embodiments.

A physician or veterinarian having ordinary skill in the art, in some cases, readily determines and prescribes the effective amount ($ED_{50}$) of the composition required. For example, the physician or veterinarian could start doses of the compounds employed in the composition at levels lower than that required to achieve the desired therapeutic effect and gradually increase the dosage until the desired effect is achieved. Alternatively, a dose remains constant in some embodiments.

In some embodiments, other antibodies, small molecule therapeutics, and/or other agents are combined in separate compositions for simultaneous or sequential administration. In one embodiment, simultaneous administration comprises one or more compositions that are administered at the same time, or within 30 minutes of each other. In some embodiments, administration occurs at the same or different sites.

Toxicity and therapeutic efficacy of such ingredient are, in some embodiments, determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). In some embodiments, the dose ratio between toxic and therapeutic effects is the therapeutic index and it are expressed as the ratio $LD_{50}/ED_{50}$. While compounds that exhibit toxic side effects are used in some embodiments, care should be taken to design a delivery system that targets such compounds to the site of affected tissue to minimize potential damage to healthy cells and, thereby, reduce side effects.

Data obtained from cell culture assays and animal studies is used in formulating a range of dosage for use in humans in some embodiments. The dosage of such compounds lies preferably within a range of circulating concentrations that include the $ED_{50}$ with little or no toxicity. In some embodiments, the dosage varies within this range depending upon the dosage form employed and the route of administration utilized. For any compound used in the method of the disclosure, the therapeutically effective dose is estimated initially from cell culture assays in some embodiments. In some embodiments, a dose is formulated in animal models to achieve a circulating plasma concentration range that includes the $IC_{50}$ (i.e., the concentration of the test compound which achieves a half-maximal inhibition) as determined in cell culture. Levels in plasma are measured, for example, by high performance liquid chromatography. Such information is, in some cases, used to more accurately determine useful doses in humans.

In some embodiments the disclosure provides a method of treating a patient having a cancer, comprising administering to the patient a therapeutically effective amount of an antibody as described herein and further comprising treating the subject with an anticancer therapy selected from surgical therapy, chemotherapy, radiation therapy, cryotherapy, hormonal therapy, immunotherapy, or cytokine therapy. In some embodiments, the antibody, or antigen-binding fragment thereof, and another anticancer therapy are administered concurrently or sequentially.

Diagnostic Products and Methods

In some embodiments, disclosed herein, are methods of detection of a huCD163 protein or M2 macrophages in a sample or a subject to assess a treatment state of a patient or diagnose a disease or disorder associated or correlated with the activity of M2 macrophages or TAMs, such as those diseases and disorders described herein.

In the in vivo detection, diagnosis or monitoring of soluble huCD163 protein, expression of a huCD163 protein by cells or tissues, or presence or activity of M2 macrophages, a subject is administered an antibody or antigen-binding fragment as described herein, which antibody or antigen-binding fragment is bound to a detectable moiety. The detectable moiety is visualized, in some embodiments, using art-recognized methods such as, but not limited to, magnetic resonance imaging (MRI), fluorescence, radioimaging, light sources supplied by endoscopes, laparoscopes, or intravascular catheter (i.e., via detection of photoactive agents), photoscanning, positron emission tomography (PET) scanning, whole body nuclear magnetic resonance (NMR), radioscintigraphy, single photon emission computed tomography (SPECT), targeted near infrared region (NIR) scanning, X-ray, ultrasound. Labels for detecting compounds using such methods are also known in the art. Visualization of the detectable moiety allows, in some embodiments, for detection, diagnosis, and/or monitoring of a condition or disease associated with M2 macrophage activity or activity of another cell that expresses a huCD163 protein. Additional diagnostic assays that utilize antibodies specific to the desired target protein, i.e., a huCD163 protein, are known in the art and are also contemplated herein.

For in vitro detection methods, samples to be obtained from a subject include, but are not limited to, blood, tissue biopsy samples, and fluid therefrom.

Thus, the disclosure provides antibodies and antigen-binding fragments thereof that are useful for detecting or diagnosing levels of M2 macrophages or TAM macrophages associated with a disease or disorder, potentially indicating need for therapeutic treatment. In other embodiments the antibody further comprises a second agent. Such an agent, in some embodiments, is a molecule or moiety such as, for example, a reporter molecule or a detectable label. Detectable labels/moieties for such detection methods are known in the art and are described in more detail below. Reporter molecules are any moiety which are detected using an assay, for example. Non-limiting examples of reporter molecules which have been conjugated to polypeptides include enzymes, radiolabels, haptens, fluorescent labels, phosphorescent molecules, chemiluminescent molecules, chromophores, luminescent molecules, photoaffinity molecules, colored particles or ligands, such as biotin. In some embodiments, detectable labels include compounds and/or elements that are detected due to their specific functional properties, and/or chemical characteristics, the use of which allows the polypeptide to which they are attached to be detected, and/or further quantified if desired. Many appropriate detectable (imaging) agents are known in the art, as are methods for their attachment to polypeptides.

Polypeptides are conjugated to a wide variety of fluorescent dyes, quenchers, and haptens such as fluorescein, R-phycoerythrin, and biotin in some embodiments. In some embodiments, conjugation occurs either during polypeptide synthesis or after the polypeptide has been synthesized and purified.

Alternatively, an antibody, antigen-binding fragment or binding protein is conjugated with a fluorescent moiety in some embodiments. Conjugating polypeptides with fluorescent moieties (e.g., R-Phycoerythrin, fluorescein isothiocyanate (FITC), etc.) is, for example, accomplished using art-recognized techniques. Numerous commercially available fluorescent dyes and dye-conjugation kits are commercially available for particular applications, such as fluorescence microscopy, flow cytometry, fluorescence-activated cell sorting (FACS), etc.

In one non-limiting embodiment, an antibody antigen-binding fragment is associated with (conjugated to) a detectable label, such as a radionuclide, a dye, an imaging agent, or a fluorescent agent for immunodetection of binding to antigen which is used to visualize binding of the antibodies to M2 macrophages or soluble or bound huCD163 protein in vitro and/or in vivo.

Non-limiting examples of radiolabels include, for example, $^{32}P$, $^{33}P$, $^{43}K$, $^{52}Fe$, $^{57}Co$, $^{64}Cu$, $^{67}Ga$, $^{67}Cu$, $^{68}Ga$, $^{71}Ge$, $^{75}Br$, $^{76}Br$, $^{77}Br$, $^{77}As$, $^{77}Br$, $^{81}Rb/^{81m}Kr$, $^{87m}Sr$, $^{90}Y$, $^{97}Ru$, $^{99}Tc$, $^{99m}Tc$, $^{100}Pd$, $^{101}Rh$, $^{103}Pb$, $^{105}Rh$, $^{109}Pd$, $^{111}Ag$, $^{111}In$, $^{113}In$, $^{119}Sb$, $^{121}Sn$, $^{123}I$, $^{125}I$, $^{127}Cs$, $^{128}Ba$, $^{129}Cs$, $^{131}I$, $^{131}Cs$, $^{143}Pr$, $^{153}Sm$, $^{161}Tb$, $^{166}Ho$, $^{169}Eu$, $^{177}Lu$, $^{186}Re$, $^{188}Re$, $^{189}Re$, $^{191}OS$, $^{193}Pt$, $^{194}Ir$, $^{197}Hg$, $^{199}Au$, $^{203}Pb$, $^{211}At$, $^{212}Pb$, $^{212}Bi$, and $^{213}Bi$. In some embodiments, radiolabels are attached to compounds using conventional chemistry known in the art of antibody imaging. Radiolabeled compounds are useful in in vitro diagnostics techniques and in in vivo radioimaging techniques and in radioimmunotherapy.

Compositions of antibodies and antigen-binding fragments described herein are also used as non-therapeutic agents (e.g., as affinity purification agents) in some embodiments.

Antibody Technology

As will be understood by the skilled artisan, general description of antibodies herein and methods of preparing and using the same also apply to individual antibody polypeptide constituents and antibody fragments.

The antibodies of the present disclosure are polyclonal or monoclonal antibodies. However, in preferred embodiments, they are monoclonal. In particular embodiments, antibodies of the present disclosure are human antibodies. Methods of producing polyclonal and monoclonal antibodies are known in the art.

Antibodies, antigen-binding fragments, and other proteins that bind huCD163 expressed by M2 macrophages are generated using such methods are tested for one or more of their binding affinity, avidity, and modulating capabilities in some embodiments.

Conventional methods, in some embodiments, are utilized to identify antibodies or antigen-binding fragments thereof that bind to a huCD163 protein. In some embodiments, antibodies and antigen-binding fragments are evaluated for one or more of binding affinity, association rates, disassociation rates, and avidity. Measurement of such parameters is, for example, accomplished using assays including, but not limited to, an enzyme-linked-immunosorbent assays (ELISA), ELISpot assays, Scatchard analysis, surface plasmon resonance (e.g., BIACORE) analysis, etc., competitive binding assays, and the like. In one non-limiting embodiment, an ELISA assay is used to measure the binding capability of specific antibodies or antigen-binding fragments that bind to a huCD163 protein. A surface plasmon resonance technique is described in Liljeblad et al., *Glyco J* 17:323-9 (2000).

In some embodiments, antibodies according to the disclosure are produced recombinantly, using vectors and methods available in the art, as described further below. In some embodiments, human antibodies are also be generated by in vitro activated B cells (see U.S. Pat. Nos. 5,567,610 and 5,229,275).

In some embodiments, human antibodies are produced in transgenic animals (e.g., mice) that are capable of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice results in the production of human antibodies upon antigen challenge. See, e.g., Jakobovits et al., *Proc Nat Acad Sci USA*, 90:2551 (1993); Jakobovits et al., *Nature* 362:255-58 (1993); Bruggemann et al., Year in Immunol., 7:33 (1993); U.S. Pat. Nos. 5,545,806, 5,569,825, 5,591, 669; 5,545,807; and WO 97/17852. In some embodiments, such animals are genetically engineered to produce human antibodies comprising a polypeptide of the present disclosure.

The antibodies are, for example, isolated and purified from a culture supernatant or ascites (if produced in an animal) using methods known in the art, such as by saturated ammonium sulfate precipitation, euglobulin precipitation method, caproic acid method, caprylic acid method, ion exchange chromatography (DEAE or DE52), or affinity chromatography using anti-Ig column or a protein A, G, or L column.

As noted above, the disclosure further provides antibody fragments. In certain circumstances there are advantages of using antibody fragments, rather than whole antibodies. For example, the smaller size of the fragments allows for rapid clearance, and leads to improved access to certain tissues, such as solid tumors, in some embodiments. Examples of antibody fragments include: Fab, Fab', F(ab')2, and Fv fragments; diabodies; linear antibodies; single-chain antibodies; and multispecific antibodies formed from antibody fragments.

Various techniques have been developed to produce antibody fragments. Traditionally, these fragments were derived via proteolytic digestion of intact antibodies (see, e.g., Morimoto et al., *J Biochem Biophys Methods* 1992 24(1-2): 107-17; and Brennan et al., Science 1985 229:81). However, these fragments are now be produced directly by recombinant host cells in some embodiments. In some embodiments, Fab, Fv, and ScFv antibody fragments all are expressed in and secreted from *E. coli*, thus allowing the facile production of large amounts of these fragments. In some embodiments, Fab'-SH fragments are directly recovered from *E. coli* and chemically coupled to form F(ab')$_2$ fragments (Carter et al., Bio/Technology 10:163-167 (1992)). According to another approach, in some embodiments, F(ab')$_2$ fragments are isolated directly from recombinant host cell culture. Fab and F(ab')2 fragment with increased in vivo half-life comprising a salvage receptor binding epitope taken from two loops of a $C_H2$ domain of an Fc region of an IgG are described in U.S. Pat. Nos. 5,869,046 and 6,121,022. Other techniques for producing antibody fragments will be apparent to the skilled practitioner.

In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions. Thus, they are suitable for reduced nonspecific binding during in vivo use. In some embodiments, sFv fusion proteins are constructed to yield fusion of an effector protein at either the amino or the carboxy terminus of an sFv. See Antibody Engineering, ed. Borrebaeck, supra. In some embodiments, the antibody fragment is also be a "linear antibody," e.g., as described in U.S. Pat. No. 5,641,870 for example. In some embodiments, such linear antibody fragments are monospecific or bispecific.

Methods for making bispecific or other multispecific antibodies are known in the art and include chemical cross-linking, use of leucine zippers (Kostelny et al., *J Immunol* 148:1547-53 (1992)); diabody technology (Hollinger et al., *Proc Nat Acad Sci USA* 90:64448 (1993)); scFv dimers [Gruber et al., *J Immunol* 152:5368 (1994)), linear antibodies (Zapata et al., *Protein Eng* 8:1057-62 (1995)); and chelating recombinant antibodies (Neri et al., *J Mol Biol* 246:367-73 (1995)).

Traditional production of full-length bispecific antibodies is based on the co-expression of two immunoglobulin heavy chain-light chain pairs, where the two chains have different specificities (Millstein et al., *Nature* 305:537-9 (1983)). Because of the random assortment of immunoglobulin heavy and light chains, these hybridomas (quadromas) produce a potential mixture of ten different antibody molecules, of which only one has the correct bispecific structure. Purification of the correct molecule are done, for example, by affinity chromatography. Similar procedures are disclosed in WO 93/08829, and in Traunecker et al., *EMBO J* 10:3655-9 (1991).

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred that the first heavy-chain constant region ($C_H1$) containing the site necessary for light chain bonding, be present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the four polypeptide fragments in embodiments when unequal ratios of the four polypeptide chains used in the construction provide the optimum yield of the desired bispecific antibody. It is, however, possible to insert the coding sequences for two or all four polypeptide chains into a single expression vector when the expression of at least two polypeptide chains in equal ratios results in high yields or when the ratios have no significant effect on the yield of the desired chain combination.

Bispecific antibodies are composed of, for example, a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods Enzymol* 121:210 (1986).

According to another approach described in U.S. Pat. No. 5,731,168, the interface between a pair of antibody molecules are engineered to maximize the percentage of heterodimers that are recovered from recombinant cell culture in some embodiments. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate are coupled to avidin, the other to biotin. Such antibodies have, for example, been proposed to target immune system cells to unwanted cells (U.S. Pat. No. 4,676,980), and for treatment of HIV infection (WO 91/00360, WO 92/20373, and EP 03089). In some embodiments, heteroconjugate antibodies are made using any convenient cross-linking methods. Suitable cross-linking agents are well known in the art, and are disclosed in U.S. Pat. No. 4,676,980, along with a number of cross-linking techniques. Another method is designed to make tetramers by adding a streptavidin-coding sequence at the C-terminus of the scFv. Streptavidin is composed of four subunits, so when the scFv-streptavidin is folded, four subunits associate to form a tetramer (Kipriyanov et al., *Hum Antibodies Hybridomas* 6(3):93-101 (1995)).

According to another approach for making bispecific antibodies, the interface between a pair of antibody molecules are engineered to maximize the percentage of heterodimers which are recovered from recombinant cell culture in some embodiments. One interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. See WO 96/27011.

Techniques for generating bispecific antibodies from antibody fragments have also been described in the literature. For example, bispecific antibodies are prepared using chemical linkage. Brennan et al., *Science* 229: 81 (1985) describes a procedure wherein intact antibodies are proteolytically cleaved to generate F(ab')$_2$ fragments. These fragments are reduced in the presence of the dithiol complexing agent, sodium arsenite, to stabilize vicinal dithiols, and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. In some embodiments, the bispecific antibodies produced are used as agents for the selective immobilization of enzymes.

Recent progress has facilitated the direct recovery of Fab'-SH fragments from E. coli, which are, for example, chemically coupled to form bispecific antibodies. Shalaby et al., J Exp Med 175: 217-25 (1992) describes the production of a humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J Immunol 148(5):1547-53 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method is used to produce antibody heterodimers in some embodiments.

Identification and Preparation of Antibodies

Polynucleotide sequences encoding the antibodies, variable regions thereof, or antigen-binding fragments thereof are, in some embodiments, determined using conventional sequencing techniques, and subcloned into expression vectors for the recombinant production of the antibodies. This was accomplished by obtaining mononuclear cells from the blood of a subject, e.g., a cancer patient; producing B cell clones from the mononuclear cells; inducing the B cells to become antibody-producing plasma cells; and screening the supernatants produced by the plasma cells to determine if it contains an antibody. Identification of other antibodies having the specificity of the antibodies of the disclosure are accomplished using a similar method in some embodiments. For example, once a B cell clone that produces an antibody is identified, reverse-transcription polymerase chain reaction (RT-PCR) is performed to clone the DNAs encoding the variable regions or portions thereof of the antibody. These sequences are then subcloned into expression vectors suitable for the recombinant production of human antibodies. The binding specificity is confirmed, in some embodiments, by determining the antibody's or the recombinant antibody's ability to bind M2 cells or other cells expressing a human CD163 polypeptide that is expressed by M2 cells.

In particular embodiments of the methods described herein, B cells isolated from peripheral blood or lymph nodes are sorted, e.g., based on their being CD19 positive, and plated, e.g., as low as a single cell specificity per well, e.g., in 96-, 384-, or 1536-well configurations. The cells are induced to differentiate into antibody-producing cells, e.g., plasma cells, and the culture supernatants are harvested and tested for binding to cells expressing the target polypeptide on their surface using, e.g., FMAT or FACS analysis. Positive wells are then subjected to whole well RT-PCR to amplify heavy and light chain variable regions of the IgG molecule expressed by the clonal daughter plasma cells. The resulting PCR products encoding the heavy and light chain variable regions, or portions thereof, are subcloned into human antibody expression vectors for recombinant expression. The resulting recombinant antibodies are then tested to confirm their original binding specificity and are further tested, in some embodiments, for cross-reactivity against other cells or proteins.

Thus, in one embodiment, a method of identifying antibodies is practiced as follows. First, full-length or approximately full-length CD163 cDNAs are transfected into a cell line for expression of CD163 polypeptides. Secondly, individual human plasma or sera samples are tested for antibodies that bind the cell-expressed polypeptides. And lastly, MAbs derived from plasma- or serum-positive individuals are characterized for binding to the same cell-expressed CD163 polypeptides. Further definition of the fine specificities of the MAbs are performed at this point in some embodiments.

Polynucleotides that encode the antibodies or portions thereof of the present disclosure are isolated from cells expressing the antibodies, according to methods available in the art and described herein, including amplification by polymerase chain reaction using primers specific for conserved regions of human antibody polypeptides, in some embodiments. For example, light chain and heavy chain variable regions is cloned from the B cell according to molecular biology techniques described in WO 92/02551; U.S. Pat. No. 5,627,052; or Babcook et al., Proc Nal Acad Sci USA 93:7843-48 (1996). In certain embodiments, polynucleotides encoding all or a region of both the heavy and light chain variable regions of the IgG molecule expressed by the clonal daughter plasma cells expressing the antibody are subcloned and sequenced. In some embodiments, the sequence of the encoded polypeptide is readily determined from the polynucleotide sequence.

Isolated polynucleotides encoding a polypeptide of the present disclosure is subcloned into an expression vector to recombinantly produce antibodies and polypeptides of the present disclosure, using procedures known in the art and described herein.

In some embodiments, binding properties of an antibody (or fragment thereof) to CD163 polypeptides or M2 cells are generally determined and assessed using immunodetection methods including, for example, immunofluorescence-based assays, such as immuno-histochemistry (IHC) and/or fluorescence-activated cell sorting (FACS). Immunoassay methods include, in some embodiments, controls and procedures to determine whether antibodies bind specifically to CD163 polypeptides or to M2 macrophages, and do not recognize or cross-react with control cells, e.g., M1 cells, or host cells transfected to express a control protein.

Following pre-screening of serum to identify patients that produce antibodies to a CD163 polypeptide or to M2 macrophages or TAMs, the methods of the present disclosure typically include the isolation or purification of B cells from a biological sample previously obtained from a patient or subject. In some embodiments, the patient or subject are currently or have previously been diagnosed with or suspect of having a cancer or particular disease of interest, or the patient or subject is considered free of cancer or disease. Typically, the patient or subject is a mammal and, in particular embodiments, a human. In some embodiments, the biological sample is any sample that contains B cells, including but not limited to, lymph node or lymph node tissue, pleural effusions, peripheral blood, ascites, tumor tissue, or cerebrospinal fluid (CSF). In some embodiments, B cells are isolated from different types of biological samples, such as a tumor biopsy or other biological sample affected by a particular disease. However, in some embodiments, it is understood that any biological sample comprising B cells is used for any of the embodiments of the present disclosure.

Once isolated, the B cells are induced to produce antibodies, e.g., by culturing the B cells under conditions that support B cell proliferation or development into a plasmacyte, plasmablast, or plasma cell. The antibodies are then screened, typically using high throughput techniques, to identify an antibody that specifically binds to a target antigen, e.g., a particular tissue, cell, or polypeptide. In certain embodiments, the specific antigen, e.g., cell surface polypeptide bound by the antibody is not known, while in other embodiments, the antigen specifically bound by the antibody is known.

According to the present disclosure, B cells are, in some embodiments, isolated from a biological sample, e.g., a tumor, tissue, peripheral blood or lymph node sample, by any means known and available in the art. B cells are typically sorted by FACS based on the presence on their surface of a B cell-specific marker, e.g., CD19, CD138, and/or surface IgG. However, other methods known in the art are employed in some embodiments, such as, e.g., column purification using CD19 magnetic beads or IgG-specific magnetic beads, followed by elution from the column. However, magnetic isolation of B cells utilizing any marker results in loss of certain B cells in some embodiments. Therefore, in certain embodiments, the isolated cells are not sorted but, instead, Ficoll-purified mononuclear cells isolated from tumor are directly plated to the appropriate or desired number of specificities per well.

To identify B cells that produce an antibody, the B cells are typically plated at low density (e.g., a single cell specificity per well, 1-10 cells per well, 10-100 cells per well, 1-100 cells per well, less than 10 cells per well, or less than 100 cells per well) in multi-well or microtiter plates, e.g., in 96, 384, or 1536 well configurations. When the B cells are initially plated at a density greater than one cell per well, then the methods of the present disclosure include the step of subsequently diluting cells in a well identified as producing an antigen-specific antibody, until a single cell specificity per well is achieved, thereby facilitating the identification of the B cell that produces the antigen-specific antibody in some embodiments. In some embodiments, cell supernatants or a portion thereof and/or cells are frozen and stored for future testing and later recovery of antibody polynucleotides.

In certain embodiments, the B cells are cultured under conditions that favor the production of antibodies by the B cells. For example, the B cells are cultured under conditions favorable for B cell proliferation and differentiation to yield antibody-producing plasmablasts, plasmacytes, or plasma cells. In particular embodiments, the B cells are cultured in the presence of a B cell mitogen, such as lipopolysaccharide (LPS) or CD40 ligand. In one specific embodiment, B cells are differentiated to antibody-producing cells by culturing them with feed cells and/or other B cell activators, such as CD40 ligand.

Cell culture supernatants or antibodies obtained therefrom are tested for their ability to bind to a target antigen, using routine methods available in the art, including those described herein, in some embodiments. In particular embodiments, culture supernatants are tested for the presence of antibodies that bind to a target antigen using high-throughput methods. For example, B cells are cultured in multi-well microtiter dishes, such that robotic plate handlers are used to simultaneously sample multiple cell supernatants and test for the presence of antibodies that bind to a target antigen. In particular embodiments, antigens are bound to beads (e.g., paramagnetic or latex beads) to facilitate the capture of antibody/antigen complexes. In other embodiments, antigens and antibodies are fluorescently labeled (with different labels) and FACS analysis is performed to identify the presence of antibodies that bind to target antigen. In one embodiment, antibody binding is determined using FMAT™ analysis and instrumentation (Applied Biosystems, Foster City, Calif.). FMAT is a fluorescence macro-confocal platform for high-throughput screening, which enables mix-and-read, non-radioactive assays using live cells or beads.

In comparing the binding of an antibody to a particular target antigen (e.g., a biological sample such as cancer tissue or cells, or infectious agents) to the antibody's binding to a control sample (e.g., a biological sample such as normal cells, comparator cells from another species, a different cancer tissue or cell, or different infectious agent), in some embodiments, the antibody is considered to preferentially bind a particular target antigen if at least two-fold, at least three-fold, at least five-fold, or at least ten-fold more antibody binds to the particular target antigen as compared to the amount that binds a control sample.

Polynucleotides encoding antibody chains, variable regions thereof, or fragments thereof, are isolated from cells utilizing any means available in the art in some embodiments. In one embodiment, polynucleotides are isolated using polymerase chain reaction (PCR), e.g., reverse transcription-PCR (RT-PCR) using oligonucleotide primers that specifically bind to heavy or light chain encoding polynucleotide sequences or complements thereof using routine procedures available in the art. In one embodiment, positive wells are subjected to whole well RT-PCR to amplify the heavy and light chain variable regions of the IgG molecule expressed by the clonal daughter plasma cells. These PCR products, in some embodiments, are sequenced, and products encoding the heavy and light chain variable regions or portions thereof are then subcloned into human antibody expression vectors and recombinantly expressed according to routine procedures in the art (see, e.g., U.S. Pat. No. 7,112,439). The nucleic acid molecules encoding a M2 macrophage-specific antibody or fragment thereof as described herein are, in some embodiments, propagated and expressed according to any of a variety of well-known procedures for nucleic acid excision, ligation, transformation, and transfection. Thus, in certain embodiments expression of an antibody fragment are preferred in a prokaryotic host cell, such as *E. coli* (see, e.g., Pluckthun et al., *Methods Enzymol* 178:497-515 (1989)). In certain other embodiments, expression of the antibody or an antigen-binding fragment thereof are preferred in a eukaryotic host cell, such as yeast (e.g., *Saccharomyces cerevisiae, S. pombe, Pichia pastoris*); animal cells (including mammalian cells); or plant cells. Examples of suitable animal cells include, but are not limited to, myeloma, COS, CHO, or hybridoma cells. Examples of plant cells include tobacco, corn, soybean, and rice cells. By methods known to those having ordinary skill in the art and based on the present disclosure, a nucleic acid vector is designed for expressing foreign sequences in a particular host system, and then polynucleotide sequences encoding the tumor-specific antibody (or fragment thereof) is inserted, in some embodiments. The regulatory elements will vary according to the particular host.

One or more replicable expression vectors containing a polynucleotide encoding a variable and/or constant region is, in some embodiments, prepared and used to transform an appropriate cell line, for example, a non-producing myeloma cell line, such as a mouse NSO line or a bacterium, such as *E. coli*, in which production of the antibody will occur. In order to obtain efficient transcription and translation, the polynucleotide sequence in each vector should include appropriate regulatory sequences, particularly a promoter and leader sequence operatively linked to the variable region sequence.

Particular methods for producing antibodies in this way are generally well known and routinely used. For example, molecular biology procedures are described by Sambrook et al., *Molecular Cloning, A Laboratory Manual*, 2nd ed., Cold Spring Harbor Laboratory, New York, 1989; see also Sambrook et al., 3rd ed., Cold Spring Harbor Laboratory, New York, (2001). While not required, in certain embodiments, regions of polynucleotides encoding the recombinant antibodies are sequenced. DNA sequencing are performed, for example, in any manner or using any systems known in the art. Basic sequencing technology is described for example, in Sanger et al., *Proc Natl Acad Sci USA* 74:5463 (1977) and the Amersham International plc sequencing handbook and including improvements thereto.

In particular embodiments, the resulting recombinant antibodies or fragments thereof are then tested to confirm their original specificity, and are further tested for cross-reactivity, e.g., with related polypeptides, in some embodiments. In particular embodiments, an antibody identified or produced according to methods described herein is tested for ability to internalize or other effector function using conventional methods.

Packages, Kits, and Pre-Filled Containers

Also provided herein are kits containing one or more compounds described above. The kit comprises, in some embodiments, an antibody or antigen-binding fragment thereof as described herein in suitable container means.

In some embodiments, there is provided is a container means comprising a composition described herein. In some embodiments, the container means is any suitable container which houses, for example, a liquid or lyophilized composition including, but not limited to, a vial, syringe, bottle, an intravenous (IV) bag or ampoule. A syringe holds any volume of liquid suitable for injection into a subject, in some embodiments, including, but not limited to, 0.5 cc, 1 cc, 2 cc, 5 cc, 10 cc, or more.

Provided herein are kits, comprising a composition or compositions described herein. In some embodiments, provided herein is a kit for treating a subject having a cancer, comprising an antibody as described herein and an anticancer therapy.

In some embodiments, provided herein is a kit for treating a cancer, comprising an antibody as described herein, and a label attached to or packaged with the container, the label describing use of the antibody in combination with an anticancer therapy.

In some embodiments, provided herein is a kit for treating a cancer, comprising an anticancer therapy and a label attached to or packaged with the container, the label describing use of the anticancer therapy with an antibody as described herein.

In some embodiments, the container means of the kits will generally include at least one vial, test tube, flask, bottle, ampoule, syringe, an intravenous (IV) bag, and/or other container means, into which the at least one polypeptide are placed, and/or preferably, suitably aliquoted. Provided herein is a container means comprising a composition described herein.

The kits, in some embodiments, include a means for containing at least one fusion protein, detectable moiety, reporter molecule, and/or any other reagent containers in close confinement for commercial sale. In some embodiments, such containers include injection and/or blow-molded plastic containers into which the desired vials are retained. In some embodiments, kits also include printed material for use of the materials in the kit.

Packages and kits additionally include a buffering agent, a preservative, and/or a stabilizing agent in a pharmaceutical formulation in some embodiments. In some embodiments, each component of the kit is enclosed within an individual container and all of the various containers can be within a single package. In some embodiments, disclosure kits are designed for cold storage or room temperature storage.

Additionally, in some embodiments, the preparations contain stabilizers to increase the shelf-life of the kits and include, for example, bovine serum albumin (BSA). Where the compositions are lyophilized, the kit contains, in some embodiments, further preparations of solutions to reconstitute the lyophilized preparations. Acceptable reconstitution solutions are well known in the art and include, for example, pharmaceutically acceptable phosphate buffered saline (PBS).

In some embodiments, packages and kits further include one or more components for an assay, such as, for example, an ELISA assay. Samples to be tested in this application include, for example, blood, plasma, tissue sections and secretions, urine, lymph, and products thereof. In some embodiments, packages and kits further include one or more components for collection of a sample (e.g., a syringe, a cup, a swab, etc.).

In some embodiments, packages and kits further include a label specifying information required by US FDA or similar regulatory authority, for example, a product description, amount and mode of administration, and/or indication of treatment. Packages provided herein can include any of the compositions as described herein.

The term "packaging material" refers to a physical structure housing the components of the kit. In some embodiments, the packaging material maintains the components sterilely and are made of material commonly used for such purposes (e.g., paper, corrugated fiber, glass, plastic, foil, ampules, etc.). In some embodiments, the label or packaging insert includes appropriate written instructions. Kits, therefore, additionally includes, in some embodiments, labels or instructions for using the kit components in any method of the disclosure. In some embodiments, a kit includes a compound in a pack, or dispenser together with instructions for administering the compound in a method described herein.

In still further embodiments, a kit further comprises a container means for an anticancer therapy.

Instructions include instructions for practicing any of the methods described herein including treatment methods in some embodiments. Instructions additionally include indications of a satisfactory clinical endpoint or any adverse symptoms that occur, or additional information required by regulatory agencies such as the Food and Drug Administration for use on a human subject in some embodiments.

The instructions are, in some embodiments, on "printed matter," e.g., on paper or cardboard within or affixed to the kit, or on a label affixed to the kit or packaging material, or attached to a vial or tube containing a component of the kit. Instructions are additionally included on a computer readable medium, such as, for example, CD-ROMs, DVDs, flash memory devices, solid state memory, magnetic disks and disk devices, magnetic tapes, cloud computing systems and services, and the like, in some embodiments. In some cases, the program and instructions are permanently, substantially permanently, semi-permanently, or non-transitorily encoded on the media.

Provided herein is a container means comprising a composition described herein. In some embodiments, the container means is any suitable container which houses a liquid or lyophilized composition including, but not limited to, a vial, syringe, bottle, intravenous (IV) bag, or ampoule. A syringe, in some embodiments, holds any volume of liquid suitable for injection into a subject including, but not limited to, 0.5 cc, 1 cc, 2 cc, 5 cc, 10 cc or more.

Provided herein are kits comprising a composition described herein. In some embodiments, provided herein is a kit for treating a cancer, comprising an antibody as described herein in combination with an anticancer therapy agent.

In some embodiments, provided herein is a kit for treating a cancer, comprising an antibody as described herein, and a label attached to or packaged with the container, the label describing use of the antibody, or an antigen-binding fragment thereof, with an anticancer therapy.

In some embodiments, provided herein is a kit for treating a cancer, comprising an anticancer therapy and a label attached to or packaged with the container, the label describing use of the anticancer therapy with an antibody as described herein.

EXAMPLES

The present disclosure will be further illustrated in the following Examples which are given for illustration purposes only and are not intended to limit the disclosure in any way.

Example 1—Identification and Cloning

Antibodies that specifically bind to human myeloid-derived suppressor cells (MDSCs) produced by patients who respond to checkpoint inhibitor anti-PD-1 treatment were isolated and cloned. These monoclonal antibodies were further interrogated for their immunomodulatory properties with the goal of identifying antibodies that have therapeutic potential to target and reverse the immunosuppressive effects of MDSCs, thereby enhancing tumor clearance.

Cancer patients who achieved partial or complete response to immune checkpoint inhibitor for at least 6 months of duration were identified and selected for memory B cell repertoire analysis via the I-STAR platform. This platform utilized a short-term B cell culture system to interrogate the memory B cell repertoire. More than 15,000 memory B cells based on CD19 and IgG surface-expression were isolated from ten million peripheral blood mononuclear cells (PBMCs) of each donor patient. These memory B cells were then seeded in forty 384-well microtiter plates, at approximately 1 cell/well, under conditions that promoted B cell activation, proliferation, terminal differentiation, and antibody secretion. The plating density of 1 cell/well allowed for expansion of single B cell clones such that the authentic antibody heavy and light chain pair could be reconstituted from each culture well. Using a high throughput and miniaturized, multiplex flow cytometry assay, the secreted IgG antibodies in each well were screened for binding to MDSCs. 49 positive B cell clones were identified. A selected subset of antibodies, prioritized based on MDSCs binding profiles and antibody variable-region sequences, was sequenced, cloned, and expressed as recombinant IgG1 for further in vitro characterizations.

Heavy (VH) and light (VL) variable regions of the immunoglobulin genes from B cell clones that produce MDSC-specific antibodies were amplified by RT-PCR amplification using family-specific primer sets. From positive family-specific PCR reactions, pools of the VH- or VL-region clones were cloned into an expression vector upstream to human IgG1 constant domain sequence, resulting in a functional antibody with the same binding characteristic as the antibody produced by that B cell clone. DNA plasmids were designed and requested for gene synthesis in constant regions at GenScript, NJ, USA. These plasmids were combined in all possible heavy and light chain family-specific pairs and were used to transiently transfect HEK293 cells. All transfectant supernatants containing secreted recombinant antibodies were screened in flow-based MDSC binding assays. For wells that contained more than one B cell clone per well, multiple VH and VL domain sequences were amplified and expressed as described earlier. A MDSC screen was then used to identify the heavy and light chain combination pools that recapitulated the binding activity as observed with the antibody found in the mixed cultures. DNA sequences of the VH and light VL variable regions for all binding mAbs were confirmed by multiple sequencing reactions using purified DNA from maxipreps (GenScript source and Macherey Nagel amplified plasmids).

One B cell clone (Germline ID for heavy chain VH3.30-3/IGHG1 and light chain VK1.O12) was identified from MDSC screen and designated AB101 comprising a light chain comprising SEQ ID NO: 9 and a heavy chain comprising SEQ ID NO: 10. The donor from whom the clone was derived was a patient diagnosed with non-small-cell lung cancer (NSCLC). The patient had progressive disease to chemotherapy and then had complete remission upon anti-PD-1 treatment and was still receiving treatment at the time of blood draw. The B cell clone well was confirmed to have just one heavy and one light chain from sequencing. As observed with the secreted IgG antibodies from the single B cell clone, the recapitulated antibody also had a distinct bimodal binding on MDSCs, indicating that the antibody target is highly expressed on a select subpopulation of MDSCs. See FIG. 1. Results from recapitulation screen on two MDSC donors with relaxed block (10 µg/mL of recombinant Fc block (Abcam)) and stringent block (10 µg/mL of recombinant Fc block from Abcam+1 µg/mL of anti-CD16, anti-CD32, and anti-CD64) conditions show dose-dependent saturable binding of AB101 to human MDSCs with an IC50 of about 10 nM under relaxed block conditions. There was a decrease in overall binding of AB101, as suggested by decrease in MFI, under stringent block conditions.

Figure 2:
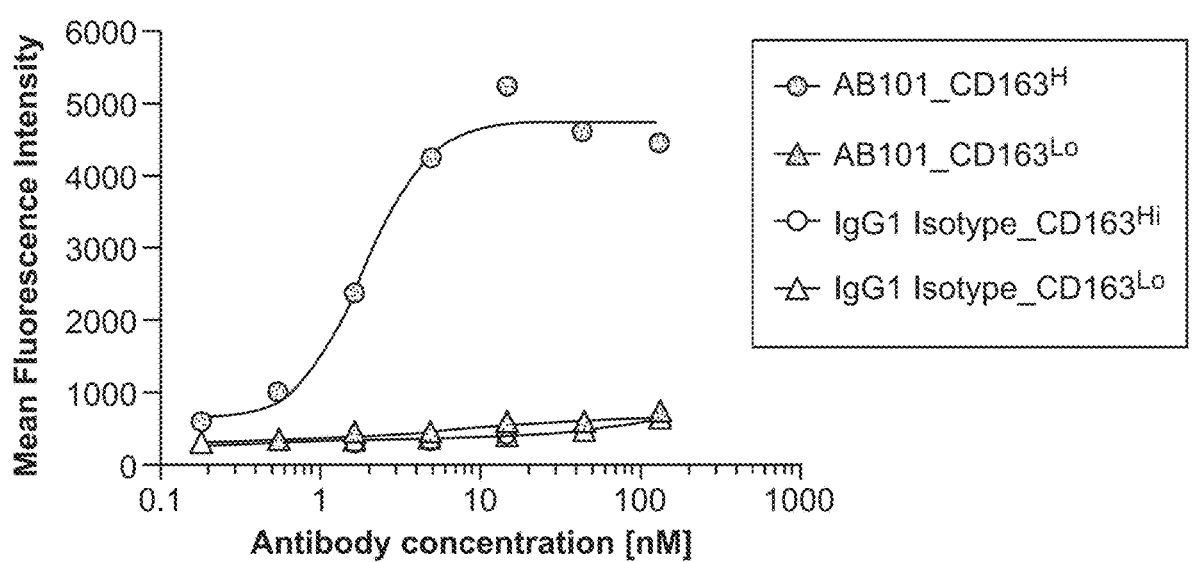
FIG. 2 shows AB101 binds to CD163$^{Hi}$ cells.

CD163 is a marker of cells from the monocyte/macrophage lineage. The expression of CD163 on in vitro differentiated MDSCs has been reported to be bimodal. It was hypothesized that bimodal binding of AB101 may correlate with CD163 expression. To test this hypothesis, in vitro MDSCs were generated (see EXAMPLE 11) and co-stained with anti-CD163 (BioLegend 333611) and with AF647 conjugated AB101 as described in EXAMPLE 8 and analyzed for binding by FACS. Cells were first gated as CD163 high or low and then examined for binding with various concentrations of AB101 or human IgG1 isotype control. The subpopulation of cells that the AB101 antibody was binding to was CD163$^{Hi}$ cells. See FIG. 2.

Example 2—Isolation of Autologous Monocytes and T Cells

This example shows the isolation of autologous monocytes and T cells. Human monocytes and T cells were obtained using techniques commonly used in the art. Human monocytes and T cells were isolated from white blood cells (WBCs) trapped within an integrated chamber, known as the LeukoReduction System (LRS) chambers, during the plateletpheresis collection process. Peripheral blood mononuclear cells (PBMC) were purified from the LRS samples by standard density gradient centrifugation (Ficoll™ Paque Premium 1.073, GE Healthcare No. 17-5449-52). The supernatant was discarded, and the pellet resuspended in 20 mL EasySep™ Buffer (StemCell Technologies No. 20144) for enumeration of PBMCs and further isolations of monocytes and T cells.

Monocytes were isolated using the EasySep Human Monocyte Isolation kit (Stem Cell No. 19359) following the manufacturer's instructions.

Total CD3, CD4, or CD8 T cells were isolated using the Human CD3$^+$ T Cell Isolation Kit (StemCell 19051), EasySep™ Human CD4$^+$ T Cell Isolation Kit (StemCell No. 17952), EasySep™ Human CD8$^+$ T Cell Isolation Kit (StemCell No. 17953), respectively, following the manufactures instructions. These negative selection kits used antibodies to label undesired cell types for removal, allowing the desired target cells to be isolated from the sample.

Example 3—AB101 Specific Binding to Immunosuppressive Myeloid Cells

Figure 4:
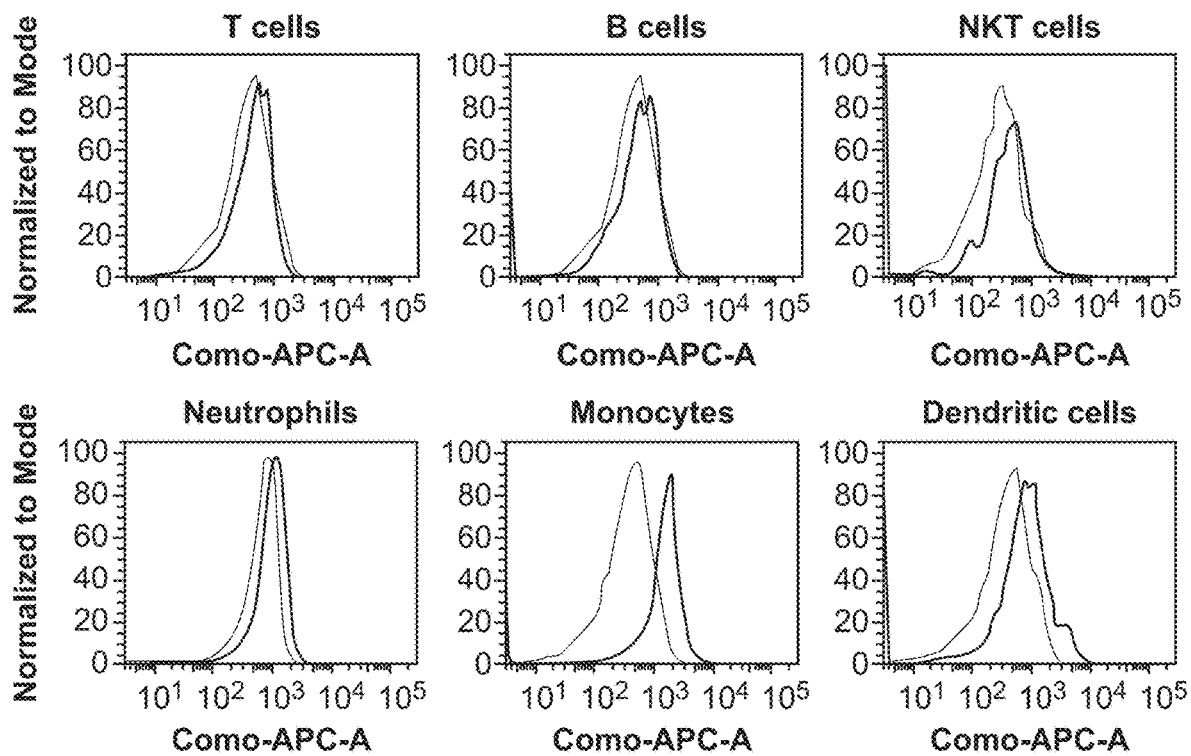
FIG. 4 shows AB101 binding to human peripheral blood T cells, B cells, NKT cells, neutrophils, monocytes, and dendritic cells, in which the isotype control is shown in gray and the AB101 binding is shown in black.
Figure 5:
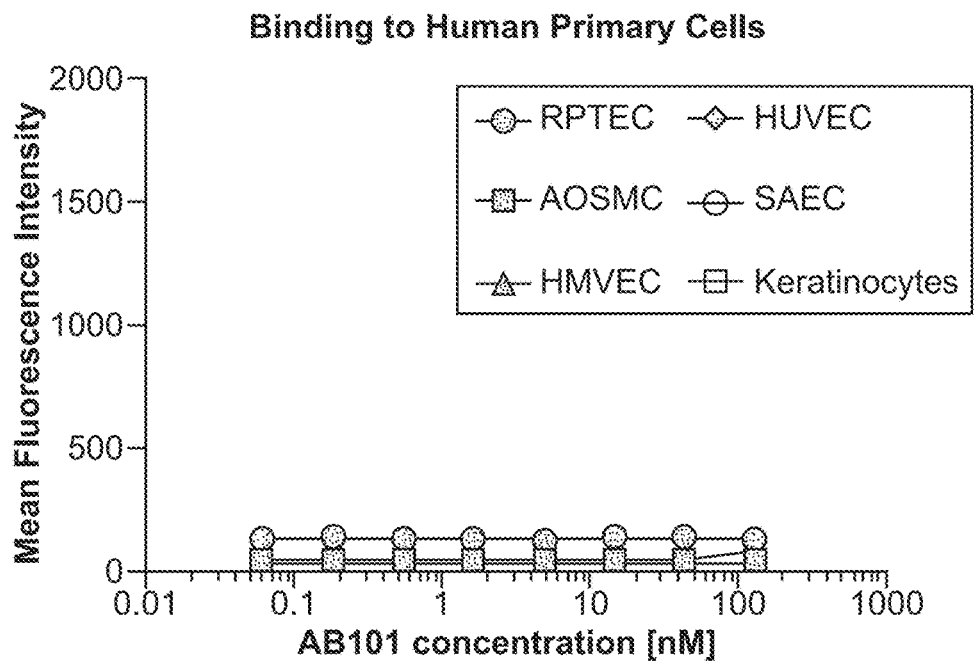
FIG. 5 shows no binding of AB101 to a panel of human primary cells, including small airway epithelial cells (SAEC), renal proximal tubule epithelial cells (RPTEC), lung microvascular endothelial cells (HMVEC), umbilical vein endothelial cells (HUVEC), aortic smooth muscle cells (AOSMC), and keratinocytes.

To assess specificity, the binding of an antibody of the invention, antibody AB101, conjugated to the far-red fluorescence dye AF647, was tested on different cell types, including MDSCs, immune suppressive M2c and pro-inflammatory M1 macrophages generated as described in EXAMPLE 11 and below. Additionally, separate immune populations from PBMCs of healthy donors were assessed for antibody binding. For each of these studies at least 3 individual donors were used. PBMCs were isolated from blood using a Ficoll gradient using standard procedures. To distinguish the immune cell populations, PBMC cells were then stained with hematopoietic lineage markers (CD45-BV421 (BD 642275), CD3-BV510 (BD 563109), CD11c-PE-Cy7 (BD 561356), CD14-FITC (BD 347493), CD20-APC-Cy7 (BD 562643), CD56-PE (BD 347747), and CD66c (BD 551478)). Separate lineage populations were further characterized by the following expression patterns and assessed for binding to AB101: T cells CD45$^+$CD3$^+$; B cells CD45$^+$CD20$^+$; monocytes CD45$^+$CD14$^+$, NK cells CD45$^+$SSC$^{low}$CD14$^-$CD3$^-$CD56+; granulocytes CD45$^+$SSC$^{Hi}$ CD4$^-$CD66+; and dendritic cells CD45+CD14$^-$CD66$^-$CD11c+. Antibody binding to primary human non-immune cells (Lonza) was also assessed, including small airway epithelial cells (SAEC, #CC-2547), renal proximal tubule epithelial cells (RPTEC, #CC-2553), lung microvascular endothelial cells (HMVEC, #CC-2527), umbilical vein endothelial cells (HUVEC, #C2519A), aortic smooth muscle cells (AOSMC, #CC2571), and keratinocytes (#00192627). These cells were cultured in cell type-specific medium and conditions per manufacturer's instructions until 60-70% confluency, den-then harvested to test for antibody binding by flow cytometry (FIG. 4 and FIG. 5).

In vitro monocytic MDSCs were generated from isolated monocytes by standard methods: Day 0, monocytes were plated in RPMI 1640 (Hyclone SH30027.02, serum-free) at 1.5×10$^5$/cm$^2$, incubated for 1 hour at 5% CO$_2$ and 37° C., then washed with pre-warmed RPMI before adding MDSC medium (RMPI+10% FBS (Hyclone SH30070.03)+50 ng/mL GM-CSF (R&D Systems 215-GM-010)+50 ng/mL IL-6 (R&D Systems 206-IL-010), 20 mL per T75 flask) to the cells. Cells were then cultured in 5% CO$_2$, 37° C. for 7 days without medium change. After 7 days, cells were harvested by washing 2× with PBS (Hyclone SH30028.03)+2 mM EDTA then adding cold Macrophage Detachment Solution (PromoCell C-41330) at 15 mL per T75 flask followed by incubation for 40 min at 2-8° C. Cells were dislodged by tapping the flask against the palm, collected and diluted 1:1 with PBS+2 mM EDTA. Cells were pelleted in a conical tube by centrifuging for 15 min at 450×g, washed once with PBS+2 mM EDTA, counted and resuspended at 1×10$^7$ per mL in FACS blocking buffer (PBS+1% FBS+0.1 µg/mL Fc block (Abcam Ab90285) for relaxed staining conditions, or PBS+1% FBS+Fc block 0.01 µg/mL CDR block (antibodies against FcR CD16, CD32, and CD64; BD Biosciences 556617, 557333, and 555525 respectively) for stringent staining conditions). Cells were incubated in FACS blocking buffer for 20 minutes (min) at room temperature (RT) then 30 min at 4° C. The cells were then diluted to 1×10$^6$ cells/mL with FACS buffer+5% BSA (Sigma A3059) and 40 µL of cells (4×10$^4$ cells) were aliquoted to wells for staining. Primary antibodies (AB101 at 20, 6, 2, 0.75, 0.25, 0.08, and 0.02 µg/mL or Human IgG1 Isotype control at 6 µg/mL) were added to the cells and incubated for 90 min at RT. The cells were washed 3× with 250 µL/well of FACS buffer+5% BSA. Secondary APC Goat anti-Human IgG (Jackson IR 109-136-097) antibodies were prepared at 1:250 in FACS buffer+BSA+e780 viability dye (at 1:1000 dilution) and added to cells (50 µL per well). After incubation at 4° C. for 45 minutes, cells were washed 3× in 250 µL FACS buffer. Cells were then fixed in 100 µL per well of 4% PFA for 10-15 min at RT, washed once with 250 µL FACS buffer, pelleted at 650×g for 5 min, then resuspended in 100 µL of FACS buffer for analysis by flow cytometry.

Figure 3:
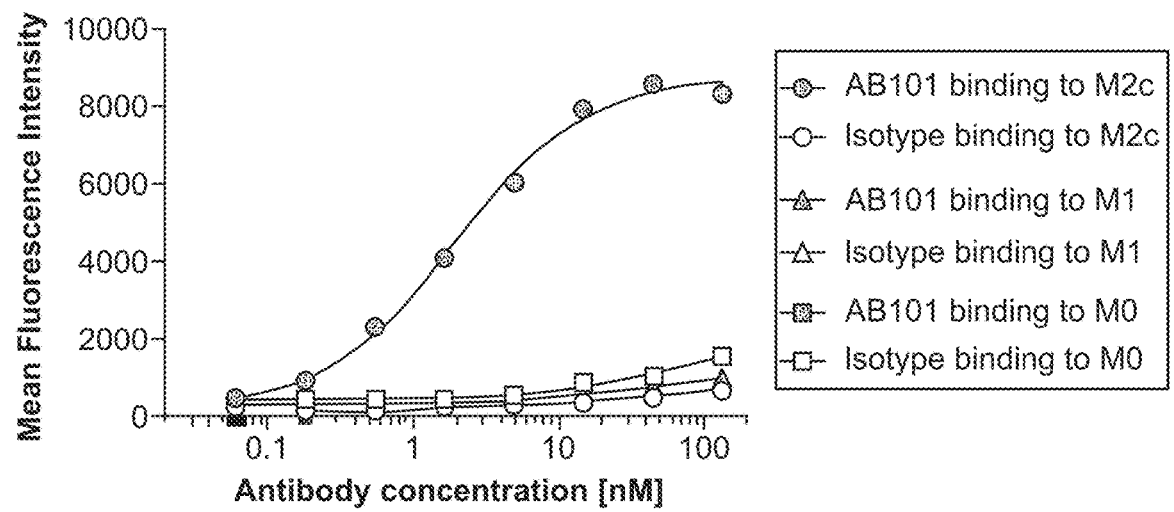
FIG. 3 shows AB101 binding to human M2c, M1, and M0 as compared to isotype controls.

The AB101 antibody binds to human immunosuppressive myeloid cells (M2c macrophages and monocytic MDSCs) as shown in FIG. 3, which plots the MFI of AB101 or isotype staining on M2c, M1, and M0. The AB101 antibody does not bind to B, T and NK cells, and granulocytes as illustrated in FIG. 4, which shows staining of AB101 on T, B and NKT cells, neutrophils, monocytes, and dendritic cells (black curve) compared to isotype control (gray curve), and non-immune cells such as SAEC, RPTEC, HMVEC, HUVEC, AOSMC, and keratinocytes as shown in FIG. 5. Thus, the AB101 antibody specifically binds to CD163-expressing immune-suppressive myeloid cells without impacting other immune or non-immune cells.

Example 4—AB101 FcNull Antibody Immunoprecipitates CD163 Polypeptide

This example shows immunoprecipitation of CD163 using an FcNull antibody comprising AB101 variable domains in an IgG1 sequence modified to substantially reduce binding of the antibody to Fc receptors (Fc null), designated AB102 comprising a light chain comprising SEQ ID NO: 9 and a heavy chain comprising SEQ ID NO: 11. Immunoprecipitation (IP) was performed based on Klockenbusch and Kast, J Biomed Biotechnol Article ID 927585 (2010). Antibodies were added prior to paraformaldehyde (PFA) fixative in a more classic cross-linked IP approach or prior to bis(sulfosuccinimidyl)suberate (BS3) crosslinking followed by an IP.

For IP involving the cross-linking using PFA approach, monocytes were isolated from human blood and then polarized into M2 cells using the protocol of EXAMPLE 2 and EXAMPLE 11, M2 macrophages were detached from the plate after incubation with macrophage detachment solution (Macrophage Detachment Solution DXF; PromoCell, No.

C-41330) at 37° C. for ~10 min, during which cells were rounded up and beginning to detach. The flasks were firmly tapped to facilitate cell detachment. After detachment the macrophage detachment solution was quenched by addition of FACS buffer to the cells. The cells were pelleted at 300×g for 10 min and the supernatant was removed. The cell pellet was resuspended in 30 mL of PBS containing 5% BSA (w/v) and 1 mM EDTA pH 8.0 and were incubated on ice for 30 min.

The cells were split into 6 aliquots of 15×10$^6$ cells per aliquot (5 mL per aliquot) and biotinylated antibodies were added to each. Two aliquots received 50 µg each of the mouse IgG1 anti-hCD163 (R&D, No. MAB1607), two aliquots received 100 µg each of an isotype-control antibody ISO2 (in Fc null framework) and two aliquots received 100 µg each of test antibody AB102 (comprising AB101 variable domains in an IgG1 sequence modified to substantially reduce binding of the antibody to Fc receptors (Fc null)). Cells were incubated at 4° C. for 1 hour (hr), with occasional gentle mixing by inversion of the tubes. Cells were pelleted at 300×g for 5 min and washed 3× with PBS-EDTA and then resuspended in 5 mL PBS (without magnesium or calcium; HyClone, No. SH30028.02). Paraformaldehyde (PFA; 5 mL of 0.8%) was added to each tube, for a final PFA concentration of 0.4%. The cells were incubated in PFA at room temp for 5 min with gentle rocking. The cells were pelleted by centrifugation at 800×g for 5 min and the supernatant was removed. The cells were resuspended in 10 mL of ice-cold PBS containing 1.25 M glycine to quench. The cells were pelleted at 800× g for 5 min and resuspended in ice-cold PBS. The cells were pelleted at 800× g for 5 min and resuspended in 1.0 mL of RIPA buffer containing 1× protease inhibitors (ThermoFisher Scientific, No. 89900). The cells were incubated on ice for 2 hr and then passed through a 2 mL Dounce homogenizer 15 times.

Cell lysates were spun in a hanging bucket centrifuge to pellet nuclei and supernatants were used for the IPs. Protein lysate (50 µL) was set aside as the input fraction and 2.0 mL of cold PBS containing 1× protease inhibitors was added to the remaining supernatant. Dynabeads MyOne Streptavidin (250 µL) (ThermoFisher Scientific, No. 65601) was added to each sample and they were rotated overnight at 4° C. The next day beads were collected with StemCell magnets and the supernatant was removed. The beads were sequentially washed with 5 mL of Paro Buffer I, 5 mL of Paro Buffer II, and 5 mL Paro Buffer III for 5 min at 4° C. (Oncotarget. 2017; 8(7): 11105-11113). The beads were then washed 3× with cold PBS and finally resuspended in 100 µL PBS and frozen at −80° C.

The beads were analyzed by mass spectrometry. This analysis was performed generally in accordance with the method described by Yan et al., *Mol Cell Proteomics* 10(3): M110.005611 (2011). In this method, the reversal of formaldehyde crosslinking and the elution of proteins from streptavidin beads was carried out the with 6 M guanidine, 150 mM Tris buffer (pH 8.3) at 60° C. for 3 hr with constant agitation. The supernatant was denatured, reduced, and alkylated in the same buffer with 10 mM tris(2-carboxyethyl)-phosphine (TCEP) and 50 mM chloroacetamide (CAA) at 95° C. for 10 min. The samples were then diluted 10× and digested with 1.3 µg trypsin each overnight at 37° C. The peptides were cleaned by C18 cartridges. One replicate of AB102 IP and one replicate of anti-CD163 IP were eluted from C18 cartridges for direct MS/MS analysis. One replicate of AB102 IP and one replicate of anti-CD163 were incubated with 0.1 M formaldehyde-d2, 0.4 M sodium cyanoborohydride in PBS buffer pH 7.5 for one hour to label with heavy dimethylation (d4) and both replicates of ISO2 (Fc null) IPs were incubated with 0.1 M formaldehyde, 0.4 M sodium cyanoborohydride in PBS buffer pH 7.5 for one hour to label with light dimethylation (d0) on C18 cartridges. Then the C18 cartridges were washed with 0.1% trifluoroacetic acid (TFA) and eluted by 80% acetonitrile (ACN). The d0/d4 dimethylated peptides were resuspended in Buffer A (20% ACN, 0.1% TFA) and then mixed. The peptides were fractionated using an in-house prepared microcapillary HPLC strong cation exchange column (SCX) (200 mm×20 cm; Proteomix SCX 3 µm, Sepax Technologies). Peptides were loaded onto the microcapillary column equilibrated in Buffer A and washed with Buffer A. Bound peptides were eluted with 20 µL of Buffer A containing 30%, 50% of Buffer B (800 mM ammonium formate, 20% ACN, pH 2.8), followed by 20 µL elution with Buffer D (0.5 M ammonium acetate, 50% ACN). All the samples were dried by Speed-Vac and directly analyzed by Thermo-Oritrap-Fusion. The spectra were searched against human UniProt database by Comet search engine (https://sourceforge.net/projects/comet-ms/). For demethylation labels, differential modification of 28.03 Da (for d0 dimethylation) and 32.06 Da (for d4 dimethylation) on the N-termini and Lys side-chain were used.

The heavy/light samples were run through an in-line HPLC column using strong cation exchange column (200 mm×20 cm; Proteomix SCX 3 µm, Sepax Technologies) and subjected to MS/MS using Thermo-Oritrap-Fusion. For heavy and light labeled samples only spectra that were fully methylated were included. Eighty-nine proteins were identified where all peptides contained the heavy isotope, indicating that the protein was identified in the AB102 IP but not in the negative control. Of the 89 proteins unique to the AB102 IP, 12 were considered to be plausibly on the cell surface: CD163, RIPK1, NEUA, SLC31, LRP8, SLIT1, RAF, ILK, ATRN1, MCA32, FNBP2, and LRRN3. One additional protein, TNR5, was found to have two heavy methylated peptides and one unmethylated peptide (IP origin unknown), suggesting it could also be exclusive to the AB102 IP.

Peptides from one replicate of AB102 IP and one replicate of the control anti-CD163 IP were individually analyzed by mass spectrometry. Of the 360 proteins identified in the AB102 IP, 45 of them were curated as potentially membrane-bound or secreted. Of the proteins identified in other data sets, the following were found in the AB102 IP: CD163, Galectin-1, Galectin-3, and Peptidyl-Prolyl Cis-Trans Isomerase A (PPIA). Casein kinase IIb, which has been reported to interact directly with CD163, was also identified in this dataset.

For IP by cross-linking using BS3 approach, macrophages were harvested by collecting supernatants from flasks into 250 mL centrifuge tubes. Cold Macrophage Detachment Solution (30 mL) was added to each flask and incubated for 45 min at 4° C. The flasks were then scraped with a scraper and cells were collected into 250 mL centrifuge tubes and centrifuged at 650×g for 10 min. The medium was aspirated, leaving the cell pellet in the tube. The cells were then resuspended in 20 mL cold PBS+2 mM EDTA.

The cells were then diluted to 1×10$^7$ cells/mL with PBS+2 mM EDTA and were split into three volumes of 40%, 40%, and 20% total volume. AB102 (2.5 mg) was added to one of the 40% fractions. An anti-PDL1 antibody in an FcNull framework (2.5 mg) was added to the other 40% fraction, which was the positive control. The isotype control (ISO2 in FcNull framework, 1.25 mg) was added to the 20% fraction, which was the negative control. Each fraction was incubated with gentle mixing for 2 hr at 4° C. They were then centrifuged at 650×g for 10 min and the supernatant was carefully decanted. The pellets were each resuspended in 15 mL PBS+EDTA and then centrifuged at 650×g for 10 min. This wash step was then repeated. The wash buffer was next carefully removed without disturbing the pellets. The pellets from the 40% fractions were resuspended in 2 mL cross-linking buffer. The pellet from the 20% fraction was resuspended in 1 mL cross-linking buffer. A stock concentration of 50 mM BS3 was dissolved in 70 μL of UltraPure water per each 8 mg vial. BS3 (60 μl/mL of cells) was added to each resuspended cell fraction, for a final concentration of 3 mM BS3, and each cell fraction was mixed gently by swirling. Cell fractions were then incubated on ice for 1 hour, swirling to mix every 10 minutes. After BS3 incubation, 15 mL quench solution was added directly to cells and incubated for 15 minutes at room temperature. The cells were centrifuged for 15 min at 1200× g, and the quench buffer was carefully decanted. The pellets were washed 1x with PBS+EDTA as previously described. The cells were then lysed by adding 20 mL of lysis buffer (Pierce™ IP Lysis Buffer #87788) to each of the 40% fractions and 10 mL to the 20% fraction and subsequently incubated on ice for 15 min. The cell lysates were then centrifuged for 10 min at 13,000×g at 4° C.

MabSelect SuRe resin (GE Healthcare Life Sciences, No. 17543801) was prepared for use in the IP and protein purification of the prepared cells. Sterile Mab Select Sure was equilibrated with 20 column volumes (CV) sterile PBS. One hundred and fifty microliters of Mab Select SuRe was used for the AB102 and positive control samples and 75 μL was used for the ISO sample. The sterile and equilibrated MabSelect SuRe resin was then transferred to 50 mL conical tubes. After centrifugation, supernatant was added to tubes with prepared MabSelect SuRe resin. Samples were incubated overnight with end-over-end mixing at 4° C. The next day, samples were allowed to settle on ice for 10 min. MabSelect SuRe resin was transferred by pipet to a disposable drip column. Resin was washed with 20 column volumes sterile PBS. Prior to elution, the column was placed in a collection tube and centrifuged for 30 seconds (s) at 9,000 rpm in an Eppendorf benchtop microcentrifuge to remove excess liquid. A stopper was placed on the bottom of the column. Sample was eluted from the resin by adding one column volume of 50 mM glycine pH 2.5 as elution buffer to the stoppered column and mixing with pipet, then allowing the mixture to incubate at RT for 8 min. (One-tenth of the total volume (resin and elution buffer) was removed from each sample and set aside for determination of cross-linking by western blot analysis. See below. The remaining samples were neutralized by adding ⅒ volume of 2 M Tris pH 8.0. Eluate was collected by removing stopper from bottom of the column and immediately placing drip column in a 1.8 mL Eppendorf centrifuge tube. Column assembly was centrifuged for 30 s at 9,000 rpm in a benchtop microcentrifuge unit. Eluate was neutralized by adding ⅒$^{th}$ eluate volume of sterile 2 M Tris pH 8.0 to the eluate fraction. Elution protocol was repeated to ensure complete protein removal. Eluate fractions were stored at −80° C. until western blot confirmed cross-linking. Western blot analysis for confirmation of cross linking The reserved eluate fractions were mixed with Laemmli Sample Buffer (Bio-Rad, No. 161-0747)+10% 2-mercaptoethanol. Samples were heated at 90° C. for 10 minutes. Samples were loaded on a 4-12% Bis-Tris gradient polyacrylamide gel. The gel was run for 80 min at 200 V. After the running, the gel was transferred to PVDF western blot membrane and run overnight at 4° C. at 25 V. The next morning the blot was blocked for 3 hr at RT with SuperBlock (ThermoFisher Scientific, No. 37515). After blocking, the membrane was washed 1× in SuperBlock. The western blot was probed with 1:1000 anti-human IgG HRP overnight at 4° C. The following day, the blot was washed 4× with PBST at 10 min per wash. The western blot was washed with PBS 1× for 10 min. The western blot was then developed with SuperSignal West Dura Extended Duration Substrate (ThermoFisher Scientific, No. 34076). Upon exposure, the western blot showed clear super-shifted bands representing positive cross-linking for AB102. Cross-linked bands were also observed for the positive control antibody. As expected, no molecular weight shift was observed for ISO.

The remainder of the samples were then acetone precipitated, run on SDS-PAGE gels in which the cross-linked bands were then excised and prepared for mass spectrometry evaluation. The eluate samples (AB101, ISO, and positive control from above) were thawed. Four times the eluate volume of cold (−20° C.) acetone was added to each sample. The samples were then vortexed vigorously and incubated at −20° C. for 1 hr. The samples were centrifuged for 10 min at 15,000×g. The supernatant was decanted, being careful not to disrupt pellet. The pellets were dried in speed vac for 5 min or until liquid has evaporated. The pellets were resuspended in 15 μL per tube and mixed until dissolved. Eluates were combined for each condition. Sample loading buffer+10% 2-mercaptoethanol was added and the samples were heated for 5 min at 90° C. Five microliters of each sample was reserved for SYPRO Ruby Protein Gel Stain (ThermoFisher Scientific, No. S12000) analysis. The entire remaining volume of sample was loaded on 4-12% Bis-Tris gradient polyacrylamide gel and run on the gel for 80 min at 200 V. The gel was removed from the cassette and washed 3×10 min with Mass Spectrometry grade water. The gel was then stained with Safe Stain blue for 1 hr. The stain was decanted and then the gel was destained with mass spectrometry grade water by 2 washes at 30 min per wash. Scalpels and tweezers were extensively sprayed with ethanol (EtOH) before the cross-linked bands were excised from the gel and placed in sterile Eppendorf tubes. The tubes were filled with enough sterile, ultrapure water to cover gel sections, packed on wet ice, and shipped to MS Bioworks.

The mass spectrometry analysis by MS Bioworks was performed. For the mass spectrometry, all of each submitted sample was processed by in-gel digestion with trypsin using a ProGest robot (DigiLab) by first washing with 25 mM ammonium bicarbonate followed by acetonitrile, reducing with 10 mM dithiothreitol at 60° C. followed by alkylation with 50 mM iodoacetamide at RT, digesting with trypsin (Promega) at 37° C. for 4 hr, and then quenching with formic acid, digests were pooling and analyzing without further processing. Each digested sample was then analyzed by nano LC-MS/MS with a Waters M-Class NanoAcquity HPLC system interfaced to a ThermoFisher Fusion Lumos. Peptides were loaded on a trapping column and eluted over a 75 μm analytical column at 350 nL/min; both columns were packed with Luna C18 resin (Phenomenex, No. 00C-4041-E0). The mass spectrometer was operated in data-dependent mode, with the Orbitrap operating at 60,000 FWHM and 15,000 FWHM for MS and MS/MS with a 3 s cycle time. Advanced Peak Determination was enabled. 4 hr of instrument time was used/sample. For the data processing by MS Bioworks, data were searched using a local copy of Mascot (Matrix Science) with the following parameters: Enzyme: Trypsin/P; Database: SwissProt Human (concatenated forward and reverse plus common potential contaminants); Fixed modification: Carbamidomethyl (C); Variable modifications: Oxidation (M), Acetyl (N-term), Pyro-Glu (N-term Q), Deamidation (N/Q); Mass values: Monoisotopic; Peptide Mass Tolerance: 10 ppm; Fragment Mass Tolerance: 0.02 Da; and Max Missed Cleavages: 2. Mascot DAT files were parsed into Scaffold (Proteome Software) for validation, filtering and to create a non-redundant list per sample. Data were filtered at 1% protein and peptide FDR and requiring at least two unique peptides per protein. Spectral Abundance Factor (SAF) was converted to Normalized Spectral Abundance Factor (NSAF), which was used to approximate relative abundance of proteins within a given sample, and relative abundance of a given protein between samples.

Figure 6A:
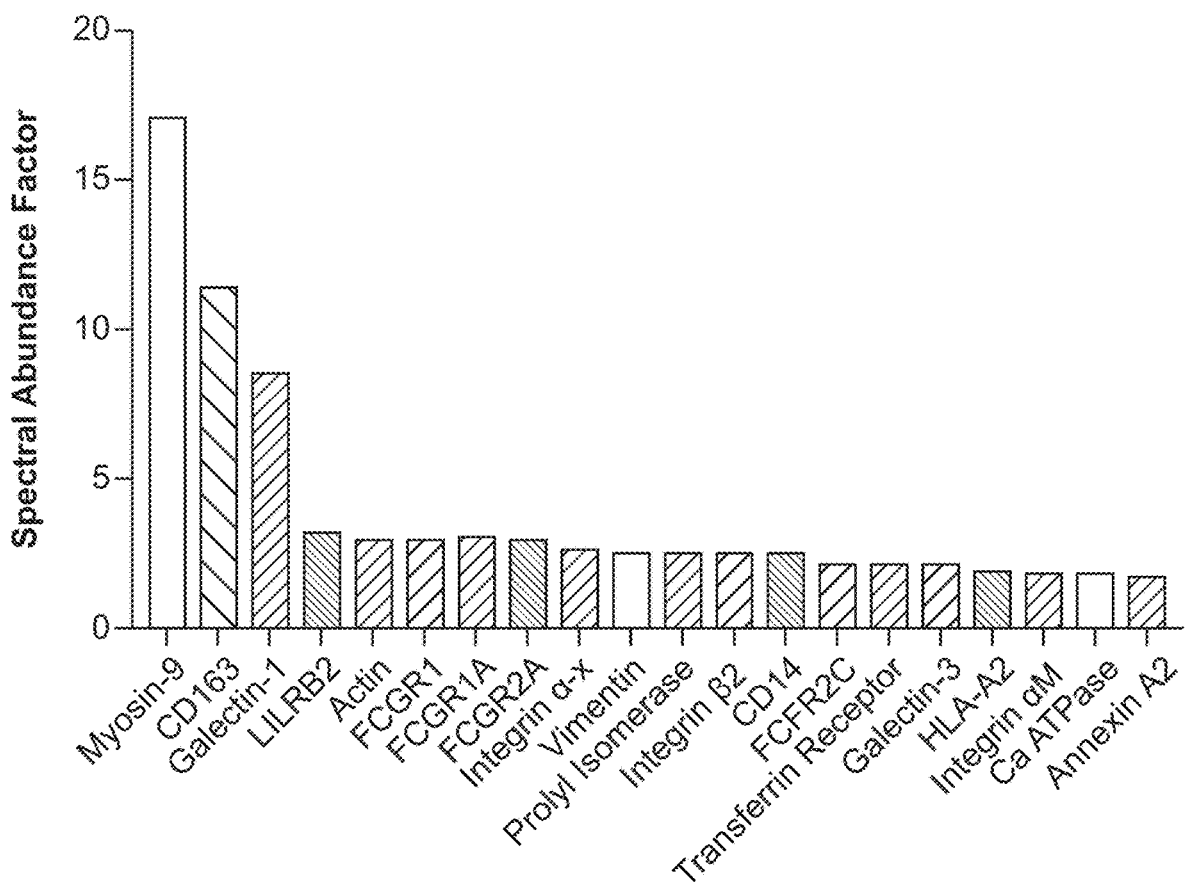
FIG. 6A shows the top 20 targets for AB102 based on mass spectrometry analysis of a sample after immunoprecipitation.
Figure 6B:
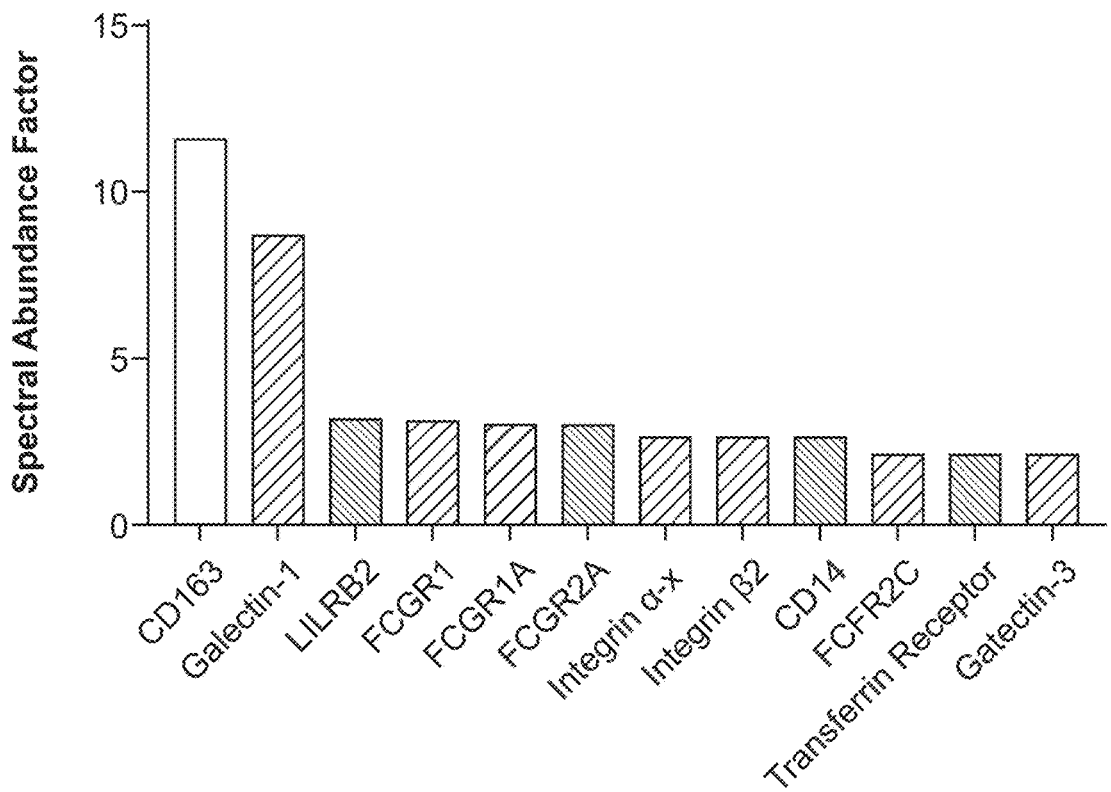
FIG. 6B shows the top cell surface targets for AB102 based on mass spectrometry analysis of a sample after immunoprecipitation.
Figure 6C:
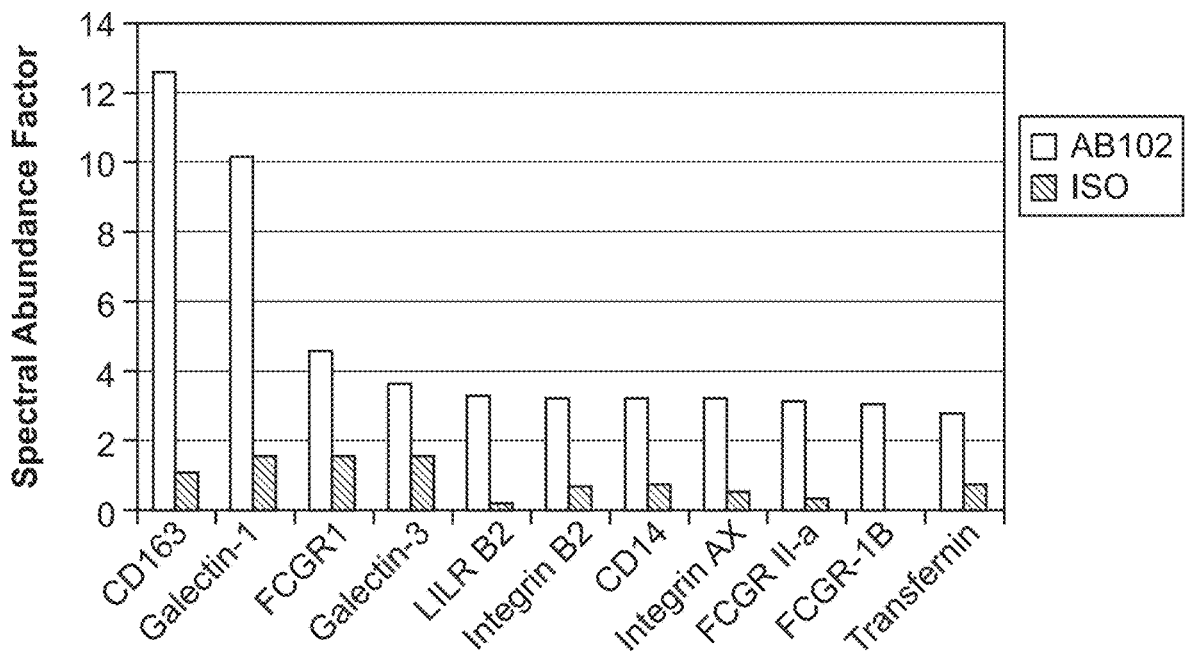
FIG. 6C shows the top cell surface targets for AB102 compared to ISO (isotype negative control) based on mass spectrometry analysis of AB102 and ISO samples after immunoprecipitation.

Examination of proteins observed in the BS3-cross-linked data from MS Bioworks did not support the full list of targets identified in the above IP involving PFA. Galectin-3 was found in both the heavy and light data with greater representation in the light data set. Galectin-1 was found in both the heavy and light data with only 3/5 peptides labeled with the heavy isotope. LILRB2 was not observed. uPAR was not observed. PPIA was found in both the heavy and light data with near equal representation in both. FIG. 6A shows the top 20 targets for AB102. FIG. 6B shows the top cell surface targets for AB102. FIG. 6C shows the top cell surface targets for AB102 compared to isotype negative control (ISO). Of the cell surface proteins immunoprecipitated with AB102 using a BS3 cross-linker, CD163 had the highest spectral abundance factor (SAF). CD163 was immunoprecipitated with AB102 by both the PFA and BS3 methods. SAF=spectral counts normalized to protein size (molecular weight) for each target, and SAF values in FIG. 6A and FIG. 6B are values for AB102 subtracted from SAF for isotype control for each target.

Example 5—AB101 Antibody in FcNull Framework Immunoprecipitates a Glycoform of CD163

Glycosylation is a highly regulated post-translational modification that affects the protein conformation, stability and function, and it plays a critical role in establishing protein-protein interactions (i.e., the binding of ligand to its cognate receptor). The AB102 antibody, and by extension AB101, has specificity for a distinct higher molecular weight glycoform of CD163, which potentially affects CD163 interactions with other proteins necessary for the activity of immune suppressive macrophages.

The AB101 FcNull antibody comprises AB101 variable domains in an IgG1 sequence modified to substantially reduce binding of the antibody to Fc receptors (Fc null), and is designated as AB102. For analysis by western blot and SYPRO Ruby Protein Gel Stain, 12 μL of 4× NuPAGE LDS Sample Buffer (ThermoFisher, No. NP0007) with 10% 2-mercaptoethanol was added to a 25 μL aliquot of PBS-beads from EXAMPLE 4 and incubated at 95° C. for 25 min. Samples were run on 4-12% Bis-Tris gradient polyacrylamide gels. For direct visualization, gels were stained with SYPRO Ruby Protein Gel Stain per the manufacturer's instructions. For western blots, proteins were transferred to a PVDF membrane at 20 V overnight at 4° C. The following morning, the membranes were blocked in 5.0 mL of Super-Block (ThermoFisher, No. 37515; no Tween 20) for 1 hr. Primary anti-CD163 antibody (goat IgG polyclonal; R&D, No. AF1607) was added to the membrane at a concentration of 1 μg/mL. After an approximately 3-hr incubation in primary Ab (rocking at room temp) the membrane was washed 3× with approximately 5 mL of PBST, 5 minutes per wash. Following washes, a 5 mL of SuperBlock (no Tween 20) containing 1:10,000 (v/v) HRP-conjugated anti-goat F(ab')2-specific secondary Ab (various vendors) was added to the membrane and incubated at room temp for approximately 1 hr. After incubation with the secondary Ab, the membrane was washed 3× with 5 mL PBST for approximately 5 min per wash. The membrane was imaged using SuperSignal West Dura Extended Duration Substrate with a FotoDyne Analyst Luminary Convertible transilluminator FX workstation according to the manufacturer's instructions.

Figure 7:
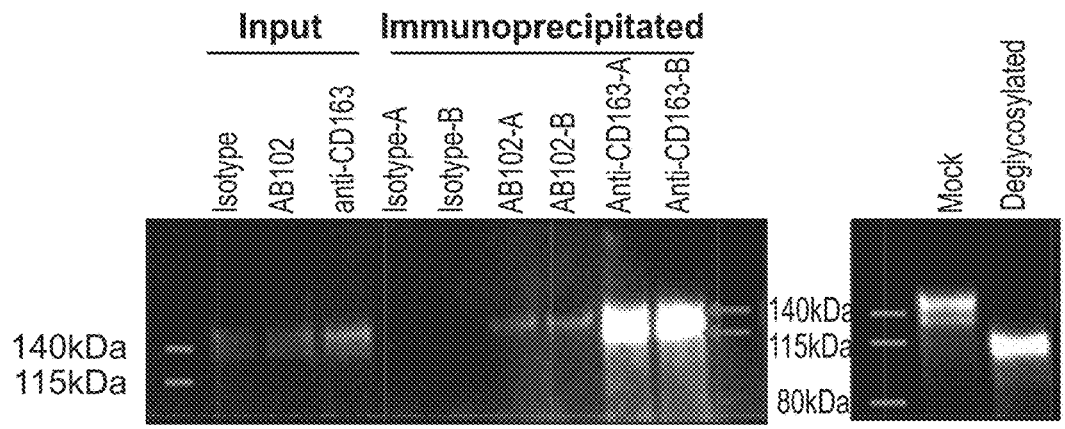
FIG. 7 shows AB102 coimmunoprecipitates a distinct higher molecular weight glycoform of CD163.

As shown in FIG. 7, AB102 immunoprecipitates a distinct higher molecular weight glycoform of CD163. Both bands in the doublet indicated by arrows appear to be distinct glycoforms of CD163.

Example 6—AB101 Binds to Human, but not Mouse, Recombinant CD163 Protein

This example shows that AB101 binds to human, but not to mouse, recombinant CD163 protein. AB101 binding to His-tagged recombinant human CD163 (R&D Systems, No. 1607-CD-050) and recombinant murine CD163 (R&D Systems, No. 7435-CD-050) proteins was determined using ELISA. Recombinant proteins were diluted in PBS to 5 μg/mL and added to 384-well High binding ELISA plates (Greiner Bio-One, No. 781061) at 25 μL per well and incubated at 4° C. overnight. The plates were washed three times with PBS, using the BioTek ELx405 Select microplate washer (wash program ELISA_384_PBS_3x_wash) and then blocked with 90 μL/well of blocking buffer (2% nonfat, dry milk/PBS+0.05% Tween 20) for 1 hr at RT.

After blocking, 25 μL per well of primary antibodies were added to the plates and incubated for 1 hr at room temp. The test antibody was AB101; the control anti-huCD163 antibody was a commercially available antibody in murine IgG1 framework (R&D Systems, #MAB1607); the isotype controls were a proprietary mAb, in human IgG1, human FcNull, and murine IgG1 frameworks, with known specificity. After primary antibody binding, plates were washed three times with PBS using the EL405x (wash program ELISA_384_PBS_3x_wash). The secondary antibody for anti-hu CD163 was the goat anti-mouse IgG F(ab)'2 HRP (Jackson Immunoresearch, No. 115-035-072), and secondary antibody for AB101 and AB102 was goat anti-human IgG F(ab)'2 HRP (Jackson Immunoresearch, No. 109-035-097). Secondary antibodies were diluted to 1:2500 in 2% nonfat, dry milk/PBS and 25 μL per well was added to the respective plate and incubated at room temp for 1 hr. The plates were washed four times with PBS, using the EL405x (Wash program ELISA_384_PBS_4x_wash). After removal of the final wash, 25 μL/well of neat Ultra-TMB was added and the plates were incubated for 10-15 min at room temp, protected from light. After development, the reaction was stopped by adding 25 μL per well of 0.3 M HCl and plates were read using the SpectraMax M5e instrument at 450 nm.

Figure 8:
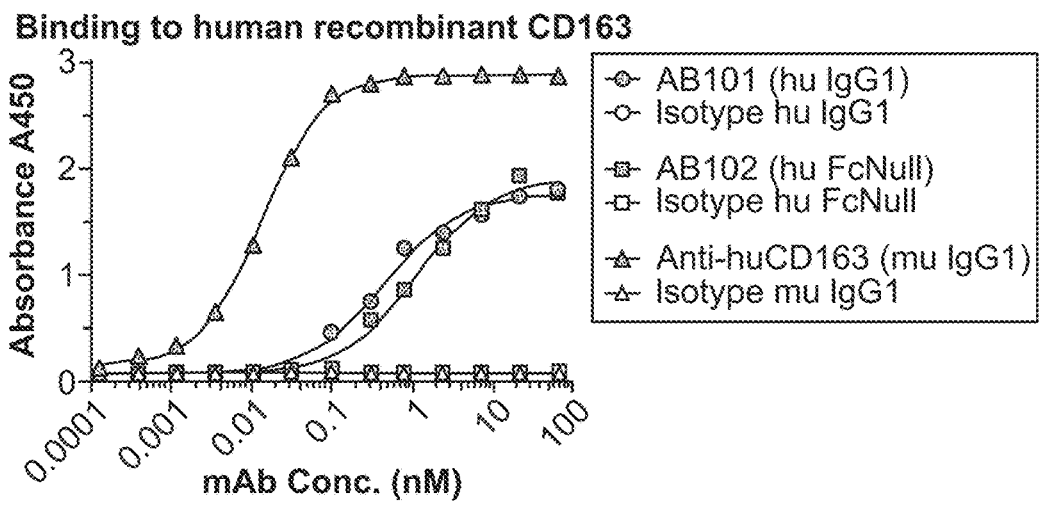
FIG. 8 shows AB101, AB102, and the control CD163 antibody bind to huCD163, while the isotype control showed no appreciable binding.
Figure 9:
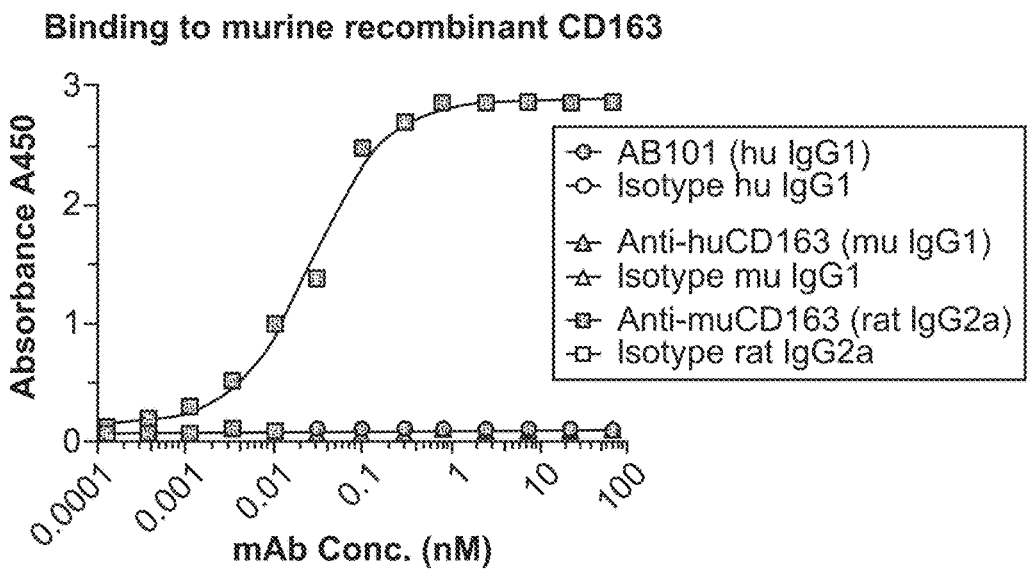
FIG. 9 shows neither AB101 nor the control anti-huCD163 antibody bound to the recombinant murine CD163 compared to a commercially available anti-muCD163 antibody, which did bind to murine CD163.

As shown in FIG. 8, the AB101, AB102, and the control CD163 antibody bound to huCD163 in this assay, while the isotype control showed no appreciable binding. Neither AB101 nor the control anti-huCD163 antibody bound to the recombinant murine CD163, while a commercially available anti-muCD163 antibody bound as expected (FIG. 9).

Example 7—Polyclonal Anti-CD163 Antibody Blocks Binding of AB101 to M2c Macrophages This example shows polyclonal anti-CD163 antibody blocks binding of AB101 to M2c cells. To examine the specificity of AB101 binding to CD163 on M2c cells, blocking experiments were performed using a commercial polyclonal antibody to human CD163.

The harvested M2c cells were resuspended (1 million cells per 100 µL) in FACS buffer (PBS containing 2 mM EDTA) (ThermoFisher No. 15575-038) and an appropriate volume of human Fc-block (10 µg of recombinant human Fc block per million cells) was added. The cells were incubated at RT for 20 min. Goat anti-huCD163 polyclonal antibody (R&D, #AF1607) and Goat control polyclonal antibody (Sigma, #PP40) were added at a final concentration of 200 µg/mL and incubated at RT for 1 hr. The cells were diluted with FACS buffer to a final volume of 1 million cells/mL and 40 µL/well were transferred to v-bottom polypropylene opaque 96-well plates.

Alexa Fluor® 647 labeled AB101 and APC-labeled anti-huCD163 (R&D Systems, #FAB1607A) antibodies were added, and the cells incubated for 90 min at 4° C. The cells were washed by adding 250 µL of FACS buffer containing 5% BSA to each well using a multidrop, centrifuged at 350×g for 5 min, and the buffers were removed. The wash step was repeated 2× with wash volume of 300 µL FACS buffer. 50 µL of FACS buffer with viability dye e780 (1:1000 dilution) was added to each well, and the plates incubated for 20 min at RT. The cells were then washed by adding 250 µL of FACS buffer to each well using the multidrop, centrifuged at 350×g for 5 min, and the buffers were removed. FACS buffer (75 µL) was added to each well and sample analysis performed using a BD Canto II flow cytometer.

Figure 10:
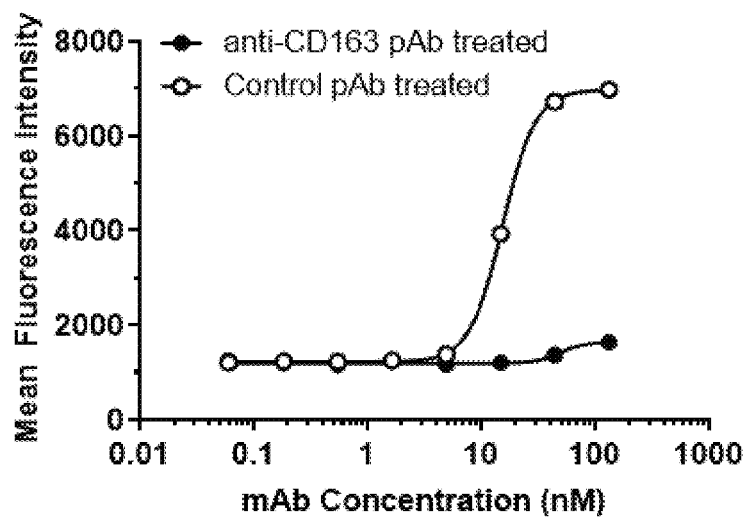
FIG. 10 shows pretreatment of M2c macrophages with polyclonal anti-CD163 antibody blocked binding of the AB101 antibody compared to treatment with goat control polyclonal antibody, which did not block binding of AB101.
Figure 11:
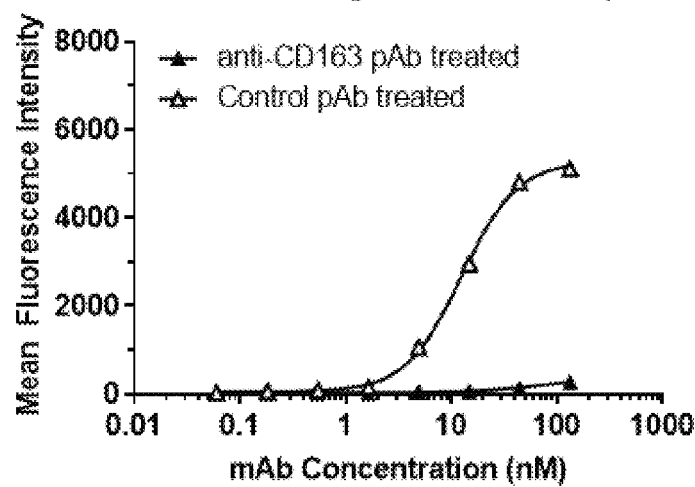
FIG. 11 shows pretreatment of M2c macrophages with polyclonal anti-CD163 antibody blocked binding of a control monoclonal anti-huCD163 antibody compared to treatment with goat control polyclonal antibody, which did not block binding of the control monoclonal anti-huCD163 antibody.

The pretreatment of M2c macrophages with polyclonal anti-CD163 antibody blocked binding of the AB101 antibody (FIG. 10) and a control monoclonal anti-huCD163 antibody (FIG. 11) to M2c macrophages. The pretreatment of M2c macrophages with goat control polyclonal antibody did not block binding of the AB101 antibody (FIG. 10) and a control monoclonal anti-huCD163 antibody (FIG. 11) to M2c macrophages.

Example 8—sIRNA Knockdown of CD163 in Human M2c Macrophages After Polarization Reduces Binding of AB102

This example shows siRNA knockdown of CD163 in human M2c macrophages after polarization reduces binding of AB102. The methods used in this example are based on Troegeler et al., *Immunol Cell Biol* 92:699-708 (2014).

Isolated monocytes (from three donors) were separately plated at 1.5×10$^6$ cells per well in 6-well plates. On Day 4, the medium was removed and fresh X-VIVO medium containing 10% FBS, 100 ng/ml M-CSF (Peprotech No. 300-25), and 50 ng/mL IL-10 (Peprotech No. 200-10) was added to each well. On Day 6, the medium was removed, and the cells were washed twice with warm X-VIVO medium containing 10% FBS. One milliliter of X-VIVO medium+10% FBS was added to each well and cells were returned to the incubator while the siRNA transfection solutions were prepared.

The following human ON-TARGETplus siRNA— SMARTpool Reagents (Dharmacon) were tested: CD163 (Cat. No. L-007847-00-0005); SCRAM (Cat. No. D-001810-10-05); CD206 (Cat. No. L-011730-00-0005); CD163L1 (Cat. No. L-008024-00-0005); PPIA (Cat. No. L-004979-04-0005); FCGR2A (Cat. No. L-014152-00-0005); FCGR3A (Cat. No. L-016308-00-0005); LGALS1 (Cat. No. L-011718-00-0005); LGALS3 (Cat. No. L-010606-00-0005); LILRB2 (Cat. No. L-020017-00-0005); FCGR2C (Cat. No. L-027340-02-0005); and UPAR (Cat. No. L-006388-00-0005).

To prepare the siRNA transfections, ON-TARGETplus SMART siRNA pools were used to make 200 µM master stocks. Lyophilized oligonucleotides (5 nmol each) were resuspended in 25 µL of 1× Thermo siRNA buffer (Thermo No. B002000). Aliquots were stored at −80° C. These master stocks were then diluted with cell grade ultrapure water (Hyclone No. SH3052902) to make 20 µM working stocks. To make the master mix (enough for 6 wells of a 6-well plate), the following reagents were mixed: 120 µL 20 µM siRNA pool (final concentration 200 nM), 270 µL of HiPerFect (Qiagen No. 301705), and 2.64 mL warm RPMI (with no FBS or other additives). The master mix for siSCRAM (scrambled siRNA) contained the following amounts: 720 µL 20 µM siSCRAM, 1.23 mL HiPerFect, and 12.1 mL RPMI. The mixtures were combined and incubated at RT for 15 min, with periodic mixing by inversion. Just before use, tubes were centrifuged briefly, and the siRNA mix (495 µL/well) was added dropwise to cells. Plates were rocked gently to mix and then incubated at 37° C. for 6 hr. Following incubation, 2 mL of X-VIVO medium containing 10% FBS and IL-10 (final concentration 50 ng/mL) and M-CSF (Peprotech No. 300-25; final concentration 50 µg/mL) was added. The following day the medium was changed (keeping in IL-10 and M-CSF) to remove transfection reagent and any dying cells.

On day 8, the macrophages were either lifted and stained with antibodies for flow cytometry or lysed for RT-qPCR.

For those macrophages used for flow cytometry, the following method was used. siRNA-treated M2 macrophages were harvested with macrophage detachment solution, incubated in detachment solution at 4° C. for 45 min, and then gently scraped off the plates. The macrophage detachment solution was replaced with cold PBS−/− (PBS without calcium and magnesium; Hyclone No. SH30028.02) containing 0.2 mM EDTA and 0.1% HSA. The cells were spun down at 650× g for 5 min and then resuspended in 0.5 mL cold Block solution (FACS buffer+10% NGS+10 µg of human IgG Fc fragment protein (Abcam No. ab90285)) per million cells. The cells were counted and an average of 1×10$^6$ per mL was used for further calculations. The cells were incubated at RT for 15 min (to increase FcR binding), followed by a 30 min incubation on ice for full blocking. An aliquot of unstained cells was set aside for compensation controls. e780 viability dye (ThermoFisher eBioscience No. 65-0865-18) was added to the remainder at a final dilution of 1:1000. Cells were aliquoted into 96-well plates (40 µL per well), and 10 µL of antibody solution was added to each well. Antibodies were prepared with a starting concentration of 100 µg/mL in FACS buffer and serially diluted in FACS buffer. After addition of antibodies, each set of cells was tested with an antibody panel (AB101 in FcNull framework conjugated to AF647 and commercial anti-CD163 conjugated to BV421 [BioLegend No. 333612]) and an isotype panel (ISO2 in FcNull framework conjugated to AF647 and commercial mIgG1 conjugated to BV421). Final antibody concentration ranged from 20 µg/mL to 0.3 µg/mL. Cells were incubated in primary antibody for 1 hr at 4° C., then pelleted at 450× g and washed three times with 150 µL PBS-EDTA. After pelleting, cells were then resuspended in 100 µL 4% paraformaldehyde (in PBS −/−) and incubated at RT for 15 min (protected from light). After fixation, cells were spun down at 650× g for 5 min and washed once with PBS-EDTA. Cells were resuspended in 100 µL PBS-EDTA and stored at 4° C. over the weekend (protected from light). Cells were then analyzed by flow cytometry on a BD Canto II machine.

A second set of cells was harvested for use in RT-qPCR assays, as follows. Cells were harvested in buffer RLT and RNA was isolated using the Qiagen RNeasy kit (Qiagen No. 74104), including QIAshredders (Qiagen No. 79654). After elution, RNA was used to make cDNA using the SuperScript III first-strand synthesis system (Invitrogen No. 18080051). To 1.5 µg RNA, RNase-free water was added to a final volume of 10 µL. Added to this was 5 µL of DnaseI master mix ((per sample)=1.5 µL 10× DnaseI buffer+2 µL RNase-free water+1.5 µL DnaseI enzyme). Samples were mixed well and incubated at room temp for 15 min. After incubation, 1.5 µL EDTA solution was added to stop the reaction, the samples incubated at 65° C. for 10 min (to kill the enzyme), and then returned to ice to cool down. dNTPs (1.5 µL) and oligo-dT (1.5 µL) were added to each sample and mixed well. The samples were incubated at 65° C. for 5 min and then returned to ice for 2 min. After samples were chilled, 13 µL of sample was removed to fresh tubes and +RT master mix (7 µL) was added to each. To the remaining 7.5 µL of sample, -RT master mix (3.5 µL) was added for the negative control samples. For the +RT master mix (per sample): 4 µL 5× First strand buffer, 1 µL 0.1 M DTI, 1 µL RNaseOUT, and 1 µL SuperScript III reverse transcriptase enzyme (all part of the SuperScript III system referenced above). For the -RT master mix, the SuperScript III enzyme was replaced with RNase-free water.

Samples were mixed well and incubated at 25° C. for 5 min. After incubation, the samples were incubated at 50° C. for 30 min, followed by incubation at 55° C. for 30 min, and then incubation at 70° C. for 15 min. Samples were then cooled to 4° C. before proceeding and kept on ice. Before use, 20 µL of RNase-free water was added to the +RT samples and 10 µL of RNase-free water added to the -RT samples to dilute the cDNA for RT-qPCR.

For the qPCR, 2 µL of diluted cDNA was mixed with 0.2 µL of each primer (10 µM stock concentrations), 2.6 µL RNase-free water, and 5 µL of 2×SYBR Green qPCR mix (BioRad No. 1725271). Standard curves were made using a dilution series of the untreated control cells. Samples were run on the StepOne qPCR instrument using the default settings, including a temperature melt curve. Samples were normalized to amplification of Rp117a as an internal control.

Figure 12:
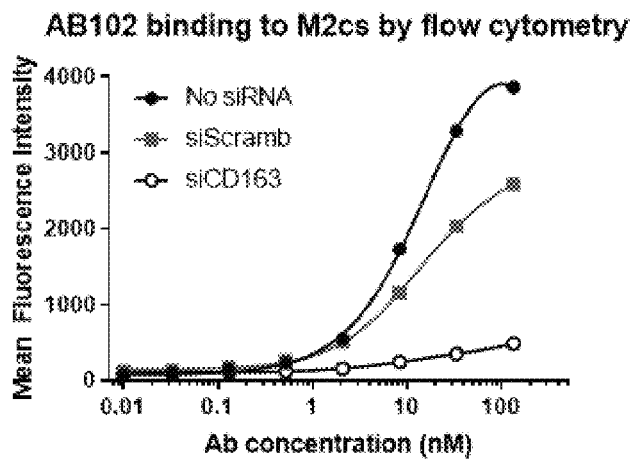
FIG. 12 shows treatment of polarized M2c macrophages with siRNA to CD163 substantially reduced binding of the AB102 antibody compared to the scrambled siRNA (siScramb) or no siRNA treated M2c macrophages, and is representative of the three replicates.

As shown in FIG. 12, (representative of the three replicates) treatment of polarized M2c macrophages with siRNA to CD163 substantially reduced binding of the AB102 antibody compared to the scrambled siRNA (siSCRAM) or no siRNA treated M2c macrophages.

Example 9—AB102 Binding to Polarized Human M2c Macrophages after siRNA Knockdown This example shows AB102 binding to polarized human M2c macrophages after siRNA knockdown using various siRNAs.

Figure 13:
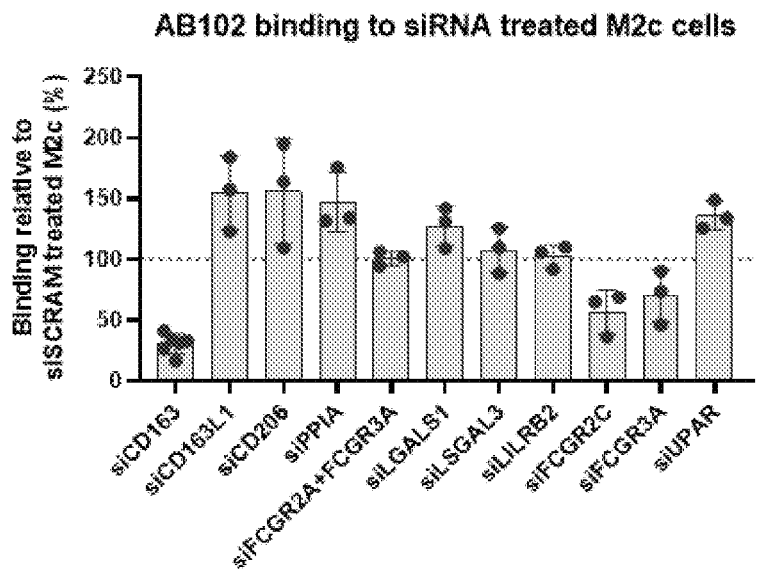
FIG. 13 shows siRNA knockdown of CD163 reduced binding of the AB102 antibody, a slight decrease in AB102 antibody binding after knockdown with siRNAs against FCGR2A+FCGR3A (in 1 out 3 donors), FCGR2C, or FCGR3A, and no evidence of reduction in AB102 binding after knockdown with siCD206; siCD163L1; siPPIA; siLGALS1; siLGALS3; siLILRB2; and siUPAR.

Monocytes were isolated from whole blood, plated at $1.5 \times 10^6$ cells per well (6-well plates), and cultured under M2-polarizing conditions as described in EXAMPLE 8, above. On day 6, medium was changed and 100 ng/mL M-CSF and 50 ng/mL IL-10 were added.

siRNA treatment was done on day 8 with various siRNA as described previously (see EXAMPLE 8). The following day the medium was aspirated to remove the transfection reagent and any dying cells, and fresh medium was added (still containing IL-10 and M-CSF). On day 10, FACS analysis was performed on siRNA-treated cells, and a second set of cells was harvested in buffer RLT for RT-qPCR (see EXAMPLE 8). The data was normalized, using AB102 binding geometric MFI to siSCRAM treated M2c as 100%, and isotype control antibody binding geometric MFI to untreated M2c as 0%.

siRNA knockdown of CD163 reduced binding of the AB102 antibody. In contrast, no evidence was seen of reduction in AB102 binding after knockdown with siCD206; siCD163L1; siPPIA; siLGALS1; siLGALS3; siLILRB2; or siUPAR, except some slight decrease with siRNAs against FCGR2A+FCGR3A (in 1 out 3 donors), FCGR2C, or FCGR3A as shown in FIG. 13. In fact, the binding intensity of AB102 increased in several of the siRNA conditions. The RT-qPCR showed strong knockdown of the targets.

Example 10—LPS-Induced Decrease of CD163 Expression on the Cell Surface of M2c Macrophages Reduces AB101 Binding to Macrophages This example shows that reduced binding of AB101 to M2c macrophages after LPS-induced shedding of CD163. Monocytes were isolated as described in EXAMPLE 2 and plated at $1 \times 10^4$ cells/well in flat bottom, tissue culture treated 96 well plates in X-VIVO medium containing 10% FBS, 50 ng/mL M-CSF and 50 ng/mL IL-10 at 100 µL/well. On day 7, half of the cells were treated for 24 hr with 10 ng/mL LPS (lipopolysaccharides from *E. coli* 0111:B4; Sigma No. L5293-2ML). Cells were labeled with titrations of unconjugated primary antibodies, anti-CD163 (R&D Systems MAB1607-100) and AB101, according to methods previously described, using eight serial 5-fold dilutions of each, starting at 200 nM. Alexa Fluor® 647 AffiniPure F(ab')2 Fragment Goat Anti-Human IgG, F(ab')2 fragment antibody was used as the secondary (Jackson ImmunoResearch 109-606-006). Cells were analyzed by flow cytometry.

Figure 14:
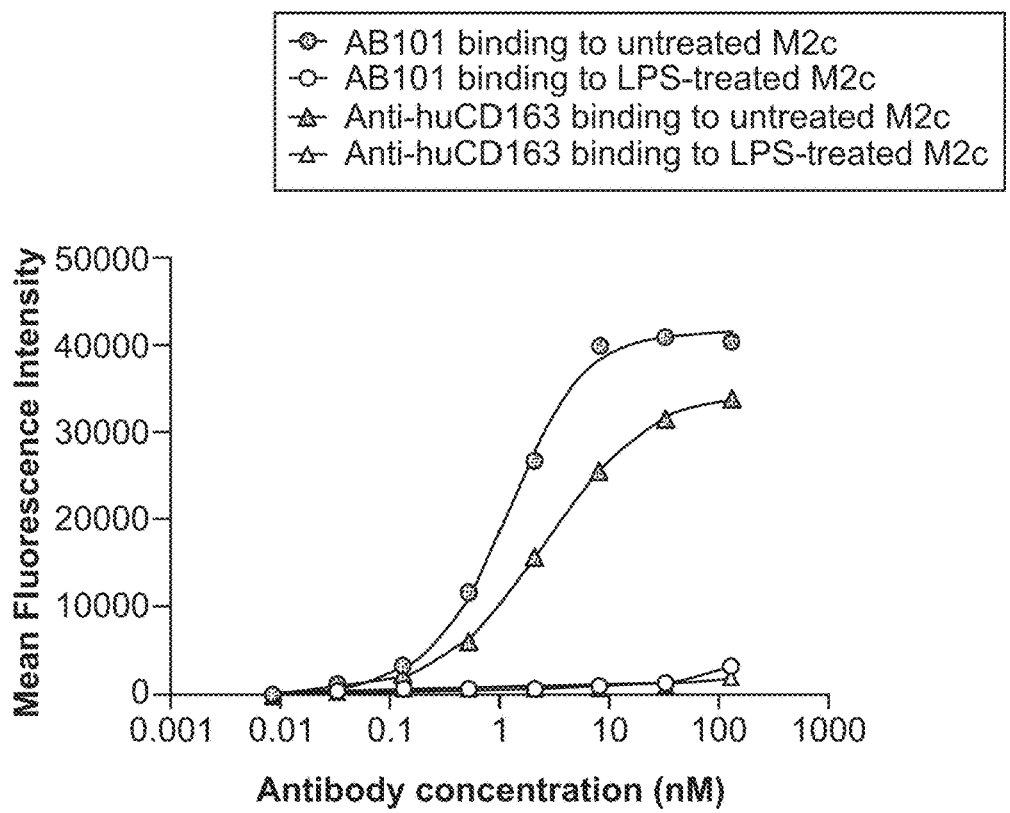
FIG. 14 shows treatment of the cultured M2 macrophages with LPS resulted in a loss of binding by both AB101 antibody and control anti-CD163 antibody.

As shown in FIG. 14, treatment of the cultured M2c macrophages with LPS resulted in a loss of binding by both AB101 antibody and the control anti-CD163 antibody.

Example 11—AB101 Blockage of Myeloid Cell Suppression of T Cell Activation (IL-2 Production) and Proliferation This example shows AB101 blocks myeloid cell suppression of T cell activation (IL-2 production) and proliferation.

To assess the ability of to relieve the M2 macrophage-mediated suppression of T cell activation, M0, M1 and M2c macrophages were generated from human monocytes. M0 macrophages were cultured with AB101 or Isotype control under three treatment protocols: 1) In the presence of AB101 (or isotype control antibody) during polarization from M0 to M2c macrophage (Day 5-7, "pre"-condition), 2) in the presence of AB101 (or isotype antibody) post polarization (Day 7 onward, "post"-condition), or 3) conditions 1 and 2 combined ("pre" and "post" polarization).

Generation of M0 macrophages. At Day 0, monocytes from individual donors (isolated as described in EXAMPLE 2) were plated at $2.5 \times 10^5$ cells/well of a 96-well tissue culture plate in M0 medium (X-VIVO medium+10% FBS+ 100 ng/mL M-CSF), and incubated at 37° C., 5% $CO_2$ for 5 days.

Polarization of M0 macrophages to M1 or M2c macrophages. 5-day old M0 macrophages were polarized to M2c by culturing the cells in M0 medium+100 ng/mL IL-10

(Peprotech No. 200-10), and to M1 by culturing in M0 medium+100 ng/mL IFN-gamma (Peprotech No. 300-03). For cells treated with AB101 or IgG1 isotype control, those antibodies were added at 20 µg/mL in M2c medium. At Day 6, for M1 macrophages, medium was discarded and fresh M0 medium+100 ng/mL IFN-gamma+1 ng/mL LPS (lipopolysaccharides from E. coli 0111:B4; Sigma No. L5293-2ML) was added.

PBMCs from autologous donors were used to isolate CD8+ T cells (as described in EXAMPLE 2). T cells were plated into T75 flasks overnight in X-VIVO+10% FBS until the day of co-culture with macrophages (Day 7).

CellTrace™ Violet Proliferation Dye kit (ThermoFisher No. C34557), which allows tracing of multiple generations using dye dilution by flow cytometry, was used to stain T cells prior to co-culture. CellTrace™ staining was performed according to manufacturer's protocol.

At Day 7, supernatant was removed from plated macrophages, and medium was replaced with 100 µL of X-VIVO medium+10% FBS+0.5 µg/mL OKT3. Macrophages were incubated at 37° C., 5% $CO_2$ for 1 hr. T cells were harvested from flasks and resuspended at 115,000 T cells in 100 µL/well (1.15 million/mL) in flat bottom 96 well plates in the absence or presence of AB101 (20 µg/mL) or isotype control (20 µg/mL) for "Pre/Post-polarization" and "post-polarization" treatments. T cells were added to macrophages at a volume of 100 µL, to give a final volume of 200 µL/well and final concentration of 0.25 µg/mL OKT3. Plates were incubated at 37° C., 5% $CO_2$ for 24 hr. On Day 8, supernatants were collected. IL-2 levels were measured using a CisBio HTRF IL-2 kit (No. 62HIL02PEG) according to the manufacturer's protocol, with the following modifications: the assay was performed in low-volume 384-well plates (Greiner Bio-One No. 784075); all volumes were halved; and the plates were briefly spun to bring bubbles to the surface.

Figure 15:
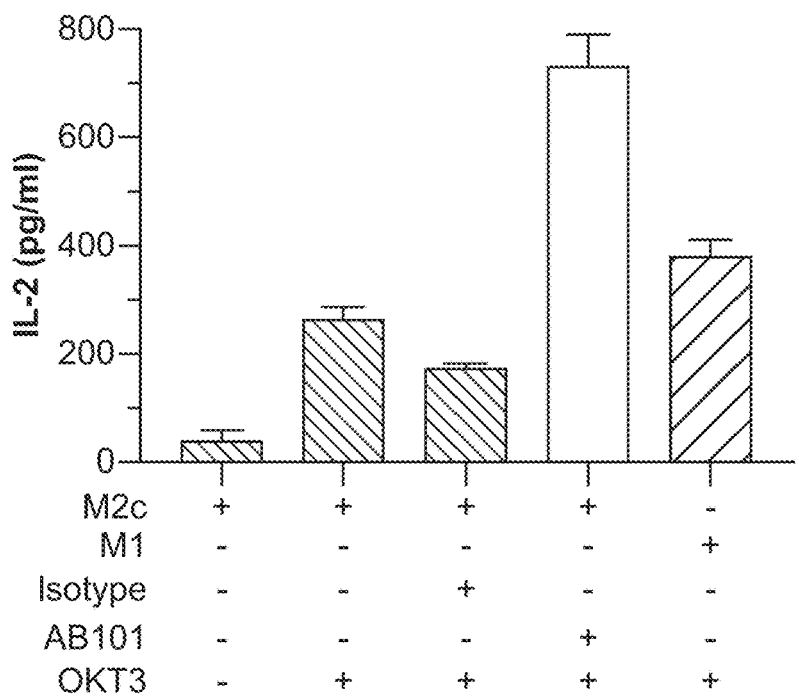
FIG. 15 shows increased IL-2 production after treatment of myeloid cells with AB101 antibody.

As shown in FIG. 15, AB101 antibody blocked the ability of myeloid cells to suppress T-cell activation, as evidenced by increased IL-2 production, a marker of T-cell stimulation and proliferation. Cells were treated with AB101 or isotype control during polarization (with IL-10), the "Pre" condition.

On Day 10, co-cultured T cells from each 96-well plate were transferred to a V-bottomed 96-well plate (ThermoFisher No. 249946), and pelleted by centrifuging at 300× g for 2 min. Pellets were resuspended in 100 µL of e780 viability dye (eBiosciences No. 65-0865-14) in PBS (0.5 µL/mL) and incubated for 10 min at RT in the dark.

Following e780 staining, cells were washed by adding 150 µL FACS Buffer (1×PBS+2 mM EDTA+1% FBS) and centrifuged at 300×g for 2 min. Supernatant was removed. Cell pellets were resuspended in 50 µL/well FACS Block (human TruStain FcX™ [Fc receptor blocking solution; BioLegend No. 422302] at 5 µL/100 µL in FACS Buffer), and incubated for 30 min at 4° C.

Antibody cocktails (2×) were made using FACS Block containing APC-labeled anti-CD8 (BD Pharmingen No. 561953) at a 1:50 dilution (Final concentration is 1:100); and FITC-labeled anti-CD14 at a 1:50 dilution (Final conc is 1:100) (BD No. 347493). This antibody cocktail was added at 50 µL/well and incubated for 30 min on ice in the dark. The stain was washed with 150 µL/well FACS Buffer. Cells were pelleted at 300× g for 2 min. Supernatant was removed, and cells were fixed in 25 µL of 4% PFA for 15 min on ice in the dark. Before analysis on a flow cytometer, 75 µL/well of PBS was added.

Figure 16:
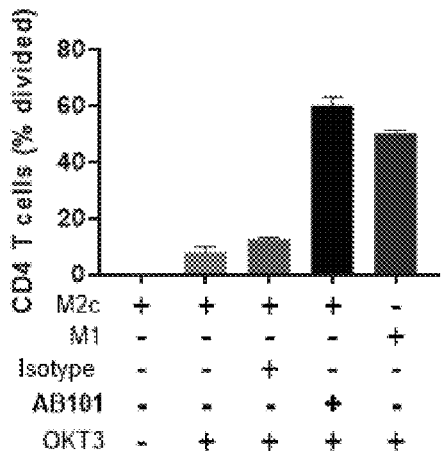
FIG. 16 shows AB101 antibody treatment during polarization promoted CD4+ T cell proliferation.
Figure 17:
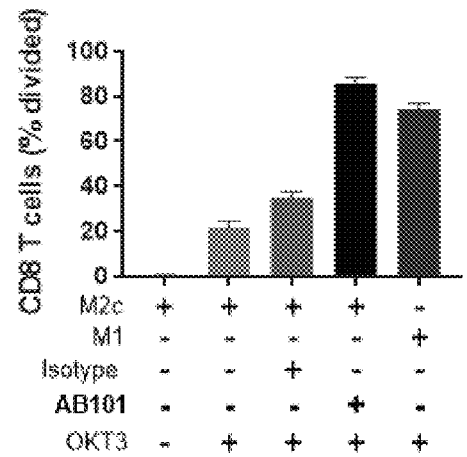
FIG. 17 shows AB101 antibody treatment during polarization promoted CD8+ T cell proliferation.
Figure 18:
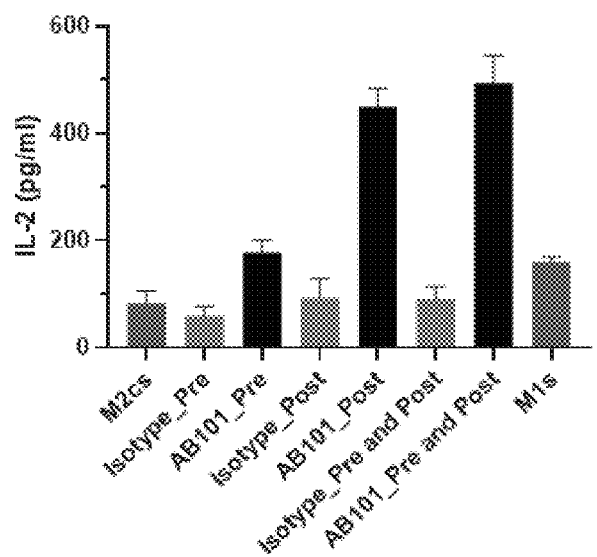
FIG. 18 shows treatment with AB101 antibody during polarization (labeled "pre" on graph), post-polarization (labeled "post" on graph), or combined during and post-polarization (labeled "pre and post" on graph) resulted in enhanced IL-2 production when compared to isotype antibody treatment.

As shown in FIG. 16 and FIG. 17, the AB101 antibody permitted OKT3-induced CD4+ and CD8+ T cell proliferation with AB101 treatment during polarization, respectively. Furthermore, as shown in FIG. 18, treatment with AB101 antibody post-polarization, during co-culture with CD3+ T cells (labeled "post" on graph), or combined during and post-polarization (labeled "Pre and Post" on graph) resulted in enhanced IL-2 production, when compared to isotype antibody treatment. These results indicate that the binding of AB101 to M2c macrophages relieves M2c-mediated suppression of T cell proliferation and IL-2 production. The AB101 treatment is effective during polarization with IL-10, overcoming a constitutively suppressive signal, and after M2c polarization, which is representative of the suppressive TAMs in the tumor microenvironment in vivo.

Example 12—Reduction of M2c Surface Marker Expression

This example shows the reduction of M2c surface maker expression after treatment with AB101.

Monocytes were isolated (as described in EXAMPLE 2) and polarized to M2c macrophages (as described in EXAMPLE 11) in the presence of AB101 or the isotype control antibody. Cells were then stained for surface marker expression of phenotyping antibodies following the protocols described in EXAMPLE 11. Normalized Median Fluorescence Intensity (MFI) is displayed in the graph below for macrophage surface expression following the treatment of M2c macrophages with AB101 or with the isotype control antibody. Live cells were gated using e780 fixable viability dye. Normalized MFI was calculated by dividing the MFI of the AB101 treated cells by the MFI of M2c cells treated with isotype control. Samples were then normalized to percent of M2c control, to show relative change in surface marker expression. Data from 7 donors was averaged and statistics were performed using 2-way ANOVA.

Figure 19:
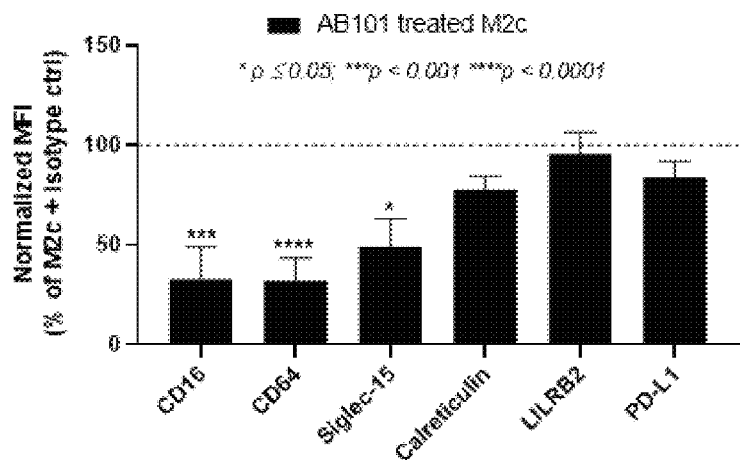
FIG. 19 shows treatment of M2 macrophages with the AB101 antibody reduced expression of CD16, CD64, Calreticulin, and Siglec-15.

As shown in FIG. 19, "Pre" treatment of M2 macrophages with the AB101 antibody during polarization reduced expression of CD16, CD64, Calreticulin, and Siglec-15. CD16(FcγRIIIa), a low-affinity IgG receptor, is highly expressed on M2 suppressive macrophages. CD64(FcγRI), a high-affinity IgG receptor, is also highly expressed on M2s. Siglec-15 is an ITIM-containing transmembrane protein involved in immune suppression, which is specifically expressed on suppressive macrophages.

No change in these markers was seen in M2c cells treated with isotype control antibody. Similarly, surface expression of PD-L1, CD11b, CD14, CD32, CD163, CD206, HLA-DR, CD204, CD33, CD80, CD86, HLA-DR, DP, DQ, CD48, MARCO, LILRB2, CD172a (SIRPα), IL10R, and IL18R were evaluated, but no change in expression of these markers was observed with AB101 treatment.

Example 13—AB101-Treated M2c Macrophages Skew OKT-3 Activated T Cells Towards a Th1 Phenotype This example shows that AB101-treated M2c macrophages induce the expression of Th1-associated surface markers by OKT3-stimulated T cells. The data suggests that AB101 treatment of M2c cells inhibits M2c-mediated immune suppression and modulates the activation of anti-tumor Th1 cells.

Myeloid cells in the tumor microenvironment, tumor associated macrophages (TAMs), have been shown to orchestrate a dampened immune response which facilitates tumor grown. Often, this effect can be seen as skewing T cells to a lower ratio of Th1/Th2 (e.g., skewing T cells to a Th2 phenotype). Therefore, we hypothesized that AB101 will affect the cross talk between the TAMs and tumor infiltrating lymphocytes (TILs), relieving the suppressive effect of the TAMs on the TILs.

The ratio of Th1 to Th2-helper cells was assessed in the presence or absence of AB101 and isotype control. M2c macrophages were treated with AB101 or isotype control on Day 5 ("Pre"=during polarization), and Day 7 ("Post" polarization, during co-culture). Starting on Day 7, treated M2c macrophages are co-cultured with OKT3 stimulated $CD3^+$ T cells for 3 days to allow for T cell proliferation. Following T cell proliferation, on Day 10, T cells were removed from co-culture and stained with cell surface marker antibody panels to determine ratio of T1 to Th2 skewing. Following surface marker and cell viability staining, T cells were fixed and analyzed for presence of Th1 or Th2 markers by flow cytometry. Panel 1 was used to determine ratio of Th1/Th2, Th17, and Treg, while panel 2 was used to determine T cell activation and exhaustion.

Monocytes were obtained and cultured to macrophages, and the macrophages were polarized as described in previous examples.

$CD3^+$ T cells were obtained as described in EXAMPLE 2, using the StemCell $CD3^+$ negative selection kits according to the manufacturer's instructions.

The macrophages and T cells were co-cultured, as described in EXAMPLE 11, for three days.

At Day 10, cells were labeled using antibodies cocktails as set forth in the Table 4 below according to the method described in EXAMPLE 11.

Antibody cocktail is made at 2× using remaining 50 μL/well of Blocking buffer, with Panel 1 antibodies at 1:50 (Final conc is 1:100), and Panel 2 antibodies at 1:50 (Final conc is 1:100).

Figure 20:
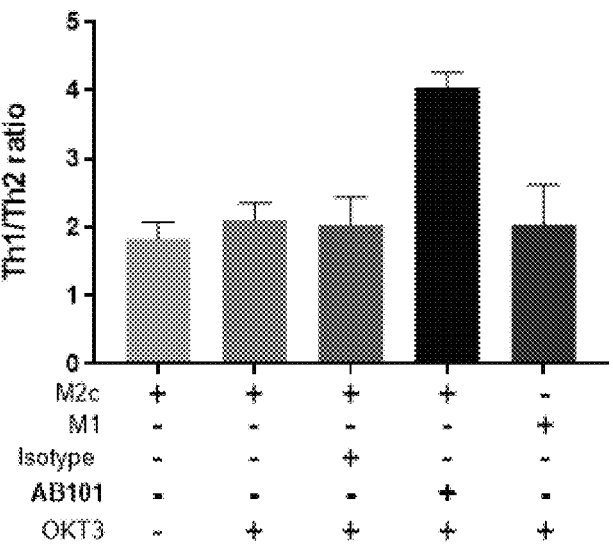
FIG. 20 shows that treatment of M2c cells with AB101 increased the Th1/Th2 ratio compared to the isotype control.
Figure 21:
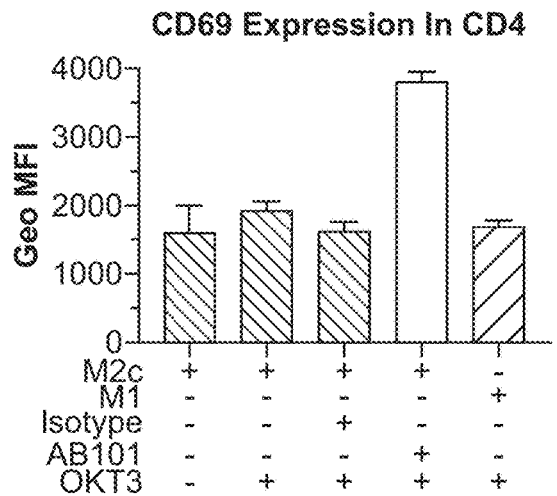
FIG. 21 shows that treatment of M2c cells with AB101 increased the expression of CD69 on CD4 T cells compared to the isotype control.
Figure 22:
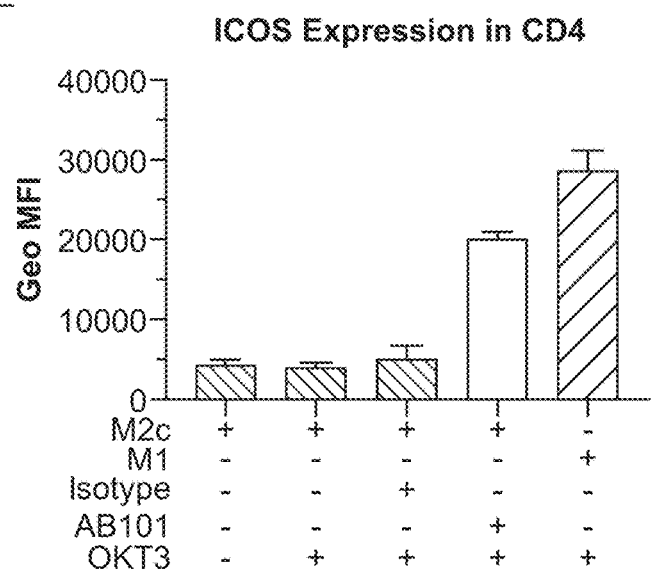
FIG. 22 show that treatment of M2c cells with AB101 increased the expression of ICOS on CD4 T cells compared to the isotype control.
Figure 23:
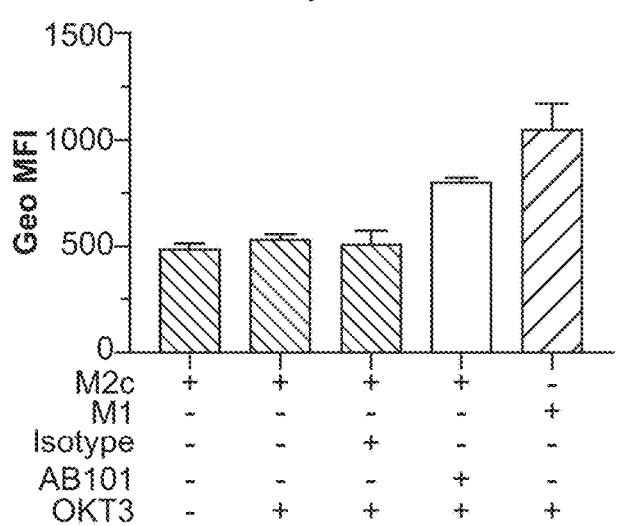
FIG. 23 show that treatment of M2c cells with AB101 increased the expression of OX40 on CD4 T cells compared to the isotype control.

Treatment with AB101 alleviated the suppressive effects of the M2c cells, resulting in the ability of the stimulated T cells to produce IL-2, proliferate (as shown in EXAMPLE 11), and be skewed them toward an activated Th1, pro-inflammatory, phenotype. FIG. 20 shows that treatment of M2c cells with AB101 increased the Th1/Th2 ratio compared to the isotype control, indicating that AB101 treatment of the M2c cells caused T cells to skew toward the Th1 phenotype. Furthermore, FIG. 21 shows that treatment of M2c cells with AB101 increased the expression of CD69 on $CD4^+$ T cells compared to the isotype control, indicating that AB101 treatment of the M2C cells caused the $CD4^+$ T cells to skew toward the Th1 phenotype when M2c cells were treated with AB101. FIG. 22 and FIG. 23 show that treatment of M2c cells with AB101 increased the expression of ICOS and OX40, respectively, on $CD4^+$ T cells compared to the isotype control, indicating that AB101 treatment of the M2c cells caused the proliferated $CD4^+$ T cells to have enhanced expression of activation markers.

Example 14—Reduction of Myeloid Cell Suppression of CD19-CD3 Bispecific T Cell Engager-Mediated Killing of Raji Cells by CD8 T Cells This example shows AB101 treatment reduces myeloid cell suppression of CD19-CD3 BiTE-mediated killing of Raji cells by CD8 T cells. Tumor cell killing was evaluated for AB101 against an isotype control antibody using a Bispecific T cell Engager (BiTE) antibody (bispecific antibody against human CD19 and human CD3; InvivoGen Bimab-hcd19cd3). M2c macrophages were treated with AB101 or isotype control on Day 5 during ("Pre") and on Day 7 after ("Post") polarization, during co-culture. Co-culture with T cells continued for 3 days starting on Day 7 to allow for T cell proliferation. On Day 10, T cells were

TABLE 4

Antibody Cocktail Mixes for assessing Th1/Th2, Th17 (Panel 1) and Exhaustion/Activation (Panel 2) of T cells.

|  | Antibody Panel 1: Th 1/Th 2, Th 17 | Antibody Panel 2: Exhaustion/Activation |
|---|---|---|
| Surface markers | CD4 - PE (BD Pharmingen No. 55347) CD69 - PE-Cy7 (BioLegend No. 104511) CD25 - APC (BioLegend No. 101909) CD127 - BV510 (BD BIO SCIENCE NO. 563086) CXCR3 - PerCP-Cy5.5 (BioLegend No. 126513) CD194 (CCR4) - BV421 (BioLegend No. 359413) CD196 (CCR6) - BV510 (BioLegend No. 353423) | CD4 - PE (BD Pharmingen No. 55347) CD8 - APC (BIOLEGEND No. 344721) LAG3 - BV421 (BioLegend No. 369313) OX40 - BV510 (BioLegend No. 745040 PD-1 - PerCP-Cy5.5 (BioLegend No. 135207) ICOS - PE-Cy7 (BioLegend No. 329805) CTLA4 - FITC (eBioscience 11-1529-42) |
| Marker Identification | Th1: $CD4^+$, $CD69^+$, $CD196^-$; $CXCR3^+$, $CCR4^-$ Th2: $CD4^+$, $CD196^-$; $CXCR3^-$, $CCR4^+$ Treg: $CD4^+$, $CD25^+$, $CD127^-$ Th17: $CD4^-$; $CD196^+$, $CXCR3^-$, $CCR4^+$ | Activated: $ICOS^+$, $OX-40^+$ Exhausted: $LAG-3^+$, $PD-1^+$, $CTLA-4^+$ Th T cells: $CD4^+$ Tc T cells: $CD8^+$ |

The in vitro myeloid cells, M2c cells, had immunosuppressive effects on activated T cells in co-culture, in which the M2c inhibited T cell proliferation and skewed T cells to a Th2 phenotype.

removed from co-culture with macrophages and subsequently incubated onto tumor cells+/−BiTE antibody to facilitate contact between the Cytotoxic T-lymphocytes (CTL) and tumor cells. Following treatment with BiTE antibody, tumor cells were stained for viability by flow cytometry.

Monocytes were cultured, and macrophages polarized as described in EXAMPLE 11. CD8$^+$ T cells were obtained as described in EXAMPLE 11. Macrophages (25,000 cells/well) were co-cultured with CD8$^+$ T cells (115,000 cells/well), using the described method, for three days.

On Day 10, Raji (ATCC No. CCL-86) and K562 (ATCC No. CCL-243) cells were stained with CellTrace Violet using the method described in EXAMPLE 11. The tumor cells were then resuspended in M0 medium at 100 k cells/well in a flat-bottom 96-well tissue culture plate. Some unstained and stained cells were set aside for single stain control for flow analysis.

On Day 10, CD8$^+$ T cells were isolated from T cell/macrophage co-culture using a StemCell CD8 Negative selection kit. The recovered T cells were plated into the Raji and K562 cell plates, 100 µL per well. Bispecific antibody was added to each Raji and K562 plates at final concentration of 10 ng/mL in final volume of 220 µL/well (some wells without BiTE as controls). Cells were cultured in BiTE treatment overnight at 37° C., 5% CO$_2$.

On Day 11, cells were placed into new V-bottom plate, and centrifuged at 300×g for 2 min. Supernatant was collected from all plates and transferred to new V-bottom 96-well plates, which were then sealed and stored at −80° C. for later cytokine analysis. Cells were resuspended in FACS buffer (PBS+1% FBS), and stained with anti-CD8, anti-CD14 (to exclude non-target cells), and e780 viability dye, as described in EXAMPLE 11. Following staining, cells were rinsed with FACS buffer, fixed using 4% PFA, and resuspended in PBS for flow cytometry analysis. CellTrace violet-labeled tumor cells were evaluated for tumor cell death by inclusion of Fixable Viability Dye eFluor™ 780 within cells. Cells positive for eFluor™ 780 dye were plotted as percent dead compared to No BiTE control wells.

Figure 24:
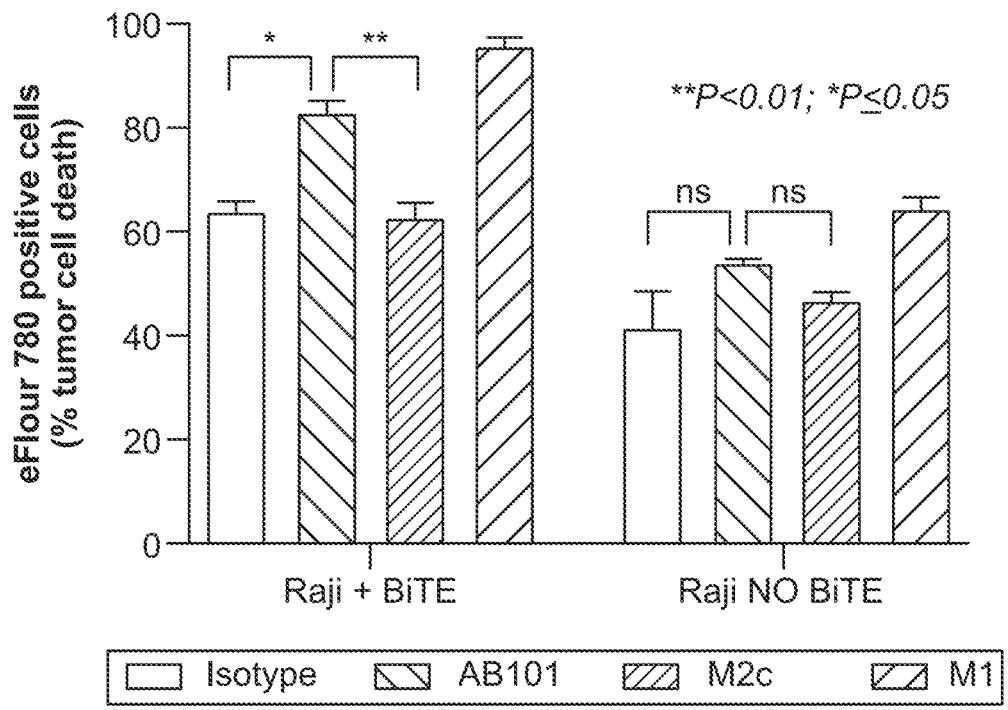
FIG. 24 shows increased CTLs in the presence of BiTE resulted in increased Raji tumor cell killing, compared to isotype control.

Treatment with AB101 relieved the suppressive effects of the M2c macrophages, which allowed for increased T cell proliferation compared to isotype control. Increased CTLs in the presence of BiTE resulted in increased Raji tumor cell killing, compared to isotype control, as shown in FIG. 24. K562 was used as a negative control and showed no increase in killing+BiTE antibody.

Example 15—Antibody Internalization by Human Primary M2c Macrophages

At Day 0, monocytes (see EXAMPLE 2) were plated in optically clear bottom, 96-well tissue culture plates at 1×10$^5$/well in 100 µL (1×10$^6$/mL) of M0 medium to differentiate to macrophages. At Day 5, the plates were swirled to dislodge floating cells and the medium was gently aspirated. Macrophages were polarized to M2c in 100 µL/well M2c medium as described in previous examples.

At Day 6, antibodies were labeled using Alexa Fluor™ 647 Antibody Labeling Kit (Invitrogen No. A20186). Each antibody (100 µg) was diluted to 2 mg/mL in 50 µL PBS. The antibodies tested were as follows: AB101 huIgG1 and AB102 huIgG1 ADCC-Null; CD163 mouse monoclonal IgG1 antibody (R&D Systems MAB1607-100); and Isotype control: ISO1 huIgG1 or ISO2 human Fc-null framework.

The entire vial of A-647 carboxylic acid succinimidyl ester from the kit was resuspended in 150 µL PBS. Aliquots (50 µL) of A-647 solution were added to each tube of diluted antibody, now at 1 mg/mL, and the mixtures incubated at RT for 45 min in the dark.

Zebra desalting columns (Thermo 87766) were washed, by first snipping the bottom and centrifuging for 1 min at 4,100 rpm to remove storage buffer. Then the columns were washed twice with 300 µL PBS (spin 1 min. at 4,100 rpm), and once w/300 µL PBS (spin 4,100 rpm for 2 min.). The columns were placed into new amber tubes and the antibodies were individually loaded. The columns were then centrifuged for 2 min at 4,100 rpm to elute the Alexa-647 labeled antibodies at 1 mg/mL.

At Day 7, FBS-containing medium was removed from the culture plates by flicking and the plates washed twice with 250 µL cold PBS, followed by addition of 90 µL of X-VIVO medium either containing 20 µg/mL unlabeled ISO1 IgG1 antibody to block Fc receptors, for staining with labeled AB101, ISO1, and anti-CD163 antibody (R&D Systems MAB1607-100), or medium without unlabeled ISO1 block for staining with AB102 and ISO2. Cells were incubated for 30 min at 37° C., 5% CO$_2$, followed by addition of labeled antibodies were at a final concentration of 5 µg/mL. After 1 hr of incubation, medium was removed and the cells washed with 250 µL cold FACS Buffer, followed by addition of 4% PFA (BD Cytofix/Cytoperm No. 554722) for 10 min at RT in the dark. Counterstains for cellular components were prepared, by adding 2 drops/mL of NucBlue™ (Molecular Probes No. R37605) and ActinGreen™ (Molecular Probes No. R37110) per mL to 1× Perm Buffer (BD Perm/Wash No. 554723, diluted 1:10 in water). The plates were flicked to remove fix and counterstain solutions (20 µL/well) were added. Staining proceeded at RT in the dark for 20 min. The cells were then washed by adding 250 µL/well PBS, which was removed and replaced with 50 µL/well PBS. Cells were imaged using a Cellomics instrument.

Figure 25:
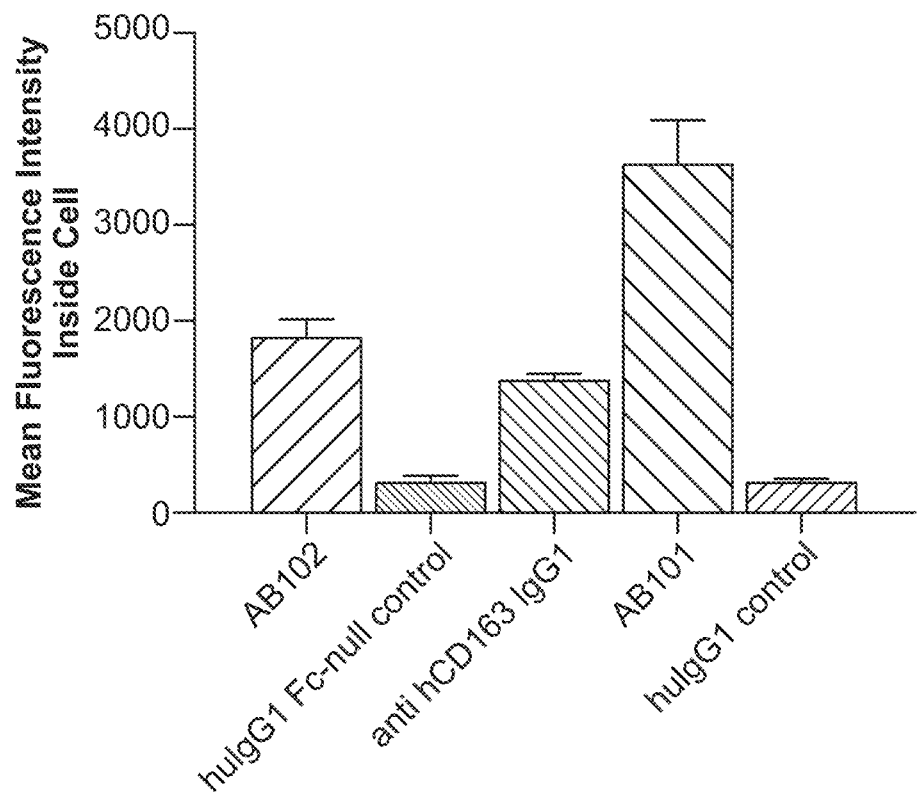
FIG. 25 shows the AB102 antibody internalized approximately as well as the commercial anti-CD163 antibody (R&D Systems MAB1607-100), and approximately 2-fold more of the AB101 antibody was internalized than that of the commercial CD163 antibody

These data are mean fluorescence values inside the cell as determined by cellomics (mean ring average intensity in AF647). The cell is defined and detected by a DAPI stained nucleus (NucBlue) and a FITC labeled cytoskeleton (Acin-Green). FIG. 25 shows representative results of at least 4 individual donors. In all cases, the isotype control antibodies did not internalize and the AB102 antibody internalized to the same extent as the commercial anti-CD163 antibody (R&D Systems MAB1607-100). AB101 (IgG1) antibody was internalized approximately 2-fold more than either AB102 (FcNull) or the commercial CD163 antibody.

Example 16—AB101 Inhibits Tumor Growth in a Human Lung Cancer Xenograft Model

AB101 was tested for tumor growth inhibition in vivo in a human lung cancer xenograft model. Following AB101 treatment, tumor size and weight were significantly reduced compared to control group, with a corresponding increase in the proportion of CD8$^+$ T cells as well as surface expressions of T cell activation markers, ICOS and OX40, on CD8$^+$ T cells in the spleen. No differences were observed for CD4$^+$ T cells. These results suggest that AB101 promotes CD8$^+$ T cell activation and proliferation, consistent with in vitro studies shown in previous examples. Furthermore, the proportion of CD11b$^+$ cells was increased. CD11b is present on monocytes, macrophages, granulocytes, dendritic cells, and natural killer cells. Taken together, these findings suggest that AB101 may have therapeutic application to augment the immune response to control tumor burden.

To determine the therapeutic potential of AB101, the effectiveness of the AB101 in reducing tumor growth in vivo was tested using the NSG-SGM3 mouse strain (The Jackson Laboratory), which supports engraftment of human CD34$^+$ hematopoietic stem cells and the reconstitution of multilineage immune cell populations.

Frozen aliquots of A549 (human lung carcinoma, p53 wild type) and NCI-H1975 (human lung adenocarcinoma, p53 mutated, p.R273H) were purchased from ATCC (cat #CCL-185 and CRL-5908, respectively). A549 cells were grown in F-12K medium (ATCC No. 30-2004) supplemented with 10% fetal bovine serum (FBS; Corning, cat #35-010-CV) and 1% penicillin-streptomycin (pen/strep, HyClone, cat #SV30010). H1975 cells were cultured in RPMI (HyClone, cat #SH30096.02) with 10% FBS and 1% Pen/Strep. Cells were expanded at 37° C./5% $CO_2$ for multiple passages prior to subcutaneous injection into mice.

NSG-SGM3 mice were transplanted with two human cord blood units, performed by The Jackson Laboratory as previous described Shultz et al., Nat Rev Immunol 7(2):118-30 (2007) [PubMed: 17259968]; Shultz et al., Nat Rev Immunol 12(11):786-98 (2012) [PubMed: 23059428]; Ishikawa et al., Curr Top Microbiol Immunol 324:87-94 (2008) [PubMed: 18481454]; Pearson et al., Curr Protoc Immunol; Chapter 15:Unit 15.21 (2008) [PubMed: 18491294]. Two of these mice became sick and were euthanized. Upon arrival to the facility, these mice were allowed to acclimate for 5 days. The right and left flanks of each mouse were shaved on day 6.

On day 7, A549 and H1975 cells were harvested from the cultures, washed 3 times with PBS (phosphate-buffered saline without $Ca^{2+}$ or $Mg^{2+}$; HyClone No. SH30028.02) and resuspended in Corning Matrigel® membrane matrix (Fisher Scientific No. CB-40234C) at a density of $5 \times 10^6$ cells/mL. A549 cells were injected into the right flank while H1975 cells were injected into the left flank of each mouse at a dose of $5 \times 10^5$ cells in 100 µL Matrigel.

Five days post injections, the tumors were measured by digital caliper (Fisher Scientific No. NC0649232). Once tumors reached 50-75 $mm^3$ (tumor volume=(W (2)×L)/2), the mice were then randomized using a web-based randomizer application (https://www.randomizer.org/) and divided into 2 groups (shown below) with 7 mice per group:

(1) Isotype control antibody (ISO1 Hu IgG1);
(2) AB101 antibody (Hu IgG1);

The mice received antibody treatments starting on the day of randomization and every three days thereafter. Each mouse received 200 µg of isotype control or of AB101 per treatment in 100 µL of PBS via intraperitoneal injection. Tumor size was measured on Mondays, Wednesdays, and Fridays until day 26. Any mice showing signs of fatal morbidity were documented and euthanized immediately. Mice were sacrificed on day 26. Tumors and spleen were harvested for further analysis.

The isolated tumors were weighed and processed by removing fat, fibrous, and necrotic areas and cutting into 2-4 mm pieces. The processed tumors were added to a gentleMACS C tube (MACS Miltenyi Biotec, No. 130-096-334) containing tumor dissociation enzyme mix solution (Tumor Dissociation Kit, Mouse; MACS Miltenyi Biotec, No. 130-096-730). The cells were dissociated using a gentleMACS dissociator (MACS Miltenyi Biotec, No. 130-093-235) and then incubated at 5% $CO_2$ and 95% humidity for 30 min. The cells were pelleted, resuspended in PBS and strained using a 100-µm cell strainer (Corning No. 352360). Dissociated single cells were analyzed by flow cytometry.

Spleens were processed and dissociated into single cells by pressing through a cell strainer. A 10-mL syringe plunger head was used to remove any fat and fibrous tissues. Splenic cells were pelleted and resuspended in PBS for analysis by flow cytometry.

Myeloid and T cells from the tumors and spleens were quantified using flow cytometry with antibody cocktail panels shown in Table 5 below. Cell viability was assessed using e780 viability dye (eBiosciences No. 65-0865-14; 1:500 in PBS). The cells were incubated for 10 min at 4° C. with e780 in FACS Buffer (PBS+1% FBS+1 mM EDTA (Fisher Scientific No. 15575-038)) prior to staining with primary or isotype control antibodies. The cells were then washed with 200 µL of FACS buffer, and blocked in 25 µL Fc Block (FACS buffer+5 pL/mL of Fc Block (BioLegend No. 422302)) at 4° C. for 30 min. The antibody stains (see Table 5 below) were added (25 µL) to the cells and incubated at 4° C. for another 30 min in the dark. Cells were washed 3× before FACS analysis.

TABLE 5

Antibody Cocktail Panels

| Myeloid Panel 1 | Source | Source Number |
|---|---|---|
| Anti-CD11b-APC | BD Biosciences | 550019 |
| Anti-CD16 - PE | BioLegend | 302007 |
| Anti-CD64 - Pacific Blue | BioLegend | 305018 |
| Anti-HLA-DR - PerCP-Cy5.5 | BioLegend | 361710 |
| Anti-CD80 - FITC | BioLegend | 305206 |
| Anti-LILRB2 - PE-Cy7 | BioLegend | 338711 |

| Myeloid Panel 2 | Source | Source Number |
|---|---|---|
| Anti-CD11b-APC | BD Biosciences | 550019 |
| Anti-CD86 - BV510 | BD Biosciences | 563697 |
| Anti-PD-L1 - BV421 | BioLegend | 329714 |
| Anti-CD83 - PE-Cy7 | BioLegend | 305325 |
| Anti-CD163 - FITC | BD Biosciences | 3563697 |
| Anti-ICOSL - PE | BioLegend | 309403 |

| T cell Panel 1 | Source | Source Number |
|---|---|---|
| Anti-CD4-FITC | BioLegend | 300505 |
| Anti-CD194 (CCR4) - BV421 | BioLegend | 359413 |
| Anti-CD196 (CCR6) - BV510 | BioLegend | 353423 |
| Anti-CXCR3 - PerCP-Cy5.5 | BioLegend | 126513 |
| Anti-CD69 - PE-Cy7 | BioLegend | 104511 |
| Anti-CD25 - APC | BioLegend | 101909 |
| Anti-IL-7Ra - PE | BioLegend | 135013 |

| T cell Panel 2 | Source | Source Number |
|---|---|---|
| CD8-APC | BD Biosciences | 561953 |
| Anti-LAG-3 - BV421 | BioLegend | 369313 |
| Anti-OX40 - BV510 | BD Biosciences | 745040 |
| Anti-PD-1 - PerCP-Cy5.5 | BioLegend | 135207 |
| Anti-ICOS - PE-Cy7 | BioLegend | 329805 |
| Anti-CTLA4 - PE | BioLegend | 106305 |

Figure 26:
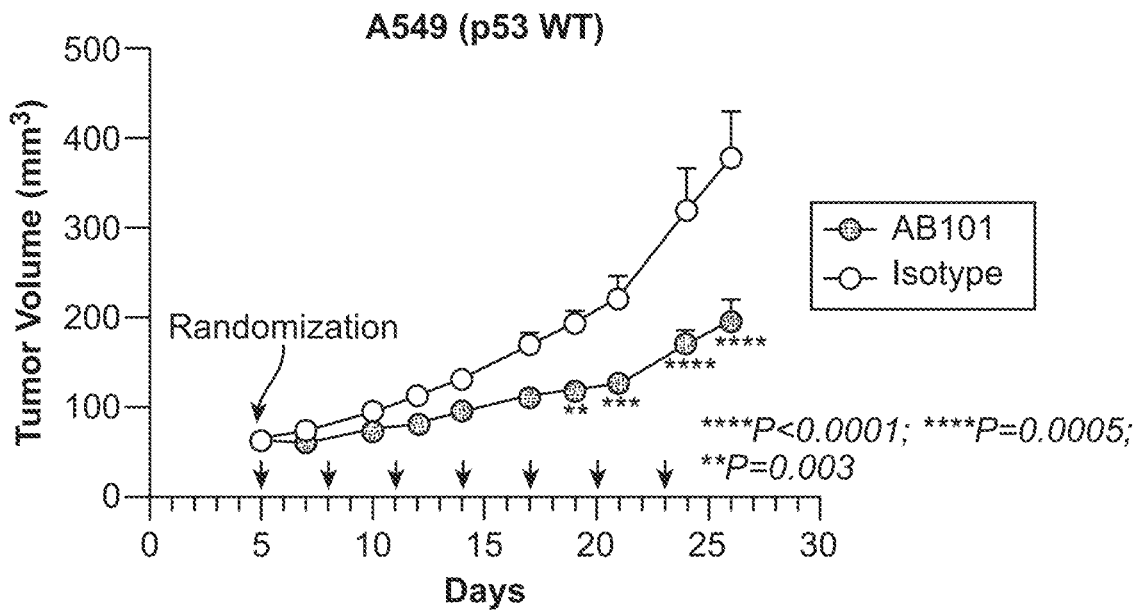
FIG. 26 shows tumor volume plotted for the A549 tumors over 30 days. Arrows indicate injections with antibody treatments. Each point represents the mean measurement from 7 mice. Error bars denote standard error of the mean (SEM). Statistical significance was calculated using Mann-Whitney test.
Figure 27:
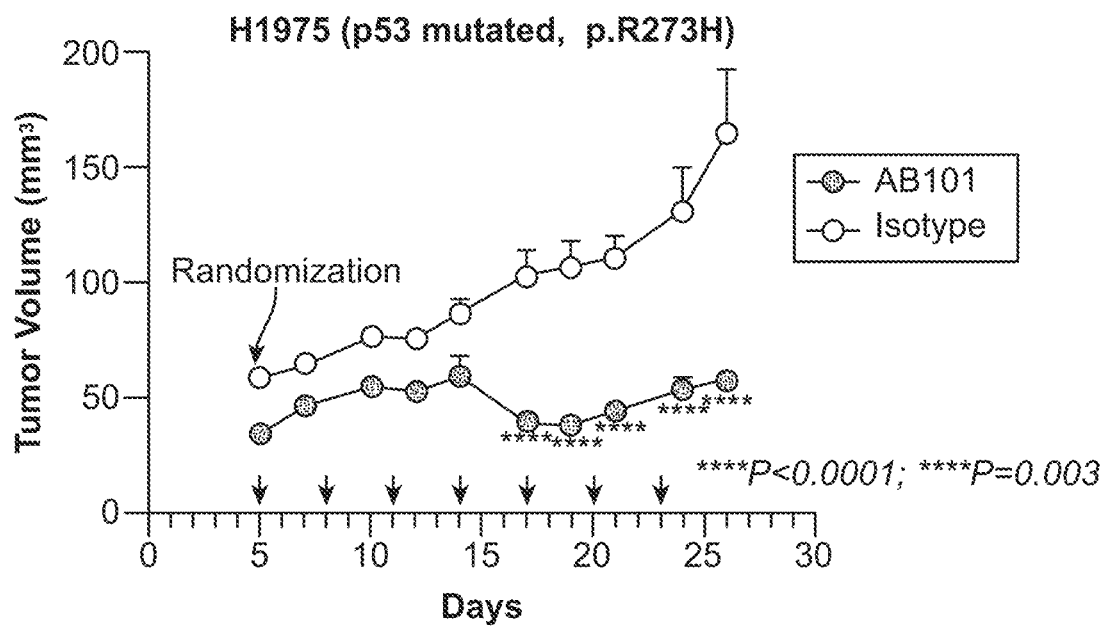
FIG. 27 shows tumor volume plotted for the H1975 tumors over 30 days. Arrows indicate injections with antibody treatments. Each point represents the mean measurement from 7 mice. Error bars denote standard error of the mean (SEM). Statistical significance was calculated using Mann-Whitney test.

AB101 treatment significantly reduces A549 and H1975 tumor growth compared to isotype control antibody. FIG. 26 and FIG. 27 show tumor volume plotted for the A549 and H1975, respectively, tumors over 30 days. Arrows indicate injections with antibody treatments. Each point represents the mean measurement from 7 mice. Error bars denote standard error of the mean (SEM). Statistical significance was calculated using Mann-Whitney test.

In the isotype control, the volume of A549 and H1975 tumors increased over time. However, in mice that received AB101 treatment, the A549 tumor exhibited slower growth compared to isotype control, while H1975 tumor showed regression at day 17 and the growth remained steady thereafter. At randomization on D5, the average A549 tumor volumes for isotype control and AB101 were 63.6 $mm^3$ and 63 $mm^3$ respectively, and on D26, the average tumor volume for isotype control was 378 $mm^3$, whereas the average tumor volume for AB101 was 198 $mm^3$. Similarly, H1975 tumor volumes on D5 were 57.8 and 34.2 for isotype control and AB101, respectively and on D26, the average tumor volume for isotype control was 164.4 mm$^3$, whereas the average tumor volume for AB101 was 57.4 mm$^3$.

AB101 treatment significantly reduced tumor size of both A549 and H1975 tumors. Tumors were excised on D26 and weighed. AB101 reduced the size of A549 tumor by 49% relative to the isotype control (average tumor weight: 538.2 mg for isotype control and 273.0 mg for AB101, p=0.003) and H1975 tumor by 60% (average tumor weight: 217.2 mg for isotype control and 85.6 mg for AB101, p=0.0009).

AB101 treatment significantly increased the proportions of CD8$^+$ T cells and myeloid cells amongst the total live cells in the spleen. The average percent CD8$^+$ T cells was increased by 1.3 for isotype control to 3.3 for AB101 and significantly increased the average percent CD11b$^+$ cells from 2.1 for isotype control to 4 for AB101.

AB101 treatment also significantly enhanced expression of activation markers on human CD8$^+$ T cells in spleen. The average MFI for ICOS expression on CD8$^+$ T cells was increased from 318 for isotype control to 841 for AB101 and average MFI for OX40 expression was increased from 586 for isotype control to 1561 for AB101.

Example 17—AB101 Relieves M2c Mediated Immune Suppression on T Cell in M2c/T Cell Coculture Assay To evaluate if AB101 can modulate the cancer mediated immune evasion in the TME, human PBMC-derived T cells were cultured with autologous immunosuppressive M2c macrophages. AB101 immunomodulatory activities to rescue anti-CD3 (OKT3) activated T cells from M2c-mediated immune suppression were assessed under three treatment regimens, with T cell proliferation and IL-2 production as read outs for treatment efficacy. FIG. 28 shows the experimental design.

To determine if AB101 interferes with the generation of M2-like tumor associated macrophages, M0 macrophages were polarized to M2c macrophages in the presence of AB101 or isotype control ("Pre" regimen). Treatment antibodies were washed out before coculture with T cells. To evaluate if AB101 treatment rescues T cells from M2c-mediated immune suppression, T cells were activated with anti-CD3 in the presence of M2c macrophages and AB101, or isotype control during M2c/T cell coculture ("Post" regimen). To mimic in vivo immunotherapy, Pre and Post regimens were combined (Pre/Post).

Figure 30:
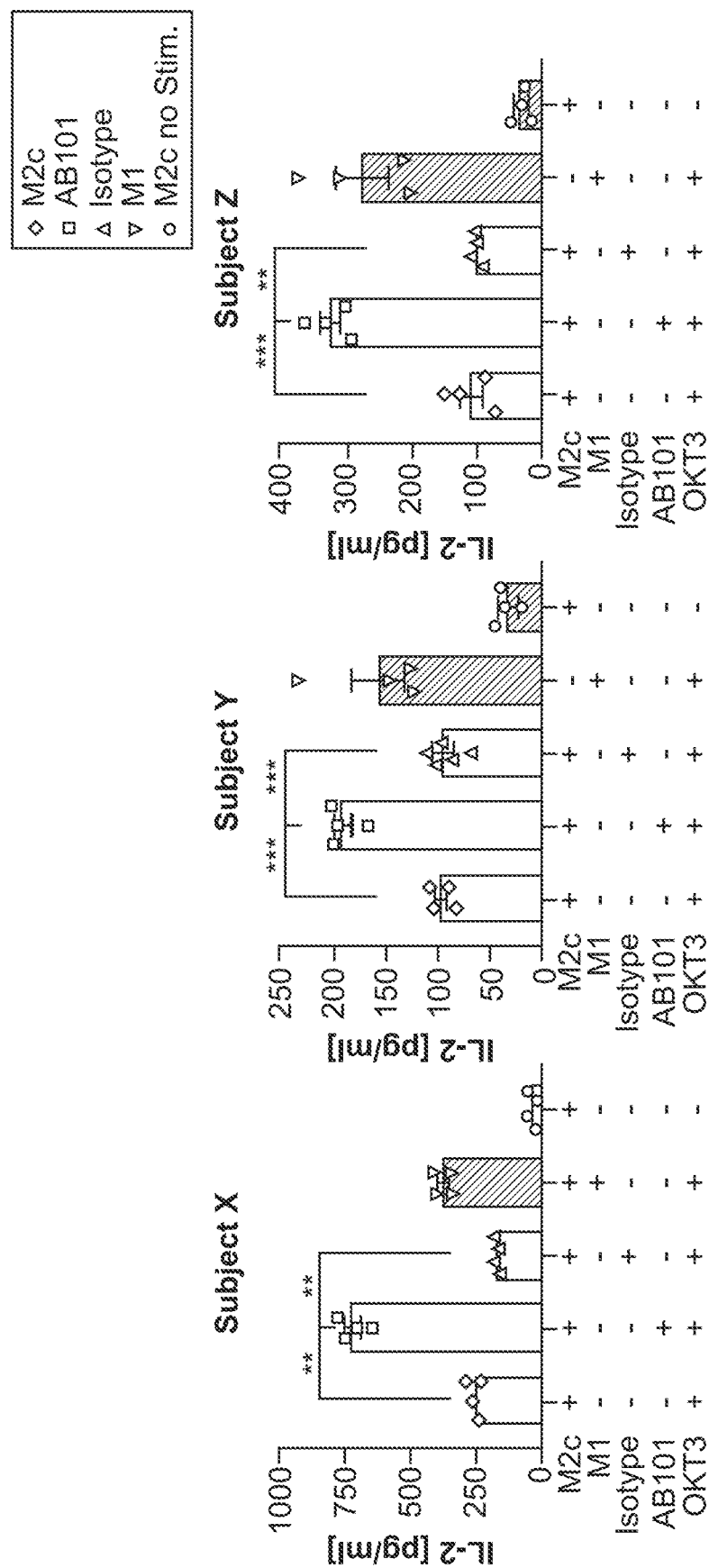
FIG. 30 shows that treatment with AB101 during M2c macrophage polarization enhanced IL-2 secretion by OKT3 activated T cells in M2c/IT cell coculture assay.

In the first set of experiments, the effect of AB101 on M2c polarization was evaluated with human monocyte derived macrophages and T cells from three healthy subjects. CD4$^+$ and CD8$^+$ T cells were activated with OKT3 in the presence of autologous M2c macrophages treated with AB101 or isotype control. OKT3 stimulated T cells cocultured with M2c macrophages alone was used to assess M2c mediated immune suppression. T cell coculture with IFN-γ+LPS polarized M1 macrophages provided a measure for optimal T cell activation. M2c/T cell coculture without OKT3 activation resembled resting T cells. FIG. 29 shows that AB101 treatment significantly enhanced the proliferation of CD4$^+$ and CD8$^+$ T cells over isotype control from 7 to 54% (p<0.01) and from 21 to 83% (p<0.05) of dividing cells, respectively. M1 macrophages and AB101 treated M2c macrophages induced similar levels of proliferation. In addition, FIG. 30 shows that AB101 Pre-treatment of M2c macrophages significantly increased IL-2 production by activated T cells from all three study subjects, when compared to IL-2 secretion by activated T cells from AB101-treated or naïve M2c groups. IL-2 levels from coculture with AB101 treated M2c macrophages were similar or higher than achieved in coculture with M1 macrophages. As expected, T cells cocultured with M2c without OKT3 activation did not produce detectable levels of IL-2.

Next, the effects of AB101 treatment on CD8$^+$ T cell/M2c cocultures under Pre-, Pre/Post- and Post-regimens were evaluated. The experiment was performed with PBMCs from three healthy subjects. CD3$^+$ T cells from 3 study subjects were activated with anti-CD3 (OKT3, 0.25 µg/mL) in the presence of M2c macrophages. M2c macrophages were treated with AB101 (20 µg/mL), human IgG1 isotype control (20 µg/mL) or media alone during polarization (Pre, before coculture). T cells were harvested 72 h after anti-CD3 stimulation and proliferation was quantified by flow cytometry. P values were calculated by Dunnett's T3 multiple comparisons test for M2c, AB101 and IgG1 isotype control treatment groups (p<0.05, *; p<0.01; p<0.001, *).

Figure 31:
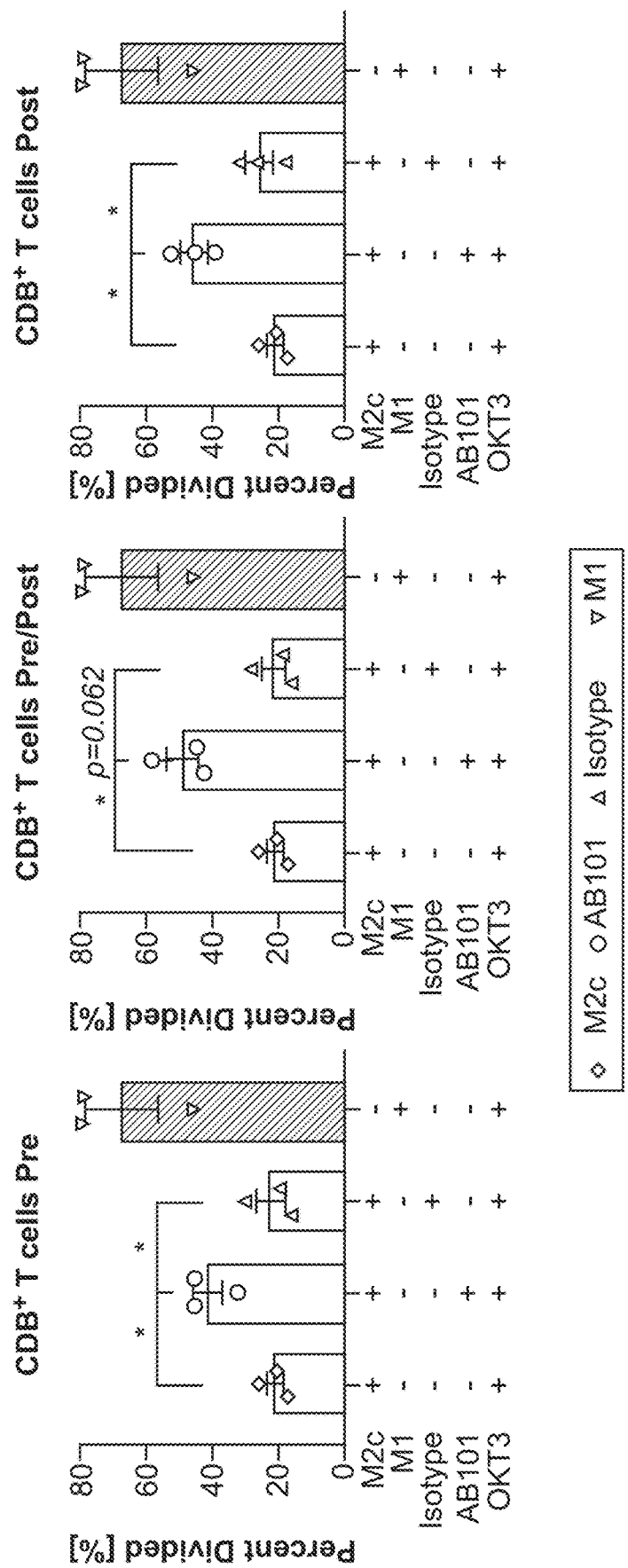
FIG. 31 shows that treatment with AB101 pre-, pre/post-, and post-regimens increased CD8+ T cell proliferation in M2c/T cell coculture assay.

FIG. 31 shows that AB101 treatment significantly enhanced CD8$^+$ T cell proliferation under Pre- and Post-regimens, when compared to the isotype control group (p<0.05). AB101 pre- and post-regimens increased the percent of divided CD8$^+$ T cells from 23 to 42% and from 26 to 47%, respectively when compared to the corresponding isotype control group values. The largest increase in CD8$^+$ T cell proliferation was observed in AB101 Pre/Post group, with 49% divided CD8$^+$ T cells, compared to the 22% dividing CD8$^+$ T cells of the isotype control Pre/Post control group (p=0.062).

Figure 32:
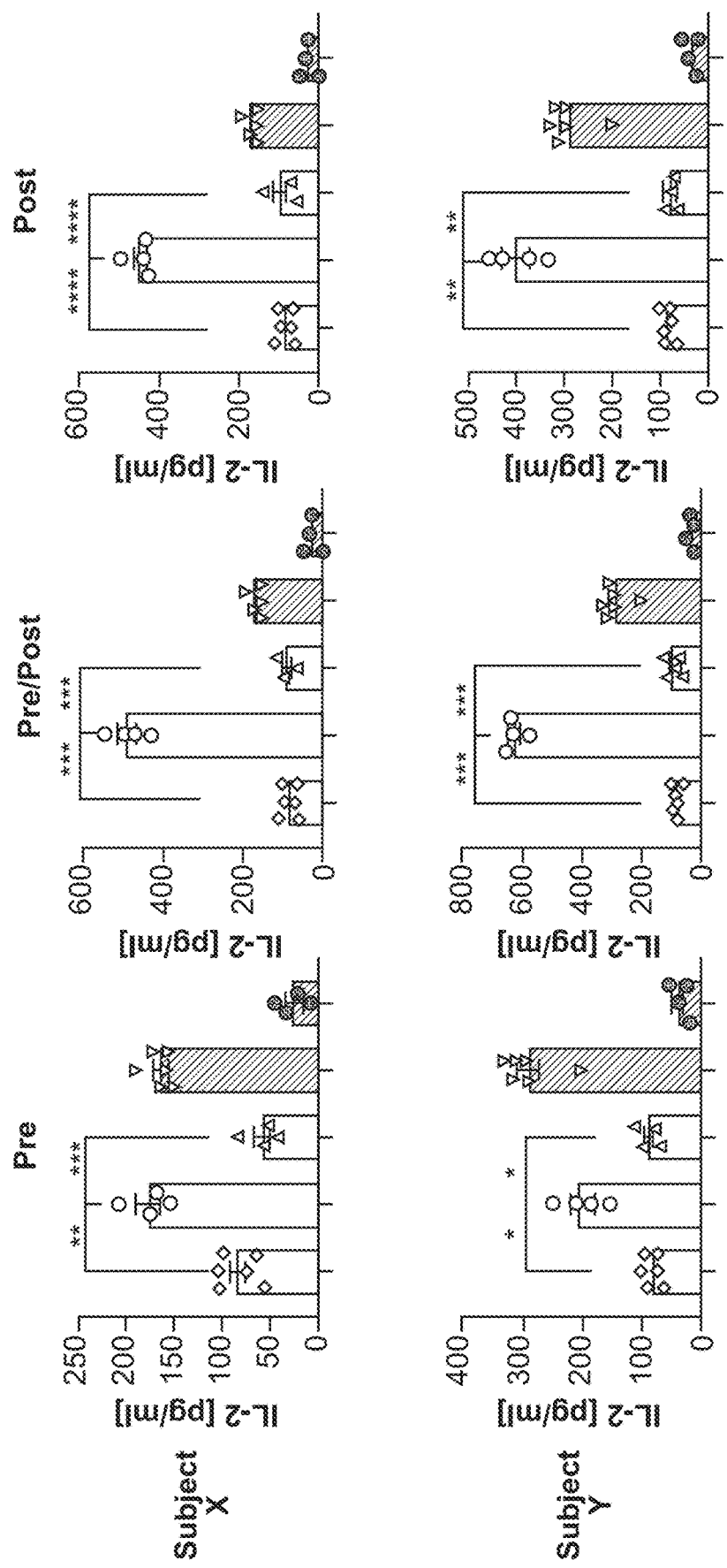
FIG. 32 shows that treatment with AB101 pre-, pre/post-, and post-regimens increased CD8+ T cell proliferation in M2c/T cell coculture assay for individual subjects.
Figure 32:
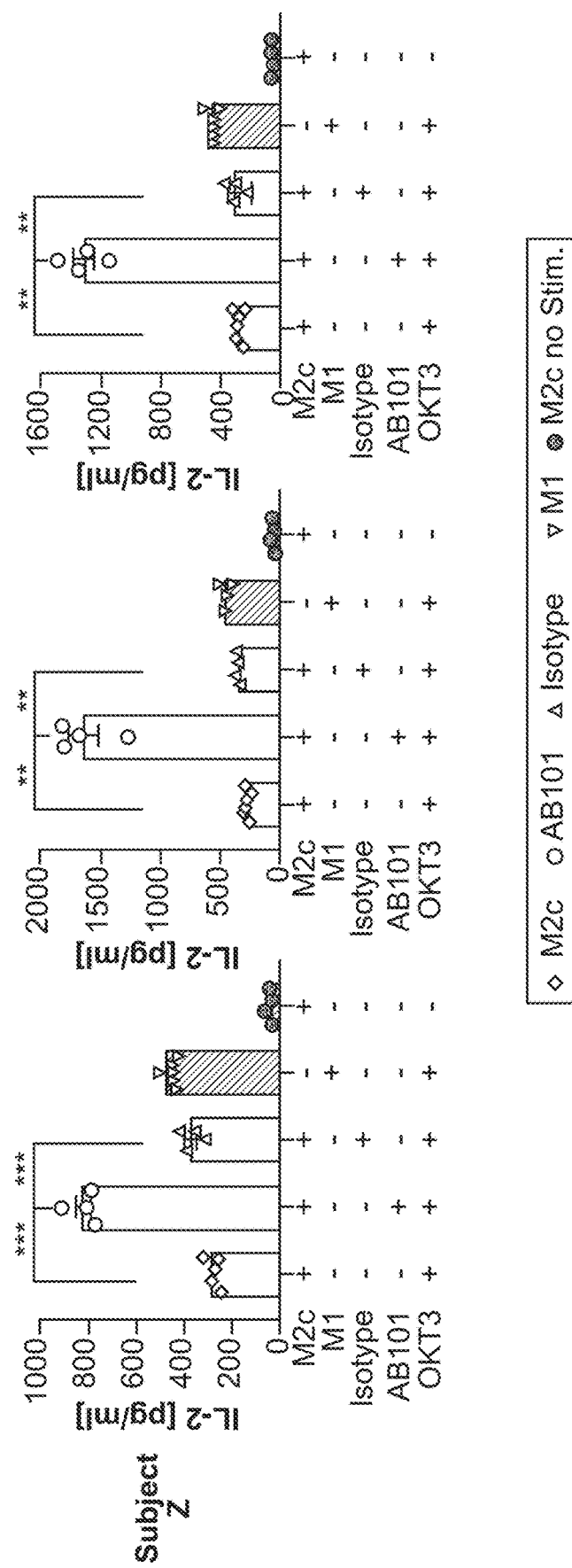

FIG. 32 shows the corresponding IL-2 data for the individual study subjects. All three subjects in the AB101 treatment groups significantly increased the IL-2 production of CD8$^+$ T cells when compared to M2c alone and isotype control groups. The highest IL-2 secretion was achieved with the Pre/Post combination treatment of M2c/T cell cocultures. The proliferation and IL-2 data of the three AB101 treatment regimens indicated that AB101 not only affected the polarization of M2c cell but also mitigated the M2c mediated immune suppression during T cell/M2c coculture.

Figure 33:
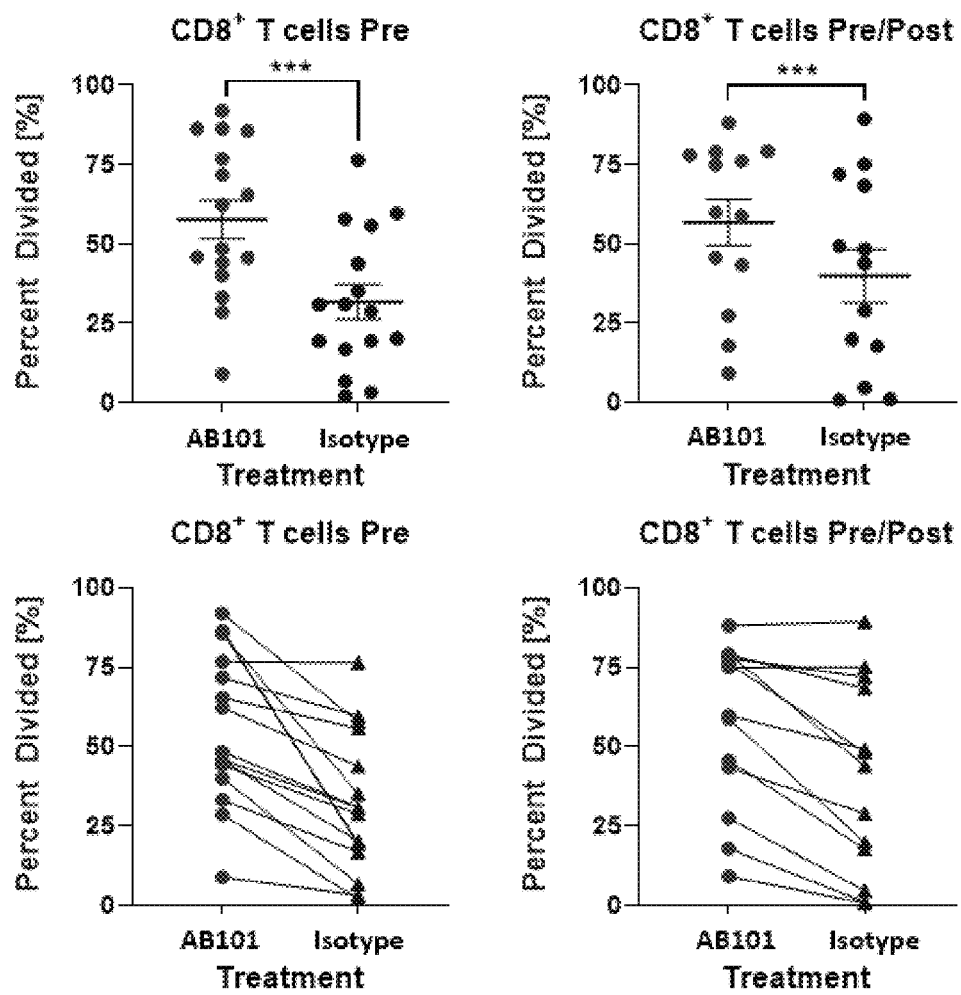
FIG. 33 shows that AB101 treatment enhanced CD8+ T cell proliferation in M2c/cocultures from multiple subjects.
Figure 34:
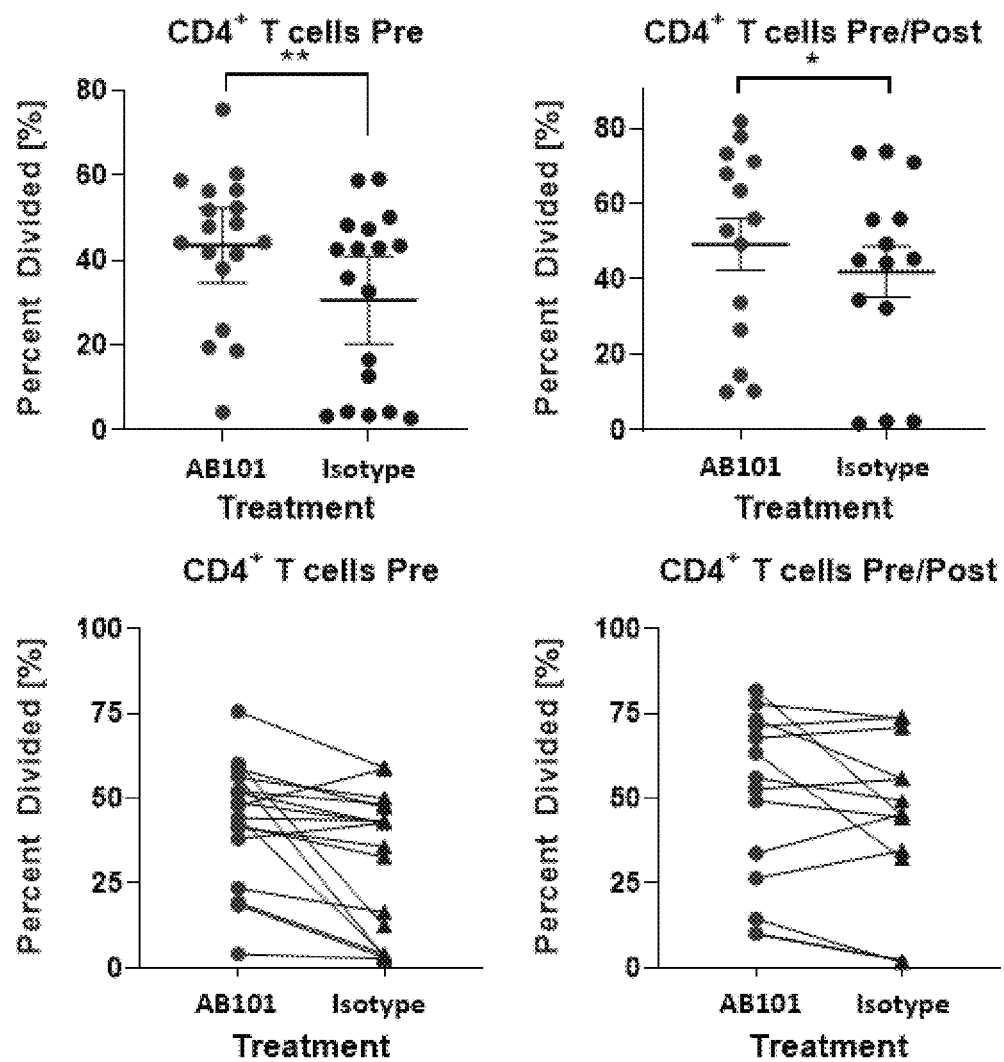
FIG. 34 shows that AB101 treatment enhanced CD4+ T cell proliferation in M2c/cocultures from multiple subjects.

FIG. 33 and FIG. 34 show the compiled proliferation data for Pre and Pre/Post AB101 treatment. AB101 had a greater effect on the proliferation of CD8$^+$ T cells than on CD4$^+$ T cell proliferation. AB101 treatment significantly enhanced the proliferation of CD8$^+$ T cells over the corresponding isotype control values under Pre (n=16, p<0.001) and Pre/Post-regimens (n=13, p<0.001), respectively. CD4$^+$ T cells proliferated in response to AB101 Pre- and Pre/Post-regimens with an increase in percent of divided cells from 31 to 44% (Pre, n=18, p<0.01) and 42 to 49% (Pre/Post, n=14, p<0.05) when compared to isotype treated M2c macrophages.

Figure 35:
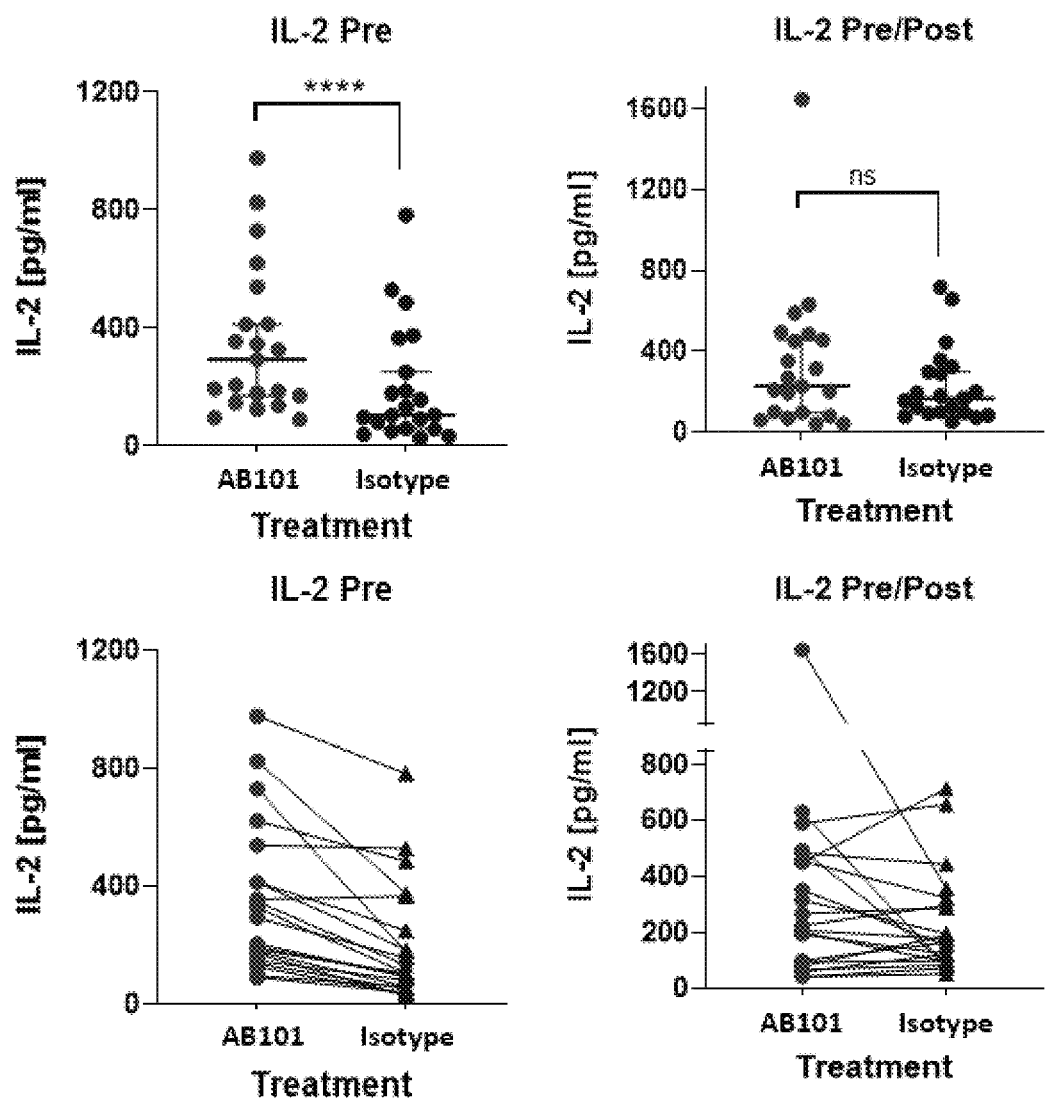
FIG. 35 shows that AB101 treatment enhanced IL-2 production by T cells from multiple human during M2c/T coculture.

FIG. 35 shows that treatment with AB101 during polarization of M2c cells also significantly enhanced IL-2 production of T cells in the M2c/T cell coculture assay. T cells in the Pre-treatment AB101 group produced significantly higher levels of IL-2, with a median of 292 ng/mL, almost three-fold higher than the 104 ng/mL from T cells in the corresponding isotype control treatment group (n=21, p<0.0001). The AB101 Pre/Post treatment generated an IL-2 response by T cells of 333 ng/mL, 50% greater than the 227 ng/mL from isotype control treated M2c/T cell cocultures; this difference, however, did not reach significance.

Example 18—AB101 is More Potent than AB104 in Restoring T Cell Proliferation and Cytokine Response by T Cells Cocultured with M2c Macrophages To determine if AB101 mediated relief of immune suppression requires interactions with Fc receptors expressed by M2c macrophages, we evaluated the AB101-IgG4 (AB104) and AB101-IgG1Fcnull (AB102) isotypes in the M2c/T cell coculture assay. The AB101 IgG1-Fc region binds to CD64, CD32 and CD16 on M2c macrophages, whereas the binding of the IgG1Fcnull isotype to Fcγ receptors is minimal. Like the IgG1 Fc region, the IgG4 Fc region has a nanomolar affinity to CD64 but does not usually bind to CD32 or CD16 Fc receptors. The ability of AB101, AB102 and AB104 isotypes to relieve M2c mediated immune suppression on T cell proliferation was compared with cells from 5 study subjects.

T cells isolated from 4 ($CD8^+$ T cells) and 5 ($CD4^+$ T cells) human subjects were activated with anti-CD3 (OKT3, 0.25 μg/mL) in the presence of M2c macrophages. M2c/T cell cocultures were treated under Pre/Post-regimens with 20 μg/mL of the indicated isotypes of AB101. M2/T cell coculture alone was used as a control for M2c mediated immune suppression. T cells were harvested 72 h after anti-CD3 stimulation and proliferation was quantified by flow cytometry. Symbols represent individual study subjects. P values were calculated by paired, two tailed t-test comparing the indicated treatment groups ($p<0.05$, *; ns, not significant).

Figure 36:
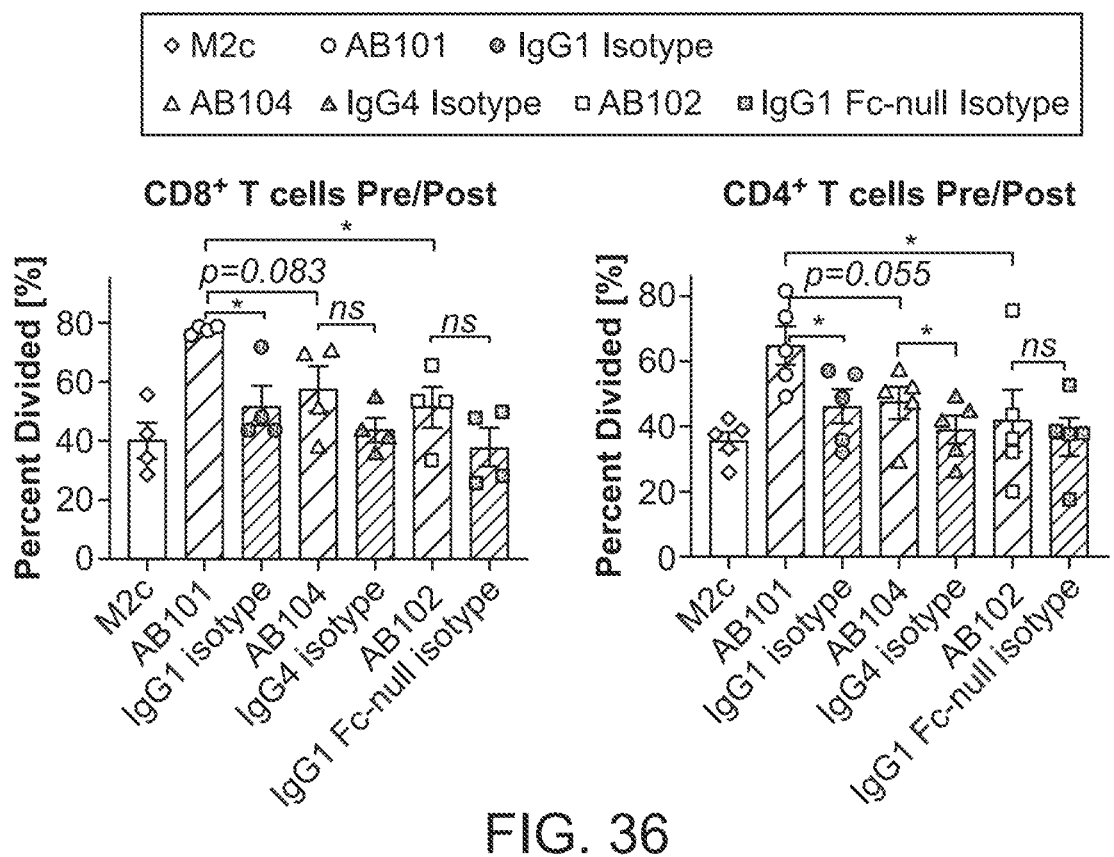
FIG. 36 shows that AB101 is more potent than AB104 and AB102 isotypes in enhancing T cell proliferation in M2c/T cell coculture assay.

FIG. 36 shows that AB101 Pre/Post-regimen significantly ($p<0.05$) enhanced the mean proliferation of anti-CD3 activated $CD8^+$ and $CD4^+$ T cells, when compared to IgG1 isotype control (52 to 78% $CD8^+$ T cells; 46 to 65% $CD4^+$ T cells) and to AB102 (52 to 78% $CD8^+$ T cells; 42 to 65% $CD4^+$ T cells). AB104 and AB102 treatment only marginally enhanced the proliferative response of T cells when compared to the respective isotype controls. Only the proliferative response of $CD4^+$ T cells in the AB104 treatment group reached significance over the IgG4 isotype control group (39 to 47% divided cells, $p<0.05$).

Figure 37:
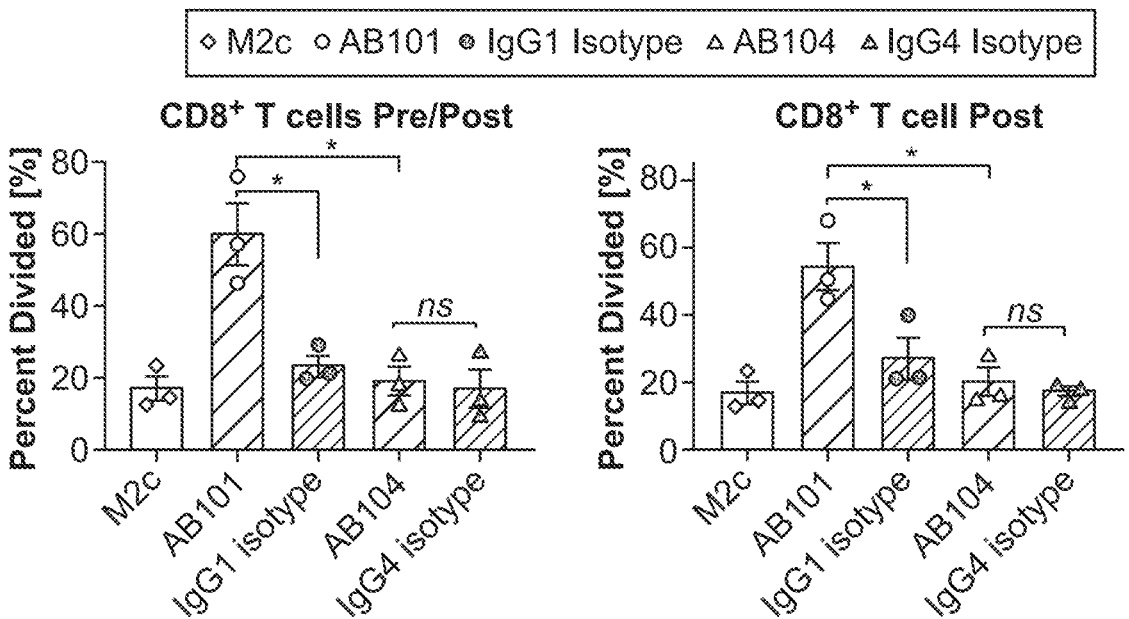
FIG. 37 shows that AB101, but not AB104, pre/post and post-regimen rescued CD8+ T cell proliferation from M2c mediated immune suppression.

FIG. 37 shows that AB101 Pre/Post-regimen had a strong and significant stimulatory effect on OKT3 mediated $CD8^+$ T cell proliferation (70% divided cells) when compared to IgG1 isotype control (40% divided cells, $p<0.05$) and AB104 treatment (41% divided cells, $p<0.05$). Additionally, AB101 Post-regimen demonstrated significantly enhanced $CD8^+$ T cell proliferation (54% divided cells), when compared to isotype control (27% divided cells, $p<0.05$), or AB104 treatment (20% divided cells, $p<0.05$). AB104 treatment did not significantly improve the proliferative response over the IgG4 isotype control in Pre/Post- or Post-regimen.

AB101 treatment during M2c/T cell coculture (Post-regimen) relieved M2c mediated immunosuppression and induced a potent cytokine response by anti-CD3 activated $CD8^+$ T cells. $CD8^+$ T cells isolated from 3 study subjects were activated with anti-CD3 (OKT3, 0.25 μg/mL) in the presence of M2c macrophages. M2c/T cell cocultures were treated under Post-regimen with 20 pg/mL of AB101, human IgG1 isotype control, AB104, human IgG4 isotype control, and media alone (M2c). Supernatants were taken 72 h after anti-CD3 stimulation and cytokine secretion was quantified by magnetic bead-based immunoassay. P values were calculated by paired, two tailed t-tests comparing the indicated treatment groups ($p<0.05$, *; $p<0.01$, ; $p<0.001$, *; ns, not significant).

Figure 38:
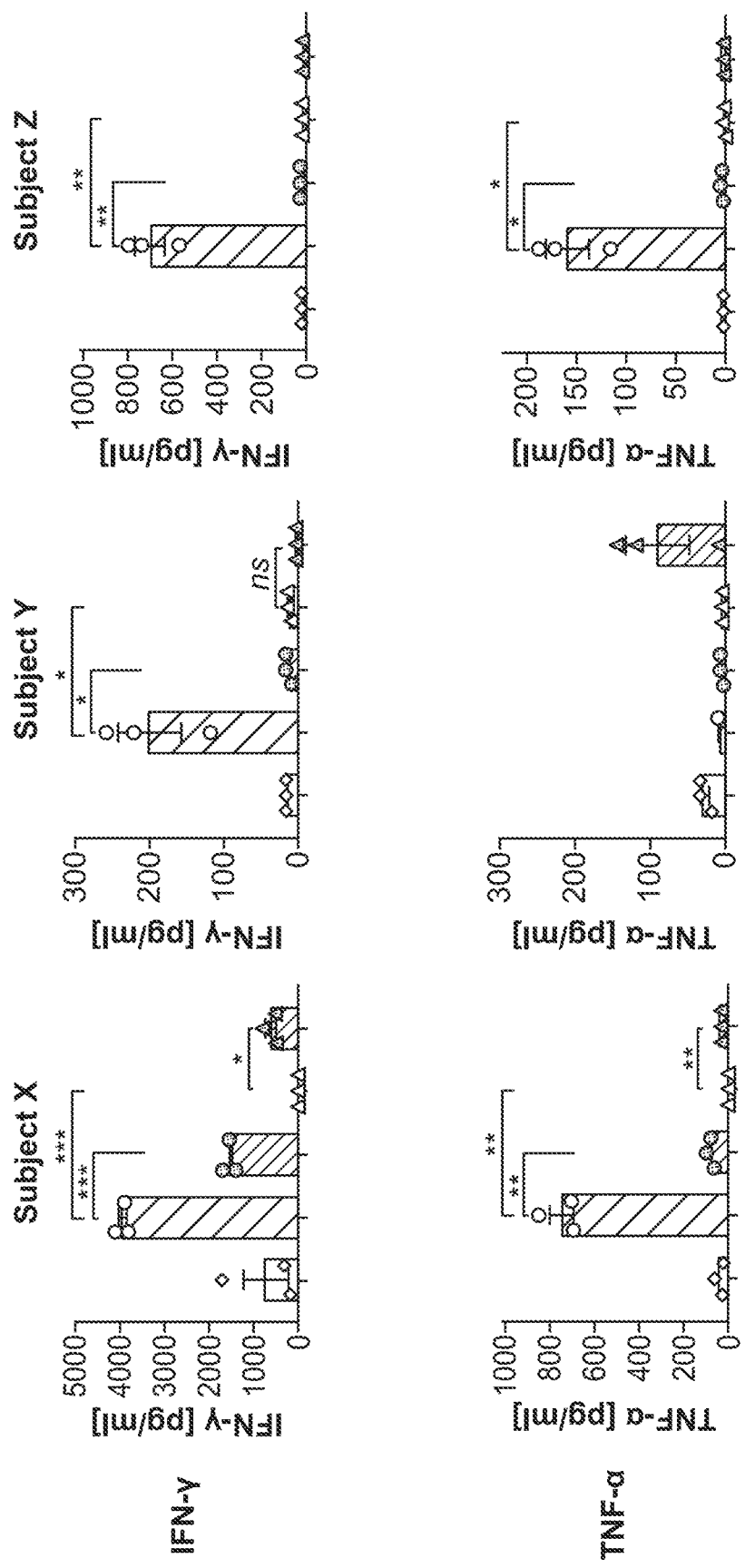
FIG. 38 shows that AB101 restored CD8+ T cell cytokine response in M2c/T cell coculture assay.
Figure 38:
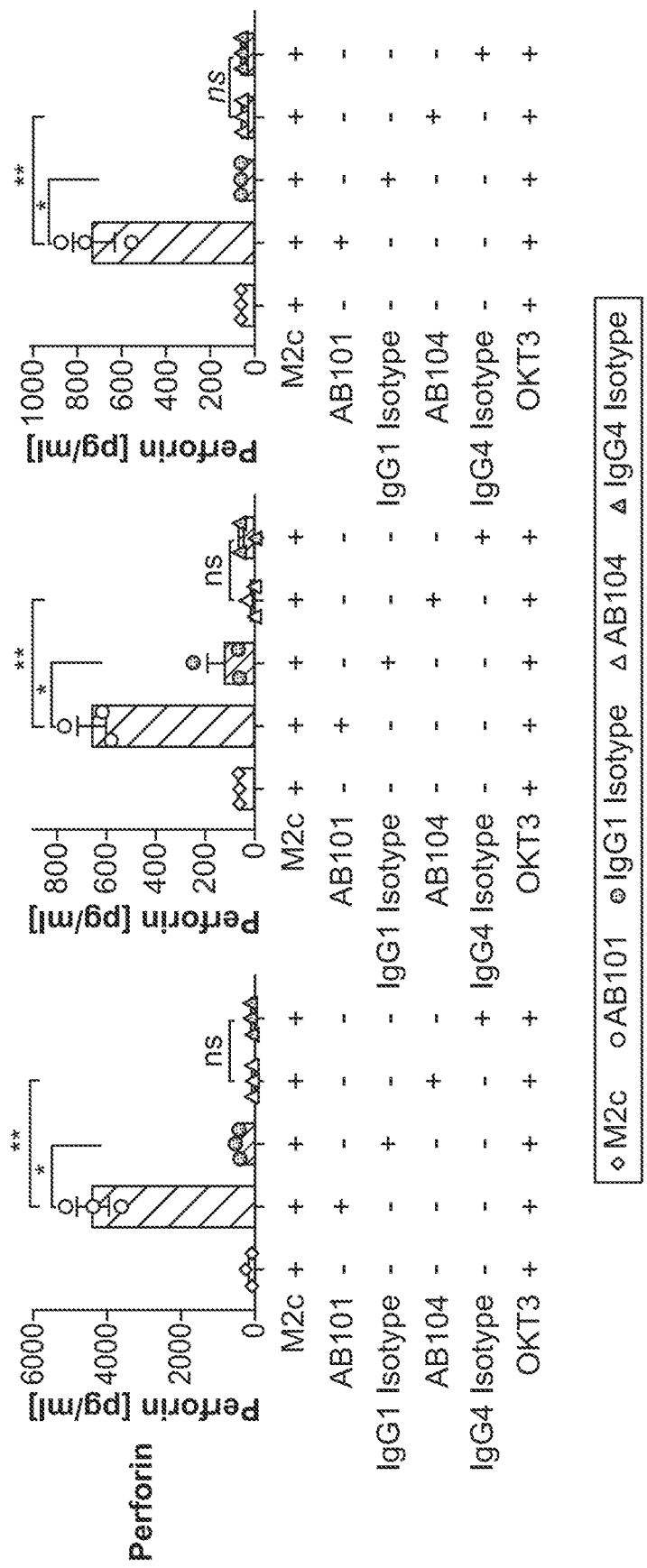

FIG. 38 shows that AB101 significantly enhanced the IFN-γ and perforin levels in all study subjects when compared to the IgG1 isotype control. Table 6 shows that the mean IFN-γ, perforin and IL-6 levels in the AB101 treatment groups increased from 530 to 1600 pg/mL (IFN-γ), 210 to 1900 pg/mL (perforin) and 203 to 690 pg/mL (IL-6) in comparison to IgG1 isotype control values. In addition, AB101 treatment restored TNF-α secretion in 2 of the 3 study subjects with significant increase over the corresponding IgG1 isotype control values from 60 to 830 pg/mL and from 1 to 120 pg/mL. As shown in Table 6 the AB101 Pre/Post-regimen confirmed the results observed with the Post-regimen group by inducing similar cytokine levels for perforin and tested cytokines. AB104 did not relieve M2c mediated immune suppression in any of the treatment groups. The IL-10 levels in the evaluated M2c cocultures were at the lower detection limit of the assay under all treatment conditions.

TABLE 6

AB101 Rescued $CD8^+$ T cell Cytokine Response from M2c Macrophage Mediated Immune Suppression
Cytokine Secretion by $CD8^+$ T cells [pg/mL]

| Cytokines | | Controls | | Pre/Post-Regimen | | | | Post-Regimen | | | |
|---|---|---|---|---|---|---|---|---|---|---|---|
| | | No antibody | | AB101 | | AB104 | | AB101 | | AB104 | |
| | | M1 | M2 | Ab | Iso | Ab | Iso | Ab | Iso | Ab | Iso |
| IL-6 | Mean | 243 | 27 | 744 | 62 | 12 | 51 | 686 | 203 | 22 | 77 |
| | SEM | 113 | 16 | 222 | 36 | 5 | 28 | 201 | 86 | 21 | 53 |
| IL10 | Mean | 4 | 20 | 26 | 11 | 9 | 13 | 20 | 16 | 10 | 13 |
| | SEM | 4 | 10 | 17 | 0 | 5 | 3 | 10 | 3 | 7 | 3 |
| IFN-γ | Mean | 3016 | 259 | 1730 | 461 | 14 | 134 | 1615 | 531 | 172 | 20 |
| | SEM | 1209 | 295 | 1441 | 549 | 5 | 153 | 1439 | 632 | 22 | 55 |
| TNF-α | Mean | 53 | 14 | 330 | 23 | 2 | 12 | 312 | 31 | 2 | 14 |
| | SEM | 24 | 15 | 310 | 25 | 1 | 12 | 272 | 32 | 2 | 15 |
| Perforin | Mean | 220 | 91 | 2459 | 144 | 57 | 72 | 1912 | 213 | 48 | 73 |
| | SEM | 129 | 34 | 1945 | 124 | 8 | 24 | 1494 | 147 | 19 | 23 |

Figure 39:
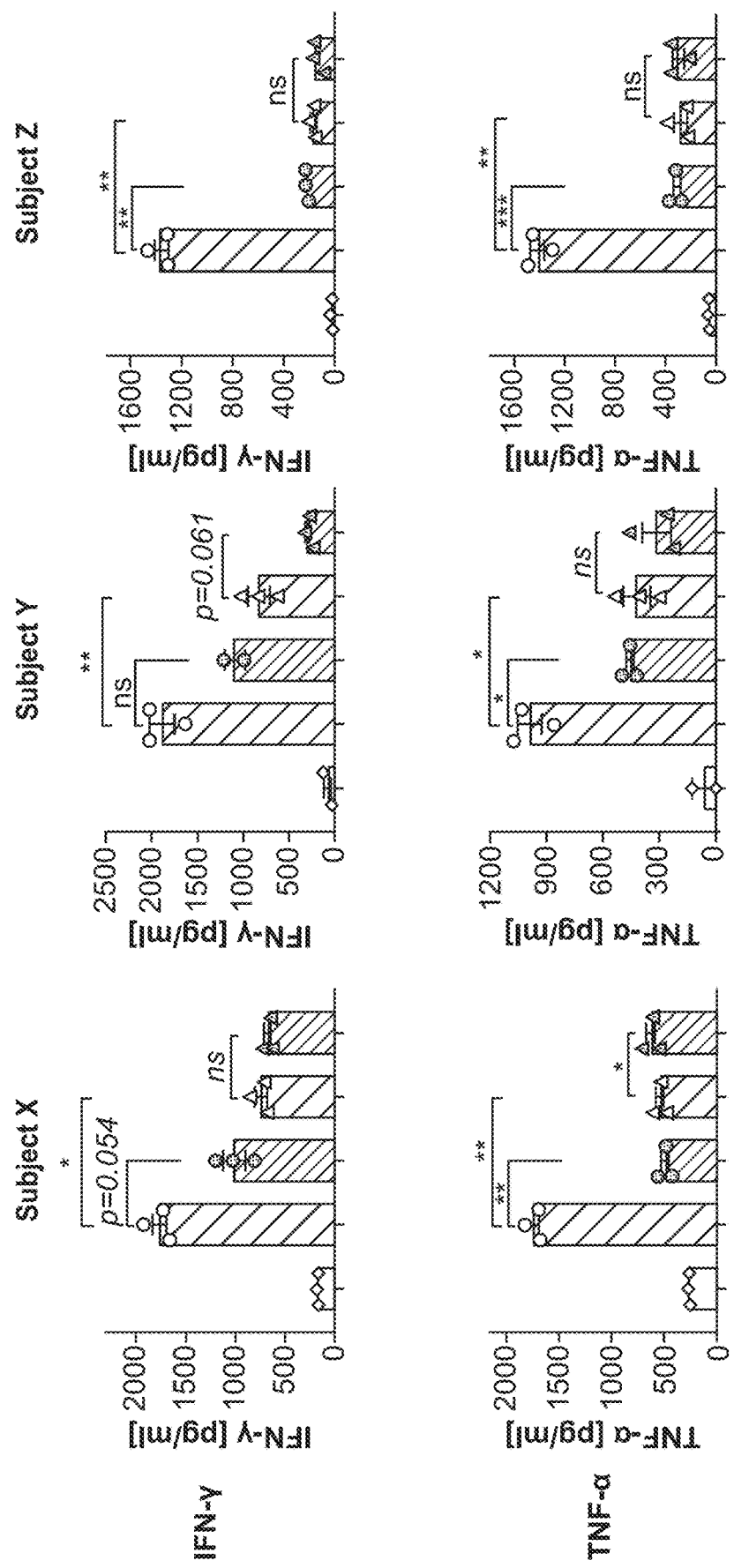
FIG. 39 shows that AB101 rescued CD4+ T cell IFN-γ, TNF-α and perforin response from M2c macrophage mediated immune suppression.
Figure 39:
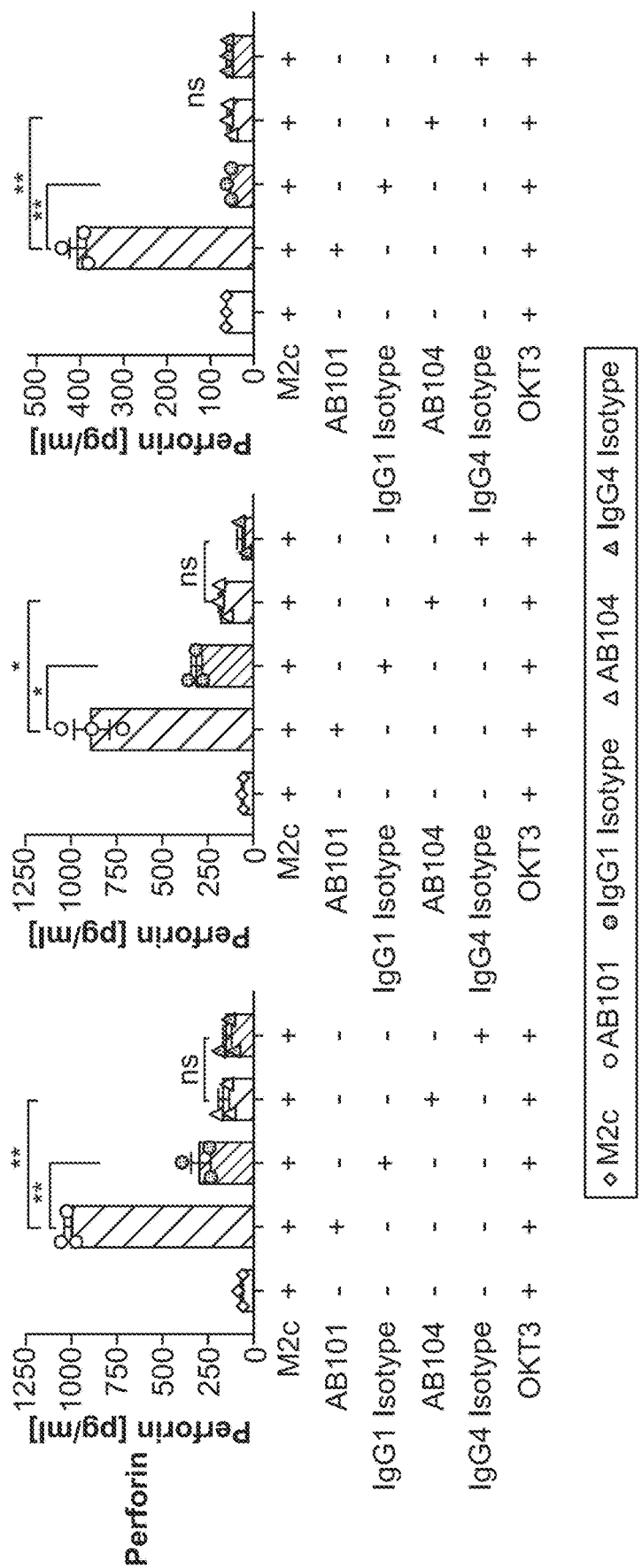

The corresponding cytokine and perforin results for AB101 Post- and Pre/Post-regimen M2c/$CD4^+$ T cell cocultures are shown in FIG. 39 and Table 7. $CD4^+$ T cells isolated from 3 healthy study subjects were activated with anti-CD3 (OKT3, 0.25 μg/mL) in the presence of M2c macrophages. M2c/T cell cocultures were treated under the Post regimens with AB101 (20 μg/mL), human IgG1 isotype control (20 μg/mL), AB104 (20 μg/mL), human IgG4 isotype control (20 μg/mL), and media alone (M2c). Supernatants were taken 72 h after anti-CD3 stimulation and cytokine secretion was quantified by magnetic bead-based immunoassay. P values were calculated by paired, two tailed t-tests comparing the indicated treatment groups ($p<0.05$, *; $p<0.01$, **; ns: not significant).

AB101 significantly enhanced the IFN-γ, TNF-α and perforin levels in all study subjects when compared to the IgG1 isotype control and AB104. The mean IFN-γ, TNF-α, perforin and IL-6 levels in the AB101 treatment groups increased from 770 to 1700 pg/mL (IFN-γ), 420 to 1400 pg/mL (TNF-α), 220 to 780 pg/mL (perforin) and 1300 to 5100 pg/mL (IL-6) in comparison to IgG 1 isotype control values. AB101 Pre/Post-regimen confirmed the results observed with the Post-regimen group by inducing similar cytokine levels for perforin and tested cytokines. AB104 did not enhance cytokine or perforin responses when compared to the corresponding levels of the IgG4-isotype control group.

TABLE 7

AB101 Rescued CD4+ T cell Cytokine Response from
M2c Macrophage Mediated Immune Suppression
Cytokine Secretion by CD4+ T cells [pg/mL]

| Cytokines | | Controls | | Pre/Post-Regimen | | | | Post-Regimen | | | |
| --- | --- | --- | --- | --- | --- | --- | --- | --- | --- | --- | --- |
| | | No antibody | | AB101 | | AB104 | | AB101 | | AB104 | |
| | | M1 | M2 | Ab | Iso | Ab | Iso | Ab | Iso | Ab | Iso |
| IL-6 | Mean | 372 | 112 | 5039 | 1092 | 1015 | 940 | 5129 | 1330 | 1101 | 738 |
| | SEM | 205 | 33 | 1813 | 236 | 214 | 362 | 2372 | 388 | 380 | 153 |
| IL10 | Mean | 93 | 67 | 576 | 232 | 171 | 132 | 533 | 218 | 164 | 129 |
| | SEM | 50 | 35 | 171 | 106 | 53 | 35 | 103 | 106 | 68 | 67 |
| IFN-γ | Mean | 4202 | 84 | 1609 | 721 | 562 | 416 | 1678 | 774 | 588 | 366 |
| | SEM | 1012 | 53 | 251 | 291 | 176 | 96 | 195 | 345 | 255 | 194 |
| TNF-α | Mean | 175 | 133 | 1356 | 424 | 427 | 500 | 1377 | 423 | 417 | 419 |
| | SEM | 95 | 82 | 402 | 70 | 70 | 95 | 261 | 59 | 87 | 121 |
| Perforin | Mean | 117 | 64 | 685 | 173 | 122 | 99 | 776 | 224 | 138 | 94 |
| | SEM | 58 | 5 | 195 | 50 | 33 | 9 | 231 | 103 | 48 | 34 |

In conclusion, the rescue of the T cell cytokine response by AB101 from M2c mediated immune suppression and the lack of efficacy by the AB104 isotype suggest that AB101 Fc receptor interactions may be required for the AB101 function.

Example 19—AB101 Treatment Enhanced the Cytotoxic Activity of CD8+ T Cells

To determine if AB101 enhances tumor cell killing by CD8+ T cells in the TME, the cytotoxic activity of CD8+ T cells stimulated with anti-CD3 antibody in the presence of M2c macrophages was evaluated. In this study, the tumor antigen specific, T cell mediated, killing of tumor cells was substituted with Bispecific T cell Engager (BiTE®) technology. BiTE antibodies are fusion proteins, consisting of variable domains of two monoclonal antibodies, that are designed to bridge cancer cells to CTLs. One variable domain targets an antigen on the cancer cell surface, and the other variable domain engages CD3 on the surface of a T cell. Upon binding of both arms of the BiTE® antibody, T cells and cancer cells are forced within proximity of one another. As a result, a cytolytic synapse is created between the T cell and cancer cell, perforin and granzymes are released from the T cell, and tumor cell death occurs.

The CD19-CD3 BiTE antibody was used to assess the efficacy of AB101 in T-cell-mediated tumor cell killing of Raji B cell lymphoma cells which express the CD19 target of BiTE. AB101 treatment of the M2c/CD8+ T cell coculture relieves M2c mediated immune suppression and may expand and enhance the cytolytic activity of CD8+ T cells. CD8+ T cells may also kill Raji cells by allogenic HLA-restricted cytolysis in the absence of BiTE. K562 cells (chronic myeloid leukemia cell line) that do not express the BiTE or HLA were included for the evaluation of non-HLA-restricted cell death by CD8+ T cells.

A coculture of M2c macrophages and autologous human primary CD8+ T cells was activated with anti-CD3 and expanded for 3 days. Cocultures were treated with AB101 (20 µg/mL), human IgG1 isotype control (20 µg/mL) or media alone under Pre-, Pre/Post-, and Post-regimen. Under Pre- and Post-regimen, therapeutic antibodies were added only during M2c polarization and during M2c T cell coculture, respectively. P values were calculated by paired, two tailed t-test comparing AB101 to M2c and isotype control treatment groups, respectively (p<0.05, *; p<0.01, ; p<0.001, *; p<0.0001, ****; ns: not significant). The workflow of the M2/T cell coculture assay with cytotoxicity readout is shown in FIG. 28.

Figure 40:
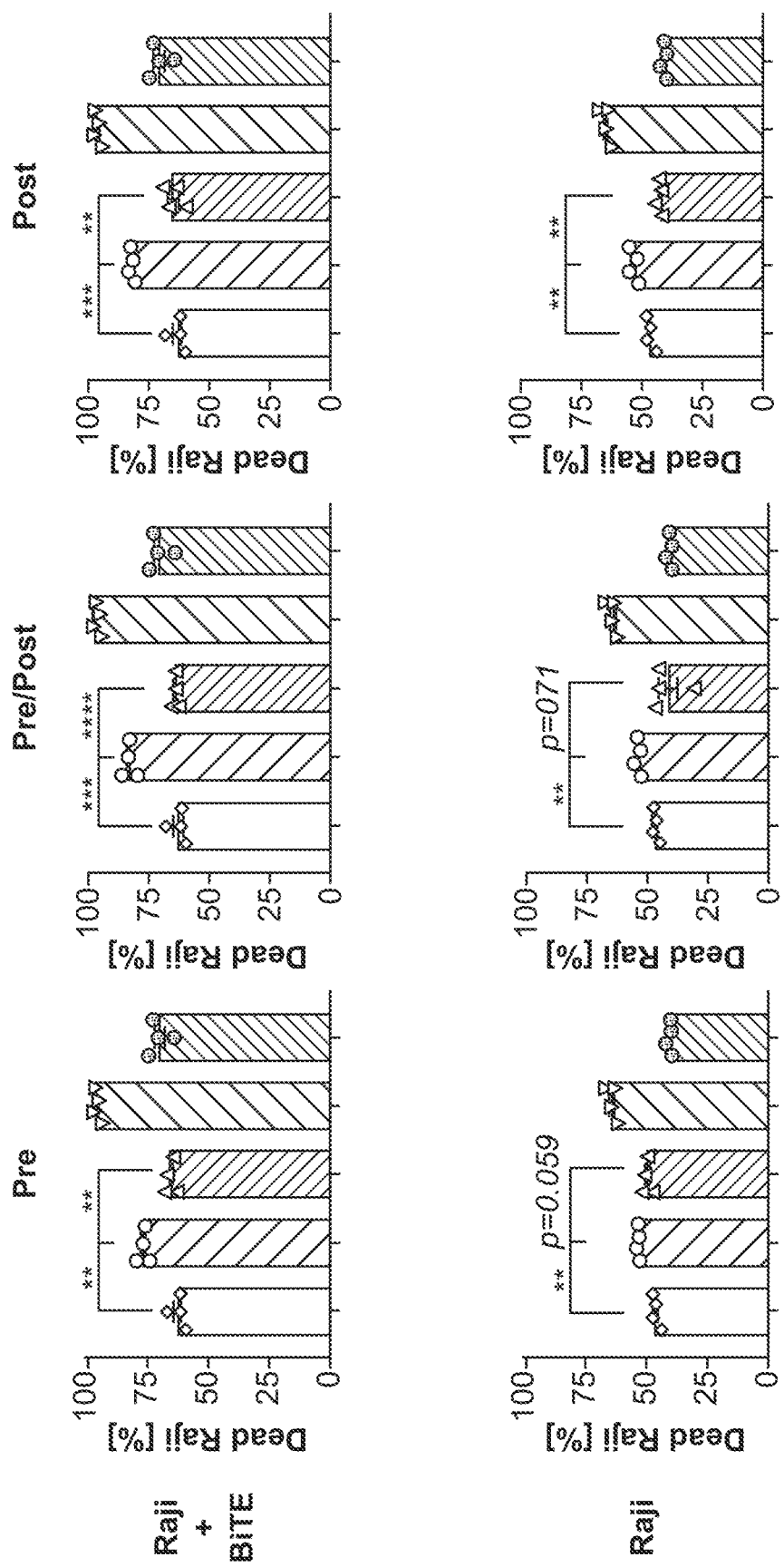
FIG. 40 shows that AB101 treatment enhanced the cytotoxic activity of CD8+ T cells.
Figure 40:
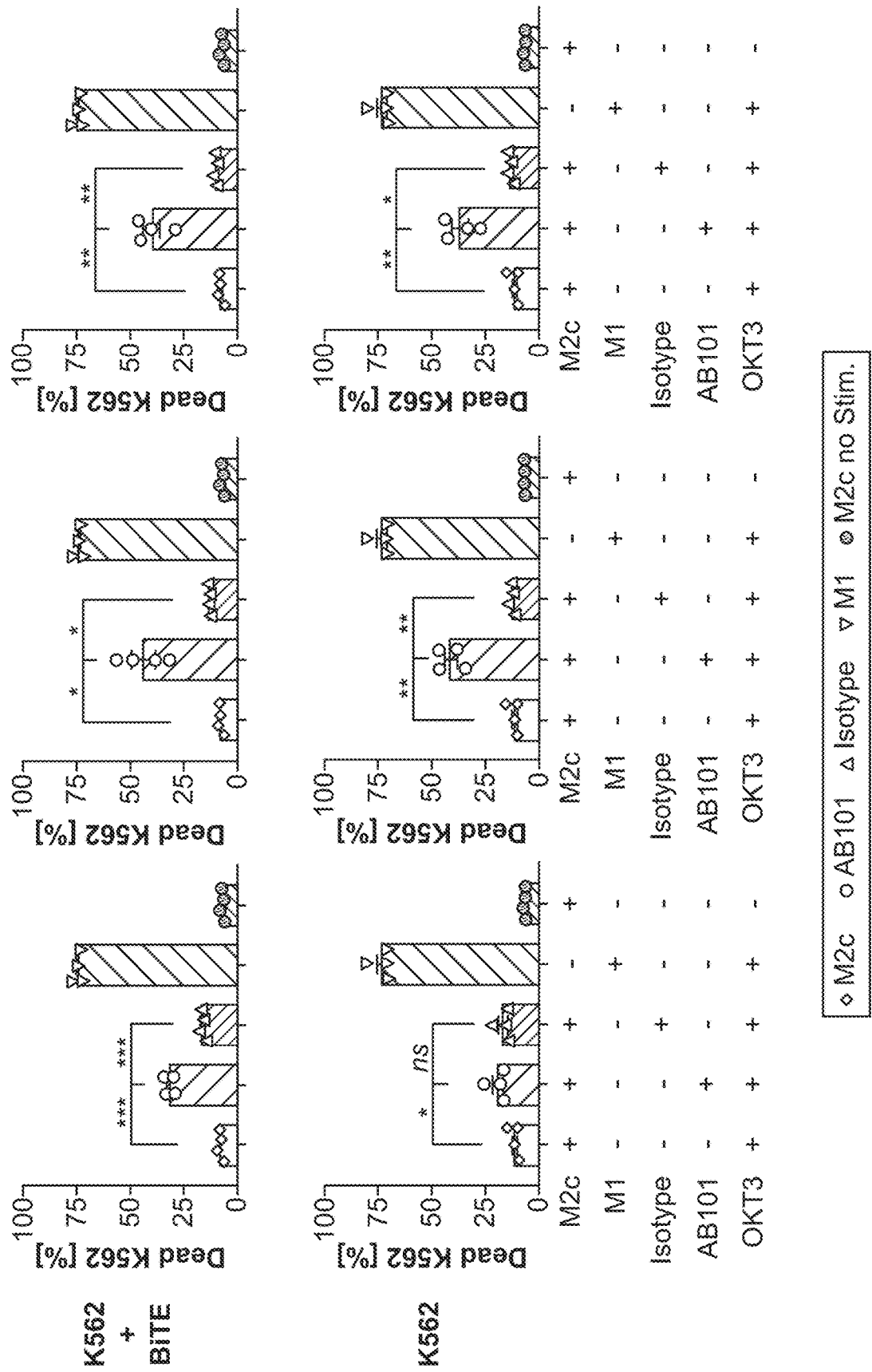

FIG. 40 shows that AB101 treatment during polarization of M0 to M2 macrophages or during M2c/T cell coculture enhanced the killing of Raji cells in the presence of the CD19-CD3 BiTE® antibody significantly, when compared to the isotype control. The percent of Raji cell death increased from 66 to 77% (p<0.01) under Pre, from 64 to 83% (p<0.001) under Pre/Post and from 65 to 82% (p<0.01) under Post-regimens. The Raji BiTE® killing assay had a small dynamic range and high background with resting CD8+ T cell (grey bar, black circles) cultured with M2c cells killing 71% of Raji cells.

Notably, AB101 treatment also increased the cytotoxic activity of non-HLA-restricted CD8+ T cells targeting K562 cancer cells. Pre/Post- and Post AB101 treatment of M2c macrophages and T cells enhanced the tumor cell killing from 12 to 41% under Pre/Post (p<0.01) and from 13 to 36% (p<0.05) under Post conditions compares to the related isotype control values.

Next, the effect of AB101 on the cytotoxic activity of CD8+ T cells from a panel of human subjects was evaluated. CD8+ T cells from 8 study subjects were propagated in the presence of autologous M2c macrophages with anti-CD3 (OKT3, 0.25 µg/mL). M2c macrophages alone and cocultures were treated with AB101 (20 µg/mL), human IgG1 isotype control (20 µg/mL) or media alone under Pre-, Pre/Post-, and Post-regimens. T cells were harvested 72 h after anti-CD3 stimulation and cultured with Raji cells in the presence or absence of CD19-CD3 BiTE antibody. Cell death of Raji cells was determined by flow cytometry 18 h after cytolysis assay setup. P values were calculated by paired, two tailed t-test comparing AB101 to M2c and human IgG1 isotype control treatment groups, respectively (p<0.01, ; p<0.001, *).

Figure 41:
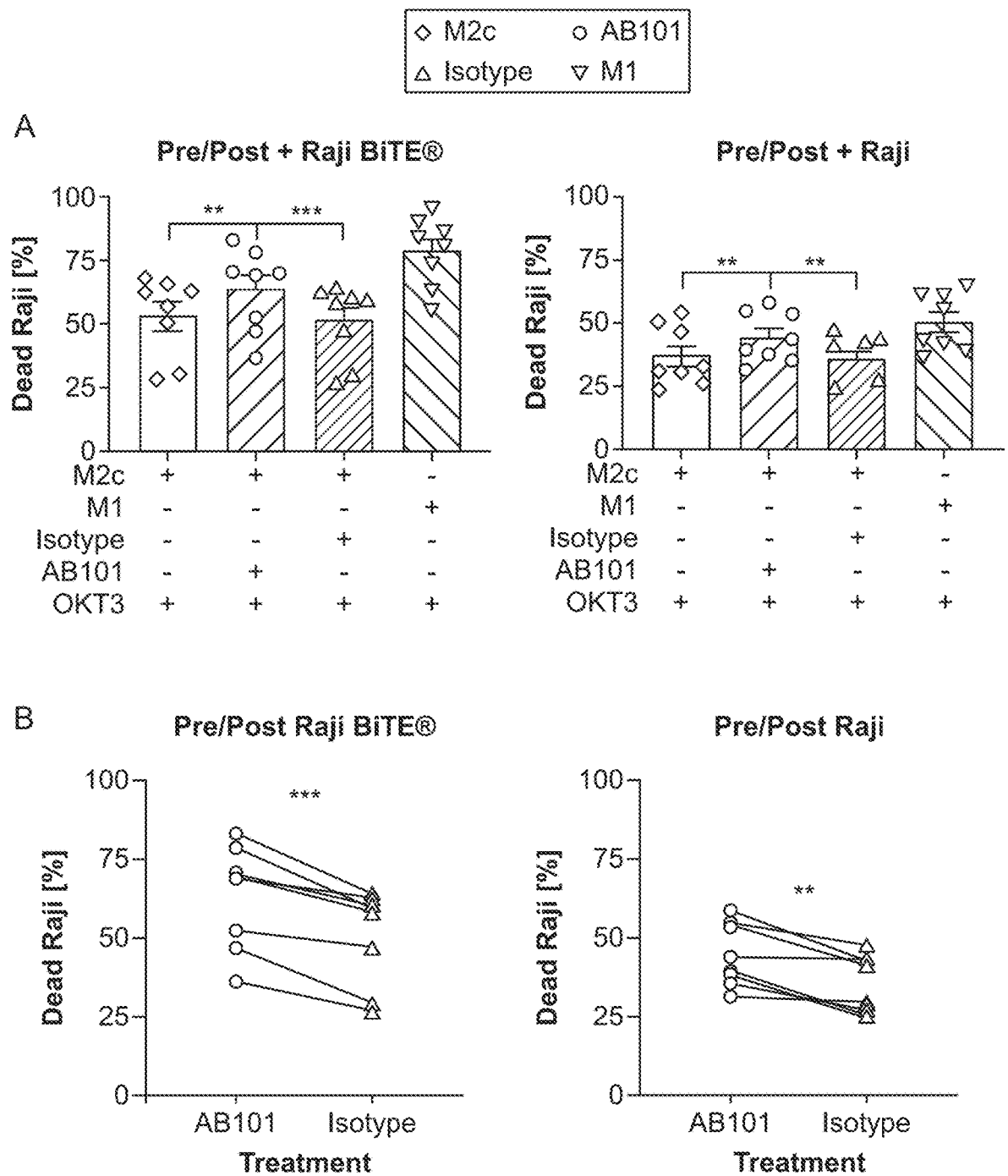
FIG. 41 shows that AB101 treatment enhanced the BiTE®-assisted cytotoxic activity of CD8+ T cells.

As shown in FIG. 41, AB101 Pre/Post treatment significantly increased the CD8+ T cell-mediated BiTE®-assisted Raji cell killing from 49.5 to 63.5% (p<0.001) when compared to the human IgG1 isotype control group. Without BiTE, CD8+ T cells from the AB101 group enhanced the cytolysis of Raji cells from 35 to 43% (p<0.01).

Next, the effect of AB101 on the cytotoxic activity of non-HLA restricted CD8+ T cells was evaluated. CD8+ T cells from 8 study subjects were propagated in the presence of autologous M2c macrophages with anti-CD3 (OKT3, 0.25 μg/mL). M2c macrophages alone and cocultures were treated with AB101 (20 μg/mL), human IgG1 isotype control (20 μg/mL), or media alone under Pre-, Pre/Post-, and Post-regimens. T cells were harvested 72 h after anti-CD3 stimulation and cultured with K562 cells. Cell death of K562 cells was determined by flow cytometry 18 h after assay setup. P values were calculated by paired, two tailed t-test comparing AB101 to M2c and human IgG1 isotype control treatment groups, respectively (p<0.01, **).

Figure 42:
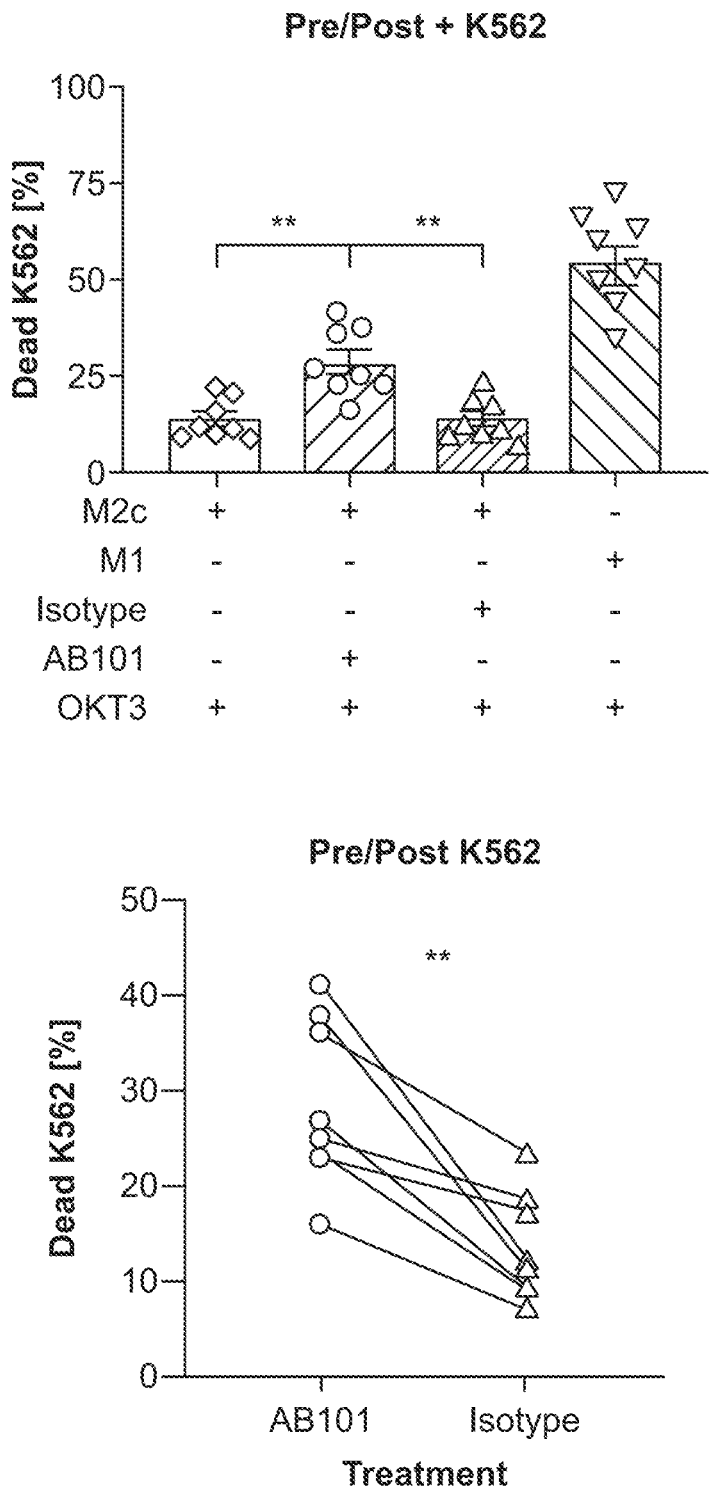
FIG. 42 shows that AB101 treatment enhanced the cytotoxic activity of non-HLA restricted CD8+ T cells.

FIG. 42 shows that AB101 treatment had the strongest effect on cytolytic CD8$^+$ T cells activity in the K562 killing assay. The mean cell death in the AB101 treatment group was twice as high as a the human IgG1 isotype control group, increasing the mean K562 killing from 14 to 29%, respectively (p<0.01).

Example 20—AB101 Modulates the Expression of Chemokine Receptors on T Cells Cocultured with M2c Macrophages To determine if AB101 alters the activation state of CD4$^+$ and CD8$^+$ T cells, the expression of chemokine receptors and markers of activation or exhaustion were evaluated in the M2c/T cell coculture assay as shown in FIG. 28.

Anti-CD3 activated T cells were cocultured with autologous M2c cells treated with AB101 or isotype control during polarization. Anti-CD3 activated T cells cocultured with naïve M2c or IFN-γ LPS activated M1 macrophages were included as controls for immune suppression and immune activation, respectively. Resting T cells were cocultured with M2c macrophages without anti-CD3 activation. Three days after anti-CD3 activation, T cells were analyzed by flow cytometry. The flow cytometry staining panel 1 (Table 8) included antibodies for activation markers (CD25 and CD69), resting T cell marker CD127, as well as chemokine receptors CXCR3, CCR4 (CD194) and CCR6 (CD196) typically used to differentiate CD4$^+$ T cell subsets. Flow cytometry antibody panel 2 (Table 8) contained the T cell activation and exhaustion markers LAG3, OX40, PD-1, ICOS and CTLA-4.

T cells isolated from 3 study subjects were activated with anti-CD3 (OKT3, 0.25 μg/mL) in the presence of M2c macrophages. M2c/T cell cocultures were treated during M2c polarization with AB101 (20 μg/mL), human IgG1 isotype control (20 μg/mL), or media alone. M1/T cell coculture was included as a positive control. Supernatants were harvested 72 h after anti-CD3 stimulation for flow cytometry. Heatmap represents the FlowSOM cluster analysis of the combined treatment groups of all study subjects.

Figure 43:
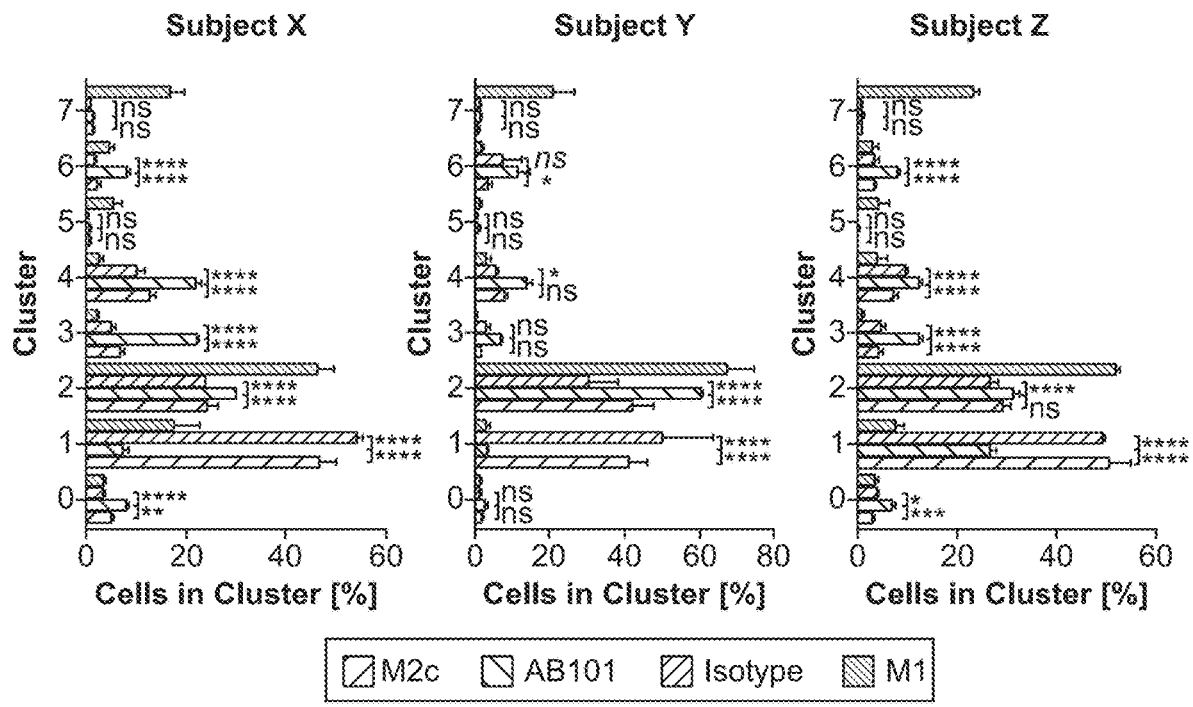
FIG. 43 shows that AB101 treatment relieved M2c cell mediated immune suppression and induces a unique expression pattern by activated CD4+ T cells.

The phenotype of CD4$^+$ T cells was evaluated using flow cytometry panel 1 and the FlowJo FlowSOM plugin for non-biased clustering. As shown in FIG. 43, FlowSOM clustering of CD4$^+$ T cells from all M2c/T cells coculture groups identified 8 clusters (numbered 0-7) with differential expression levels for the surface markers. Cluster 1 represents resting T cells and cluster 6 resembles activated Th1-like T cells.

TABLE 8

Antibody Panels Used to Assess Expression of Chemokine Receptors on CD4$^+$ T cell Subtypes and Exhaustion/Activation Markers

|  | Antibody Panel 1: T Cell Phenotyping Panel | Antibody Panel 2: Exhaustion/Activation |
|---|---|---|
| Surface markers | CD4 - FITC | CD4 - FITC |
|  | CD69 - PE-Cy7 | CD8 - APC |
|  | CD25 - APC | LAG3 - BV421 |
|  | CD127 - PE | OX40 - BV510 |
|  | CXCR3 - PerCP-Cy5.5 | PD-1 - PerCP-Cy5.5 |
|  | CD194 (CCR4) - BV421 | ICOS - PE-Cy7 |
|  | CD196 (CCR6) - BV510 | CTLA4 - PE |

A visualized representative example of how AB101 treatment influenced the proportions of CD4$^+$ T cells is shown in Table 9 and FIG. 43. The majority (mean=74%) of T cells cocultured with M2c cells without anti-CD3 activation were found in cluster 1 (from 3 out of 3 study subjects). Cluster 1 cells had a resting phenotype with low or no CD69, CXCR3, CCR4 or CD25 expression, and elevated expression of CD127. In the presence of the immune-activating M1 polarized macrophages, the majority of T cells (57%, mean of all 3 subjects) adopt an activated phenotype characterized by high expression of CXCR3 and low expression of CCR4, CD127, CCR6, and activation markers CD25 and CD69 (cluster 2). M1 coculture also induces a unique smaller subset with elevated expression of CD25, CXCR3 and CCR4 (cluster 7, 21% of T cells cocultured with M1). M2c cells had immunosuppressive effects on anti-CD3 activated CD4$^+$ T cells in coculture with 46% of the T cells in the resting phenotype cluster 1. In addition, 32% of the T cells of the M2c alone group were found in the activated T cell phenotype cluster 2.

TABLE 9

AB101 Modulates the Distribution of Activated CD4$^+$ T cells in FlowSOM Cluster

| | Distribution of CD4$^+$ T cells in FlowSOM clusters [%] | | | | | | | | | |
|---|---|---|---|---|---|---|---|---|---|---|
| FlowSOM | Resting T cells M2c | | M2c + OKT3 | | Isotype control M2c + OKT3 | | AB101 M2c + OKT3 | | M1 +OKT3 | |
| Cluster | Mean | SEM | Mean | SEM | Mean | SEM | Mean | SEM | Mean | SEM |
| 0 | 1.7 | 0.3 | 3.3 | 0.9 | 3.0 | 0.7 | 5.9 | 1.6 | 2.9 | 0.8 |
| 1 | 73.1 | 7.8 | 46.3 | 2.9 | 51.3 | 1.6 | 12.3 | 7.3 | 8.9 | 3.7 |
| 2 | 19.8 | 5.7 | 31.9 | 5.3 | 27.4 | 1.9 | 40.5 | 9.8 | 55.6 | 6.1 |
| 3 | 1.3 | 0.8 | 4.3 | 1.5 | 4.2 | 0.7 | 14.0 | 4.5 | 1.1 | 0.5 |
| 4 | 2.9 | 0.8 | 9.6 | 1.7 | 8.7 | 1.5 | 16.0 | 3.0 | 3.3 | 0.5 |
| 5 | 0.2 | 0.0 | 0.3 | 0.1 | 0.2 | 0.1 | 0.6 | 0.1 | 3.9 | 1.3 |

TABLE 9-continued

AB101 Modulates the Distribution of Activated CD4+ T cells in FlowSOM Cluster

Distribution of CD4+ T cells in FlowSOM clusters [%]

| FlowSOM Cluster | Resting T cells M2c | | M2c + OKT3 | | Isotype control M2c + OKT3 | | AB101 M2c + OKT3 | | M1 +OKT3 | |
|---|---|---|---|---|---|---|---|---|---|---|
| | Mean | SEM | Mean | SEM | Mean | SEM | Mean | SEM | Mean | SEM |
| 6 | 0.4 | 0.2 | 3.3 | 0.5 | 4.4 | 1.8 | 9.3 | 1.0 | 3.4 | 0.8 |
| 7 | 0.7 | 0.3 | 1.0 | 0.1 | 0.9 | 0.1 | 1.4 | 0.1 | 20.8 | 1.5 |

FIG. 43 shows that Anti-CD3 activated CD4+ T cells from the isotype control treatment group had a similar distribution profile to the T cells from the corresponding M2c alone group, with a mean of 51% of the T cells in cluster 1 and 27% of T cells in cluster 2 (Table 9).

In contrast, treatment with the AB101 alleviated the suppressive effects of the M2c polarized macrophages. AB101 significantly enhanced the proportion of T cells sharing the activated phenotype of cluster 2 compared to isotype control from 27 to 40% (p<0.05). In addition, AB101 significantly decreased the proportion of cells sharing the phenotype of resting cells from 51 to 13% (cluster 1; p<0.0001). This distribution resembled the phenotype patterns of T cells which have been stimulated in the presence of M1 macrophages.

Clusters 3, 4 and 6 were also elevated by treatment with AB101 when compared to isotype control group. As shown in FIG. 43, the differences in the 3 clusters reached significance in 2 out of the 3 evaluated subjects (p<0.0001) related to the respective M2c and isotype controls.

Cluster 3 and 4 are defined by high expression of CXCR3, mid expression of CCR4 and presence of CD127 with high (Cl. 3) or low (Cl. 4) expression of the activation marker CD69. The phenotype of cluster 3 is not shared with either M1 or resting T cells, appearing unique to AB101 treatment.

Cluster 6 represents the phenotype of activated Th1-like T cells with high expression of CXCR3 and CD69 and minimal expression of CCR4 and CCR6. AB101 treatment increased the mean percentage of proportion of T cells in cluster 6 from 4.4% of the isotype treatment group to 9.3% (Table 9).

In conclusion, the FlowSOM analysis of the CD4+ T cell phenotypes expanded by M2c coculture indicate that AB101 treatment relieves M2c mediated immune suppression and induces the expression of unique T cell phenotypes highlighted by the expression of CXCR3 and CCR4. AB101 treatment also increased the proportion of activated Th1-like CXCR3+ T cells in the M2c cocultures.

To further investigate the ability of AB101 to block M2c-mediated suppression resulting in enhanced activation of T cells, CD4+ and CD8+ T cells were assessed for the markers of activation and exhaustion LAG3, OX40, PD-1, ICOS and CTLA-4. Clustering of CD4+ and CD8+ T cells by FlowSOM identified 5 CD4+ (numbered 0-4) and 4 CD8+ (numbered 0-3) clusters.

The low expression of LAG3, OX40, PD-1 and CTLA-4 in Cluster 0 (CD4+ T cells) and Cluster 3 (CD8+ T cells) are indicative of a resting phenotype. The increased expression of PD-1 and ICOS in cluster 1 (CD4+ T cells) and cluster 3 (CD8+ T cells) represents the activated phenotype in this study (FIG. 44).

Figure 44:
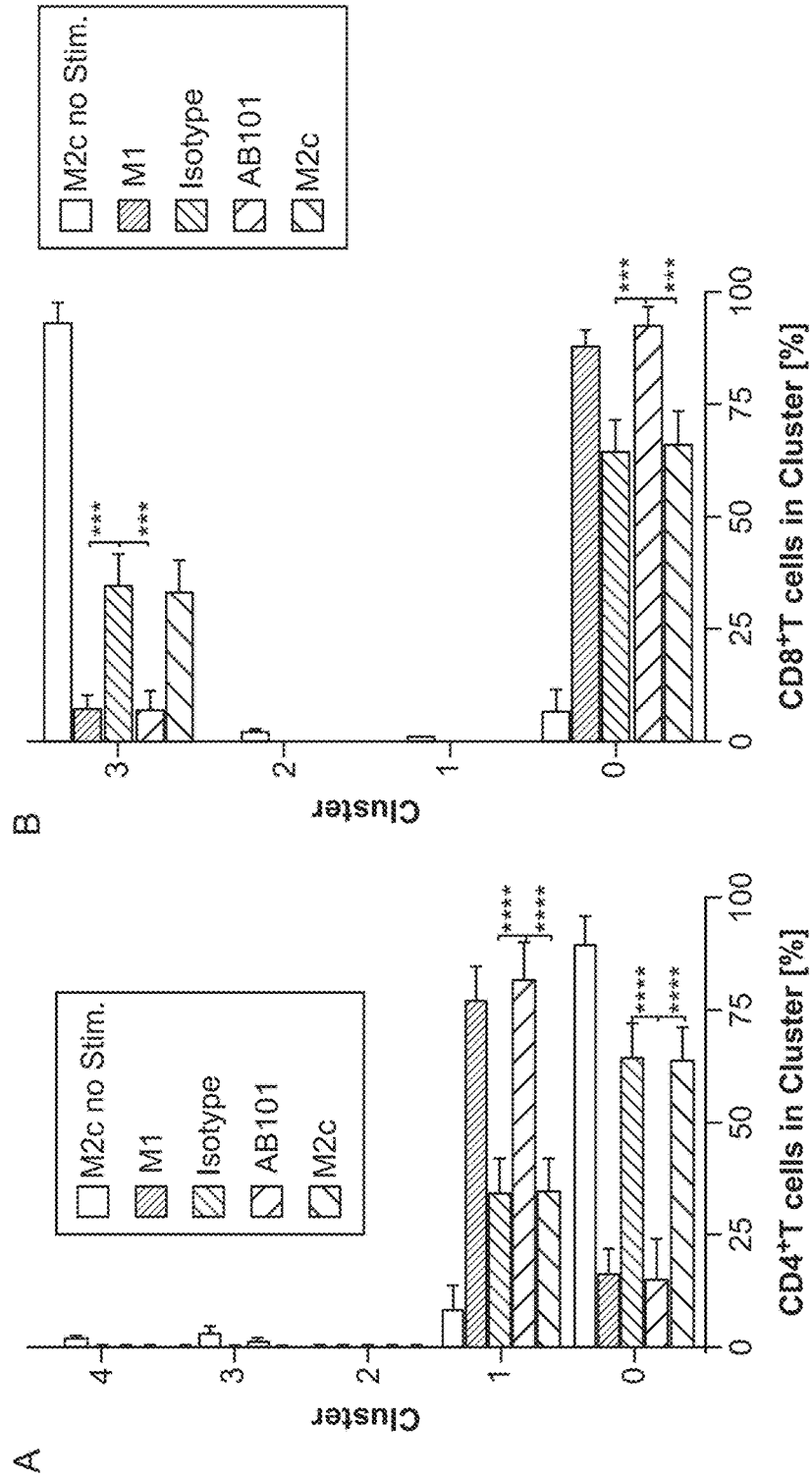
FIG. 44 shows that AB101 treatment relieves M2c macrophages immune suppression and enhances the activation of CD4+ and CD8+ T cells.

Cluster 0 (ICOS$^+$ PD-1$^-$ LAG3$^-$ CTLA4$^-$ OX40$^-$) represents 90% of un-stimulated CD4+ T cells and cluster 3 (ICOS$^{lo}$ PD-1$^-$ LAG3$^-$ CTLA4$^-$ OX40$^-$) represent 93% of resting CD8+ T cells cultured with M2c macrophages without anti-CD3 activation (FIG. 44). When cocultured with M2c polarized macrophages or treated with isotype control, anti-CD3 activated CD4+ and CD8+ T cells primarily fall into the corresponding resting cluster 0 (65% of CD4+ T cells are) and cluster 3 (64% of CD8+ T cells) confirming M2c cell mediated immune suppression.

AB101 significantly enhances the activation of CD4+ and CD8+ T cells when compared to the M2c alone or the isotype control treatment groups. Eighty-two percent of CD4+ T cells and 93% of CD8+ T cells of the AB101 treatment group are found in the respective activated T cell phenotype cluster 1 (ICOS$^{hi}$ PD-1$^+$ LAG3$^-$ CTLA4$^-$ OX40$^{lo}$) and cluster 0 (ICOS$^{hi}$ PD-1$^+$ LAG3$^{lo}$ CTLA4$^-$ OX40$^{lo}$) shared with T cells cocultured with M1 polarized macrophages.

Example 21—AB101 Modulated the Expression of m2c Surface Markers

AB101 treatment during polarization of M0 to M2c macrophages rescued anti-CD3 activated T cells from M2c-mediated immune suppression in the M2c/T cell coculture assay. To determine if AB101 modulates the expression of surface markers and immune checkpoints on M2c, 5-day old M0 macrophages were polarized with IL-10 to M2c macrophages in the presence of AB101 or isotype control (20 μg/mL) and then stained with a panel of macrophage phenotyping antibodies. The flow cytometry profiles were compared to naïve, untreated M2c cells and LPS+IFN-γ polarized M1 macrophages. M2c macrophages express the M2c markers CD163, CD206 and Mer-TK, the Fcγ receptors CD16, CD32, CD64, the pattern recognition receptor TLR2, the TNFR family member CD40. As expected, after IFN-γ treatment, M1 macrophages expressed higher levels of HLA-Class II and the checkpoint ligand PD-L1 when compared to M2c macrophages. In contrast, M2c macrophages showed higher levels of the immune suppressive ligands Siglec-15 and LILRB2 than M1 macrophages. The evaluated surface markers, costimulatory molecules, and receptors CD86, CD91, CD150, Calreticulin, Dectin-1, TIM4 and TLR4 are not expressed on M2c cells.

Figure 45:
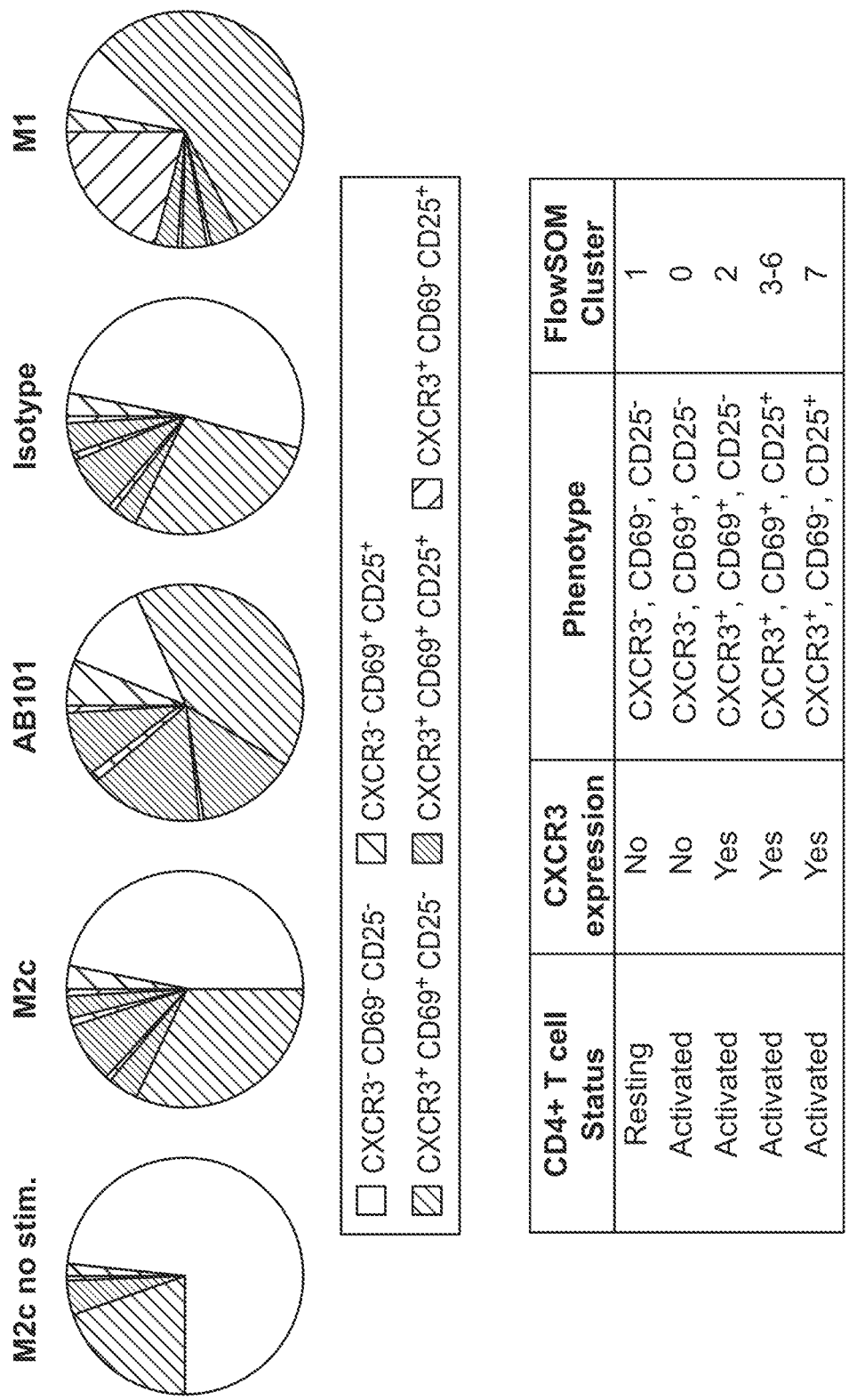
FIG. 45 shows CXCR3 expression by activated CD4+ T cells.

To further analyze the CXCR3 expression by activated CD4+ T cells the FlowSOM clusters 3 to 6 were combined based on their CXCR3+ CD69+ CD25+ T cell phenotype. The proportions of the resulting phenotypes are shown as pie charts in FIG. 45 and represent the phenotypes in the table in FIG. 45.

AB101 treatment increased the proportion of activated CXCR3+, CD4+ T cells expressing the activation markers CD69 and CD25 from 18% to 40% when compared to the isotype treatment group. The OR2572 and M2c alone treatment groups had comparable distribution profiles.

Figure 46:
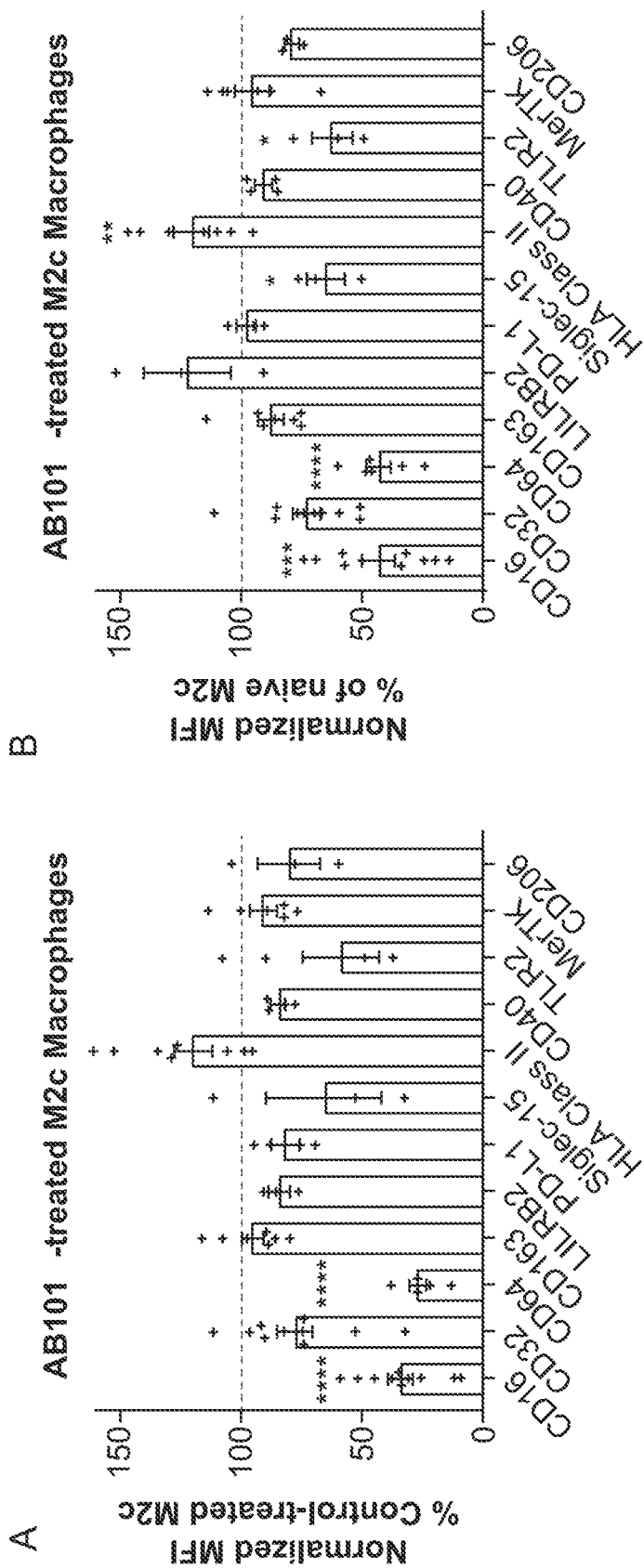
FIG. 46 shows that AB101 treatment during polarization of M2c macrophages reduced the expression of CD16, CD64, Siglex-15 and TLR2 by M2c macrophages.

To quantify the modulatory effect of AB101 on surface marker expression, the mMFI values of the phenotyping antibodies on AB101 treated M2c cells were normalized to the corresponding markers on isotype control (nMFIiso) or untreated, naïve M2c macrophages (nMFIM2c) from up to 10 study subjects (FIG. 46). AB101 induced a highly significant reduction of CD16 (34% nMFIiso, $p<0.0001$) and CD64 (30% nMFIiso, $p<0.0001$) as well as a significant decrease of TLR2 (66% nMFIiso, $p<0.05$) relative to isotype control treated M2c cells. Similar trends were observed when AB101 M2c surface marker MFIs were normalized to naïve M2c macrophages. The nMFIM2c of surface markers from AB101 treated macrophages were reduced significantly for CD16 (44% nMFIM2c, $p<0.001$), CD64 (30% nMFIM2c, $p<0.0001$), TLR2 (63% nMFIM2c, $p<0.05$) and Siglec-15 (66% nMFIM2c, $p<0.05$). AB101 treatment enhanced the expression of HLA-Class II and did not significantly affect the expression of CD163, CD206, MerkTK, LILRB2 and PD-L1, when compared to the M2c macrophage controls.

In summary, AB101 treatment during polarization of M2c macrophages reduced the expression of the innate receptor TLR2 and the checkpoint ligand Siglec-15. In addition, it inhibited IL-10 induced upregulation of CD16 and CD64 on M2c cells.

Example 22—AB101 Binding Increased Protection (Slower HD Exchange) of Regions in SRCR Domain 3 and 4 and Exposed (Faster HD Exchange) Regions in Domain 2, 5, and 9 of CD163

A comparative HDX study was conducted to examine the effects of IgG binding on the CD163. Due to the large number of peptides derived from the excess Ab present in the complex many resulted in many peptides overlapping in m/z and retention times. Ultimately, after filtering out noisy and overlapped peptides a final set of 107 peptides in the pepsin data, corresponding to a coverage of 74% with an average redundancy of 1.28. For the Nepenthesin II data set the final filtered peptide count was 230 corresponding to 87% coverage with an average redundancy of 2.8. When combining the data sets with both proteases the total sequence coverage is 93% with an average redundancy of 4.1.

Hydrogen/Deuterium Exchange with Mass Spectrometry: Starting stock solutions of recombinant human CD163 (rhCD163) was diluted to 0.36 mg/mL in phosphate buffered saline (PBS) pH7.2. Internal exchange reporters: tetrapeptide PPPF or tripeptide YPI were added to each solution for a final concentration of 1 µM. The antibody-complexed sample was made the same way but included 1.38 mg/mL of AB101, which corresponds to a 3-fold molar excess over rhCD163. These working solutions were incubated at 22° C. and stored at 4° C. for 1 day prior to starting the deuterium exchange reactions. 10 µL of the working protein solution was diluted 10-fold into 90 µL deuterated HBS buffer: (20 mM HEPES, pH7.2, 150 mM NaCl, 2 mM $CaCl_2$, 95% $D_2O$) and incubated at 22° C. for 3 sec, 15 sec, 1 min, 5 min, 30 min, 4 hrs, or 20 hrs. The deuterated HBS also contained 0.2 µg/mL of bradykinin to provide a fully deuterated reference compound in all experiments in order to monitor back-exchange. An additional sample was incubated at 37° C. for 20 hours as a highly deuterated sample. Exchanged samples were added to an equal volume (100 µL) of ice-cold quench buffer: 1M TCEP, 0.2% formic acid (FA), for a final pH of 2.5. Samples were flash frozen in an ethanol-dry ice bath (−60° C.) and subsequently stored at −80° C. until LC-MS analysis. Undeuterated reference samples were prepared identically except diluted into aqueous HBS buffer.

Sample processing with immobilized pepsin protease: Frozen samples were thawed on a 5° C. block for 4 minutes prior to injection onto a loading loop. The loaded sample was passed over a custom packed pepsin column (Porcine pepsin immobilized on POROS 20-AL resin; 2.1×50 mm column) kept at 12° C. with a flow of 0.1% trifluoroacetic acid (TFA) and 2% acetonitrile (ACN) at 200 µL/min. Digested peptic fragments were trapped onto a Waters XSelect CSH C18 XP VanGuard Cartridge (2.1×5 mm, 2.5 µm). After 5 minutes of loading, digestion, and trapping, peptides were resolved on an analytical column (Waters CSH 1×100 mm, 1.7 µm, 130 Å) using a gradient of 3% to 40% solvent B for 9 minutes (A: 0.1% FA, 0.025% TFA, 2% ACN; B) 0.1% FA in ACN). The LC system was coupled to a Waters Synapt G2-Si performing full scans over the m/z range of 300-2000 with ion mobility separation enabled. The source conditions were optimized to minimize loss of deuterium during desolvation. Undeuterated samples were run prior to and at the end of all the LC-MS runs. During the analytical separation step, a series of 250 µL injections were used to clean the pepsin column: 1) 0.1% Fos-12 with 0.1% TFA; 2) 2 M GndHCl in 0.1% TFA; 3) 10% acetic acid, 10% acetonitrile, 5% isopropanol. After each gradient the trapping column was washed with a series of 250 µL injections: 1) 10% FA; 2) 30% trifluoroethanol; 3) 80% methanol; 4) 66% isopropanol, 34% ACN; 5) 80% ACN. During the trap washes the analytical column was cleaned with three rapid gradients. These cleaning steps were necessary to ensure that the level of carry-over was below 5% for each peptide analyzed.

Sample processing with immobilized Nepenthesin II protease: Sample processing described above was repeated except Nepenthesin II protease immobilized on POROS 20-AL was used for the online digestion step.

To first ensure that the exchange and sampling conditions were identical for the unbound and antibody-bound states we first examined the exchange profile of the internal standard peptides. For both data sets the PPPI and YPI standards were consistent between the unliganded and antibody-bound data sets ensuring that the conditions were consistent and even subtle changes can be interpreted to be due to altered protein structure and/or dynamics. Furthermore, the fully deuterated bradykinin peptide that was incorporated into the deuterated buffer showed identical deuterium levels, ensuring that the level of back-exchange was not variant among samples within each data set.

Figure 50:
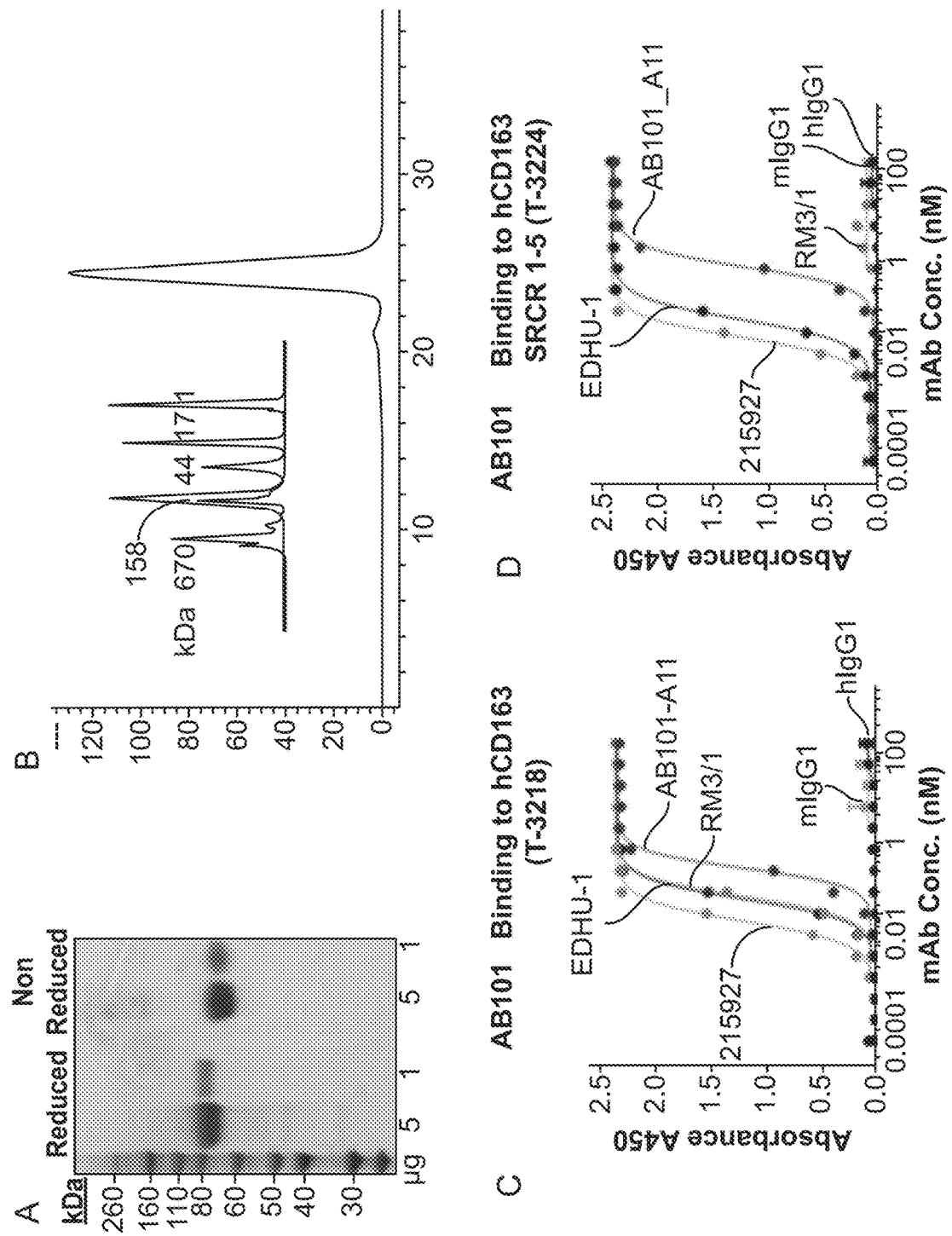
FIG. 50 shows that AB101 binds truncated CD163 ECD composed of SRCR domain 1-5.
Figure 51:
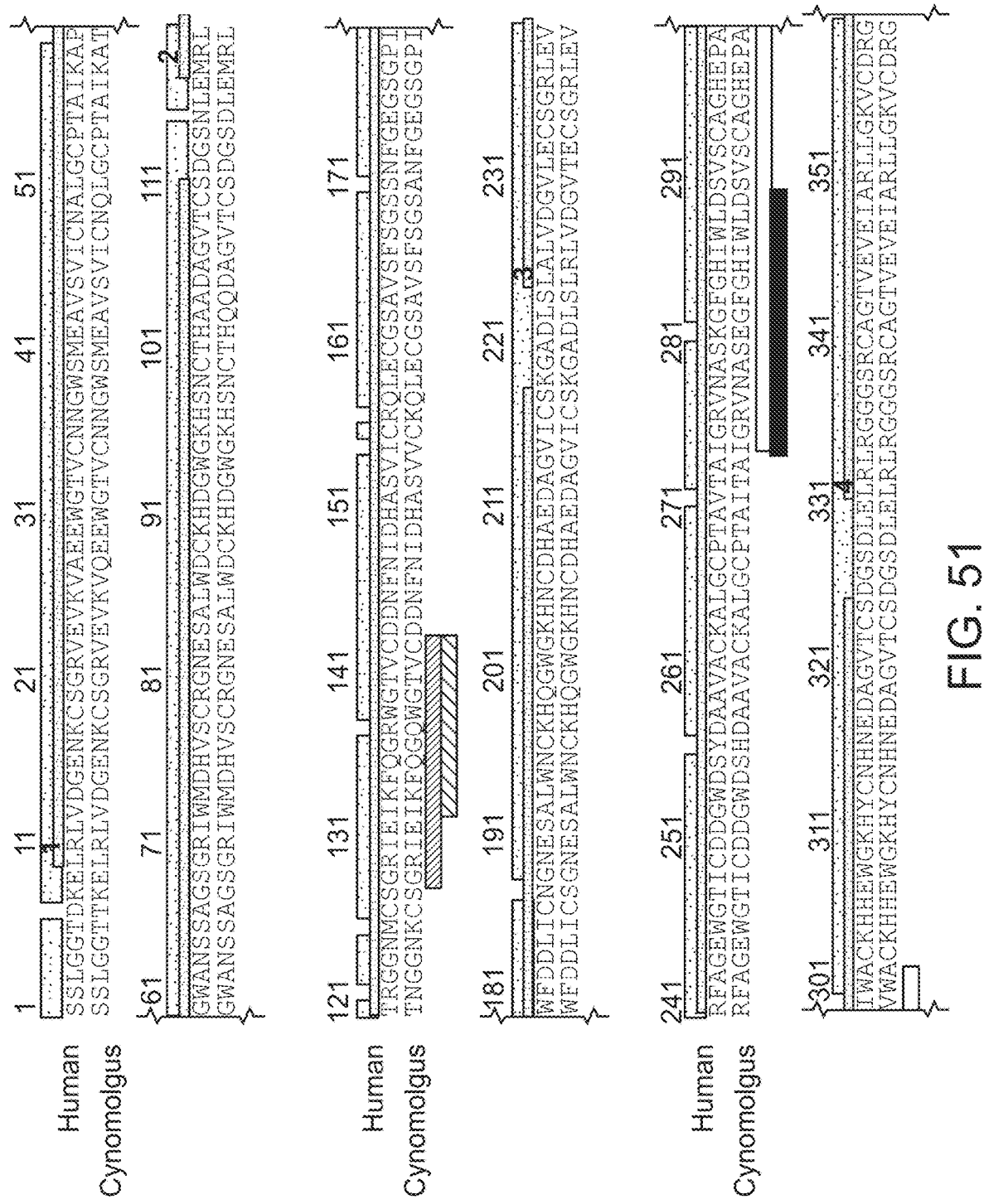
FIG. 51 shows alignment of human CD163 (SEQ ID NO: 25) against cynomolgus CD163 (SEQ ID NO: 26). Signal sequence. The sequence under black bars indicate the 9 SRCR domains and the gray lines above the sequence indicate consensus sequence. The protected and exposed regions are shown based on AB101 binding epitope as determined by observed protection in HDX-MS. The solid bars under the sequence indicate a nepenthesin II protected region. The outlined box under the sequence indicates a pepsin protected region. The hatched box under the sequence indicates a pepsin exposed region. The vertical striped box under the sequence indicates a nepenthesin II exposed region. The lysine (K) at position 323 of human CD163 and glutamic acid (E) of cynomolgus CD163 are indicated with a box.

The comparison of the HDX kinetics between the antibody-bound unbound states was used to assess the changes throughout the antigen in response to antibody binding. A summary of the changes for the pepsin and Nepenthesin II data sets are shown in FIGS. 50 and 51. The changes are colored on the primary sequence by whether there were small (small changes at a single time point) or large changes (beyond two standard deviations or seen at several time points) in HDX kinetics in response to antibody binding. We note that for these comparisons we only utilized changes that were statistically significant as assessed by the standard deviation among the replicates, along with making sure that all overlapping peptides covering nearly the same region are in agreement. By these criteria we ensure that we make only the most conservative inferences from the data sets.

In the pepsin data sets shown on FIG. 47, there were two sites that showed increased protection upon antibody binding. One site includes the glycopeptide 271-285, which showed a drastic increase in protection at several time points, and several peptides covering the C-terminally adjacent region 286-299 which also show a significant decrease in exchange kinetics. A second site includes three peptides within residues 405-418 which show a slight increase in protection. A large number of peptides showed an increase in flexibility (faster exchange) upon antibody binding. The most striking were at residues 125-139 and 479-488, while more subtle increases were observed at residues 887-910 and 918-933.

The Nepenthesin II data set shown in FIG. 48 overall showed similar changes to those observed with pepsin. The largest increases in protection were evident at residues 279-286, with the region just N-terminal to this (271-278) showing a small increase. The residues 408-415 also showed a small increase in protection upon antibody binding. As in the pepsin data, there was an increase in flexibility across large sections of the protein. The largest increase in flexibility was observed at residues 471-483, with smaller changes across many more parts of the protein. The consistency with these datasets strongly indicates the epitope of OR2805 lies with within residues 279-285 and may also include the neighboring sequence (279-299) as well as residues 405-418. Other regions may also be involved that were not observed by HDX-MS.

Figure 49:
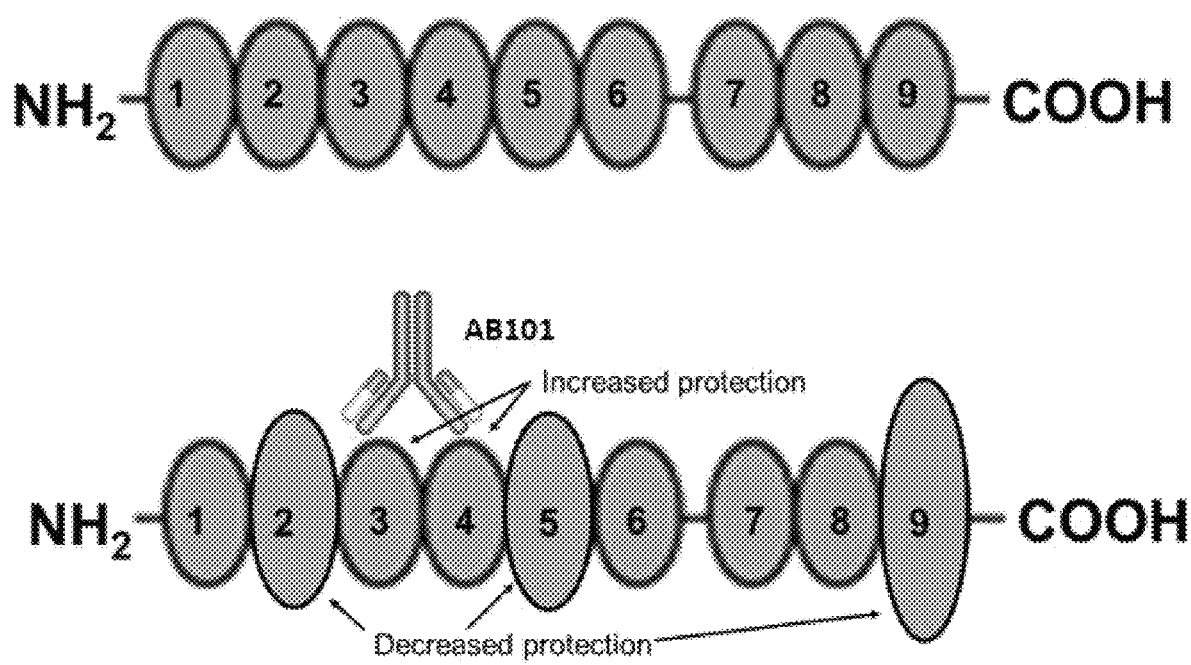
FIG. 49 shows schematic of AB101 binding to human CD163 ECD based on HDX-MS studies.

Much like in the pepsin data, there was also an increase in flexibility across large sections of the protein in the Nepenthesin II data set. The largest increase in flexibility was observed at residues 471-483, with smaller changes across many more parts of the protein (FIG. 49). Overall, the large changes distal to the proposed epitope are consistent with a large-scale allosteric effect upon antibody binding. The fact that all of the changes distal to the epitope are becoming more exposed indicate that antibody binding loosens some secondary structure across the protein, likely by influencing the interactions with neighboring protein domains. The fact that changes are seen at both the very N-terminal and C-terminal domains indicates that this protein has several inter-domain interactions in its native (unliganded) conformation.

FIG. 49 shows a schematic summary of the effect of AB101 binding to human CD163 ECD. In the presence of AB101, regions within domains SRCR 3 and 4 were protected from proton-deuterium exchange. Concomitantly with reduced exchange in domains 3 and 4, SRCR domains 2, 5, and 9 displayed increased exchange indicative of greater exposure to solvent upon AB101 binding.

Example 23—AB101 Binds Truncated Human CD163 ECD SRCR Domain 1-5 Fragment

The extracellular domain of human CD163 was truncated after SRCR domain 5 and retained a C-terminus histidine tag. This CD163 ECD fragment was expressed in HEK293-6E cells and purified using IMAC methods, as shown in FIG. 50. AB101 binds truncated ECD with sub-nanomolar EC50 as indicated in Table 10, however as expected RM3/1 does not bind. RM3/1 binding epitope has been mapped to SRCR domains 8 and 9. The truncated CD163 ECD SRCR 1-5 contains domains 3 and 4 that were identified by HDX-MS to contain the AB101 binding epitope. That AB101 maintains binding to SRCR 1-5 further supports the epitope identification results from the HDX-MS study.

TABLE 10

EC50 values for AB101, RM3/1, EDHu-1, and 215927 binding to truncated CD163 ECD SRCR 1-5.

| | EC50 (nM) | | | |
|---|---|---|---|---|
| Antigen | AB101 R11 | RM3/1 | EDHu-1 | 215927 |
| huCD163 ECD | 0.26 | 0.061 | 0.052 | 0.017 |
| huCD163 SRCR 1-5 | 0.76 | — | 0.050 | 0.020 |
| Ratio SRCR 1-5/ECD | 2.9 | — | 0.96 | 1.17 |

Example 24—AB101 Binds to Human but not Cynomolgus Recombinant CD163 ECD Protein and a Single Point Mutation, E323K, in Cynomolgus CD163 ECD Confers AB101 Binding on Par with Human CD163 ECD In EXAMPLE 6, using an ELISA assay with recombinant CD163 proteins immobilized to plastic, the AB101 binding to recombinant human was determined from 14-point dose-response curves in 26 separate experiments to have a geometric mean EC50 value of 0.52 nM. AB101 did not show binding to the recombinant murine CD163, while a commercially available rat anti-muCD163 (Thermo Fisher Scientific #14-1631-82) antibody bound as expected.

As a result of the failure of AB101 to bind murine CD163 and the low amino acid sequence identity with human CD163 (72.9%), focus was directed toward a second species often used in preclinical toxicology studies, namely non-human primate (NHP) cynomolgus. Cynomolgus CD163 shares a 96.5% amino acid sequence identity with human CD163. Production of human and cynomolgus CD163 ECD with a C-terminal 8 histidine tag in HEK293-6E cells yielded about 1 to 2 mg of purified protein per L of day 7 transient transfection CM. FIG. 51 shows the alignment of human and cynomolgus CD163 proteins.

Armed with the knowledge of the HDX-MS results that identify the binding epitope on CD163 and the significant sequence identity between human and cynomolgus CD163 and that AB101 does not bind cynomolgus CD163, allowed the identification a key residue in SRCR domain 3 implicated AB101 binding. The lysine residue at position 323 in human CD163 is a glutamic residue in all potential non-human species considered for toxicology studies (FIG. 51). This position is centered within the AB101 binding epitope of SRCR domain 3 that was defined by HDX-MS. Site-directed mutagenesis of the cynomolgus glutamic acid at position 323 to lysine confers AB101 binding to cynomolgus CD163 ECD with an EC50 near that of AB101 binding to human CD163 ECD (FIG. 52). This gain in function result strongly implicates the lysine at position 323 in AB101 binding epitope.

Example 25—Binding Affinity of AB101 to Human CD163 by SPR

Surface plasmon resonance (SPR) measurements were used to determine AB101 and anti-CD163 clone GHI/61 binding to human CD163 (AB101 avidity measurements) in different running buffer conditions.

SPR analysis of binding of AB101 and anti-CD163 clone GHI/61 to human CD163 was carried out using a Biacore T200 instrument (GE Healthcare Life Sciences). The purified recombinant CD163 protein was directly immobilized on the chip (Serie S-type CM5) using an amine coupling kit (GE Healthcare Life Sciences). A pH scouting (10 mM sodium acetate pH 5.5/5.0/4.5/4.0) was performed to determine suitable concentration and pH for amine coupling immobilization. The sodium acetate (pH5.5) was chosen as the best condition for CD163 coupling onto the sensor chip CM5. The amount of CD163 protein coupling onto the CM5 chip was 80 RU (0.08 ng/mm$^2$).

The running buffers used for the experiment: Buffer (1) 10 mM Hepes, 150 mM NaCl, 3.0 mM EDTA, and 0.05% Tween 20, pH7.4; Buffer (2) 10 mM Hepes, 150 mM NaCl, 3.0 mM CaCl$_2$), 1.0 mM EGTA, and 0.005% Tween 20, pH7.4.

MAbs were dissolved in running buffer. For AB101, sensorgrams were generated using flow rate at 30 µl/min, concentrations at 6.25/12.5/25/50/100/200 µg/ml, contact time 300 s, and dissociation time 600 s. For GHI/61, sensorgrams were generated using flow rate at 30 µl/min, concentrations at 3.125/6.25/12.5/25/50/100 µg/ml, contact time 300 s, and dissociation time 600 s. The flow cells were regenerated with 10 mM Glycine-HCl, pH3.0 (GE Healthcare Life Sciences). Data analysis was performed on the Biacore T200 computer and with the Biacore T200 evaluation software.

Figure 54:
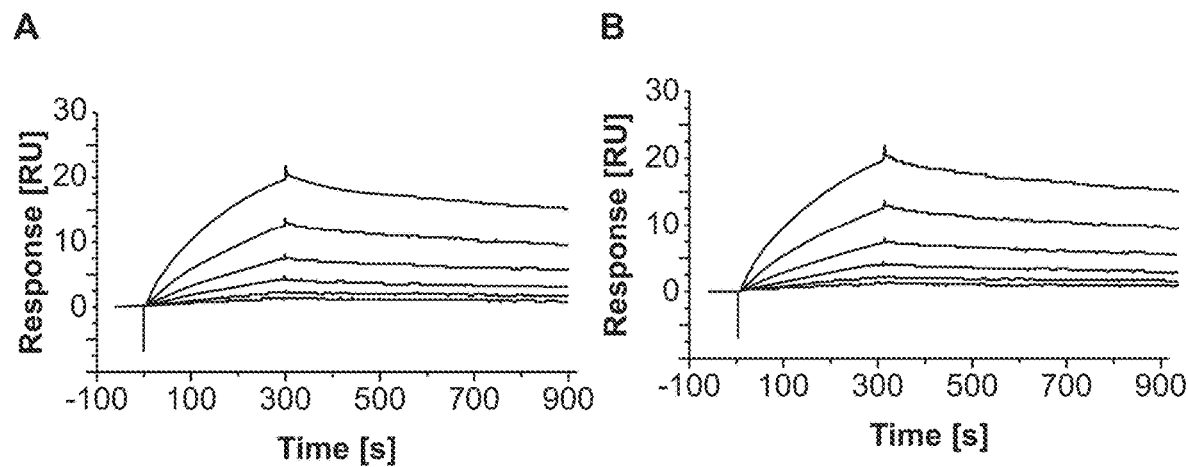
FIG. 54 shows SPR detection of binding of GHI/61 to human CD163. Anti-CD163 clone GHI/61 was serially diluted into different concentrations with (A) EDTA or (B) calcium-containing running buffer. GHI/61 was then injected into flow cell 2 with a flow rate at 30 μl/min, concentrations at 3.125/6.25/12.5/25/50/100 μg/ml, a contact time of 300 s, and a dissociation time of 600 s.

It has been shown that the binding of GHI/61 and other anti-CD163 antibodies to human CD163 is dependent on free calcium. GHI/61 had higher affinity to CD163 in calcium free buffer than in calcium-containing buffer. To determine if AB101 binding is calcium dependent, we performed SPR measurement of AB101 binding to immobilized human CD163 in 2 mM calcium-containing buffer or calcium free, EDTA buffer. As shown in Table 11 and FIG. 53, AB101 had stronger binding avidity with a $K_D$ of 45 nM in calcium-containing buffer as related to the 2-fold weaker avidity in calcium free EDTA buffer ($K_D$=89 nM). In contrast, SPR measurements observed $K_D$ values of 63 nM and 12 nM for GHI/61 binding to CD163 in calcium-containing and EDTA buffer (FIG. 54 and Table 11), respectively.

TABLE 11

SPR Binding Results of AB101 to Immobilized Human CD163 Binding of Antibodies to Immobilized Human CD163

| | AB101 | | | GHI/61 | | |
|---|---|---|---|---|---|---|
| Buffer | $K_D$ [nM] | $k_a$ [M$^{-1}$s$^{-1}$] | $K_d$ [s$^{-1}$] | $K_D$ [nM] | $k_a$ [M$^{-1}$s$^{-1}$] | $K_d$ [s$^{-1}$] |
| Calcium | 45 | 1.678 × 10$^4$ | 7.544 × 10$^{-4}$ | 63 | 0.732 × 10$^4$ | 4.668 × 10$^{-4}$ |
| EDTA | 89 | 1.280 × 10$^4$ | 11.39 × 10$^{-4}$ | 12 | 1.476 × 10$^4$ | 1.783 × 10$^{-4}$ |

The SPR results confirmed the previously reported GHI/61 findings and indicated that AB101 may require physiological calcium concentrations for optimal binding to human CD163.

Figure 55:
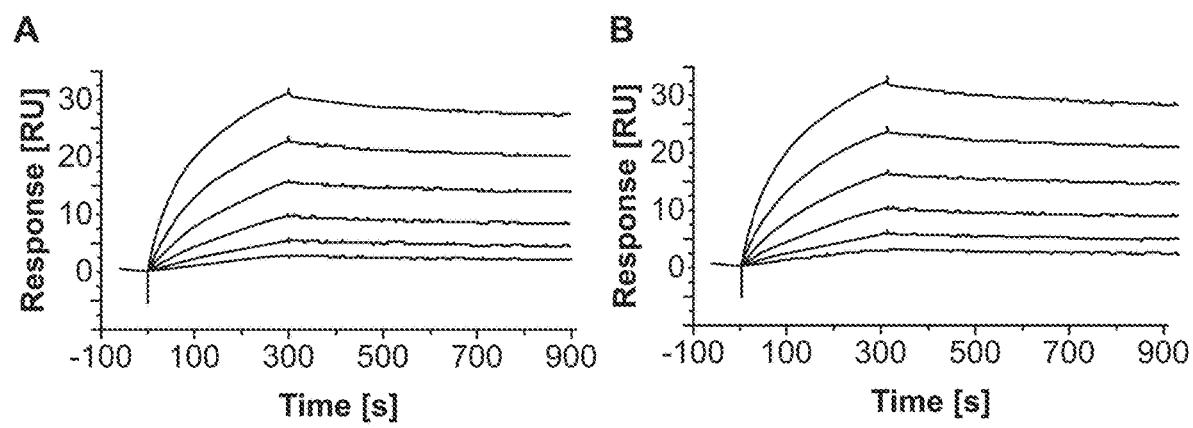
FIG. 55 shows SPR detection of binding of CD163 to AB101. Human CD163 protein was serially diluted into different concentrations with calcium-containing running buffer. CD163 protein was then injected into flow cell 2 with a flow rate at 30 μl/min, concentrations at 1.25/2.5/5.0/10.0/20.0/40.0 μg/ml, a contact time of 300 s, and a dissociation time of 600 s.

Next, we performed SPR measurements of CD163 binding affinity to immobilized AB101 in calcium-containing buffer and observed a $K_D$ of 12 nM (FIG. 55 and Table 12). CD163 binding to immobilized AB101 had a 3.7-fold higher ka of 6.213×10$^4$ (M$^{-1}$s$^{-1}$) when compared to the corresponding Ka of AB101 binding to immobilized CD163 (1.678× 10$^4$ M$^{-1}$s$^{-1}$).

TABLE 12

SPR Binding Results of human CD163 to Immobilized AB101 Human CD163 Binding to AB101

| Buffer | $K_D$ [nM] | $k_a$ [M$^{-1}$s$^{-1}$] | $K_d$ [s$^{-1}$] |
|---|---|---|---|
| Calcium | 12 | 6.213 × 10$^4$ | 7.895 × 10$^{-4}$ |

In summary, SPR measurements determined a 12 nM binding affinity and a 45 nM avidity of AB101 to CD163 in the presence of 2 mM free calcium.

Example 26—AB101 Binding to Human CD163 Protein in Solution by AlphaLISA

The binding affinity of AB101 to human CD163 in solution was determined by AlphaLisa assay.

The assay consists of human soluble CD163 with 10-histidine tag on the C-terminus, biotinylated anti-hIgG1, streptavidin acceptor beads and nickel donor beads.

The assay was performed by making serial dilutions of AB101 and isotype control in 0.5% BSA in 1×PBS without Ca$^{2+}$, Mg$^{2+}$ with a starting titration concentration of 1500 nM. CD163 was diluted in the same buffer to a concentration of 1500 nM.

Binding of AB101 to human CD163. AB101 or isotype control serial dilutions were added at a volume of 5 µl/well to 5 µl/well human CD163, sealed with aluminum plate sealer and incubated for 1 hour at room temperature with gentle shaking.

Detection of AB101: AB101 was detected using 2.5 nM biotinylated anti-human IgG1 antibody in 1× AlphaLISA Immunoassay assay buffer at a volume of 5 µl/well to the 10 µl binding mix. The plate was sealed and incubated for 1 hour at room temperature with gentle shaking.

Binding of acceptor bead: Following antibody detection step, 5 µl of 100 µg/ml streptavidin acceptor beads in 1× AlphaLISA Immunoassay assay buffer were added to each well, followed by sealing the plate and incubating at room temperature for 1 hour with gentle shaking.

Binding of donor bead: Next, 5 µl of 100 µg/ml nickel donor beads in 1× AlphaLISA Immunoassay assay buffer were added per well, followed by sealing the plate and incubating at room temperature for 1 hour with gentle shaking.

The plate was read using an Envision plate reader according to manufacturer protocol, and data was analyzed using GraphPad Prism 8 to calculate $K_d$.

Figure 56:
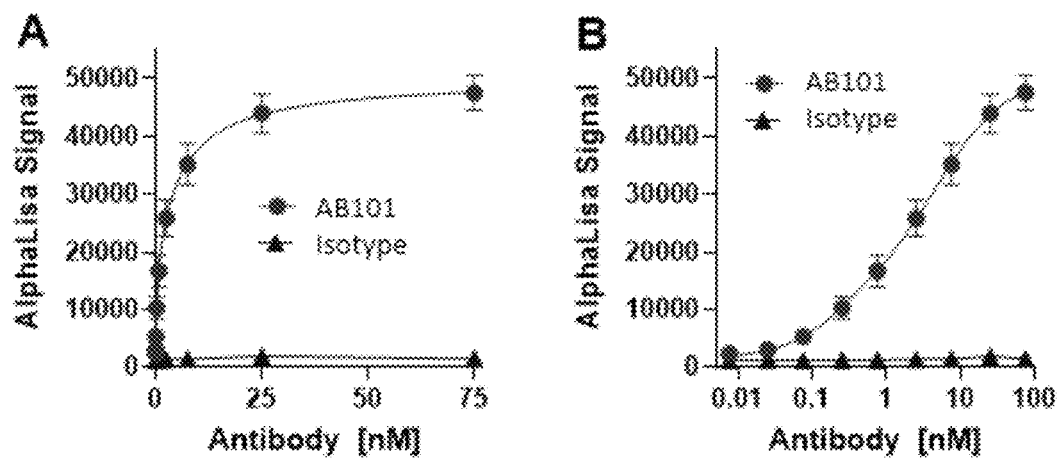
FIG. 56 shows binding of AB101 to soluble CD163 in AlphaLisa assay. AB101 (circles) or isotype control (triangles) were incubated with 750 nM CD163-His at the indicated concentration for 1 h. Binding was quantified by AlphaLisa with a biotinylated anti-hIgG1 mAb, streptavidin acceptor and nickel donor beads. Symbols represent the mean±standard error of five independent measurements. Curve fit was performed with 1 and 2-site saturated binding models (GraphPad Prism). ($R^2$=0.92). (A) linear and (B) log x-axes scale.

The AlphaLisa measurement of AB101 binding to CD163 reached saturation at 30 nM of AB101 (FIG. 56). The $K_d$ of 1.8 nM was determined by a 1-site saturated binding model combining 5 independent measurements (Table 13). The 2-site saturated binding model provided a better curve fit for the lower AB101 concentration.

TABLE 13

AlphaLisa Measurements of AB101 Binding to Soluble CD163 Protein
Binding AB101 to Soluble CD163

| Independent Assays | 1-Site Binding Model | | |
|---|---|---|---|
| | $EC_{50}$ [nM] | Max | $R^2$ |
| 1 | 4.1 | 31000 | 0.99 |
| 2 | 1.5 | 37000 | 0.97 |
| 3 | 1.9 | 52000 | 0.98 |
| 4 | 1.7 | 48000 | 0.99 |
| 5 | 0.51 | 44000 | 0.98 |
| Mean | 1.9 | 42400 | |
| SD | 1.3 | 8444 | |
| Geometrical Mean | 1.6 | 41692 | |

Example 27—Binding of AB101 to M2c Macrophages

To determine the binding kinetics of AB101 to CD163 expressed on cells, we performed binding studies with immunosuppressive M2c macrophages from 4 study subjects.

AB101 binding to M2c macrophages was evaluated from four healthy human subjects (39-year-old female, 24 year old male, 39 year old male and 54 year old male). Monocytes were isolated from LeukoPaks purchased from Blood-Works.

At Day 7, M2c cells were incubated for 15 minutes at room temperature in Macrophage Detachment Solution DXF and removed from the flask into X-VIVO-15™ medium. Following centrifugation, the cells were washed once with PBS and resuspended in Zombie UV live/dead stain (1:500) at room temperature for 20 minutes. Cells were then washed with FACS buffer and resuspended in FACS Block (FACS buffer containing 10% FBS and 0.5 mg/ml human IgG1) at room temperature for 20 minutes. Cells in blocking buffer were transferred to a 384 well plate at $2.5 \times 10^4$ cells/well and titrated antibodies were added directly to each well at 2× final assay concentration. Cells were incubated with antibodies at room temperature for 20 min. Cells were washed three times with FACS buffer, then resuspended in FACS buffer for acquisition on a Symphony flow cytometer (BD Biosciences).

Figure 57:
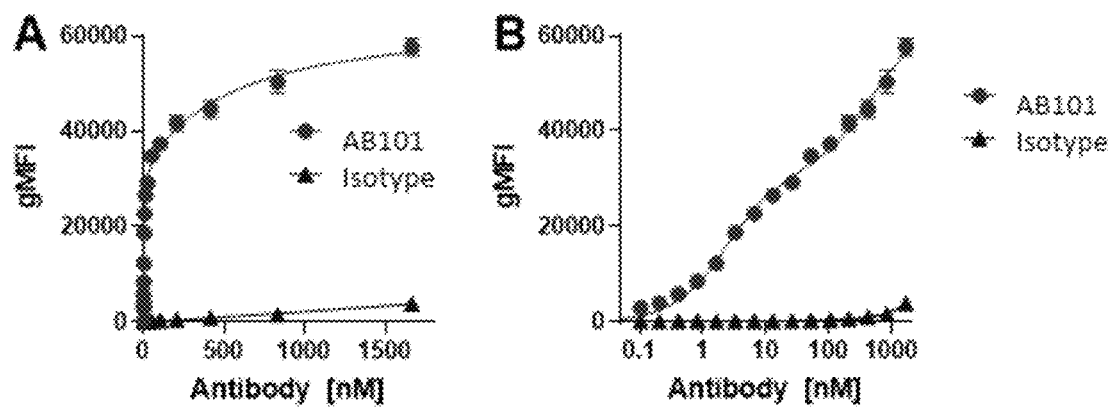
FIG. 57 shows AB101 binding to M2c macrophages. M2c macrophages were blocked with stringent FACS blocking buffer containing 0.5 mg/ml human IgG1 and then stained with AB101 (circles) or isotype control (triangles) at the indicated concentration for 30 min. Binding of AlexaFluor 647 labeled AB101 and isotype control to M2c macrophages was quantified by fluorescence intensity and reported as gMFI. Symbols represent the mean t standard error of four study subjects. Curve fits was performed with the 2-site saturated binding model (GraphPad Prism). ($R^2$=0.99). (A) linear and (B) log x-axes scale.

AB101 binding to M2c macrophages exhibited a bimodal binding curve (FIG. 57) suggesting that AB101 binding to the Fc receptor may affect binding to CD163 expressed on M2c cells. The calculated $K_d$ values for AB101 in 1-site specific saturated binding curves are shown in Table 14. The $K_d$ value for binding of AB101 to CD163 calculated by the 1-site model was 7.7 nM with a Bmax of 46103 gMFI ($R^2$=0.91). Two-site curve fit modelling provided a better curve fit ($R^2$=0.98).

TABLE 14

Equilibrium Binding of AB101 Binding to Human M2c Macrophages
Binding Kinetics of AB101

| Human Subject IDs | 1-Site Binding Model | | |
|---|---|---|---|
| | $K_d$ [nM] | Bmax | $R^2$ |
| W | 7.2 | 45800 | 0.93 |
| X | 6.6 | 41700 | 0.91 |
| Y | 8.1 | 45400 | 0.91 |
| Z | 8.9 | 51513 | 0.93 |
| Mean | 7.7 | 46103 | |
| SD | 1.0 | 4051 | |
| Geometrical Mean | 7.7 | 45972 | |

Although the present disclosure and its advantages have been described in detail, it should be understood that various changes, substitutions, and alterations are made herein without departing from the spirit and scope of the disclosure as defined in the appended claims.

SEQUENCE LISTING

```
Sequence total quantity: 28
SEQ ID NO: 1          moltype = AA  length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 1
RASQSISSYL N                                                              11

SEQ ID NO: 2          moltype = AA  length = 7
FEATURE               Location/Qualifiers
REGION                1..7
                      note = Description of Artificial Sequence: Synthetic peptide
source                1..7
                      mol_type = protein
                      organism = synthetic construct
SEQUENCE: 2
AASSLQS                                                                    7

SEQ ID NO: 3          moltype = AA  length = 10
FEATURE               Location/Qualifiers
REGION                1..10
                      note = Description of Artificial Sequence: Synthetic peptide
source                1..10
```

```
                        mol_type = protein
                        organism = synthetic construct
SEQUENCE: 3
QQSYSTPRGT                                                              10

SEQ ID NO: 4            moltype = AA   length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 4
SYAMH                                                                   5

SEQ ID NO: 5            moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 5
VISYDGSNKY YADSVKG                                                      17

SEQ ID NO: 6            moltype = AA   length = 24
FEATURE                 Location/Qualifiers
REGION                  1..24
                        note = Description of Artificial Sequence: Synthetic peptide
source                  1..24
                        mol_type = protein
                        organism = synthetic construct
SEQUENCE: 6
ENVRPYYDFW SGYYSEYYYY GMDV                                              24

SEQ ID NO: 7            moltype = AA   length = 109
FEATURE                 Location/Qualifiers
REGION                  1..109
                        note = Description of Artificial Sequence: Synthetic
                         polypeptide
source                  1..109
                        mol_type = protein
                        organism = synthetic construct
SEQUENCE: 7
DIQMTQSPSS LSASVGDRVT ITCRASQSIS SYLNWYQQKP GKAPKLLIYA ASSLQSGVPS        60
RFSGSGSGTD FTLTISSLQP EDFATYYCQQ SYSTPRGTFG QGTKVEIKR                   109

SEQ ID NO: 8            moltype = AA   length = 166
FEATURE                 Location/Qualifiers
REGION                  1..166
                        note = Description of Artificial Sequence: Synthetic
                         polypeptide
source                  1..166
                        mol_type = protein
                        organism = synthetic construct
SEQUENCE: 8
EVQLVESGGG VVQPGRSLRL SCAASGFTFS SYAMHWVRQA PGKGLEWVAV ISYDGSNKYY        60
ADSVKGRFTI SRDNSKNTLY LQMNSLRAED TAVYYCAREN VRPYYDFWSG YYSEYYYYGM       120
DVWGQGTTVT VSSASTKGPS VFPLAPSSKS TSGGTAALGC LVKDYF                     166

SEQ ID NO: 9            moltype = AA   length = 215
FEATURE                 Location/Qualifiers
REGION                  1..215
                        note = Description of Artificial Sequence: Synthetic
                         polypeptide
source                  1..215
                        mol_type = protein
                        organism = synthetic construct
SEQUENCE: 9
DIQMTQSPSS LSASVGDRVT ITCRASQSIS SYLNWYQQKP GKAPKLLIYA ASSLQSGVPS        60
RFSGSGSGTD FTLTISSLQP EDFATYYCQQ SYSTPRGTFG QGTKVEIKRT VAAPSVFIFP       120
PSDEQLKSGT ASVVCLLNNF YPREAKVQWK VDNALQSGNS QESVTEQDSK DSTYSLSSTL       180
TLSKADYEKH KVYACEVTHQ GLSSPVTKSF NRGEC                                 215

SEQ ID NO: 10           moltype = AA   length = 463
FEATURE                 Location/Qualifiers
REGION                  1..463
                        note = Description of Artificial Sequence: Synthetic
                         polypeptide
```

```
source                   1..463
                         mol_type = protein
                         organism = synthetic construct
SEQUENCE: 10
EVQLVESGGG VVQPGRSLRL SCAASGFTFS SYAMHWVRQA PGKGLEWVAV ISYDGSNKYY   60
ADSVKGRFTI SRDNSKNTLY LQMNSLRAED TAVYYCAREN VRPYYDFWSG YYSEYYYYGM  120
DVWGQGTTVT VSSASTKGPS VFPLAPSSKS TSGGTAALGC LVKDYFPEPV TVSWNSGALT  180
SGVHTFPAVL QSSGLYSLSS VVTVPSSSLG TQTYICNVNH KPSNTKVDKR VEPKSCDKTH  240
TCPPCPAPEL LGGPSVFLFP PKPKDTLMIS RTPEVTCVVV DVSHEDPEVK FNWYVDGVEV  300
HNAKTKPREE QYNSTYRVVS VLTVLHQDWL NGKEYKCKVS NKALPAPIEK TISKAKGQPR  360
EPQVYTLPPS REEMTKNQVS LTCLVKGFYP SDIAVEWESN GQPENNYKTT PPVLDSDGSF  420
FLYSKLTVDK SRWQQGNVFS CSVMHEALHN HYTQKSLSLS PGK                   463

SEQ ID NO: 11            moltype = AA   length = 463
FEATURE                  Location/Qualifiers
REGION                   1..463
                         note = Description of Artificial Sequence: Synthetic
                         polypeptide
source                   1..463
                         mol_type = protein
                         organism = synthetic construct
SEQUENCE: 11
EVQLVESGGG VVQPGRSLRL SCAASGFTFS SYAMHWVRQA PGKGLEWVAV ISYDGSNKYY   60
ADSVKGRFTI SRDNSKNTLY LQMNSLRAED TAVYYCAREN VRPYYDFWSG YYSEYYYYGM  120
DVWGQGTTVT VSSASTKGPS VFPLAPSSKS TSGGTAALGC LVKDYFPEPV TVSWNSGALT  180
SGVHTFPAVL QSSGLYSLSS VVTVPSSSLG TQTYICNVNH KPSNTKVDKR VEPKSCDKTH  240
TCPPCPAPEF EGGPSVFLFP PKPKDTLMIS RTPEVTCVVV DVSHEDPEVK FNWYVDGVEV  300
HNAKTKPREE QYNSTYRVVS VLTVLHQDWL NGKEYKCKVS NKALPASIEK TISKAKGQPR  360
EPQVYTLPPS REEMTKNQVS LTCLVKGFYP SDIAVEWESN GQPENNYKTT PPVLDSDGSF  420
FLYSKLTVDK SRWQQGNVFS CSVMHEALHN HYTQKSLSLS PGK                   463

SEQ ID NO: 12            moltype = AA   length = 463
FEATURE                  Location/Qualifiers
REGION                   1..463
                         note = Description of Artificial Sequence: Synthetic
                         polypeptide
source                   1..463
                         mol_type = protein
                         organism = synthetic construct
SEQUENCE: 12
EVQLVESGGG VVQPGRSLRL SCAASGFTFS SYAMHWVRQA PGKGLEWVAV ISYDGSNKYY   60
ADSVKGRFTI SRDNSKNTLY LQMNSLRAED TAVYYCAREN VRPYYDFWSG YYSEYYYYGM  120
DVWGQGTTVT VSSASTKGPS VFPLAPSSKS TSGGTAALGC LVKDYFPEPV TVSWNSGALT  180
SGVHTFPAVL QSSGLYSLSS VVTVPSSSLG TQTYICNVNH KPSNTKVDKR VEPKSCDKTH  240
TCPPCPAPEL LGGPDVFLFP PKPKDTLMIS RTPEVTCVVV DVSHEDPEVK FNWYVDGVEV  300
HNAKTKPREE QYNSTYRVVS VLTVLHQDWL NGKEYKCKVS NKALPLPEEK TISKAKGQPR  360
EPQVYTLPPS REEMTKNQVS LTCLVKGFYP SDIAVEWESN GQPENNYKTT PPVLDSDGSF  420
FLYSKLTVDK SRWQQGNVFS CSVMHEALHN HYTQKSLSLS PGK                   463

SEQ ID NO: 13            moltype = AA   length = 460
FEATURE                  Location/Qualifiers
REGION                   1..460
                         note = Description of Artificial Sequence: Synthetic
                         polypeptide
source                   1..460
                         mol_type = protein
                         organism = synthetic construct
SEQUENCE: 13
EVQLVESGGG VVQPGRSLRL SCAASGFTFS SYAMHWVRQA PGKGLEWVAV ISYDGSNKYY   60
ADSVKGRFTI SRDNSKNTLY LQMNSLRAED TAVYYCAREN VRPYYDFWSG YYSEYYYYGM  120
DVWGQGTTVT VSSASTKGPS VFPLAPCSRS TSESTAALGC LVKDYFPEPV TVSWNSGALT  180
SGVHTFPAVL QSSGLYSLSS VVTVPSSSLG TKTYTCNVDH KPSNTKVDKR VESKYGPPCP  240
PCPAPEFLGG PSVFLFPPKP KDTLMISRTP EVTCVVVDVS QEDPEVQFNW YVDGVEVHNA  300
KTKPREEQFN STYRVVSVLT VLHQDWLNGK EYKCKVSNKG LPSSIEKTIS KAKGQPREPQ  360
VYTLPPSQEE MTKNQVSLTC LVKGFYPSDI AVEWESNGQP ENNYKTTPPV LDSDGSFFLY  420
SRLTVDKSRW QEGNVFSCSV MHEALHNHYT QKSLSLSLGK                       460

SEQ ID NO: 14            moltype = AA   length = 215
FEATURE                  Location/Qualifiers
REGION                   1..215
                         note = Description of Artificial Sequence: Synthetic
                         polypeptide
source                   1..215
                         mol_type = protein
                         organism = synthetic construct
SEQUENCE: 14
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ SYSTPRGTFG QGTKVEIKRT DAAPTVSIFP  120
PSSEQLTSGG ASVVCFLNNF YPKDINVKWK IDGSERQNGV LNSWTDQDSK DSTYSMSSTL  180
```

```
TLTKDEYERH NSYTCEATHK TSTSPIVKSF NRNEC                              215

SEQ ID NO: 15           moltype = AA  length = 462
FEATURE                 Location/Qualifiers
REGION                  1..462
                        note = Description of Artificial Sequence: Synthetic
                        polypeptide
source                  1..462
                        mol_type = protein
                        organism = synthetic construct
SEQUENCE: 15
EVQLVESGGG VVQPGRSLRL SCAASGFTFS SYAMHWVRQA PGKGLEWVAV ISYDGSNKYY   60
ADSVKGRFTI SRDNSKNTLY LQMNSLRAED TAVYYCAREN VRPYYDFWSG YYSEYYYYGM  120
DVWGQGTTVT VSSKTTAPSV YPLAPVCGDT TGSSVTLGCL VKGYFPEPVT LTWNSGSLSS  180
GVHTFPAVLQ SDLYTLSSSV TVTSSTWPSQ SITCNVAHPA SSTKVDKKIE PRGPTIKPCP  240
PCKCPAPNLL GGPSVFIFPP KIKDVLMISL SPIVTCVVVD VSEDDPDVQI SWFVNNVEVH  300
TAQTQTHRED YNSTLRVVSA LPIQHQDWMS GKEFKCKVNN KDLPAPIERT ISKPKGSVRA  360
PQVYVLPPPE EEMTKKQVTL TCMVTDFMPE DIYVEWTNNG KTELNYKNTE PVLDSDGSYF  420
MYSKLRVEKK NWVERNSYSC SVVHEGLHNH HTTKSFSRTP GK                    462

SEQ ID NO: 16           moltype = AA  length = 462
FEATURE                 Location/Qualifiers
REGION                  1..462
                        note = Description of Artificial Sequence: Synthetic
                        polypeptide
source                  1..462
                        mol_type = protein
                        organism = synthetic construct
SEQUENCE: 16
EVQLVESGGG VVQPGRSLRL SCAASGFTFS SYAMHWVRQA PGKGLEWVAV ISYDGSNKYY   60
ADSVKGRFTI SRDNSKNTLY LQMNSLRAED TAVYYCAREN VRPYYDFWSG YYSEYYYYGM  120
DVWGQGTTVT VSSKTTAPSV YPLAPVCGDT TGSSVTLGCL VKGYFPEPVT LTWNSGSLSS  180
GVHTFPAVLQ SDLYTLSSSV TVTSSTWPSQ SITCNVAHPA SSTKVDKKIE PRGPTIKPCP  240
PCKCPAPNLE GGPSVFIFPP KIKDVLMISL SPIVTCVVVD VSEDDPDVQI SWFVNNVEVH  300
TAQTQTHRED YNSTLRVVSA LPIQHQDWMS GKAFACAVNN KDLPAPIERT ISKPKGSVRA  360
PQVYVLPPPE EEMTKKQVTL TCMVTDFMPE DIYVEWTNNG KTELNYKNTE PVLDSDGSYF  420
MYSKLRVEKK NWVERNSYSC SVVHEGLHNH HTTKSFSRTP GK                    462

SEQ ID NO: 17           moltype = AA  length = 1121
FEATURE                 Location/Qualifiers
source                  1..1121
                        mol_type = protein
                        organism = Homo sapiens
SEQUENCE: 17
MSKLRMVLLE DSGSADFRRH FVNLSPFTIT VVLLLSACFV TSSLGGTDKE LRLVDGENKC   60
SGRVEVKVQE EWGTVCNNGW SMEAVSVICN QLGCPTAIKA PGWANSSAGS GRIWMDHVSC  120
RGNESALWDC KHDGWGKHSN CTHQQDAGVT CSDGSNLEMR LTRGGNMCSG RIEIKFQGRW  180
GTVCDDNFNI DHASVICRQL ECGSAVSFSG SSNFGEGSGP IWFDDLICNG NESALWNCKH  240
QGWGKHNCDH AEDAGVICSK GADLSLRLVD GVTECSGRLE VRFQGEWGTI CDDGWDSYDA  300
AVACKQLGCP TAVTAIGRVN ASKGFGHIWL DSVSCQGHEP AIWQCKHHEW GKHYCNHNED  360
AGVTCSDGSD LELRLRGGGS RCAGTVEVEI QRLLGCSVCD GWGLKEADVV CRQLGCGSAL  420
KTSYQVYSKI QATNTWLFLS SCNGNETSLW DCKNWQWGGL TCDHYEEAKI TCSAHREPRL  480
VGGDIPCSGR VEVKHGDTWG SICDSDFSLE AASVLCRELQ CGTVVSILGG AHFGEGNGQI  540
WAEEFQCEGH ESHLSLCPVA PRPEGTCSHS RDVGVVCSRY TEIRLVNGKT PCEGRVELKT  600
LGAWGSLCNS HWDIEDAHVL CQQLKCGVAL STPGGARFGK GNGQIWRHMF HCTGTEQHMG  660
DCPVTALGAS LCPSEQVASV ICSGNQSQTL SSCNSSSLGP TRPTIPEESA VACIESGQLR  720
LVNGGGRCAG RVEIYHEGSW GTICDDSWDL SDAHVVCRQL GCGEAINATG SAHFGEGTGP  780
IWLDEMKCNG KESRIWQCHS HGWGQQNCRH KEDAGVICSE FMSLRLTSEA SREACAGRLE  840
VFYNGAWGTV GKSSMSETTV GVVCRQLGCA DKGKINPASL DKAMSIPMWV DNVQCPKGPD  900
TLWQCPSSPW EKRLASPSEE TWITCDNKIR LQEGPTSCSG RVEIWHGGSW GTVCDDSWDL  960
DDAQVVCQQL GCGPALKAFK EAEFGQGTGP IWLNEVKCKG NESSLWDCPA RRWGHSECGH 1020
KEDAAVNCTD ISVQKTPQKA TTGRSSRQSS FIAVGILGVV LLAIFVALFF LTKKRRQRQR 1080
LAVSSRGENL VHQIQYREMN SCLNADDLDL MNSSGGHSEP H                    1121

SEQ ID NO: 18           moltype = AA  length = 27
FEATURE                 Location/Qualifiers
source                  1..27
                        mol_type = protein
                        organism = Homo sapiens
SEQUENCE: 18
IGRVNASKGF GHIWLDSVSC QGHEPAI                                       27

SEQ ID NO: 19           moltype = AA  length = 11
FEATURE                 Location/Qualifiers
source                  1..11
                        mol_type = protein
                        organism = Homo sapiens
SEQUENCE: 19
VVCRQLGCGS A                                                        11
```

```
SEQ ID NO: 20            moltype = AA  length = 14
FEATURE                  Location/Qualifiers
source                   1..14
                         mol_type = protein
                         organism = Homo sapiens
SEQUENCE: 20
WDCKNWQWGG LTCD                                                           14

SEQ ID NO: 21            moltype = AA  length = 6
FEATURE                  Location/Qualifiers
REGION                   1..6
                         note = Description of Artificial Sequence: Synthetic 6xHis
                           tag
source                   1..6
                         mol_type = protein
                         organism = synthetic construct
SEQUENCE: 21
HHHHHH                                                                     6

SEQ ID NO: 22            moltype = AA  length = 8
FEATURE                  Location/Qualifiers
REGION                   1..8
                         note = Description of Artificial Sequence: Synthetic 8xHis
                           tag
source                   1..8
                         mol_type = protein
                         organism = synthetic construct
SEQUENCE: 22
HHHHHHHH                                                                   8

SEQ ID NO: 23            moltype = AA  length = 10
FEATURE                  Location/Qualifiers
REGION                   1..10
                         note = Description of Artificial Sequence: Synthetic 10xHis
                           tag
source                   1..10
                         mol_type = protein
                         organism = synthetic construct
SEQUENCE: 23
HHHHHHHHHH                                                                10

SEQ ID NO: 24            moltype = AA  length = 1015
FEATURE                  Location/Qualifiers
REGION                   1..1015
                         note = Description of Artificial Sequence: Synthetic
                           polypeptide
source                   1..1015
                         mol_type = protein
                         organism = synthetic construct
SEQUENCE: 24
GTDKELRLVD GENKCSGRVE VKVQEEWGTV CNNGWSMEAV SVICNQLGCP TAIKAPGWAN           60
SSAGSGRIWM DHVSCRGNES ALWDCKHDGW GKHSNCTHQQ DAGVTCSDGS NLEMRLTRGG          120
NMCSGRIEIK FQGRWGTVCD DNFNIDHASV ICRQLECGSA VSFSGSSNFG EGSGPIWFDD          180
LICNGNESAL WNCKHQGWGK HNCDHAEDAG VICSKGADLS LRLVDGVTEC SGRLEVRFQC          240
EWGTICDDGW DSYDAAVACK QLGCPTAVTA IGRVNASKGF GHIWLDSVSC QGHEPAVWQC          300
KHHEWGKHYC NHNEDAGVTC SDGSDLELRL RGGGSRCAGT VEVEIQRLLG KVCDRGWGLK          360
EADVVCRQLG CGSALKTSYQ VYSKIQATNT WLFLSSCNGN ETSLWDCKNW QWGGLTCDHY          420
EEAKITCSAH REPRLVGGDI PCSGRVEVKH GDTWGSICDS DFSLEAASVL CRELQCGTVV          480
SILGGAHFGE GNGQIWAEEF QCEGHESHLS LCPVAPRPEG TCSHSRDVGV VCSRYTEIRL          540
VNGKTPCEGR VELKTLGAWG SLCNSHWDIE DAHVLCQQLK CGVALSTPGG ARFGKGNGQI          600
WRHMFHCTGT EQHMGDCPVT ALGASLCPSE QVASVICSGN QSQTLSSCNS SSLGPTRPTI          660
PEESAVACIE SGQLRLVNGG GRCAGRVEIY HEGSWGTICD DSWDLSDAHV VCRQLGCGEA          720
INATGSAHFG EGTGPIWLDE MKCNGKESRI WQCHSHGWGQ QNCRHKEDAG VICSEFMSLR          780
LTSEASREAC AGRLEVFYNG AWGTVGKSSM SETTVGVVCR QLGCADKGKI NPASLDKAMS          840
IPMWVDNVQC PKGPDTLWQC PSSPWEKRLA SPSEETWITC DNKIRLQEGP TSCSGRVEIW          900
HGGSWGTVCD DSWDLDDAQV VCQQLGCGPA LKAFKEAEFG QGTGPIWLNE VKCKGNESSL          960
WDCPARRWGH SECGHKEDAA VNCTDISVQK TPQKATTGRS SRQSSHHHHH HHHHH             1015

SEQ ID NO: 25            moltype = AA  length = 1009
FEATURE                  Location/Qualifiers
source                   1..1009
                         mol_type = protein
                         organism = Homo sapiens
SEQUENCE: 25
SSLGGTDKEL RLVDGENKCS GRVEVKVQEE WGTVCNNGWS MEAVSVICNQ LGCPTAIKAP           60
GWANSSAGSG RIWMDHVSCR GNESALWDCK HDGWGKHSNC THQQDAGVTC SDGSNLEMRL          120
TRGGNMCSGR IEIKFQGRWG TVCDDNFNID HASVICRQLE CGSAVSFSGS SNFGEGSGPI          180
WFDDLICNGN ESALWNCKHQ GWGKHNCDHA EDAGVICSKG ADLSLRLVDG VTECSGRLEV          240
```

```
RFQGEWGTIC DDGWDSYDAA VACKQLGCPT AVTAIGRVNA SKGFGHIWLD SVSCQGHEPA    300
IWQCKHHEWG KHYCNHNEDA GVTCSDGSDL ELRLRGGGSR CAGTVEVEIQ RLLGKVCDRG    360
WGLKEADVVC RQLGCGSALK TSYQVYSKIQ ATNTWLFLSS CNGNETSLWD CKNWQWGGLT    420
CDHYEEAKIT CSAHREPRLV GGDIPCSGRV EVKHGDTWGS ICDSDFSLEA ASVLCRELQC    480
GTVVSILGGA HFGEGNGQIW AEEFQCEGHE SHLSLCPVAP RPEGTCSHSR DVGVVCSRYT    540
EIRLVNGKTP CEGRVELKTL GAWGSLCNSH WDIEDAHVLC QQLKCGVALS TPGGARFGKG    600
NGQIWRHMFH CTGTEQHMGD CPVTALGASL CPSEQVASVI CSGNQSQTLS SCNSSSLGPT    660
RPTIPEESAV ACIESGQLRL VNGGGRCAGR VEIYHEGSWG TICDDSWDLS DAHVVCRQLG    720
CGEAINATGS AHFGEGTGPI WLDEMKCNGK ESRIWQCHSH GWGQQNCRHK EDAGVICSEF    780
MSLRLTSEAS REACAGRLEV FYNGAWGTVG KSSMSETTVG VVCRQLGCAD KGKINPASLD    840
KAMSIPMWVD NVQCPKGPDT LWQCPSSPWE KRLASPSEET WITCDNKIRL QEGPTSCSGR    900
VEIWHGGSWG TVCDDSWDLD DAQVVCQQLG CGPALKAFKE AEFGQGTGPI WLNEVKCKGN    960
ESSLWDCPAR RWGHSECGHK EDAAVNCTDI SVQKTPQKAT TGRSSRQSS              1009

SEQ ID NO: 26           moltype = AA  length = 1009
FEATURE                 Location/Qualifiers
source                  1..1009
                        mol_type = protein
                        organism = Macaca fascicularis
SEQUENCE: 26
SSLGGTTKEL RLVDGENKCS GRVEVKVQEE WGTVCNNGWS MEAVSVICNQ LGCPTAIKAT     60
GWANSSAGSG RIWMDHVSCR GNESALWDCK HDGWGKHSNC THQQDAGVTC SDGSDLEMRL    120
TNGGNKCSGR IEIKFQGQWG TVCDDNFNID HASVVCKQLE CGSAVSFSGS ANFGEGSGPI    180
WFDDLICSGN ESALWNCKHQ GWGKHNCDHA EDAGVICSKG ADLSLRLVDG VTECSGRLEV    240
RFQGEWGTIC DDGWDSHDAA VACKQLGCPT AITAIGRVNA SEGFGHIWLD SVSCQGHEPA    300
VWQCKHHEWG KHYCNHNEDA GVTCSDGSDL ELRLRGGGSR CAGTVEVEIQ RLLGKVCDRG    360
WGLKEADVVC RQLGCGSALK TSYQVYSKIQ ATNTWLFLSS CNGNETSLWD CKNWQWGGLT    420
CDHYEEAKIT CSAHREPRLV GGDIPCSGRV EVKHGDTWGS VCDSDFSLEA ASVLCRELQC    480
GTVVSILGGA HFGEGNGQIW AEEFQCEGHE SHLSLCPVAP RPEGTCSHSR DVGVVCSRYT    540
EIRLVNGKTP CEGRVELKTL DAWGSLCNSH WDIEDAHVLC QQLKCGVALS TPGGAHFGKG    600
NGQVWRHMFH CTGTEQHMGD CPVTALGASL CPSGQVASVI CSGNQSQTLS SCNSSSLGPT    660
RPTIPEESAV ACIESGQLRL VNGGGRCAGR VEIYHEGSWG TICDDSWDLS DAHVVCRQLG    720
CGEAINATGS AHFGEGTGPI WLDEMKCNGK ESRIWQCHSH GWGQQNCRHK EDAGVICSEF    780
MSLRLTSEAS REACAGRLEV FYNGAWGSVG RSSMSETTVG VVCRQLGCAD KGKINPASLD    840
KAMSIPMWVD NVQCPKGPDT LWQCPSSPWE KRLARPSEET WITCDNKIRL QEGPTSCSGR    900
VEIWHGGSWG TVCDDSWDLN DAQVVCQQLG CGPALKAFKE AEFGQGTGPI WLNEVKCKGN    960
ESSLWDCPAR RWGHNECGHK EDAAVNCTDI SAHKTPQKAP TGHTSRQSS              1009

SEQ ID NO: 27           moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 27
PPPF                                                                  4

SEQ ID NO: 28           moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 28
PPPI                                                                  4
```

What is claimed is:

1. A pharmaceutical composition, comprising:
    (a) an antibody or antigen-binding fragment, comprising
        (i) a light chain having at least 90% identity to amino acid sequence SEQ ID NO: 9, and
        (ii) a heavy chain having at least 90% identity to any one of amino acid sequences SEQ ID NO: 10, SEQ ID NO: 11, or SEQ ID NO: 12,
    wherein the antibody or the recombinant antibody comprises a heavy chain complementarity determining region (CDR) H1 having 100% identity to amino acid sequence SEQ ID NO: 4, a heavy chain CDR H2 having 100% identity to amino acid sequence SEQ ID NO: 5, a heavy chain CDR H3 having 100% identity to amino acid sequence SEQ ID NO: 6, and a light chain sequence CDR L1 having 100% identity to amino acid sequence SEQ ID NO: 1, a light chain CDR L2 having 100% identity to amino acid sequence SEQ ID NO: 2, and a light chain CDR L3 having 100% identity to amino acid sequence SEQ ID NO: 3; and
    (b) a pharmaceutically acceptable excipient.

2. The pharmaceutical composition of claim 1, wherein the antibody or antigen-binding fragment comprises (i) a light chain having at least 95% identity to amino acid sequence SEQ ID NO: 9 and (ii) a heavy chain having at least 95% identity to any one of amino acid sequences SEQ ID NO: 10, SEQ ID NO: 11, or SEQ ID NO: 12.

3. The pharmaceutical composition of claim 1, wherein the antibody or antigen-binding fragment comprises (i) a light chain having at least 99% identity to amino acid sequence SEQ ID NO: 9 and (ii) a heavy chain having at least 99% identity to any one of amino acid sequences SEQ ID NO: 10, SEQ ID NO: 11, or SEQ ID NO: 12.

4. The pharmaceutical composition of claim 1, wherein the antibody or antigen-binding fragment comprises (i) a light chain having 100% identity to amino acid sequence SEQ ID NO: 9 and (ii) a heavy chain having 100% identity to any one of amino acid sequences SEQ ID NO: 10, SEQ ID NO: 11, or SEQ ID NO: 12.

5. The pharmaceutical composition of claim 1, wherein the antibody or antigen-binding fragment further comprises a constant domain that binds to an Fc receptor expressed on a macrophage.

6. The pharmaceutical composition of claim 1, wherein the antibody or antigen-binding fragment binds to a CD163-expressing immunosuppressive human myeloid cell.

7. The pharmaceutical composition of claim 1, wherein the antibody or antigen-binding fragment binds to a CD163-expressing macrophage.

8. The pharmaceutical composition of claim 1, wherein the pharmaceutically acceptable excipient is selected from the group consisting of: one or more surfactants, water, and one or more excipients that improve the stability of the antibody, antigen-binding fragment, or a combination thereof.

9. A method of treating a solid tumor in an individual in need thereof, the method comprising administering to the individual the pharmaceutical composition of claim 1.

10. The method of claim 9, wherein the solid tumor is a lung carcinoma or sarcoma.

11. The method of claim 10, wherein the lung carcinoma is a lung adenocarcinoma.

12. The method of claim 10, further comprising administering to the individual an additional anticancer therapy.

13. The method of claim 12, wherein the additional anticancer therapy is surgical therapy, chemotherapy, radiation therapy, cryotherapy, hormonal therapy, immunotherapy, or cytokine therapy, or combinations thereof.

14. The method of claim 13, wherein the immunotherapy is a composition comprising a checkpoint inhibitor.

* * * * *